US012686954B2

(12) United States Patent
Abe et al.

(10) Patent No.: US 12,686,954 B2
(45) Date of Patent: Jul. 21, 2026

(54) RECOMBINANT-STRUCTURE PROTEIN MULTIFILAMENT AND METHOD FOR MANUFACTURING SAME

(71) Applicant: Spiber Inc., Tsuruoka (JP)

(72) Inventors: Yunosuke Abe, Tsuruoka (JP); Hideto Ishii, Tsuruoka (JP); Ryoko Sato, Tsuruoka (JP); Akito Sato, Tsuruoka (JP); Hirotada Ando, Kariya (JP); Hiroshi Kano, Tsuruoka (JP); Koichi Kotaka, Tsuruoka (JP); Jun Kobayashi, Tsuruoka (JP)

(73) Assignee: CRANE Inc., Tsuruoka (JP)

( * ) Notice: Subject to any disclaimer, the term of this patent is extended or adjusted under 35 U.S.C. 154(b) by 1124 days.

(21) Appl. No.: 17/427,895

(22) PCT Filed: Feb. 7, 2020

(86) PCT No.: PCT/JP2020/004961
§ 371 (c)(1),
(2) Date: Aug. 2, 2021

(87) PCT Pub. No.: WO2020/162626
PCT Pub. Date: Aug. 13, 2020

(65) Prior Publication Data
US 2022/0010460 A1 Jan. 13, 2022

(30) Foreign Application Priority Data

Feb. 7, 2019 (JP) ................................. 2019-021014
Jun. 11, 2019 (JP) ................................. 2019-109041

(51) Int. Cl.
*D01F 4/02* (2006.01)
*C07K 14/435* (2006.01)
(Continued)

(52) U.S. Cl.
CPC .......... *D01F 4/02* (2013.01); *C07K 14/43518* (2013.01); *D01D 5/06* (2013.01); *D02G 3/045* (2013.01); *D10B 2211/22* (2013.01)

(58) Field of Classification Search
CPC ...... D01F 4/02; C07K 14/43518; D01D 5/06; D02G 3/045
(Continued)

(56) References Cited

U.S. PATENT DOCUMENTS

2004/0072328 A1 4/2004 Yashiro
2004/0102614 A1 5/2004 Islam et al.
(Continued)

FOREIGN PATENT DOCUMENTS

CN 106267309 A 1/2017
CN 109071619 A 12/2018
(Continued)

OTHER PUBLICATIONS

Patent Coopertation Treaty, International Preliminary Report on Patentability and Written Opinion issued in PCT/JP2020/004961, Apr. 21, 2020, pp. 1-9.
(Continued)

*Primary Examiner* — Vincent Tatesure
(74) *Attorney, Agent, or Firm* — Studebaker Brackett PLLC

(57) ABSTRACT

An object of the present invention is to provide a method for producing a modified fibroin multifilament excellent in productivity and a multifilament produced by the same. The multifilament of the present invention contains modified fibroin, in which the multifilament has 100 or more constituent single yarns, a coefficient of variation in elastic modulus is 15% or less, a coefficient of variation in strength
(Continued)

is 15% or less, and a coefficient of variation in elongation is less than 33%.

15 Claims, 15 Drawing Sheets

Specification includes a Sequence Listing.

(51) Int. Cl.
  *D01D 5/06* (2006.01)
  *D02G 3/04* (2006.01)

(58) Field of Classification Search
  USPC .......................................................... 428/364
  See application file for complete search history.

(56) References Cited

U.S. PATENT DOCUMENTS

| | | |
|---|---|---|
| 2012/0231499 A1 | 9/2012 | Lee et al. |
| 2018/0216260 A1 | 8/2018 | Breslauer et al. |
| 2019/0135880 A1 | 5/2019 | Morita et al. |
| 2019/0186051 A1 | 6/2019 | Lehmann et al. |
| 2020/0207817 A1 | 7/2020 | Morita et al. |

FOREIGN PATENT DOCUMENTS

| | | |
|---|---|---|
| EP | 3502169 A1 | 6/2019 |
| EP | 3789525 A1 | 3/2021 |
| JP | H06-346314 A | 12/1994 |
| JP | 2002-238569 A | 4/1995 |
| JP | H0797714 A | 4/1995 |
| JP | 2003-530491 A | 10/2003 |
| JP | 2010-024586 A | 2/2010 |
| JP | 2018-512407 A | 5/2018 |
| WO | 2001/77422 A1 | 10/2001 |
| WO | 2016/149414 A1 | 9/2016 |
| WO | 2018/087239 A1 | 5/2017 |
| WO | 2017/194103 A1 | 11/2017 |
| WO | 2018/034111 A1 | 2/2018 |
| WO | 2018/053204 A1 | 3/2018 |
| WO | 2019/022163 A1 | 1/2019 |
| WO | 2019/194263 A1 | 10/2019 |

OTHER PUBLICATIONS

Cohen et al., Nonchromosomal Antibiotic Resistance in Bacteria: Genetic Transormation of *Escherichia coli* by R-Factor DNA, Proc. Nat. Acad. Sci. USA, Aug. 1972, pp. 2110-2114, vol. 69(8).

Zoller et al., "Oligonucleotide-directed mutagenesis using M13-derived vectors: an efficient and general procedure for the production of point mutations in any fragment of DNA", Nucleic Acids Research, 1982, pp. 6487-6500, vol. 10 (20).

Morre et al., "Plasma and Internal Membranes from Cultured Mammalian Cells", Partitioning of Particulates, Methods in Enzymology, 1994, pp. 448-450, vol. 228.

Kyte et al., "A Simple Method for Displaying the Hydropathic Character of a Protein", J. Mol. Biol., 1982, pp. 105-132, vol. 157.

147 TEMPERATURE CONTROLLER

150

146 SPEED CONTROLLER

143

140

144

142

141

17

32

31

4

RECOMBINANT-STRUCTURE PROTEIN MULTIFILAMENT AND METHOD FOR MANUFACTURING SAME

RELATED PATENT APPLICATIONS

This application is based on and claims the benefit of priority from International Application No. PCT/JP2020/004961, filed on Feb. 7, 2020, which claims priority to Japanese Patent Application No. 2019-021014, filed on Feb. 7, 2019, and Japanese Patent Application No. 2019-109041, filed on Jun. 11, 2019, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 27, 2021, is named "051723-0562575_SequenceListing.txt" and is 255 KB in size.

TECHNICAL FIELD

The present invention relates to a recombinant structural protein multifilament and a method for producing the same.

BACKGROUND ART

Conventionally, silk fibroin fibers which are regenerated silk fibers, spider silk fibroin fibers, and the like have been known as artificial fibroin fibers, and many spinning methods thereof have also been reported.

For example, a multifilament of spider silk fibroin derived from a natural spider silk fibroin structure, which is composed of 50 single yarns and produced using a spinning nozzle having 50 holes, has been reported (Patent Literature 1).

However, a recombinant structural protein multifilament composed of a large number of single yarns as many as the number of holes of the spinning nozzle, which is produced in a large scale using a spinning nozzle having a larger number of holes, have not yet been reported.

CITATION LIST

Patent Literature

Patent Literature 1: International Patent Publication No. WO2018/053204

SUMMARY OF INVENTION

Technical Problem

An object of the present invention is to provide a large number of new recombinant structural protein multifilaments composed of a large number of single yarns.

Solution to Problem

That is, the present invention relates to, for example, the following inventions.

[1] A multifilament containing modified fibroin, in which the multifilament has 100 or more constituent single yarns, a coefficient of variation in elastic modulus is 15% or less, a coefficient of variation in strength is 15% or less, and a coefficient of variation in elongation is less than 33%.

[2] The multifilament according to [1], in which the coefficient of variation in elongation of the multifilament is 20% or less.

[3] The multifilament according to [1] or [2], in which the coefficient of variation in elongation of the multifilament is 0.01% or more and 20% or less.

[4] The multifilament according to any one of [1] to [3], in which the coefficient of variation in elongation of the multifilament is 0.01% to less than 0.1%, more than 0.1% to less than 1%, more than 1% to less than 5%, more than 5% to less than 10%, more than 10% to less than 15%, or more than 15% to less than 20%.

[5] The multifilament according to any one of [1] to [4], in which the coefficient of variation in elongation of the multifilament is 15% or less.

[6] The multifilament according to any one of [1] to [4], in which the coefficient of variation in elongation of the multifilament is 10% or less.

[7] The multifilament according to any one of [1] to [6], in which a coefficient of variation in fineness of the multifilament is 20% or less.

[8] The multifilament according to any one of [1] to [7], in which the coefficient of variation in strength of the multifilament is 10% or less, and the coefficient of variation in elastic modulus of the multifilament is 10% or less.

[9] The multifilament according to any one of [1] to [8], in which an average hydropathy index of the modified fibroin is more than −0.8.

[10] The multifilament according to any one of [1] to [9], in which the modified fibroin is modified spider silk fibroin.

[11] The multifilament according to any one of [1] to [10], in which the multifilament has a shrinkage history of being irreversibly shrunk after spinning.

[12] The multifilament according to [11], in which the shrinkage history is a shrinkage history of being irreversibly shrunk by bringing the multifilament into contact with water or a shrinkage history of being irreversibly shrunk by heating and relaxing the multifilament.

[13] The multifilament according to [11] or [12], in which a shrinkage rate of the multifilament having a shrinkage history of being irreversibly shrunk after spinning is 5% or less, the shrinkage rate being defined by the following equation:

$$\text{Shrinkage rate } [\%]=(1-(\text{length of multifilament when dried from wet state/length of multifilament when in wet state}))\times 100.$$

[14] The multifilament according to any one of [1] to [13], in which a coefficient of variation in fineness of the multifilament is 0.01% to 6.5%.

[15] The multifilament according to any one of [1] to [14], in which the coefficient of variation in strength of the multifilament is 0.01% to 3.8%.

[16] A multifilament containing a recombinant structural protein, in which the multifilament has 100 or more constituent single yarns, and a coefficient of variation in elongation is less than 33%.

[17] The multifilament according to [16], in which the recombinant structural protein satisfies the following (1) or (2):

(1) the number of amino acid residues is 150 or more, a content of alanine residues is 12 to 40%, and a content of glycine residues is 11 to 55%, and (2) a total of a content of at least one amino acid residue selected from the group consisting of serine, threonine, and tyrosine, the content of alanine residues, and the content of glycine residues is 56% or more.

[18] The multifilament according to [16] or [17], in which the recombinant structural protein satisfies both (1) and (2).

[19] The multifilament according to any one of [16] to [18], in which the recombinant structural protein has a plurality of repeat sequence units, and the number of amino acid residues of the repeat sequence unit is 6 to 200.

[20] The multifilament according to any one of [16] to [19], in which the recombinant structural protein is at least one selected from the group consisting of fibroin, collagen, resilin, elastin, and keratin, and proteins derived therefrom.

[21] The multifilament according to any one of [16] to [20], in which the recombinant structural protein has an $(A)_n$ motif.

[22] A method for producing a multifilament, including a step of discharging a spinning raw material solution containing a recombinant structural protein and a solvent from a spinning nozzle having 100 or more holes, and bringing the spinning raw material solution into contact with a coagulation liquid to coagulate the recombinant structural protein.

[23] The method for producing a multifilament according to [22], in which the recombinant structural protein satisfies the following (1) or (2):

(1) the number of amino acid residues is 150 or more, a content of alanine residues is 12 to 40%, and a content of glycine residues is 11 to 55%, and (2) a total of a content of at least one amino acid residue selected from the group consisting of serine, threonine, and tyrosine, the content of alanine residues, and the content of glycine residues is 56% or more.

[24] The method for producing a multifilament according to [22] or [23], in which the recombinant structural protein satisfies both (1) and (2).

[25] The method for producing a multifilament according to any one of [22] to [24], in which the recombinant structural protein has a plurality of repeat sequence units, and the number of amino acid residues of the repeat sequence unit is 6 to 200.

[26] The production method according to any one of [22] to [25], in which the recombinant structural protein is at least one selected from the group consisting of fibroin, collagen, resilin, elastin, and keratin, and proteins derived therefrom.

[27] The multifilament according to any one of [22] to [26], in which the recombinant structural protein has an $(A)_n$ motif.

[28] A method for producing a multifilament, including a step of discharging a spinning raw material solution containing modified fibroin and a solvent from a spinning nozzle having 100 or more holes, and bringing the spinning raw material solution into contact with a coagulation liquid to coagulate the modified fibroin.

[29] The production method according to [28], in which the number of holes of the spinning nozzle is 100 to 9,000.

[30] The production method according to [28] or [29], in which an average hydropathy index of the modified fibroin is more than −0.8.

[31] The production method according to any one of [28] to [30], in which the modified fibroin is modified spider silk fibroin.

[32] The production method according to any one of [28] to [31], in which the solvent is at least one organic solvent selected from the group consisting of formic acid, dimethyl sulfoxide (DMSO), and hexafluoroisopropanol (HFIP).

[33] The production method according to any one of [28] to [32], in which the coagulation liquid contains at least one component selected from the group consisting of a lower alcohol having 1 to 5 carbon atoms, ketone, water, and an aqueous solution having a pH of 0.25 to 10.00.

[34] The production method according to [33], in which a content of the component is 70 mass % or more with respect to 100 mass % of a total amount of the coagulation liquid.

[35] The production method according to any one of [28] to [34], in which the coagulation liquid contains at least one selected from the group consisting of methanol, acetone, water, an aqueous sodium chloride solution, an aqueous sodium sulfate solution, and an aqueous formic acid solution.

[36] The production method according to any one of [28] to [35], in which the coagulation liquid contains at least one selected from the group consisting of methanol, an aqueous sodium sulfate solution, and an aqueous formic acid solution.

[37] The method according to any one of [28] to [36], in which the coagulation liquid contains an organic solvent, and a content of the organic solvent is 30 mass % or less with respect to 100 mass % of a total amount of the coagulation liquid.

Advantageous Effects of Invention

According to the present invention, it is possible to provide a new recombinant protein multifilament composed of a large number of single yarns and a method for producing the same. The recombinant protein multifilament according to the present invention has a smaller coefficient of variation in elongation, elastic modulus, strength, and/or fineness, and particularly has a smaller coefficient of variation in elongation as compared to that of the related art (for example, Patent Literature 1). That is, the recombinant protein multifilament of the present invention has a relatively small variation in physical properties and extremely excellent quality stability.

BRIEF DESCRIPTION OF DRAWINGS

FIG. 5 is a schematic view illustrating an example of a domain sequence of modified fibroin.

FIG. 12 is an explanation view schematically illustrating speed control means and temperature control means that can be provided in a high temperature heating furnace of FIG. 11.

DESCRIPTION OF EMBODIMENTS (Recombinant Structural Protein)

Figure 1:
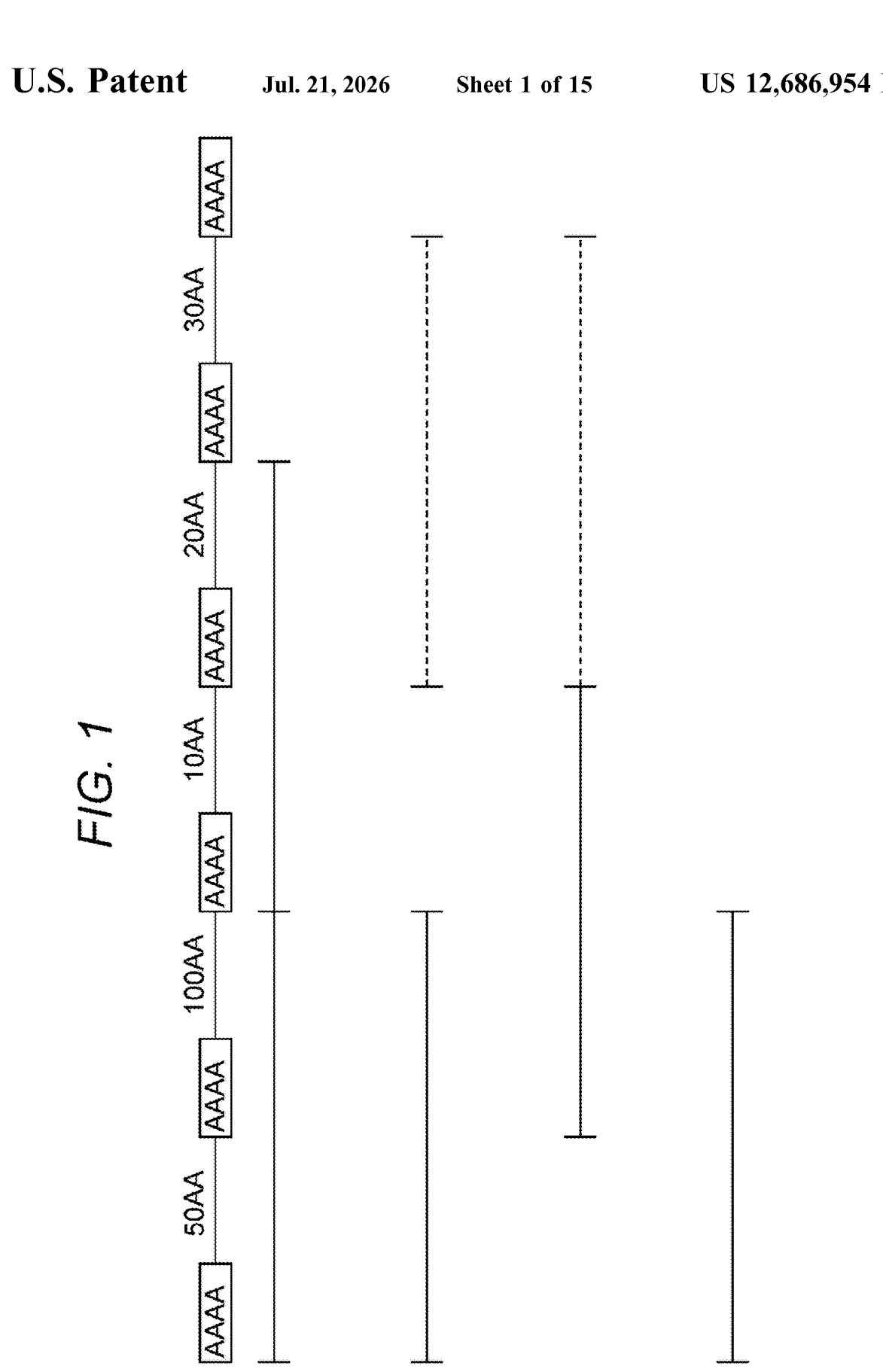
FIG. 1 is a schematic view illustrating an example of a domain sequence of modified fibroin.

A structural protein refers to a protein forming a biological structure or a protein derived therefrom. A recombinant structural protein is a structural protein produced by genetic recombination technology. The recombinant structural protein may have an amino acid sequence of a naturally derived structural protein, and may be a modified structural protein in which an amino acid sequence is partially modified based on an amino acid sequence of a naturally derived structural protein.

The recombinant structural protein according to the present embodiment may satisfy either the following (1) or (2).

(1) the number of amino acid residues is 150 or more, a content of alanine residues is 12 to 40%, and a content of glycine residues is 11 to 55%, and (2) a total of a content of at least one amino acid residue selected from the group consisting of serine, threonine, and tyrosine, the content of alanine residues, and content of glycine residues is 56% or more.

In the present specification, the "content of alanine residues" is a value represented by the following equation.

Content of alanine residues=(number of alanine residues contained in recombinant structural protein/total number of amino acid residues of polypeptide)×100(%)

In addition, a content of glycine residues, a content of serine residues, a content of threonine residues, and a content of tyrosine residues have the same meanings as those obtained by replacing an alanine residue with the glycine residue, the serine residue, the threonine residue, and the tyrosine residue, respectively, in the equation.

The recombinant structural protein satisfying (1) may have 150 or more amino acid residues. The number of amino acid residues may be, for example, 200 or more or 250 or more, and preferably 300 or more, 350 or more, 400 or more, 450 or more, or 500 or more.

In the recombinant structural protein satisfying (1), the content of alanine residues may be 12 to 40%. The content of alanine residues may be, for example, 15 to 40%, 18 to 40%, 20 to 40%, or 22 to 40%.

In the recombinant structural protein satisfying (1), the content of glycine residues may be 11 to 55%. The content of glycine residues may be, for example, 11% to 55%, 13% to 55%, 15% to 55%, 18% to 55%, 20% to 55%, 22% to 55%, or 25% to 55%.

In the recombinant structural protein satisfying (2), a content (total content) obtained by summing up a content of at least one amino acid residue selected from the group consisting of serine, threonine, and tyrosine (that is, any one of a content of serine residues, a content of threonine residues, a content of tyrosine residues, a total of a content of serine residues and a content of threonine residues, a total of a content of serine residues and a content of tyrosine residues, a total of a content of threonine residues and a content of tyrosine residues, and a total of a content of serine residues, a content of threonine residues, a content of tyrosine residues), a content of alanine residues, and a content of glycine residues, may be 56% or more. The total content may be, for example, 57% or more, 58% or more, 59% or more, or 60% or more. An upper limit of the total content is not particularly limited, but may be, for example, 90% or less, 85% or less, or 80% or less.

In one embodiment, in the recombinant structural protein satisfying (2), a total of the content of serine residues, the content of threonine residues, and the content of tyrosine residues may be 4% or more, 4.5% or more, 5% or more, 5.5% or more, 6% or more, 6.5% or more, or 7% or more. The total of the content of serine residues, the content of threonine residues, and the content of tyrosine residues may be, for example, 35% or less, 33% or less, 30% or less, 25% or less, or 20% or less.

It is preferable that the recombinant structural protein according to the present embodiment satisfies both (1) and (2). Therefore, the effects of the present invention are more remarkably exhibited.

The recombinant structural protein according to the present embodiment has an average distribution of the serine residues, the threonine residues, or the tyrosine residues, and the total content of serine residues, threonine residues, and tyrosine residues among arbitrary 20 consecutive amino acid residues may be 5% or more, 10% or more, or 15% or more, and may be 50% or less, 40% or less, 30% or less, or 20% or less.

The recombinant structural protein according to one embodiment may have a repeat sequence. That is, a plurality of amino acid sequences (repeat sequence units) having high sequence identity in the recombinant structural protein may be present in the recombinant structural protein according to the present embodiment. The amino acid sequence of the repeat sequence unit is not particularly limited as long as the entire recombinant structural proteins may satisfy (1) or (2) described above. The number of amino acid residues of the repeat sequence unit is preferably 6 to 200. In addition, the sequence identity between the repeat sequence units may be, for example, 85% or more, 90% or more, 95% or more, 96% or more, 97% or more, 98% or more, or 99% or more.

The recombinant structural protein according to one embodiment may have an $(A)_n$ motif. In the present specification, the $(A)_n$ motif means an amino acid sequence mainly containing an alanine residue. The number of amino acid residues in the $(A)_n$ motif may be an integer of 2 to 27, 2 to 20, 2 to 16, or 2 to 12. In addition, a proportion of the number of alanine residues to a total number of amino acid residues in the $(A)_n$ motif may be 40% or more, and may also be 60% or more, 70% or more, 80% or more, 83% or more, 85% or more, 86% or more, 90% or more, 95% or more, or 100% (which means that the $(A)_n$ motif consists of only alanine residues).

In one embodiment, the $(A)_n$ motif may be included in the repeat sequence unit. Since the $(A)_n$ motif mainly includes an alanine residue, it is easy to have an α-helix structure or a β-sheet structure. When the $(A)_n$ motif is included in the repeat sequence unit, the recombinant structural protein according to the present embodiment has a secondary structure in which the $(A)_n$ motifs are repeated, such that the recombinant structural protein is formed into a fiber. Therefore, it is expected that high strength is exerted by the secondary structure.

An example of the recombinant structural protein can include any structural protein that can be preferably produced in an industrial scale, and specific examples thereof can include a structural protein that can be used for industrial purposes and a structural protein that can be used for medical purposes. Specific examples of the structural protein that can be used for industrial purposes or medical purposes may include fibroin, collagen, resilin, elastin, and keratin, which are sparingly soluble proteins, and proteins derived therefrom, and the structural protein may be a water-soluble protein. Fibroin may be, for example, one or more selected from the group consisting of silk fibroin, spider silk fibroin (spider silk protein), and hornet silk fibroin.

The fibroin according to the present embodiment includes naturally derived fibroin and modified fibroin. In the present specification, the "naturally derived fibroin" means fibroin having an amino sequence identical to that of naturally derived fibroin, and the "modified fibroin" means fibroin having an amino sequence identical to that of naturally derived fibroin. In the present specification, the term "modified fibroin" means artificially produced fibroin (artificial fibroin). The modified fibroin may be fibroin in which a domain sequence is different from an amino acid sequence of naturally derived fibroin or may be fibroin in which a domain sequence is the same as an amino acid sequence of naturally derived fibroin.

The fibroin according to the present embodiment is preferably spider silk fibroin (spider silk protein). The spider silk fibroin includes natural spider silk fibroin and modified spider silk fibroin derived from natural spider silk fibroin. Examples of the natural spider silk fibroin include spider silk proteins produced by spiders.

The fibroin according to the present embodiment may be, for example, a protein containing a domain sequence represented by Formula 1: $[(A)_n$ motif-REP]m or Formula 2: $[(A)_n$ motif-REP]$_m$-$(A)_n$ motif. An amino acid sequence (N-terminal sequence and C-terminal sequence) may be further added to either or both of the N-terminus and the C-terminus of the domain sequence of the fibroin according to the present embodiment. The N-terminal sequence and the C-terminal sequence, although not limited thereto, are typically regions that do not have repetitions of amino acid motifs characteristic of fibroin and consist of amino acids of about 100 residues.

[Modified Fibroin]

The modified fibroin as a raw material is not particularly limited, but may be fibroin produced by a microorganism or the like by genetic recombination technology, or may be fibroin produced by synthesis. However, naturally derived fibroin is excluded from the modified fibroin. In the present embodiment, when the modified fibroin is modified spider silk fibroin, the heat retaining properties, hygroscopic and exothermic properties, and/or flame retardancy are more excellent.

Modified fibroin according to the present embodiment is a protein containing a domain sequence represented by Formula 1: $[(A)_n$ motif-REP]m or Formula 2: $[(A)_n$ motif-REP]m-$(A)_n$ motif. An amino acid sequence (N-terminal sequence and C-terminal sequence) may be further added to either or both of the N-terminus and the C-terminus of the domain sequence of the modified fibroin. The N-terminal sequence and the C-terminal sequence, although not limited thereto, are typically regions that do not have repetitions of amino acid motifs characteristic of fibroin and consist of amino acids of about 100 residues.

In the present specification, the term "modified fibroin" means artificially produced fibroin (artificial fibroin). The modified fibroin may be fibroin in which a domain sequence is different from an amino acid sequence of naturally derived fibroin or may be fibroin in which a domain sequence is the same as an amino acid sequence of naturally derived fibroin. The "naturally derived fibroin" referred to in the present specification is also a protein containing a domain sequence represented by Formula 1: $[(A)_n$ motif-REP]$_m$ or Formula 2: $[(A)_n$ motif-REP]$_m$-$(A)_n$ motif.

The "modified fibroin" may be fibroin obtained by using an amino acid sequence of naturally derived fibroin as it is, fibroin in which an amino acid sequence is modified based on an amino acid sequence of naturally derived fibroin (for example, fibroin in which an amino acid sequence is modified by modifying a cloned gene sequence of naturally derived fibroin), or fibroin artificially designed and synthesized independently of naturally derived fibroin (for example, fibroin having a desired amino acid sequence by chemically synthesizing a nucleic acid encoding a designed amino acid sequence).

The term "domain sequence" as used herein refers to an amino acid sequence which produces a crystalline region (typically, equivalent to $(A)_n$ motif of an amino acid sequence) and an amorphous region (typically, equivalent to REP of an amino acid sequence) peculiar to fibroin and means an amino acid sequence represented by Formula 1: $[(A)_n$ motif-REP]m or Formula 2: $[(A)_n$ motif-REP]m-$(A)_n$ motif. Here, the $(A)_n$ motif represents an amino acid sequence mainly consisting of alanine residues, and the number of amino acid residues in the $(A)_n$ motif is 2 to 27. The number of amino acid residues in the $(A)_n$ motif may be an integer of 2 to 20, 4 to 27, 4 to 20, 8 to 20, 10 to 20, 4 to 16, 8 to 16, or 10 to 16. In addition, a proportion of the number of alanine residues to a total number of amino acid residues in the $(A)_n$ motif may be 40% or more, and may also be 60% or more, 70% or more, 80% or more, 83% or more, 85% or more, 86% or more, 90% or more, 95% or more, or 100% (which means that the $(A)_n$ motif consists of only alanine residues). At least a plurality of seven $(A)_n$ motifs present in the domain sequence may consist of only alanine residues. The REP represents an amino acid sequence consisting of 2 to 200 amino acid residues. The REP may be an amino acid sequence consisting of 10 to 200 amino acid residues, or may be an amino acid sequence consisting of 10 to 40, 10 to 60, 10 to 80, 10 to 100, 10 to 120, 10 to 140, 10 to 160, or 10 to 180 amino acid residues. m represents an integer of 2 to 300, and may be an integer of 8 to 300, 10 to 300, 20 to 300, 40 to 300, 60 to 300, 80 to 300, 10 to 200, 20 to 200, 20 to 180, 20 to 160, 20 to 140, or 20 to 120. The plurality of $(A)_n$ motifs may be the same amino acid sequence or different amino acid sequences. The plurality of REPs may be the same amino acid sequence or different amino acid sequences.

The modified fibroin according to the present embodiment can be obtained by, for example, performing modification of an amino acid sequence corresponding to substitution, deletion, insertion, and/or addition of one or a plurality of amino acid residues with respect to a cloned gene sequence of naturally derived fibroin. Substitution, deletion, insertion, and/or addition of the amino acid residues can be performed by methods well known to those skilled in the art, such as site-directed mutagenesis. Specifically, the modification may be performed according to a method described in literatures such as Nucleic Acid Res. 10, 6487 (1982), and Methods in Enzymology, 100, 448 (1983).

The naturally derived fibroin is a protein containing a domain sequence represented by Formula 1: $[(A)_n$ motif-REP$]_m$ or Formula 2: $[(A)_n$ motif-REP$]_m$-$(A)_n$ motif, and a specific example thereof includes fibroin produced by insects or spiders.

Examples of the fibroin produced by insects include silk proteins produced by silkworms such as *Bombyx mori*, *Bombyx mandarina*, *Antheraea yamamai*, *Anteraea pernyi*, *Eriogyna pyretorum*, *Pilosamia Cynthia ricini*, *Samia cynthia*, *Caligura japonica*, *Antheraea mylitta*, and *Antheraea assama*, and hornet silk proteins discharged from larvae of *Vespa simillima xanthoptera*.

A more specific example of the fibroin produced by insects includes a silkworm fibroin L chain (GenBank Accession No. M76430 (base sequence) and AAA27840.1 (amino acid sequence)).

Examples of the fibroin produced by spiders include spider silk proteins produced by spiders belonging to the genus *Araneus* such as *Araneus ventricosus*, *Araneus diadematus*, *Araneus pinguis*, *Araneus pentagrammicus*, and *Araneus nojimai*, spiders belonging to the genus *Neoscona* such as *Neoscona scylla*, *Neoscona nautica*, *Neoscona adianta*, and *Neoscona scylloides*, spiders belonging to the genus *Pronus* such as *Pronous minutes*, spiders belonging to the genus *Cyrtarachne* such as *Cyrtarachne bufo* and *Cyrtarachne inaequalis*, spiders belonging to the genus *Gasteracantha* such as *Gasteracantha kuhli* and *Gasteracantha mammosa*, spiders belonging to the genus *Ordgarius* such as *Ordgarius hobsoni* and *Ordgarius sexspinosus*, spiders belonging to the genus *Argiope* such as *Argiope amoena*, *Argiope minuta*, and *Argiope bruennich*, spiders belonging to the genus *Arachnura* such as *Arachnura logio*, spiders belonging to the genus *Acusilas* such as *Acusilas coccineus*, spiders belonging to the genus *Cytophora* such as *Cyrtophora moluccensis*, *Cyrtophora exanthematica*, and *Cyrtophora unicolor*, spiders belonging to the genus *Poltys* such as *Poltys illepidus*, spiders belonging to the genus *Cyclosa* such as *Cyclosa octotuberculata*, *Cyclosa sedeculata*, *Cyclosa vallata*, and *Cyclosa atrata*, and spiders belonging to the genus *Chorizopes* such as *Chorizopes nipponicus*; and spider silk proteins produced by spiders belonging to the genus *Tetragnatha* such as *Tetragnatha praedonia*, *Tetragnatha maxillosa*, *Tetragnatha extensa*, and *Tetragnatha squamata*, spiders belonging to the genus *Leucauge* such as *Leucauge magnifica*, *Leucauge blanda*, and *Leucauge subblanda*, spiders belonging to the genus *Nephila* such as *Nephila clavata* and *Nephila pilipes*, spiders belonging to the genus *Menosira* such as *Menosira ornata*, spiders belonging to the genus *Dyschiriognatha* such as *Dyschiriognatha tenera*, spiders belonging to the genus *Latrodectus* such as *Latrodectus mactans*, *Latrodectus hasseltii*, *Latro-*

*dectus geometricus*, and *Latrodectus tredecimguttatus*, and spiders belonging to the family Tetragnathidae such as spiders belonging to the genus *Euprosthenops*. Examples of spider silk proteins include traction yarn proteins such as MaSp (MaSp1 and MaSp2) and ADF (ADF3 and ADF4), and MiSp (MiSp1 and MiSp2).

More specific examples of the spider silk protein produced by spiders include fibroin-3 (adf-3) [derived from *Araneus diadematus*] (GenBank Accession No. AAC47010 (amino acid sequence), U47855 (base sequence)), fibroin-4 (adf-4) [derived from *Araneus diadematus*] (GenBank Accession No. AAC47011 (amino acid sequence), U47856 (base sequence)), dragline silk protein spidroin 1 [derived from *Nephila clavipes*] (GenBank Accession No. AAC04504 (amino acid sequence), U37520 (base sequence)), major ampullate spidroin 1 [derived from *Latrodectus hesperus*] (Gen Bank Accession No. ABR68856 (amino acid sequence), EF595246 (base sequence)), dragline silk protein spidroin 2 [derived from *Nephila clavata*] (GenBank Accession No. AAL32472 (amino acid sequence), AF441245 (base sequence)), major ampullate spidroin 1 [derived from *Euprosthenops australis*] (GenBank Accession No. CAJ00428 (amino acid sequence), AJ973155 (base sequence)), and major ampullate spidroin 2 [*Euprosthenops australis*] (GenBank Accession No. CAM32249.1 (amino acid sequence), AM490169 (base sequence)), minor ampullate silk protein 1 [*Nephila clavipes*] (GenBank Accession No. AAC14589.1 (amino acid sequence)), minor ampullate silk protein 2 [*Nephila clavipes*] (GenBank Accession No. AAC14591.1 (amino acid sequence)), and minor ampullate spidroin-like protein [*Nephilengys cruentata*] (GenBank Accession No. ABR37278.1 (amino acid sequence).

As a more specific example of the naturally occurring fibroin, fibroin whose sequence information is registered in NCBI GenBank may be mentioned. For example, sequences thereof may be confirmed by extracting sequences in which spidroin, ampullate, fibroin, "silk and polypeptide", or "silk and protein" is described as a keyword in DEFINITION among sequences containing INV as DIVISION among sequence information registered in NCBI GenBank, sequences in which a specific character string of products is described from CDS, or sequences in which a specific character string is described from SOURCE to TISSUE TYPE.

The modified fibroin according to the present embodiment may be modified silk fibroin (in which an amino acid sequence of silk protein produced by silkworm is modified), or may be modified spider silk fibroin (in which an amino acid sequence of a spider silk protein produced by spiders is modified). Modified spider silk fibroin is preferred as the modified fibroin.

Specific examples of the modified fibroin include modified spider silk fibroin derived from a major dragline silk protein produced in a major ampullate gland of a spider (first modified fibroin), modified spider silk fibroin containing a domain sequence in which a content of glycine residues is reduced (second modified fibroin), modified spider silk fibroin containing a domain sequence in which a content of an $(A)_n$ motif is reduced (third modified fibroin), modified spider silk fibroin containing a domain sequence in which a content of glycine residues and a content of an $(A)_n$ motif are reduced (fourth modified fibroin), modified spider silk fibroin containing a domain sequence including a region locally having a high hydropathy index (fifth modified fibroin), and modified spider silk fibroin containing a domain sequence in which a content of glutamine residues is reduced (sixth modified fibroin). These modified fibroins are excellent in flame retardancy, hygroscopic and exothermic properties, and heat retaining properties, and are preferably used for fireproof clothes (for fireman uniforms and for rescue), fireproof gloves (for example, for laboratory, for industries, and for cooking), winter clothes (cold protection clothes) such as gloves, mufflers, sweaters, outerwear, and jackets, batting for cold protection clothes, innerwear, sportswear, shirts, bedding, and batting for bedding.

An example of the first modified fibroin includes a protein containing a domain sequence represented by Formula 1: $[(A)_n$ motif-REP$]_m$. In the first modified fibroin, the number n of amino acid residues in the $(A)_n$ motif is preferably an integer of 3 to 20, more preferably an integer of 4 to 20, still more preferably an integer of 8 to 20, still more preferably an integer of 10 to 20, still more preferably an integer of 4 to 16, particularly preferably an integer of 8 to 16, and most preferably an integer of 10 to 16. In the first modified fibroin, in Formula 1, the number of amino acid residues constituting the REP is preferably 10 to 200 residues, more preferably 10 to 150 residues, still more preferably 20 to 100 residues, and even still more preferably 20 to 75 residues. In the first modified fibroin, a total number of glycine residues, serine residues, and alanine residues contained in the amino acid sequence represented by Formula 1: $[(A)_n$ motif-REP$]_m$ is preferably 40% or more, more preferably 60% or more, and still more preferably 70% or more, with respect to a total number of amino acid residues.

The first modified fibroin may be a polypeptide having an amino acid sequence unit represented by Formula 1: $[(A)_n$ motif-REP$]_m$, and having a C-terminal sequence which is an amino acid sequence set forth in any one of SEQ ID NOs: 1 to 3 or a C-terminal sequence which is an amino acid sequence having 90% or more homology with the amino acid sequence set forth in any one of SEQ ID NOs: 1 to 3.

The amino acid sequence set forth in SEQ ID NO: 1 is identical to an amino acid sequence consisting of 50 amino acid residues of the C-terminal of an amino acid sequence of ADF3 (GI: 1263287, NCBI). The amino acid sequence set forth in SEQ ID NO: 2 is identical to an amino acid sequence set forth in SEQ ID NO: 1 in which 20 amino acid residues have been removed from the C-terminal. The amino acid sequence set forth in SEQ ID NO: 3 is identical to an amino acid sequence set forth in SEQ ID NO: 1 in which 29 amino acid residues have been removed from the C-terminal.

A more specific example of the first modified fibroin can include modified fibroin having an amino acid sequence set forth in (1-i) SEQ ID NO: 4 (recombinant spider silk protein ADF3KaiLargeNRSH1), or (1-ii) an amino acid sequence having 90% or more sequence identity with the amino acid sequence set forth in (1-i) SEQ ID NO: 4. The sequence identity is preferably 95% or more.

The amino acid sequence set forth in SEQ ID NO: 4 is an amino acid sequence obtained by the following mutation: in an amino acid sequence of ADF3 in which an amino acid sequence (SEQ ID NO: 5) consisting of a start codon, a His 10-tag and an HRV3C protease (Human rhinovirus 3C protease) recognition site is added to the N-terminal, the $1^{st}$ to $13^{th}$ repetitive regions are about doubled and the translation ends at the 1,154th amino acid residue. The C-terminal amino acid sequence of the amino acid sequence set forth in SEQ ID NO: 4 is identical to the amino acid sequence set forth in SEQ ID NO: 3.

The modified fibroin of (1-i) may consist of the amino acid sequence set forth in SEQ ID NO: 4.

The domain sequence of the second modified fibroin has an amino acid sequence in which a content of glycine residues is reduced, as compared with the naturally derived fibroin. It can be said that the second modified fibroin has an amino acid sequence corresponding to an amino acid sequence in which at least one or a plurality of glycine residues in REP are substituted with another amino acid residue, as compared with the naturally derived fibroin.

The domain sequence of the second modified fibroin may have an amino acid sequence corresponding to an amino acid sequence in which one glycine residue in at least one or the plurality of motif sequences is substituted with another amino acid residue, in at least one motif sequence selected from GGX and GPGXX (where G represents a glycine residue, P represents a proline residue, and X represents an amino acid residue other than glycine) in REP, as compared with the naturally derived fibroin.

In the second modified fibroin, the proportion of the motif sequence in which the glycine residue has been substituted with another amino acid residue may be 10% or more relative to the entire motif sequence.

The second modified fibroin may contain a domain sequence represented by Formula 1: $[(A)_n$ motif-REP$]_m$ and may have an amino acid sequence in which z/w is 30% or more, 40% or more, 50% or more, or 50.9% or more, in which a total number of amino acid residues in an amino acid sequence consisting of XGX (where X represents an amino acid residue other than glycine) contained in all REP's in a sequence excluding the sequence from the $(A)_n$ motif located at the most C-terminal side to the C-terminus of the domain sequence from the domain sequence is z, and a total number of amino acid residues in a sequence excluding the sequence from the $(A)_n$ motif located at the most C-terminal side to the C-terminus of the domain sequence from the domain sequence is w. The number of alanine residues with respect to the total number of amino acid residues in the $(A)_n$ motif is 83% or more, preferably 86% or more, more preferably 90% or more, still more preferably 95% or more, and still more preferably 100% (which means that the $(A)_n$ motif consists of only alanine residues).

The second modified fibroin is preferably one in which the content ratio of the amino acid sequence consisting of XGX is increased by substituting one glycine residue of the GGX motif with another amino acid residue. In the second modified fibroin, a content ratio of an amino acid sequence consisting of GGX in the domain sequence is preferably 30% or less, more preferably 20% or less, still more preferably 10% or less, still more preferably 6% or less, still more preferably 4% or less, and particularly preferably 2% or less. The content ratio of the amino acid sequence consisting of GGX in the domain sequence can be calculated by the same method as the calculation method of the content ratio (z/w) of the amino acid sequence consisting of XGX described below.

The calculation method of z/w will be described in more detail. First, the amino acid sequence consisting of XGX is extracted from all the REP's contained in the sequence excluding the sequence from the $(A)_n$ motif located at the most C-terminal side to the C-terminus of the domain sequence from the domain sequence in the fibroin containing the domain sequence represented by Formula 1: $[(A)_n$ motif-REP$]_m$ (modified fibroin or naturally derived fibroin). A total number of amino acid residues consisting of XGX is z. For example, in a case where 50 amino acid sequences consisting of XGX are extracted (there is no overlap), z is 50×3=150. In addition, for example, in a case where two Xs (central X) contained in XGX are present as in a case of an amino acid sequence consisting of XGXGX, it is calculated by subtracting the overlapping portion (in the case of XGXGX, z is 5 amino acid residues). w is a total number of amino acid residues contained in the sequence excluding the sequence from the $(A)_n$ motif located at the most C-terminal side to the C-terminus of the domain sequence from the domain sequence. For example, in the case of the domain sequence illustrated in FIG. 1, w is 4+50+4+100+4+10+4+20+4+30=230 (excluding the $(A)_n$ motif located at the most C-terminal side). Next, z/w (%) can be calculated by dividing z by w.

Figure 2:
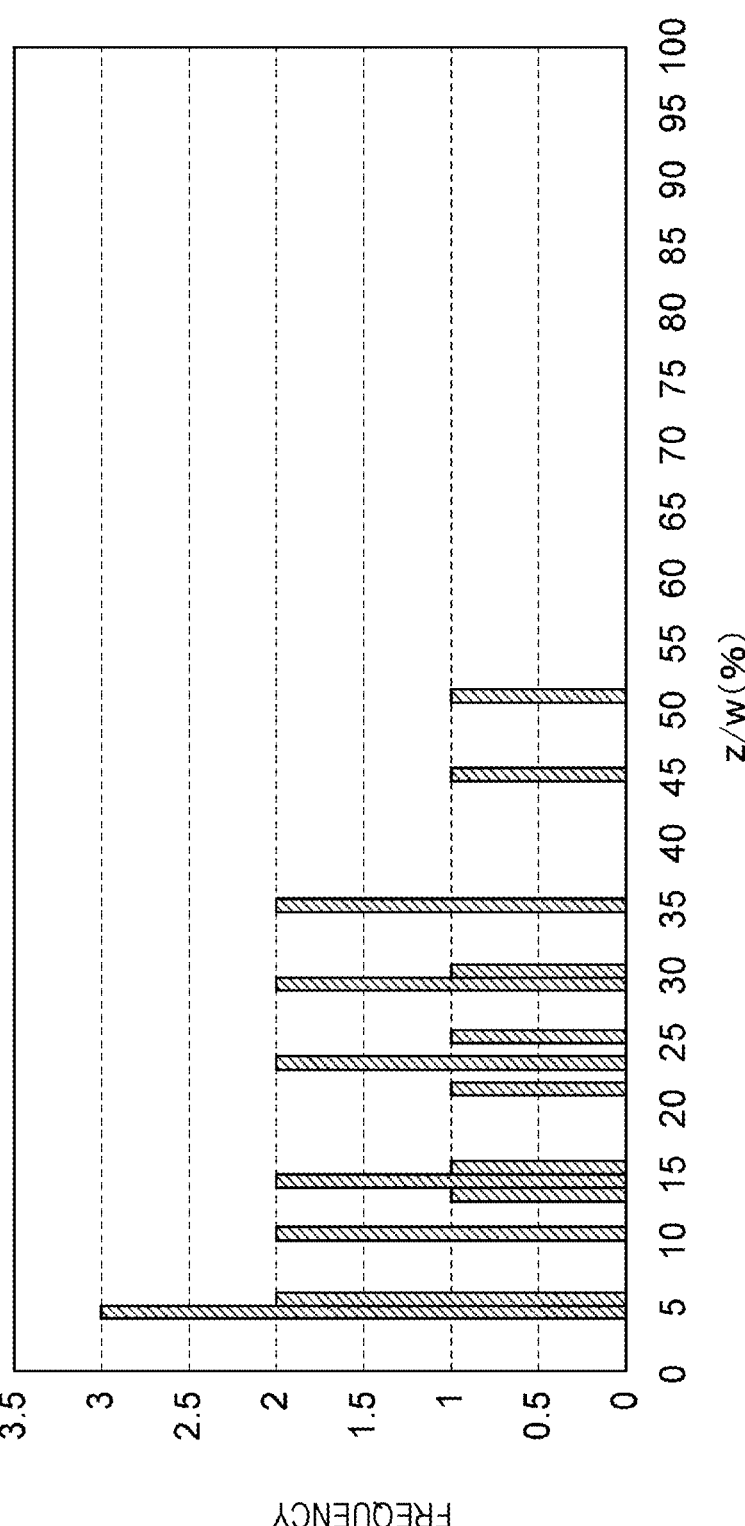
FIG. 2 is a view illustrating a distribution of values of z/w (%) in naturally derived fibroin.

Here, z/w in the naturally derived fibroin will be described. First, as described above, 663 types of fibroins (415 types of fibroins derived from spiders among them) were extracted by confirming fibroins with amino acid sequence information registered in NCBI GenBank by an exemplified method. Among all extracted fibroin, values of z/w were calculated, using the calculation method described above, from amino acid sequences of naturally derived fibroin which contained domain sequences represented by Formula 1: $[(A)_n \text{ motif-REP}]_m$ and in which the content ratios of the amino acid sequences consisting of GGX in the fibroins were 6% or less. The results are shown in FIG. 2. In FIG. 2, the horizontal axis represents z/w (%), and the vertical axis represents a frequency. As is clear from FIG. 2, the values of z/w in the naturally derived fibroin are all less than 50.9% (the largest value is 50.86%).

In the second modified fibroin, z/w is preferably 50.9% or more, more preferably 56.1% or more, still more preferably 58.7% or more, even still more preferably 70% or more, and still further preferably 80% or more. The upper limit of z/w is not particularly limited, but may be, for example, 95% or less.

The second modified fibroin can be obtained by, for example, substituting and modifying at least a part of a base sequence encoding a glycine residue from a cloned gene sequence of naturally derived fibroin so as to encode another amino acid residue. In this case, one glycine residue in a GGX motif or a GPGXX motif may be selected as the glycine residue to be modified, and substitution may be performed so that z/w is 50.9% or more. In addition, the second modified fibroin can also be obtained by, for example, designing an amino acid sequence satisfying each of the above aspects from the amino acid sequence of the naturally derived fibroin, and chemically synthesizing a nucleic acid encoding the designed amino acid sequence. In any case, in addition to the modification corresponding to substitution of a glycine residue in the REP with another amino acid residue from the amino acid sequence of the naturally derived fibroin, modification of the amino acid sequence corresponding to substitution, deletion, insertion, and/or addition of one or a plurality of amino acid residues may be performed.

The above-described another amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, more preferably a valine (V) residue, a leucine (L) residue, an isoleucine (I) residue, a phenylalanine (F) residue, or a glutamine (Q) residue, and still more preferably a glutamine (Q) residue.

A more specific example of the second modified fibroin can include a modified fibroin having (2-i) an amino acid sequence set forth in SEQ ID NO: 6 (Met-PRT380), SEQ ID NO: 7 (Met-PRT410), SEQ ID NO: 8 (Met-PRT525), or SEQ ID NO: 9 (Met-PRT799), or (2-ii) an amino acid sequence having 90% or more sequence identity with the amino acid sequence set forth in SEQ ID NO: 6, SEQ ID NO: 7, SEQ ID NO: 8, or SEQ ID NO: 9.

The modified fibroin of (2-i) will be described. The amino acid sequence set forth in SEQ ID NO: 6 is obtained by substituting GQX for all GGXs in REP of the amino acid sequence set forth in SEQ ID NO: 10 (Met-PRT313) corresponding to the naturally derived fibroin. The amino acid sequence set forth in SEQ ID NO: 7 is obtained by deleting every other two $(A)_n$ motifs from the N-terminus to the C-terminus from the amino acid sequence set forth in SEQ ID NO: 6 and further inserting one $[(A)_n \text{ motif-REP}]$ before the C-terminal sequence. The amino acid sequence set forth in SEQ ID NO: 8 is obtained by inserting two alanine residues at the C-terminus of each $(A)_n$ motif of the amino acid sequence set forth in SEQ ID NO: 7 and further substituting a part of glutamine (Q) residues with a serine (S) residue to delete a part of amino acids at the C-terminus so as to be almost the same as a molecular weight of SEQ ID NO: 7. The amino acid sequence set forth in SEQ ID NO: 9 is an amino acid sequence obtained by adding a predetermined hinge sequence and a His tag sequence to the C-terminus of a sequence obtained by repeating a region of 20 domain sequences (where several amino acid residues on the C-terminal side of the region are substituted) present in the amino acid sequence set forth in SEQ ID NO: 7 four times.

A value of z/w in the amino acid sequence set forth in SEQ ID NO: 10 (corresponding to naturally derived fibroin) is 46.8%. The values of z/w in the amino acid sequence set forth in SEQ ID NO: 6, the amino acid sequence set forth in SEQ ID NO: 7, the amino acid sequence set forth in SEQ ID NO: 8, and the amino acid sequence set forth in SEQ ID NO: 9 are 58.7%, 70.1%, 66.1%, and 70.0%, respectively. In addition, the values of x/y in the amino acid sequences set forth in SEQ ID NO: 10, SEQ ID NO: 6, SEQ ID NO: 7, SEQ ID NO: 8, and SEQ ID NO: 9 at a Giza ratio (described below) of 1:1.8 to 11.3 are 15.0%, 15.0%, 93.4%, 92.7%, and 89.8%, respectively.

The modified fibroin of (2-i) may consist of the amino acid sequence set forth in SEQ ID NO: 6, SEQ ID NO: 7, SEQ ID NO: 8, or SEQ ID NO: 9.

The modified fibroin of (2-ii) includes an amino acid sequence having a sequence identity of 90% or more with the amino acid sequence set forth in SEQ ID NO: 6, SEQ ID NO: 7, SEQ ID NO: 8, or SEQ ID NO: 9. The modified fibroin of (2-ii) is also a protein containing the domain sequence represented by Formula 1: $[(A)_n \text{ motif-REP}]_m$. The sequence identity is preferably 95% or more.

It is preferred that the modified fibroin of (2-ii) has a sequence identity of 90% or more with the amino acid sequence set forth in SEQ ID NO: 6, SEQ ID NO: 7, SEQ ID NO: 8, or SEQ ID NO: 9, and z/w is 50.9% or more in a case where the total number of amino acid residues in the amino acid sequence consisting of XGX (where X represents an amino acid residue other than glycine) included in REP is defined as z, and the total number of amino acid residues of REP in the domain sequence is defined as w.

The second modified fibroin may include a tag sequence at either or both of the N-terminal and the C-terminal. This makes it possible to isolate, immobilize, detect, and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel. Thus, the His tag can be used for isolation of modified fibroin by chelating metal chromatography. A specific example of the tag sequence includes an amino acid sequence set forth in SEQ ID NO: 11 (amino acid sequence having a His tag sequence and a hinge sequence).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) illustrating antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin having a tag sequence can include modified fibroin having (2-iii) an amino acid sequence set forth in SEQ ID NO: 12 (PRT380), SEQ ID NO: 13 (PRT410), SEQ ID NO: 14 (PRT525), or SEQ ID NO: 15 (PRT799), or (2-iv) an amino acid sequence having 90% or more sequence identity with the amino acid sequence set forth in SEQ ID NO: 12, SEQ ID NO: 13, SEQ ID NO: 14, or SEQ ID NO: 15.

Each of amino acid sequences set forth in SEQ ID NO: 16 (PRT313), SEQ ID NO: 12, SEQ ID NO: 13, SEQ ID NO: 14, and SEQ ID NO: 15 is obtained by adding the amino acid sequence set forth in SEQ ID NO: 11 (having a His tag sequence and a hinge sequence) to the N-terminus of each of the amino acid sequences set forth in SEQ ID NO: 10, SEQ ID NO: 6, SEQ ID NO: 7, SEQ ID NO: 8, and SEQ ID NO: 9.

The modified fibroin of (2-iii) may consist of the amino acid sequence set forth in SEQ ID NO: 12, SEQ ID NO: 13, SEQ ID NO: 14, or SEQ ID NO: 15.

The modified fibroin of (2-iv) may consist of an amino acid sequence having 90% or more sequence identity with the amino acid sequence set forth in SEQ ID NO: 12, SEQ ID NO: 13, SEQ ID NO: 14, or SEQ ID NO: 15. The modified fibroin of (2-iv) is also a protein containing the domain sequence represented by Formula 1: $[(A)_n$ motif-REP$]_m$. The sequence identity is preferably 95% or more.

The modified fibroin of (2-iv) preferably has 90% or more sequence identity with the amino acid sequence set forth in SEQ ID NO: 12, SEQ ID NO: 13, SEQ ID NO: 14, or SEQ ID NO: 15, and z/w is preferably 50.9% or more, in which the total number of amino acid residues in the amino acid sequence consisting of XGX (where X represents the amino acid residue other than glycine) in the REP is z, and the total number of amino acid residues in the REP in the domain sequence is w.

The second modified fibroin may include a secretory signal for releasing the protein produced in the recombinant protein production system to the outside of a host. The sequence of the secretory signal can be appropriately set depending on the type of the host.

The domain sequence of the third modified fibroin has an amino acid sequence in which a content of an $(A)_n$ motif is reduced, as compared with the naturally derived fibroin. It can be said that the domain sequence of the third modified fibroin has an amino acid sequence corresponding to an amino acid sequence in which at least one or a plurality of $(A)_n$ motifs are deleted, as compared with the naturally derived fibroin.

The third modified fibroin may have an amino acid sequence corresponding to an amino acid sequence in which 10 to 40% of the $(A)_n$ motifs are deleted from the naturally derived fibroin.

The third modified fibroin may have an amino acid sequence corresponding to an amino acid sequence obtained by deleting one $(A)_n$ motif of every one to three $(A)_n$ motifs at least from the N-terminus to the C-terminus, as compared with the naturally derived fibroin.

The third modified fibroin may have an amino acid sequence corresponding to an amino acid sequence obtained by repeating deletion of at least two consecutive $(A)_n$ motifs and deletion of one $(A)_n$ motif in this order from the N-terminus to the C-terminus, as compared with the naturally derived fibroin.

The domain sequence of the third modified fibroin may have an amino acid sequence corresponding to an amino acid sequence obtained by deleting every other two $(A)_n$ motifs at least from the N-terminus to the C-terminus.

The third modified fibroin may contain a domain sequence represented by Formula 1: $[(A)_n$ motif-REP$]_m$, and may have an amino acid sequence in which x/y may be 20% or more, 30% or more, 40% or more, or 50% or more, in which when the number of amino acid residues in REP's in two $[(A)_n$ motif-REP] units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent $[(A)_n$ motif-REP] units where the ratio of the number of amino acid residues in the other REP is 1.8 to 11.3 is x, and the total number of amino acid residues in the domain sequence is y. The number of alanine residues with respect to the total number of amino acid residues in the $(A)_n$ motif is 83% or more, preferably 86% or more, more preferably 90% or more, still more preferably 95% or more, and still more preferably 100% (which means that the $(A)_n$ motif consists of only alanine residues).

A method of calculating x/y will be described in more detail with reference to FIG. 1. FIG. 1 illustrates a domain sequence excluding the N-terminal sequence and the C-terminal sequence from the modified fibroin. This domain sequence has a sequence of $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminal side (left side).

The two adjacent $[(A)_n$ motif-REP] units are sequentially selected from the N-terminus to the C-terminus so as not to overlap. In this case, an unselected $[(A)_n$ motif-REP] unit may exist. FIG. 1 illustrates a pattern 1 (a comparison between first REP and second REP and a comparison between third REP and fourth REP), a pattern 2 (a comparison between first REP and second REP and a comparison between fourth REP and fifth REP), a pattern 3 (a comparison between second REP and third REP and a comparison between fourth REP and fifth REP), and a pattern 4 (a comparison between first REP and second REP). There are other selection methods besides this.

Next, for each pattern, the number of amino acid residues in each REP in the selected two adjacent [(A)$_n$ motif-REP] units is compared. The comparison is performed by determining a ratio of the number of amino acid residues in the other REP when one REP having a smaller number of amino acid residues is 1. For example, in the case of comparing the first REP (50 amino acid residues) with the second REP (100 amino acid residues), a ratio of the number of amino acid residues in the second REP when the first REP having a smaller number of amino acid residues is 1 is 100/50=2. Similarly, in a case of comparing the fourth REP (20 amino acid residues) and the fifth REP (30 amino acid residues), the ratio of the number of amino acid residues of the fifth REP is 30/20=1.5 in a case where the fourth REP having a smaller number of amino acid residues is defined as 1.

In FIG. 1, a set of [(A)$_n$ motif-REP] units in which the ratio of the number of amino acid residues in the other REP when one REP having a smaller number of amino acid residues is 1 is 1.8 to 11.3 is indicated by a solid line. In the present specification, the ratio is referred to as a Giza ratio. A set of [(A)$_n$ motif-REP] units in which the ratio of the number of amino acid residues in the other REP when one REP having a smaller number of amino acid residues is 1 is less than 1.8 or more than 11.3 is indicated by a broken line.

In each pattern, the number of all amino acid residues in two adjacent [(A)$_n$ motif-REP] units indicated by solid lines (including not only the number of amino acid residues in REP but also the number of amino acid residues in (A)$_n$ motif) are summed up. Then, the total values thus summed up are compared and the total value in the patterns at which the total value is maximized (the maximum value of the total value) is x. In the example shown in FIG. 1, the total value of the pattern 1 is the maximum.

Then, x/y (%) can be calculated by dividing x by the total number of amino acid residues y of the domain sequence.

In the third modified fibroin, x/y is preferably 50% or more, more preferably 60% or more, still more preferably 65% or more, even still more preferably 70% or more, still further preferably 75% or more, and particularly preferably 80% or more. An upper limit of x/y is not particularly limited, but may be, for example, 100% or less. In a case where the Giza ratio is 1:1.9 to 11.3, x/y is preferably 89.6% or more; in a case where the Giza ratio is 1:1.8 to 3.4, x/y is preferably 77.1% or more; in a case where the Giza ratio is 1:1.9 to 8.4, x/y is preferably 75.9% or more; and in a case where the Giza ratio is 1:1.9 to 4.1, x/y is preferably 64.2% or more.

In the case where the third modified fibroin is modified fibroin in which at least a plurality of seven (A)$_n$ motifs present in the domain sequence consist of only alanine residues, x/y is preferably 46.4% or more, more preferably 50% or more, still more preferably 55% or more, still more preferably 60% or more, still more preferably 70% or more, and particularly preferably 80% or more. The upper limit of x/y is not particularly limited, but is only required to be 100% or less.

Figure 3:
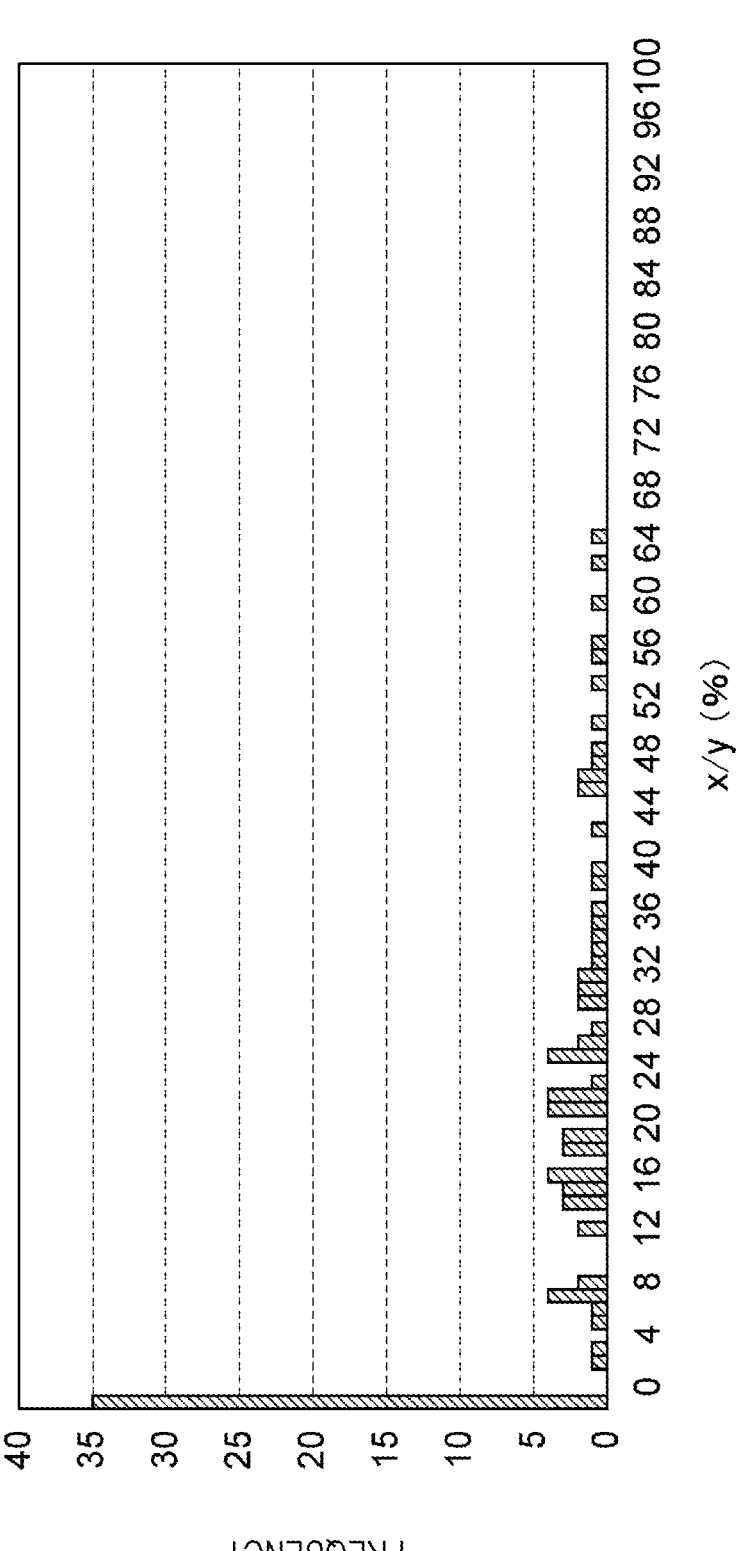
FIG. 3 is a view illustrating a distribution of values of x/y (%) in naturally derived fibroin.

Here, x/y in the naturally derived fibroin will be described. First, as described above, 663 types of fibroins (415 types of fibroins derived from spiders among them) were extracted by confirming fibroins with amino acid sequence information registered in NCBI GenBank by an exemplified method. Among all extracted fibroin, values of x/y were calculated, using the calculation method described above, from amino acid sequences of naturally derived fibroin consisting of domain sequences represented by Formula 1: [(A)$_n$ motif-REP]$_m$. The results in a case where the Giza ratio was 1:1.9 to 4.1 are shown in FIG. 3. The horizontal axis in FIG. 3 represents x/y (%), and the vertical axis represents a frequency. As is clear from FIG. 3, the values of x/y in the naturally derived fibroin are all less than 64.2% (the largest value is 64.14%).

The third modified fibroin can be obtained from, for example, a cloned gene sequence of naturally derived fibroin, by deleting one or a plurality of sequences encoding an (A)$_n$ motif so that x/y is 64.2% or more. In addition, for example, the third modified fibroin can also be obtained, from the amino acid sequence of naturally derived fibroin, by designing an amino acid sequence corresponding to deletion of one or a plurality of (A)$_n$ motifs so that x/y is 64.2% or more, and chemically synthesizing a nucleic acid encoding the designed amino acid sequence. In any case, in addition to the modification corresponding to deletion of the (A)$_n$ motif from the amino acid sequence of the naturally derived fibroin, modification of the amino acid sequence corresponding to substitution, deletion, insertion, and/or addition of one or a plurality of amino acid residues may be performed.

A more specific example of the third modified fibroin can include a modified fibroin having (3-i) an amino acid sequence set forth in SEQ ID NO: 17 (Met-PRT399), SEQ ID NO: 7 (Met-PRT410), SEQ ID NO: 8 (Met-PRT525), or SEQ ID NO: 9 (Met-PRT799), or (3-ii) an amino acid sequence having 90% or more sequence identity with the amino acid sequence set forth in SEQ ID NO: 17, SEQ ID NO: 7, SEQ ID NO: 8, or SEQ ID NO: 9.

The modified fibroin of (3-i) will be described. The amino acid sequence set forth in SEQ ID NO: 17 is obtained by deleting every other two (A)$_n$ motifs from the N-terminus to the C-terminus from the amino acid sequence set forth in SEQ ID NO: 10 (Met-PRT313) corresponding to the naturally derived fibroin and further inserting one [(A)$_n$ motif-REP] before the C-terminal sequence. The amino acid sequence set forth in SEQ ID NO: 7, SEQ ID NO: 8, or SEQ ID NO: 9 is as described in the second modified fibroin.

The value of x/y in the amino acid sequence set forth in SEQ ID NO: 10 (corresponding to naturally derived fibroin) at a Giza ratio of 1:1.8 to 11.3 is 15.0%. Both the value of x/y in the amino acid sequence set forth in SEQ ID NO: 17 and the value of x/y in the amino acid sequence set forth in SEQ ID NO: 7 are 93.4%. The value of x/y in the amino acid sequence set forth in SEQ ID NO: 8 is 92.7%. The value of x/y in the amino acid sequence set forth in SEQ ID NO: 9 is 89.8%. The values of z/w in the amino acid sequences set forth in SEQ ID NO: 10, SEQ ID NO: 17, SEQ ID NO: 7, SEQ ID NO: 8, and SEQ ID NO: 9 are 46.8%, 56.2%, 70.1%, 66.1%, and 70.0%, respectively.

The modified fibroin of (3-i) may consist of the amino acid sequence set forth in SEQ ID NO: 17, SEQ ID NO: 7, SEQ ID NO: 8, or SEQ ID NO: 9.

The modified fibroin of (3-ii) may consist of an amino acid sequence having 90% or more sequence identity with the amino acid sequence set forth in SEQ ID NO: 17, SEQ ID NO: 7, SEQ ID NO: 8, or SEQ ID NO: 9. The modified fibroin of (3-ii) is also a protein containing the domain sequence represented by Formula 1: [(A)$_n$ motif-REP]$_m$. The sequence identity is preferably 95% or more.

The modified fibroin of (3-ii) preferably has 90% or more sequence identity with the amino acid sequence set forth in SEQ ID NO: 17, SEQ ID NO: 7, SEQ ID NO: 8, or SEQ ID NO: 9, and x/y is preferably 64.2% or more, in which when the number of amino acid residues in REP's in two [(A)$_n$ motif-REP] units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent [(A)$_n$ motif-REP] units where the ratio of the number of amino acid residues in the other REP is 1.8 to 11.3 (the Giza ratio is 1:1.8 to 11.3) is x, and the total number of amino acid residues in the domain sequence is y.

The third modified fibroin may include the above-described tag sequence at either or both of the N-terminal and the C-terminal.

A more specific example of the modified fibroin having a tag sequence can include modified fibroin having (3-iii) an amino acid sequence set forth in SEQ ID NO: 18 (PRT399), SEQ ID NO: 13 (PRT410), SEQ ID NO: 14 (PRT525), or SEQ ID NO: 15 (PRT799), or (3-iv) an amino acid sequence having 90% or more sequence identity with the amino acid sequence set forth in SEQ ID NO: 18, SEQ ID NO: 13, SEQ ID NO: 14, or SEQ ID NO: 15.

Each of the amino acid sequences set forth in SEQ ID NO: 18, SEQ ID NO: 13, SEQ ID NO: 14, and SEQ ID NO: 15 is obtained by adding the amino acid sequence set forth in SEQ ID NO: 11 (having a His tag sequence and a hinge sequence) to the N-terminus of each of the amino acid sequences set forth in SEQ ID NO: 17, SEQ ID NO: 7, SEQ ID NO: 8, and SEQ ID NO: 9.

The modified fibroin of (3-iii) may consist of the amino acid sequence set forth in SEQ ID NO: 18, SEQ ID NO: 13, SEQ ID NO: 14, or SEQ ID NO: 15.

The modified fibroin of (3-iv) may consist of an amino acid sequence having 90% or more sequence identity with the amino acid sequence set forth in SEQ ID NO: 18, SEQ ID NO: 13, SEQ ID NO: 14, or SEQ ID NO: 15. The modified fibroin of (3-iv) is also a protein containing the domain sequence represented by Formula 1: [(A)$_n$ motif-REP]$_m$. The sequence identity is preferably 95% or more.

The modified fibroin of (3-iv) preferably has 90% or more sequence identity with the amino acid sequence set forth in SEQ ID NO: 18, SEQ ID NO: 13, SEQ ID NO: 14, or SEQ ID NO: 15, and x/y is preferably 64.2% or more, in which when the number of amino acid residues in REP's in two [(A)$_n$ motif-REP] units adjacent to each other are sequentially compared from the N-terminus to the C-terminus, and then the number of amino acid residues in REP having a small number of amino acid residues is set as 1, a maximum value of the total value obtained by summing up the number of amino acid residues in the two adjacent [(A)$_n$ motif-REP] units where the ratio of the number of amino acid residues in the other REP is 1.8 to 11.3 is x, and the total number of amino acid residues in the domain sequence is y.

The third modified fibroin may include a secretory signal for releasing the protein produced in the recombinant protein production system to the outside of a host. The sequence of the secretory signal can be appropriately set depending on the type of the host.

The domain sequence of the fourth modified fibroin has an amino acid sequence in which a content of an (A)$_n$ motif and a content of glycine residues are reduced, as compared with the naturally derived fibroin. It can be said that the domain sequence of the fourth modified fibroin has an amino acid sequence corresponding to an amino acid sequence in which at least one or a plurality of (A)$_n$ motifs are deleted and at least one or a plurality of glycine residues in REP are substituted with another amino acid residue, as compared with the naturally derived fibroin. That is, the fourth modified fibroin is modified fibroin having the characteristics of the above-described second modified fibroin and third modified fibroin. Specific embodiments thereof, and the like are as in the descriptions for the second modified fibroin and the third modified fibroin.

A more specific example of the fourth modified fibroin can include modified fibroin having (4-i) an amino acid sequence set forth in SEQ ID NO: 7 (Met-PRT410), SEQ ID NO: 8 (Met-PRT525), SEQ ID NO: 9 (Met-PRT799), SEQ ID NO: 13 (PRT410), SEQ ID NO: 14 (PRT525), or SEQ ID NO: 15 (PRT799), or (4-ii) an amino acid sequence having 90% or more sequence identity with the amino acid sequence set forth in SEQ ID NO: 7, SEQ ID NO: 8, SEQ ID NO: 9, SEQ ID NO: 13, SEQ ID NO: 14, or SEQ ID NO: 15. Specific aspects of the modified fibroin having the amino acid sequence set forth in SEQ ID NO: 7, SEQ ID NO: 8, SEQ ID NO: 9, SEQ ID NO: 13, SEQ ID NO: 14, or SEQ ID NO: 15 are as described above.

The domain sequence of the fifth modified fibroin may have an amino acid sequence including a region locally having a high hydropathy index corresponding to an amino acid sequence in which one or a plurality of amino acid residues in REP are substituted with amino acid residues having a high hydropathy index and/or one or a plurality of amino acid residues having a high hydropathy index are inserted into REP, as compared with the naturally derived fibroin.

The region with locally high hydropathy index preferably consists of consecutive two to four amino acid residues.

The above-described amino acid residue with a high hydropathy index is more preferably an amino acid residue selected from isoleucine (I), valine (V), leucine (L), phenylalanine (F), cysteine (C), methionine (M), and alanine (A).

The fifth modified fibroin may be further subjected to modification of an amino acid sequence corresponding to substitution, deletion, insertion, and/or addition of one or a plurality of amino acid residues as compared with the naturally derived fibroin, in addition to modification corresponding to substitution of one or a plurality of amino acid residues in REP with amino acid residues having a high hydropathy index and/or insertion of one or a plurality of amino acid residues having a high hydropathy index into REP, as compared with the naturally derived fibroin.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) from a cloned gene sequence of naturally derived fibroin, and/or inserting one or a plurality of hydrophobic amino acid residues into REP. In addition, the fifth modified fibroin can be obtained by, for example, designing an amino acid sequence corresponding to substitution of one or a plurality of hydrophilic amino acid residues in REP with hydrophobic amino acid residues from an amino acid sequence of naturally derived fibroin, and/or insertion of one or a plurality of hydrophobic amino acid residues into REP, and chemically synthesizing a nucleic acid encoding the designed amino acid sequence. In any case, in addition to modification corresponding to substitution of one or a plurality of hydrophilic amino acid residues in REP with hydrophobic amino acid residues from amino acid sequences of naturally derived fibroin, and/or insertion of one or a plurality of hydrophobic amino acid residues into REP, modification of an amino acid sequence corresponding to substitution, deletion, insertion, and/or addition of one or a plurality of amino acid residues may be further performed.

The fifth modified fibroin may contain a domain sequence represented by Formula 1: $[(A)_n \text{ motif-REP}]_m$, and may have an amino acid sequence in which p/q is 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

A known index (Hydropathy index: Kyte J, & Doolittle R (1982), "A simple method for displaying the hydropathic character of a protein", J. Mol. Biol., 157, pp. 105-132) is used as the hydropathy index of the amino acid residue. Specifically, the hydropathy index (hereinafter, also referred to as "HI") of each amino acid is as shown in Table 1.

TABLE 1

| Amino acid | HI | Amino acid | HI |
|---|---|---|---|
| Isoleucine (Ile) | 4.5 | Tryptophan (Trp) | −0.9 |
| Valine (Val) | 4.2 | Tyrosine (Tyr) | −1.3 |
| Leucine (Leu) | 3.8 | Proline (Pro) | −1.6 |
| Phenylalanine (Phe) | 2.8 | Histidine (His) | −3.2 |
| Cysteine (Cys) | 2.5 | Asparagine (Asn) | −3.5 |
| Methionine (Met) | 1.9 | Asparaginic acid (Asp) | −3.5 |
| Alanine (Ala) | 1.8 | Glutamine (Gln) | −3.5 |
| Glycine (Gly) | −0.4 | Glutamic acid (Glu) | −3.5 |
| Threonine (Thr) | −0.7 | Lysine (Lys) | −3.9 |
| Serine (Ser) | −0.8 | Arginine (Arg) | −4.5 |

The calculation method of p/q will be described in more detail. In the calculation, the sequence excluding the sequence from the $(A)_n$ motif located at the most C-terminal side to the C-terminus of the domain sequence from the domain sequence represented by Formula 1: $[(A)_n \text{ motif-REP}]_m$ (hereinafter, referred to as "sequence A") is used. First, in all REP's contained in the sequence A, an average value of hydropathy indices of four consecutive amino acid residues is calculated. The average value of the hydropathy indices is determined by dividing the sum of HI of each of the amino acid residues contained in the four consecutive amino acid residues by 4 (the number of amino acid residues). The average value of the hydropathy indices is determined for all of the four consecutive amino acid residues (each of the amino acid residues is used for calculating the average value 1 to 4 times). Next, a region where the average value of the hydropathy indices of the four consecutive amino acid residues is 2.6 or more is specified. Even in a case where certain amino acid residues correspond to a plurality of "four consecutive amino acid residues having an average value of hydropathy indices of 2.6 or more", the amino acid residue is counted as one amino acid residue in the region. Then, the total number of amino acid residues contained in the region is p. Also, the total number of amino acid residues contained in the sequence A is q.

Figure 4:
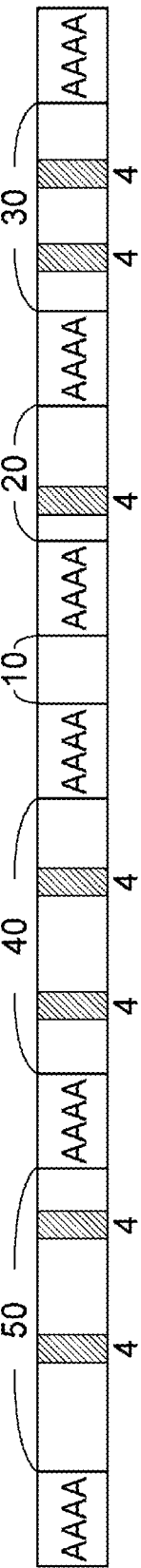
FIG. 4 is a schematic view illustrating an example of a domain sequence of modified fibroin.

For example, in a case where the "four consecutive amino acid residues having an average value of the hydropathy indices of 2.6 or more" are extracted from 20 places (no overlap), in the region where the average value of the hydropathy indices of four consecutive amino acid residues is 2.6 or more, the number of the four consecutive amino acid residues (no overlap) is 20, and thus p is 20×4=80. In addition, for example, in a case where two of the "four consecutive amino acid residues having an average value of the hydropathy indices of 2.6 or more" overlap by only one amino acid residue, in the region where the average value of the hydropathy indices of four consecutive amino acid residues is 2.6 or more, the number of amino acid residues is 7 (p=2×4−1=7, "−1" is the deduction of overlap). For example, in a case of the domain sequence shown in FIG. 4, seven sets of "four consecutive amino acid residues of which the average value of hydropathy indices is 2.6 or higher" are present without overlaps, and thus, p is 7×4=28. Furthermore, for example, in the case of the domain sequence shown in FIG. 4, q is 4+50+4+40+4+10+4+20+4+30=170 (the $(A)_n$ motif located at the end in the C-terminal side is excluded). Next, p/q (%) can be calculated by dividing p by q. In the case of FIG. 4, 28/170=16.47%.

In the fifth modified fibroin, p/q is preferably 6.2% or more, more preferably 7% or more, still more preferably 10% or more, even still more preferably 20% or more, and still further preferably 30% or more. The upper limit of p/q is not particularly limited, but may be, for example, 45% or less.

The fifth modified fibroin can be obtained by, for example, substituting one or a plurality of hydrophilic amino acid residues in REP (for example, amino acid residues having a negative hydropathy index) with hydrophobic amino acid residues (for example, amino acid residues having a positive hydropathy index) so that a cloned amino acid sequence of naturally derived fibroin satisfies the condition of p/q, and/or modifying the cloned amino acid sequence of naturally derived fibroin with an amino acid sequence including a region locally having a high hydropathy index by inserting one or a plurality of hydrophobic amino acid residues into REP. In addition, the fifth modified fibroin can also be obtained by, for example, designing an amino acid sequence satisfying the condition of p/q from the amino acid sequence of the naturally derived fibroin, and chemically synthesizing a nucleic acid encoding the designed amino acid sequence. In any case, modification corresponding to substitution, deletion, insertion, and/or addition of one or a plurality of amino acid residues may also be performed, in addition to modification corresponding to substitution of one or a plurality of amino acid residues in REP with amino acid residues having a high hydropathy index, and/or insertion of one or a plurality of amino acid residues having a high hydropathy index into REP, as compared with the naturally derived fibroin.

The amino acid residue with a high hydropathy index is not particularly limited, but is preferably isoleucine (I), valine (V), leucine (L), phenylalanine (F), cysteine (C), methionine (M), and alanine (A), and more preferably valine (V), leucine (L), and isoleucine (I).

A more specific example of the fifth modified fibroin can include modified fibroin having (5-i) an amino acid sequence set forth in SEQ ID NO: 19 (Met-PRT720), SEQ ID NO: 20 (Met-PRT665), or SEQ ID NO: 21 (Met-PRT666), or (5-ii) an amino acid sequence having 90% or more sequence identity with the amino acid sequence set forth in SEQ ID NO: 19, SEQ ID NO: 20, or SEQ ID NO: 21.

The modified fibroin of (5-i) will be described. The amino acid sequence set forth in SEQ ID NO: 19 is obtained by inserting an amino acid sequence consisting of three amino acid residues (VLI) at two sites for each REP into the amino acid sequence set forth in SEQ ID NO: 7 (Met-PRT410), except for the domain sequence at the end on the C-terminal side, and further substituting a part of glutamine (Q) residues with serine (S) residues and deleting a part of amino acids on the C-terminal side. The amino acid sequence set forth in SEQ ID NO: 20 is obtained by inserting the amino acid sequence consisting of three amino acid residues (VLI) at one site for each REP into the amino acid sequence set forth in SEQ ID NO: 8 (Met-PRT525). The amino acid sequence set forth in SEQ ID NO: 21 is obtained by inserting the amino acid sequence consisting of three amino acid residues (VLI) at two sites for each REP into the amino acid sequence set forth in SEQ ID NO: 8.

The modified fibroin of (5-i) may consist of the amino acid sequence set forth in SEQ ID NO: 19, SEQ ID NO: 20, or SEQ ID NO: 21.

The modified fibroin of (5-ii) includes an amino acid sequence having a sequence identity of 90% or more with the amino acid sequence set forth in SEQ ID NO: 19, SEQ ID NO: 20, or SEQ ID NO: 21. The modified fibroin of (5-ii) is also a protein containing the domain sequence represented by Formula 1: $[(A)_n$ motif-REP$]_m$. The sequence identity is preferably 95% or more.

The modified fibroin of (5-ii) preferably has 90% or more sequence identity with the amino acid sequence set forth in SEQ ID NO: 19, SEQ ID NO: 20, or SEQ ID NO: 21, and p/q is preferably 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

The fifth modified fibroin may include a tag sequence at either or both of the N-terminal and the C-terminal.

A more specific example of the modified fibroin having a tag sequence can include modified fibroin having (5-iii) an amino acid sequence set forth in SEQ ID NO: 22 (PRT720), SEQ ID NO: 23 (PRT665), or SEQ ID NO: 24 (PRT666), or (5-iv) an amino acid sequence having 90% or more sequence identity with the amino acid sequence set forth in SEQ ID NO: 22, SEQ ID NO: 23, or SEQ ID NO: 24.

Each of the amino acid sequences set forth in SEQ ID NO: 22, SEQ ID NO: 23, and SEQ ID NO: 24 is obtained by adding the amino acid sequence set forth in SEQ ID NO: 11 (having a His tag sequence and a hinge sequence) to the N-terminus of each of the amino acid sequences set forth in SEQ ID NO: 19, SEQ ID NO: 20, and SEQ ID NO: 21.

The modified fibroin of (5-iii) may consist of the amino acid sequence set forth in SEQ ID NO: 22, SEQ ID NO: 23, or SEQ ID NO: 24.

The modified fibroin of (5-iv) may consist of an amino acid sequence having 90% or more sequence identity with the amino acid sequence set forth in SEQ ID NO: 22, SEQ ID NO: 23, or SEQ ID NO: 24. The modified fibroin of (5-iv) is also a protein containing the domain sequence represented by Formula 1: $[(A)_n$ motif-REP$]_m$. The sequence identity is preferably 95% or more.

The modified fibroin of (5-iv) preferably has 90% or more sequence identity with the amino acid sequence set forth in SEQ ID NO: 22, SEQ ID NO: 23, or SEQ ID NO: 24, and p/q is preferably 6.2% or more, in which in all REP's contained in a sequence excluding a sequence from a $(A)_n$ motif located the most C-terminal side to the C-terminus of the domain sequence from the domain sequence, a total number of amino acid residues contained in a region where an average value of hydropathy indices of four consecutive amino acid residues is 2.6 or more is p, and a total number of amino acid residues contained in the sequence excluding the sequence from the $(A)_n$ motif located the most C-terminal side to the C-terminus of the domain sequence from the domain sequence is q.

The fifth modified fibroin may include a secretory signal for releasing the protein produced in the recombinant protein production system to the outside of a host. The sequence of the secretory signal can be appropriately set depending on the type of the host.

The sixth modified fibroin has an amino acid sequence in which a content of glutamine residues is reduced, as compared with the naturally derived fibroin.

In the sixth modified fibroin, at least one motif selected from a GGX motif and a GPGXX motif is preferably included in the amino acid sequence of REP.

In a case where the sixth modified fibroin includes the GPGXX motif in REP, the GPGXX motif content is usually 1% or more, may also be 5% or more, and preferably 10% or more. The upper limit of the GPGXX motif content is not particularly limited, but may be 50% or less, or may also be 30% or less.

In the present specification, the "GPGXX motif content" is a value calculated by the following method.

In fibroin (modified fibroin or naturally derived fibroin) containing a domain sequence represented by Formula 1: $[(A)_n$ motif-REP$]_m$ or Formula 2: $[(A)_n$ motif-REP$]_m$-$(A)_n$ motif, the content rate of the GPGXX motif is calculated as s/t, in which the number obtained by tripling the total number of GPGXX motifs in the regions of all REP's contained in a sequence excluding the sequence from the $(A)_n$ motif located at the most C-terminal side to the C-terminus of the domain sequence from the domain sequence (that is, corresponding to the total number of G and P in the GPGXX motifs) is s, and the total number of amino acid residues in all REP's excluding the sequence from the $(A)_n$ motif located at the most C-terminal side to the C-terminus of the domain sequence from the domain sequence and further excluding the $(A)_n$ motifs is t.

For the calculation of the content rate of the GPGXX motif, the "sequence excluding a sequence from the $(A)_n$ motif located at the most C-terminal side to the C-terminus of the domain sequence from the domain sequence" is used to exclude the effect occurring due to the fact that the "sequence from the $(A)_n$ motif located at the most C-terminal side to the C-terminus of the domain sequence" (sequence corresponding to REP) may have a sequence having a low correlation with the sequence characteristic of fibroin, which influences the calculation result of the content rate of the GPGXX motif in a case where m is small (that is, in a case where the domain sequence is short). Incidentally, in a case where the "GPGXX motif" is located at the C-terminal of REP, even when "XX" is "AA", for example, it is treated as the "GPGXX motif".

Figure 5:
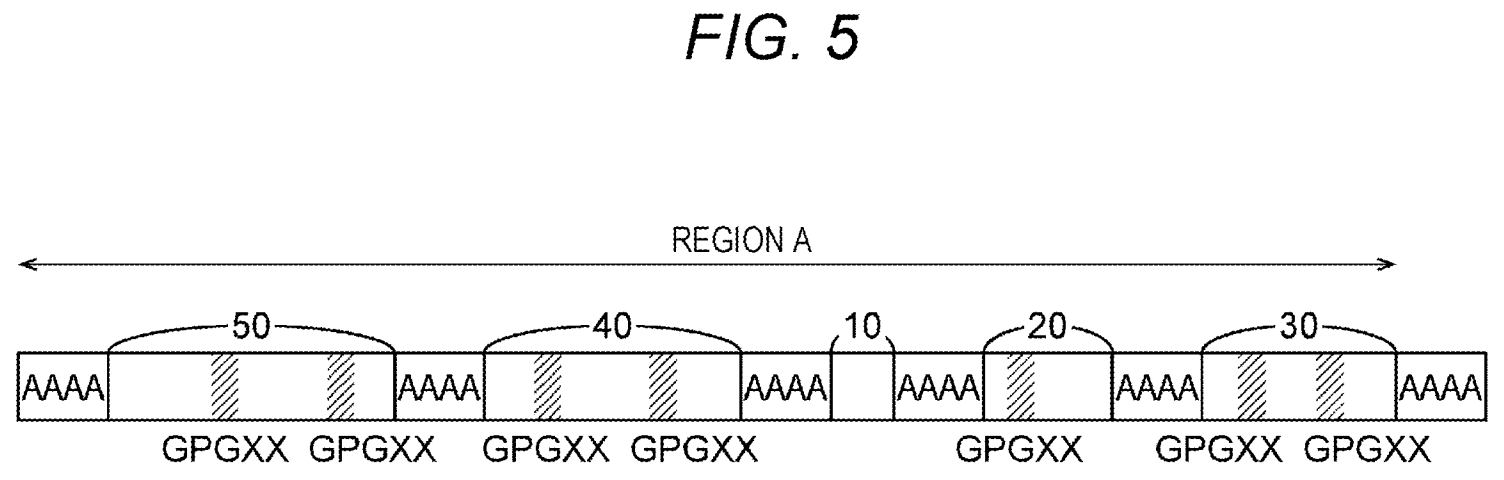

FIG. 5 is a schematic view illustrating a domain sequence of modified fibroin. The method for calculating the content rate of the GPGXX motifs will be specifically described while referring to FIG. 5. First, in the domain sequence of the modified fibroin illustrated in FIG. 5 (which is the "$[(A)_n$ motif-REP$]_m$-$(A)_n$ motif" type), all REP's are contained in "the domain sequence excluding the sequence from the $(A)_n$ motif located closest to the C-terminal side to the C-terminus of the domain sequence" (in FIG. 5, the sequence indicated as a "region A"), and therefore, the number of the GPGXX motifs for calculating s is 7, and s is $7 \times 3 = 21$. Similarly, since all REP's are contained in "the domain sequence excluding the sequence from the $(A)_n$ motif located closest to the C-terminal side to the C-terminus of the domain sequence" (in FIG. 5, the sequence indicated as the "region A"), the total number t of the amino acid residues in all REP's when the $(A)_n$ motifs are further excluded from the sequence is 50+40+10+20+30=150. Next, s/t (%) can be calculated by dividing s by t, and in the case of the modified fibroin of FIG. 5, s/t is 21/150=14.0%.

In the sixth modified fibroin, the glutamine residue content is preferably 9% or less, more preferably 7% or less, still more preferably 4% or less, and particularly preferably 0%.

In the present specification, the "content rate of the glutamine residues" is a value calculated by the following method.

The content rate of glutamine residues in fibroin having a domain sequence represented by Formula 1: $[(A)_n$ motif-$REP]_m$ or Formula 2: $[(A)_n$ motif-$REP]_m$-$(A)_n$ motif (modified fibroin or naturally derived fibroin) is calculated as u/t, in a case where a total number of glutamine residues contained in regions of all REP's contained in the domain sequence excluding a sequence from the $(A)_n$ motif located closest to the C-terminal side to the C-terminus of the domain sequence (a sequence corresponding to the "region A" in FIG. 5) is denoted by u, and a total number of amino acid residues in all REP's in the domain sequence excluding the sequence from the $(A)_n$ motif located closest to the C-terminal side to the C-terminus of the domain sequence and further excluding the $(A)_n$ motifs is denoted by t. For the calculation of the content rate of the glutamine residues, the "sequence excluding the sequence from the $(A)_n$ motif located at the most C-terminal side to the C-terminus of the domain sequence from the domain sequence" is used for the same reason described above.

The domain sequence of the sixth modified fibroin may have an amino acid sequence corresponding to deletion of one or a plurality of glutamine residues in REP, or substitution of one or a plurality of glutamine residues with another amino acid residue, as compared with the naturally derived fibroin.

The "another amino acid residue" may be an amino acid residue other than the glutamine residue, but is preferably an amino acid residue with a higher hydropathy index than that of the glutamine residue. The hydropathy index of the amino acid residue is as shown in Table 1.

As shown in Table 1, examples of the amino acid residue with a higher hydropathy index than that of the glutamine residue include amino acid residues selected from isoleucine (I), valine (V), leucine (L), phenylalanine (F), cysteine (C), methionine (M), alanine (A), glycine (G), threonine (T), serine (S), tryptophan (W), tyrosine (Y), proline (P), and histidine (H). Among them, the amino acid residue is more preferably an amino acid residue selected from isoleucine (I), valine (V), leucine (L), phenylalanine (F), cysteine (C), methionine (M), and alanine (A), and still more preferably an amino acid residue selected from isoleucine (I), valine (V), leucine (L), and phenylalanine (F).

In the sixth modified fibroin, the hydrophobicity of REP is preferably more than −0.8, more preferably −0.7 or more, still more preferably 0 or more, even still more preferably 0.3 or more, and particularly preferably 0.4 or more. An upper limit of the hydrophobicity of REP is not particularly limited, but may be 1.0 or less or 0.7 or less.

In the present specification, the "hydrophobicity of REP" is a value calculated by the following method.

The hydrophobicity of REP in fibroin having a domain sequence represented by Formula 1: $[(A)_n$ motif-$REP]_m$ or Formula 2: $[(A)_n$ Motif-$REP]_m$-$(A)_n$ motif (modified fibroin or naturally derived fibroin) is calculated as v/t, in a case where a sum of hydropathy indices of all amino acid residues in regions of all REP'S contained in the domain sequence excluding a sequence from the $(A)_n$ motif located closest to the C-terminal side to the C-terminus of the domain sequence (a sequence corresponding to the "region A" in FIG. 5) is denoted by v, and a total number of amino acid residues in all REP'S in the domain sequence excluding the sequence from the $(A)_n$ motif located closest to the C-terminal side to the C-terminus of the domain sequence and further excluding the $(A)_n$ motifs is denoted by t. For the calculation of the hydrophobicity of REP, the "sequence excluding the sequence from the $(A)_n$ motif located at the most C-terminal side to the C-terminus of the domain sequence from the domain sequence" is used for the same reason described above.

The sixth modified fibroin may be further subjected to modification of an amino acid sequence corresponding to substitution, deletion, insertion, and/or addition of one or a plurality of amino acid residues, in addition to modification corresponding to deletion of one or a plurality of glutamine residues in REP, and/or substitution of one or a plurality of glutamine residues in REP with another amino acid residue, as compared to naturally derived fibroin.

The sixth modified fibroin can be obtained by, for example, deleting one or a plurality of glutamine residues in REP from a cloned gene sequence of naturally derived fibroin, and/or substituting one or a plurality of glutamine residues in REP with another amino acid residue. In addition, the sixth modified fibroin can be obtained by, for example, designing an amino acid sequence corresponding to deletion of one or a plurality of glutamine residues in REP from an amino acid sequence of naturally derived fibroin, and/or substitution of one or a plurality of glutamine residues in REP with another amino acid residue, and chemically synthesizing a nucleic acid encoding the designed amino acid sequence.

More specific examples of the sixth modified fibroin can include modified fibroin having (6-i) an amino acid sequence set forth in SEQ ID NO: 25 (Met-PRT888), SEQ ID NO: 26 (Met-PRT965), SEQ ID NO: 27 (Met-PRT889), SEQ ID NO: 28 (Met-PRT916), SEQ ID NO: 29 (Met-PRT918), SEQ ID NO: 30 (Met-PRT699), SEQ ID NO: 31 (Met-PRT698), SEQ ID NO: 32 (Met-PRT966), SEQ ID NO: 41 (Met-PRT917), or SEQ ID NO: 42 (Met-PRT1028), and modified fibroin having (6-ii) an amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-i) will be described. The amino acid sequence set forth in SEQ ID NO: 25 is obtained by substituting all QQs in the amino acid sequence set forth in SEQ ID NO: 7 (Met-PRT410) with VL. The amino acid sequence set forth in SEQ ID NO: 26 is obtained by substituting all QQs in the amino acid sequence set forth in SEQ ID NO: 7 with TS and substituting the remaining Q with A. The amino acid sequence set forth in SEQ ID NO: 27 is obtained by substituting all QQs in the amino acid sequence set forth in SEQ ID NO: 7 with VL and substituting the remaining Q with I. The amino acid sequence set forth in SEQ ID NO: 28 is obtained by substituting all QQs in the amino acid sequence set forth in SEQ ID NO: 7 with VI and substituting the remaining Q with L. The amino acid sequence set forth in SEQ ID NO: 29 is obtained by substituting all QQs in the amino acid sequence set forth in SEQ ID NO: 7 with VF and substituting the remaining Q with I.

The amino acid sequence set forth in SEQ ID NO: 30 is obtained by substituting all QQs in the amino acid sequence set forth in SEQ ID NO: 8 (Met-PRT525) with VL. The amino acid sequence set forth in SEQ ID NO: 31 is obtained by substituting all QQs in the amino acid sequence set forth in SEQ ID NO: 8 with VL and substituting the remaining Q with I.

The amino acid sequence set forth in SEQ ID NO: 32 is obtained by substituting, with VF, all QQs in a sequence obtained by repeating a region of 20 domain sequences present in the amino acid sequence set forth in SEQ ID NO: 7 (Met-PRT410) two times and substituting the remaining Q with I.

The amino acid sequence set forth in SEQ ID NO: 41 (Met-PRT917) is obtained by substituting all QQs in the amino acid sequence set forth in SEQ ID NO: 7 with LI and substituting the remaining Q with V. The amino acid sequence set forth in SEQ ID NO: 42 (Met-PRT1028) is obtained by substituting all QQs in the amino acid sequence set forth in SEQ ID NO: 7 with IF and substituting the remaining Q with T.

The content rate of the glutamine residues in each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42 is 9% or less (Table 2).

TABLE 2

| Modified fibroin | Content of glutamine residue | Content of GPGXX motif | Hydro- phobicity of REP |
|---|---|---|---|
| Met-PTR410 (SEQ ID NO: 7) | 17.7% | 27.9% | −1.52 |
| Met-PTR888 (SEQ ID NO: 25) | 6.3% | 27.9% | −0.07 |
| Met-PTR965 (SEQ ID NO: 26) | 0.0% | 27.9% | −0.65 |
| Met-PTR889 (SEQ ID NO: 27) | 0.0% | 27.9% | 0.35 |
| Met-PTR916 (SEQ ID NO: 28) | 0.0% | 27.9% | 0.47 |
| Met-PTR918 (SEQ ID NO: 29) | 0.0% | 27.9% | 0.45 |
| Met-PTR699 (SEQ ID NO: 30) | 3.6% | 26.4% | −0.78 |
| Met-PTR698 (SEQ ID NO: 31) | 0.0% | 26.4% | −0.03 |
| Met-PTR966 (SEQ ID NO: 32) | 0.0% | 28.0% | 0.35 |
| Met-PTR917 (SEQ ID NO: 41) | 0.0% | 27.9% | 0.46 |
| Met-PTR1028 (SEQ ID NO: 42) | 0.0% | 28.1% | 0.05 |

The modified fibroin of (6-i) may consist of the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42.

The modified fibroin of (6-ii) may consist of the amino acid sequence having 90% or more sequence identity with the amino acid sequence set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, or SEQ ID NO: 42. The modified fibroin of (6-ii) is also a protein containing a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

In the modified fibroin of (6-ii), the glutamine residue content is preferably 9% or less. In addition, in the modified fibroin of (6-ii), the GPGXX motif content is preferably 10% or more.

The sixth modified fibroin may include a tag sequence at either or both of the N-terminal and the C-terminal. This makes it possible to isolate, immobilize, detect, and visualize the modified fibroin.

More specific examples of the sixth modified fibroin having a tag sequence can include modified fibroin having (6-iii) an amino acid sequence set forth in SEQ ID NO: 33 (PRT888), SEQ ID NO: 34 (PRT965), SEQ ID NO: 35 (PRT889), SEQ ID NO: 36 (PRT916), SEQ ID NO: 37 (PRT918), SEQ ID NO: 38 (PRT699), SEQ ID NO: 39 (PRT698), SEQ ID NO: 40 (PRT966), SEQ ID NO: 43 (PRT917), or SEQ ID NO: 44 (PRT1028), or modified fibroin having (6-iv) an amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

Each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, and SEQ ID NO: 44 is obtained by adding the amino acid sequence set forth in SEQ ID NO: 11 (having a His tag sequence and a hinge sequence) to the N-terminus of each of the amino acid sequences set forth in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, and SEQ ID NO: 42. Since only the tag sequence is added to the N-terminus, the content rate of the glutamine residues is not changed, and the content rate of the glutamine residues in each of the amino acid sequences set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44 is 9% or less (Table 3).

TABLE 3

| Modified fibroin | Content of glutamine residue | Content of GPGXX motif | Hydro- phobicity of REP |
|---|---|---|---|
| PRT888 (SEQ ID NO: 33) | 6.3% | 27.9% | −0.07 |
| PRT965 (SEQ ID NO: 34) | 0.0% | 27.9% | −0.65 |
| PRT889 (SEQ ID NO: 35) | 0.0% | 27.9% | 0.35 |
| PRT916 (SEQ ID NO: 36) | 0.0% | 27.9% | 0.47 |
| PRT918 (SEQ ID NO: 37) | 0.0% | 27.9% | 0.45 |
| PRT699 (SEQ ID NO: 38) | 3.6% | 26.4% | −0.78 |
| PRT698 (SEQ ID NO: 39) | 0.0% | 26.4% | −0.03 |
| PRT966 (SEQ ID NO: 40) | 0.0% | 28.0% | 0.35 |
| PRT917 (SEQ ID NO: 43) | 0.0% | 27.9% | 0.46 |
| PRT1028 (SEQ ID NO: 44) | 0.0% | 28.1% | 0.05 |

The modified fibroin of (6-iii) may consist of the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44.

The modified fibroin of (6-iv) may consist of the amino acid sequence having 90% or more sequence identity with the amino acid sequence set forth in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 43, or SEQ ID NO: 44. The modified fibroin of (6-iv) is also a protein containing a domain sequence represented by Formula 1: $[(A)_n$ motif-REP$]_m$ or Formula 2: $[(A)_n$ motif-REP$]_m$-$(A)_n$ motif. The sequence identity is preferably 95% or more.

In the modified fibroin of (6-iv), the glutamine residue content is preferably 9% or less. In addition, in the modified fibroin of (6-iv), the GPGXX motif content is preferably 10% or more.

The sixth modified fibroin may include a secretory signal for releasing the protein produced in the recombinant protein production system to the outside of a host. The sequence of the secretory signal can be appropriately set depending on the type of the host.

The modified fibroin may also be a modified fibroin having at least two or more characteristics among the characteristics of the first modified fibroin, the second modified fibroin, the third modified fibroin, the fourth modified fibroin, the fifth modified fibroin, and the sixth modified fibroin.

The modified fibroin may be hydrophilic modified fibroin or hydrophobic modified fibroin. The hydrophobic modified fibroin is modified fibroin in which a value obtained by determining the sum of hydropathy indices (HI) of all amino acid residues constituting the modified fibroin and then dividing the sum by the number of all amino acid residues (average HI) is more than −0.8. The modified fibroin is more preferably modified fibroin having an average HI of −0.6 or more, the modified fibroin is more preferably modified fibroin having an average HI of −0.4 or more, the modified fibroin is still more preferably modified fibroin having an average HI of −0.2 or more, and the modified fibroin is particularly preferably modified fibroin having an average HI of 0 or more. The hydropathy index is as shown in Table 1. In addition, a hydrophilic spider silk protein is modified fibroin having the above average HI of −0.8 or less. The average hydropathy index of the modified fibroin according to the present embodiment is preferably more than −0.8, preferably −0.7 or more, preferably −0.6 or more, more preferably −0.5 or more, preferably −0.4 or more, preferably −0.3 or more, preferably −0.2 or more, preferably −0.1 or more, more preferably 0 or more, more preferably 0.1 or more, more preferably 0.2 or more, still more preferably 0.3 or more, and particularly preferably 0.4 or more.

An example of the hydrophobic modified fibroin can include the above-described sixth modified fibroin. A more specific example of the hydrophobic modified fibroin includes modified fibroin having an amino acid sequence set forth in SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 43, or an amino acid sequence set forth in SEQ ID NO: 35, SEQ ID NO: 37, SEQ ID NO: 38, SEQ ID NO: 39, SEQ ID NO: 40, SEQ ID NO: 41, or SEQ ID NO: 44.

Examples of the hydrophilic modified fibroin can include the above-described first modified fibroin, second modified fibroin, third modified fibroin, fourth modified fibroin, and fifth modified fibroin. A more specific example of the hydrophilic modified fibroin includes modified fibroin having an amino acid sequence set forth in SEQ ID NO: 4, an amino acid sequence set forth in SEQ ID NO: 6, SEQ ID NO: 7, SEQ ID NO: 8, or SEQ ID NO: 9, an amino acid sequence set forth in SEQ ID NO: 13, SEQ ID NO: 12, SEQ ID NO: 14, or SEQ ID NO: 15, an amino acid sequence set forth in SEQ ID NO: 18, SEQ ID NO: 7, SEQ ID NO: 8, or SEQ ID NO: 9, an amino acid sequence set forth in SEQ ID NO: 17, SEQ ID NO: 12, SEQ ID NO: 14, or SEQ ID NO: 15, or an amino acid sequence set forth in SEQ ID NO: 19, SEQ ID NO: 20, or SEQ ID NO: 21.

The modified fibroin according to the present embodiment may include one kind of the modified fibroin alone or a combination of two or more kinds thereof. In addition, the modified fibroin may include a combination of modified fibroin and a structural protein other than modified fibroin.

The structural protein may be a polypeptide derived from the natural structural protein, that is, a recombinant polypeptide.

An example of a structural protein derived from collagen can include a protein containing a domain sequence represented by Formula 3: $[REP2]_p$ (in Formula 3, p represents an integer of 5 to 300, REP2 represents an amino acid sequence constituted by Gly-X-Y, and X and Y each represent any amino acid residue other than Gly, and a plurality of REP2's may be the same or different amino acid sequences). A specific example thereof can include a protein having an amino acid sequence set forth in SEQ ID NO: 45. The amino acid sequence set forth in SEQ ID NO: 45 is an amino acid sequence obtained by adding the amino acid sequence set forth in SEQ ID NO: 11 (tag sequence and hinge sequence) to the N-terminus of an amino acid sequence from the 301th residue to the 540th residue corresponding to repeated portions and motifs of a partial sequence of human collagen type 4 (NCBI GenBank Accession No.: CAA56335.1, GI: 3702452) obtained from the NCBI data base.

An example of a structural protein derived from resilin can include a protein containing a domain sequence represented by Formula 4: $[REP3]_q$ (in Formula 4, q represents an integer of 4 to 300, REP3 represents an amino acid sequence constituted by Ser-J-J-Tyr-Gly-U-Pro, J represents an optional amino acid residue and is particularly preferably an amino acid residue selected from the group consisting of Asp, Ser, and Thr, U represents an optional amino acid residue and is particularly preferably an amino acid residue selected from the group consisting of Pro, Ala, Thr, and Ser, and a plurality of REP3's may be the same or different amino acid sequences). A specific example thereof can include a protein having an amino acid sequence set forth in SEQ ID NO: 46. The amino acid sequence set forth in SEQ ID NO: 46 is an amino acid sequence obtained by adding the amino acid sequence set forth in SEQ ID NO: 49 (tag sequence and hinge sequence) to the N-terminus of an amino acid sequence from the 19th residue to the 321th residue, obtained by substituting Thr of the 87th residue with Ser and substituting Asn of the 95th residue with Asp in the amino acid sequence of resilin (NCBI GenBank Accession No.: NP 611157, GI: 24654243).

Examples of a structural protein derived from elastin can include structural proteins having amino acid sequences such as NCBI GenBank Accession Nos. AAC98395 (human), I47076 (sheep), and NP786966 (cow). A specific example thereof can include a protein having an amino acid sequence set forth in SEQ ID NO: 47. The amino acid sequence set forth in SEQ ID NO: 47 is an amino acid sequence obtained by adding the amino acid sequence set forth in SEQ ID NO: 11 (tag sequence and hinge sequence) to the N-terminus of an amino acid sequence from the 121th residue to the 390th residue of the amino acid sequence of NCBI GenBank Accession No. AAC98395.

An example of a structural protein derived from keratin can include a type 1 keratin of *Capra hircus*. A specific example thereof can include a protein having an amino acid sequence set forth in SEQ ID NO: 48 (amino acid sequence of NCBI GenBank Accession No. ACY30466).

[Method of Producing Recombinant Structural Protein]

All of the recombinant structural proteins according to the embodiment can be produced by, for example, expressing a nucleic acid by a nucleic acid sequence encoding the recombinant structural protein and a host transformed with an expression vector having one or a plurality of regulatory sequences operably linked to the nucleic acid sequence. Hereinafter, modified fibroin will be described as an example.

A method for producing a nucleic acid encoding the modified fibroin is not particularly limited. For example, the nucleic acid can be produced by a method in which a gene encoding natural fibroin is amplified and cloned by a polymerase chain reaction (PCR) or the like, and the amplified and cloned gene is modified by a genetic engineering method, or a method of chemically synthesizing a nucleic acid. A method of chemically synthesizing a nucleic acid is not particularly limited. For example, genes can be chemically synthesized by a method of linking, by PCR or the like, oligonucleotides that are automatically synthesized by AKTA oligopilot plus 10/100 (GE Healthcare Japan Ltd.) or the like, based on the amino acid sequence information of fibroin obtained from the web database of NCBI and the like. In this case, in order to facilitate purification and/or confirmation of the modified fibroin, a nucleic acid encoding modified fibroin consisting of an amino acid sequence obtained by adding an amino acid sequence consisting of a start codon and a His10 tag to the N-terminus of the above amino acid sequence may be synthesized.

The regulatory sequence is a sequence that controls the expression of modified fibroin in a host (for example, a promoter, an enhancer, a ribosome binding sequence, a transcription termination sequence, or the like), and can be appropriately selected depending on the type of the host. As a promoter, an inducible promoter which functions in host cells and is capable of inducing expression of modified fibroin may be used. An inducible promoter is a promoter that can control transcription due to the presence of an inducer (expression inducer), the absence of a repressor molecule, or a physical factor such as an increase or decrease in temperature, osmotic pressure, or pH value.

The type of the expression vector such as a plasmid vector, a viral vector, a cosmid vector, a fosmid vector, or an artificial chromosome vector can be appropriately selected depending on the type of the host. As the expression vector, an expression vector which can automatically replicate in a host cell or can be incorporated into a chromosome of a host and which contains a promoter at a position capable of transcribing the nucleic acid encoding the modified fibroin is suitably used.

Both prokaryotes and eukaryotes such as yeast, filamentous fungi, insect cells, animal cells, and plant cells can be suitably used as hosts.

Examples of the host of the prokaryote can include bacteria belonging to the genus *Escherichia*, the genus *Brevibacillus*, the genus *Serratia*, the genus *Bacillus*, the genus *Microbacterium*, the genus *Brevibacterium*, the genus *Corynebacterium*, and the genus *Pseudomonas*. An example of microorganisms belonging to the genus *Escherichia* can include *E. coli*. An example of microorganisms belonging to the genus *Brevibacillus* can include *Brevibacillus agri*. An example of microorganisms belonging to the genus *Serratia* can include *Serratia liquefaciens*. An example of microorganisms belonging to the genus *Bacillus* can include *Bacillus subtilis*. An example of microorganisms belonging to the genus *Microbacterium* can include *Microbacterium ammoniaphilum*. An example of microorganisms belonging to the genus *Brevibacterium* can include *Brevibacterium divaricatum*. An example of microorganisms belonging to the genus *Corynebacterium* can include *Corynebacterium ammoniagenes*. Examples of the microorganism belonging to the genus *Pseudomonas* include *Pseudomonas putida*, and the like.

In a case where a prokaryote is used as a host, examples of a vector into which a nucleic acid encoding the modified fibroin is introduced can include pBTrp2 (manufactured by Boehringer Mannheim GmbH), pGEX (manufactured by Pharmacia Corporation), and pUC18, pBluescriptII, pSupex, pET22b, pCold, pUB110, and pNCO2 (JP 2002-238569 A).

Examples of a host of the eukaryote include yeast and filamentous fungi (molds and the like). An example of the yeast can include yeast which belongs to the genus *Saccharomyces*, the genus *Pichia*, or the genus *Schizosaccharomyces*. Examples of the filamentous fungi include filamentous fungi belonging to *Aspergillus*, *Penicillium*, and *Trichoderma*.

In a case where a eukaryote is used as a host, examples of a vector into which a nucleic acid encoding the modified fibroin is introduced can include YEP13 (ATCC37115) and YEp24 (ATCC37051). As a method of introducing an expression vector into the host cell, any method can be used as long as a DNA is introduced into the host cell. Examples thereof include a method using calcium ions [Proc. Natl. Acad. Sci. USA, 69, 2110 (1972)], an electroporation method, a spheroplast method, a protoplast method, a lithium acetate method, and a competent method.

As a method for expressing a nucleic acid by a host transformed with an expression vector, in addition to direct expression, secretory production, fusion protein expression, and the like can be performed according to the method described in Molecular Cloning Second Edition.

The modified fibroin can be produced by, for example, culturing a host transformed with the expression vector in a culture medium, producing and accumulating the modified fibroin in the culture medium, and then collecting the modified fibroin from the culture medium. A method of culturing the host in the culture medium can be performed according to a method commonly used for culturing a host.

In the case where the host is a prokaryote such as *E. coli* or a eukaryote such as yeast, any of a natural medium and a synthetic medium may be used as a culture medium as long as it contains a carbon source, a nitrogen source, inorganic salts, and the like which can be assimilated by the host and it is a medium capable of efficiently culturing the host.

As the carbon source, any carbon source that can be assimilated by the transformed microorganisms may be used, and it is possible to use, for example, carbohydrate such as glucose, fructose, sucrose, or molasses, starch, or starch hydrolyzates containing the carbohydrate, organic acid such as acetic acid or propionic acid, and alcohol such as ethanol or propanol. As the nitrogen source, for example, it is possible to use an ammonium salt of inorganic or organic acid such as ammonia, ammonium chloride, ammonium sulfate, ammonium acetate, or ammonium phosphate, other nitrogen-containing compounds, peptone, meat extract, yeast extract, corn steep liquor, casein hydrolyzate, soybean cake, soybean cake hydrolyzate, and various fermentative bacteria and digested products thereof. Examples of the inorganic salt that can be used include monopotassium phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15 to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium during the culture, if necessary. When culturing microorganisms transformed with an expression vector using an inducible promoter as a promoter, an inducer may be added to the medium, if necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

Isolation and purification of the expressed modified fibroin can be performed by a commonly used method. For example, in the case where the modified fibroin is expressed in a dissolved state in cells, the host cells are collected by centrifugation after completion of the culture, the collected cells are suspended in an aqueous buffer, and then the host cells are disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), a cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In addition, in the case where the modified fibroin is expressed by the formation of an insoluble matter in the cell, similarly, the host cells are recovered, disrupted and centrifuged to recover the insoluble matter of the modified fibroin as a precipitated fraction. The recovered insoluble matter of the modified fibroin can be solubilized with a protein denaturing agent. After this operation, a purified preparation of the modified fibroin can be obtained by the same isolation and purification method as described above. In the case where the modified fibroin is secreted extracellularly, the modified fibroin can be recovered from the culture supernatant. That is, a culture supernatant can be obtained by treating the culture by a method such as centrifugation, and a purified preparation can be obtained from the culture supernatant using the same isolation and purification method as described above.

[Spinning Raw Material Solution]

A spinning raw material solution (dope solution) according to the present embodiment contains a recombinant structural protein (for example: modified fibroin) and a solvent. Hereinafter, a spinning raw material solution containing modified fibroin will be described as an example of the recombinant structural protein.

Any solvent of the spinning raw material solution according to the present embodiment can be used as long as the solvent can dissolve modified fibroin, and an example thereof includes an organic solvent. Examples of the organic solvent include hexafluoroisopropanol (HFIP), hexafluoroacetone (HFA), dimethyl sulfoxide (DMSO), N,N-dimethylformamide (DMF), N,N-dimethylacetamide (DMA), 1,3-dimethyl-2-imidazolidone (DMI), N-methyl-2-pyrolidone (NMP), acetonitrile, N-methylmorpholine N-oxide (NMO), and formic acid. HFIP, DMSO, or formic acid is more preferred, and DMSO or formic acid is still more preferred, from the viewpoint of more preferred solubility of the modified fibroin. These organic solvents may contain water. These solvents may be used alone or in combination of two or more kinds thereof.

A concentration of the modified fibroin in the spinning raw material solution according to the present embodiment is preferably 10 to 50 wt %, more preferably 10 to 40 wt %, more preferably 15 to 40 wt %, more preferably 15 to 35 wt %, more preferably 20 to 35 wt %, more preferably 25 to 35 wt %, still more preferably 27 to 33 wt %, and particularly preferably 28 to 32 wt %, with respect to 100 wt % of a total amount of the spinning raw material solution. When the concentration of the modified fibroin is 10 wt % or more, productivity is further improved. When the concentration of the modified fibroin is 50 wt % or less, the spinning raw material solution can be more stably discharged from a spinneret, resulting in an improvement of productivity.

An inorganic salt may be added to the spinning raw material solution according to the present embodiment, if necessary. The inorganic salt can function as a dissolution accelerator for the modified fibroin. Examples of the inorganic salt include an alkaline metal halide, an alkaline earth metal halide, and an alkaline earth metal nitrate. Specific examples of the inorganic salt include lithium carbonate, lithium chloride, calcium chloride, calcium nitrate, lithium bromide, barium bromide, calcium bromide, barium chlorate, sodium perchlorate, lithium perchlorate, barium perchlorate, calcium perchlorate, and magnesium perchlorate. At least one of these inorganic salts may be added to the solvent.

A preparation method of the spinning raw material solution according to the present embodiment is not particularly limited, but the modified fibroin and the solvent may be mixed with each other in any order. The spinning raw material solution may be stirred or shaken for a predetermined time in order to accelerate dissolution. In this case, the spinning raw material solution may be heated to a temperature at which the spinning raw material solution can be dissolved depending on the used modified fibroin and solvent, if necessary. The spinning raw material solution may be heated to, for example, 30° C. or higher, 40° C. or higher, 50° C. or higher, 60° C. or higher, 70° C. or higher, 80° C. or higher, or 90° C. or higher. The heating temperature is preferably 40° C. from the viewpoint of preventing degradation of the modified fibroin. The upper limit of the heating temperature is equal to or lower than the boiling point of the solvent, for example.

A viscosity of the spinning raw material solution according to the present embodiment may be appropriately set according to use or a spinning method of a fiber. The viscosity at 20° C. may be, for example, 60,000 to 130,000 mPa·sec, or 65,000 to 125,000 mPa·sec. In addition, the viscosity at 35° C. may be, for example, 500 to 35,000 mPa·sec, 1,000 to 35,000 mPa·sec, 3,000 to 30,000 mPa·sec, 500 to 20,000 mPa·sec, 500 to 15,000 mPa·sec, 1,000 to 15,000 mPa·sec, 1,000 to 12,000 mPa·sec, 1,500 to 12,000 mPa·sec, 1,500 to 10,000 mPa·sec, or 1,500 to 8,000 mPa·sec. In addition, the viscosity at 40° C. may be, for example, 500 to 35,000 mPa·sec, 1,000 to 35,000 mPa·sec, 5,000 to 35,000 mPa·sec, 10,000 to 30,000 mPa·sec, 5,000 to 20,000 mPa·sec, 8,000 to 20,000 mPa·sec, 9,000 to 18,000 mPa·sec, 9,000 to 16,000 mPa·sec, 10,000 to 15,000 mPa·sec, 12,000 to 30,000 mPa·sec, 12,000 to 28,000 mPa·sec, 12,000 to 18,000 mPa·sec, or 12,000 to 16,000 mPa·sec. The viscosity of the spinning raw material solution can be measured using, for example, an "EMS viscometer" (trade name) manufactured by Kyoto Electronics Manufacturing Co., Ltd.

[Coagulation Liquid]

The coagulation liquid according to the present embodiment may be a solvent that can be desolvated, and examples thereof can include a lower alcohol having 1 to 5 carbon atoms such as methanol, ethanol, or 2-propanol, ketone such as acetone, water, and an aqueous solution having a pH of 0.25 to 10.00. The above solvents may be appropriately combined and used as a mixed solvent.

The coagulation liquid according to one embodiment mainly contains water or an aqueous solution having a pH of 0.25 to 10.00. Therefore, it is possible to provide a method of producing a protein fiber capable of reducing a production cost and an environmental load. The aqueous solution may be a salt aqueous solution, an acid aqueous solution, or a mixed solution of a salt aqueous solution and an acid aqueous solution, may be a salt aqueous solution, or a mixed solution of a salt aqueous solution and an acid aqueous solution, or may be a salt aqueous solution. Here, the mixed solution of a salt aqueous solution and an acid aqueous solution is not limited to a solution in which a salt aqueous solution and an acid aqueous solution are mixed. The mixed solution includes a solution in which an acid is added to a salt aqueous solution, a solution in which a salt is added to an acid aqueous solution, and a solution in which a salt and an acid are dissolved in water.

(Acid Aqueous Solution)

Examples of the acid aqueous solution include aqueous solutions of carboxylic acid, and the like. Specific examples of the carboxylic acid include formic acid, acetic acid, propionic acid, citric acid, and oxalic acid. One type of these solvent may be used alone, or two or more types thereof may be mixed and used as an aqueous solution. The acid aqueous solution may be, for example, a citric acid aqueous solution or a formic acid aqueous solution.

(Salt Aqueous Solution)

Examples of the salt aqueous solution include a salt aqueous solution of an organic salt or an inorganic salt, and a mixed aqueous solution of an organic salt and an inorganic salt.

Examples of the organic salt include carboxylate and the like. Specific examples of the carboxylate include a formate, an acetate, a propionate, a citrate, and an oxalate. The organic salt may be, for example, a formate, an acetate, and a citrate.

Specific examples of the formate include ammonium formate, potassium formate, sodium formate, lithium formate, magnesium formate, and calcium formate.

Specific examples of the acetate include ammonium acetate, potassium acetate, sodium acetate, lithium acetate, magnesium acetate, and calcium acetate.

Specific examples of the propionate include ammonium propionate, potassium propionate, sodium propionate, lithium propionate, magnesium propionate, and calcium propionate.

Specific examples of the citrate include ammonium citrate, potassium citrate, sodium citrate, lithium citrate, magnesium citrate, and calcium citrate. For example, the citrate may include at least one type selected from the group consisting of ammonium citrate, potassium citrate, sodium citrate, magnesium citrate, and calcium citrate. The citrate may include at least one type selected from the group consisting of ammonium citrate, potassium citrate, and sodium citrate. The citrate may include at least one type selected from the group consisting of potassium citrate and sodium citrate. The citrate may be sodium citrate.

Specific examples of the oxalate include ammonium oxalate, potassium oxalate, sodium oxalate, lithium oxalate, magnesium oxalate, and calcium oxalate. The carboxylate is more preferably a sodium carboxylate, and specific examples of the sodium carboxylate include sodium formate, sodium acetate, sodium propionate, and sodium oxalate.

Specific examples of the inorganic salt include a normal salt, an acid salt, and a basic salt.

Specific examples of the normal salt include a sulfate, a chloride, a nitrate, an iodide salt, a thiocyanate, and a carbonate.

Specific examples of the sulfate include ammonium sulfate, potassium sulfate, sodium sulfate, lithium sulfate, magnesium sulfate, and calcium sulfate. For example, the sulfate may include at least one type selected from the group consisting of ammonium sulfate, sodium sulfate, magnesium sulfate, and calcium sulfate. The sulfate may include at least one type selected from the group consisting of ammonium sulfate and sodium sulfate. The sulfate may be sodium sulfate.

Specific examples of the chloride include ammonium chloride, potassium chloride, sodium chloride, lithium chloride, magnesium chloride, and calcium chloride. For example, the chloride may include at least one selected from the group consisting of ammonium chloride, potassium chloride, sodium chloride, lithium chloride, calcium chloride, and magnesium chloride, and the chloride may include at least one selected from the group consisting of potassium chloride, sodium chloride, and calcium chloride, may include at least one selected from the group consisting of sodium chloride and calcium chloride, and may be sodium chloride.

Specific examples of the nitrate include ammonium nitrate, potassium nitrate, sodium nitrate, lithium nitrate, magnesium nitrate, and calcium nitrate.

Specific examples of the iodide salt include ammonium iodide, potassium iodide, sodium iodide, lithium iodide, magnesium iodide, and calcium iodide.

Specific examples of the thiocyanate include ammonium thiocyanate, potassium thiocyanate, sodium thiocyanate, lithium thiocyanate, magnesium thiocyanate, calcium thiocyanate, and guanidine thiocyanate.

Specific examples of the carbonate include ammonium carbonate, potassium carbonate, sodium carbonate, lithium carbonate, magnesium carbonate, and calcium carbonate.

Specific examples of the acid salt include a hydrogen sulfate, a hydrogen phosphate, and a bicarbonate.

Specific examples of the hydrogen sulfate include ammonium hydrogen sulfate, potassium hydrogen sulfate, sodium hydrogen sulfate, lithium hydrogen sulfate, magnesium hydrogen sulfate, and calcium hydrogen sulfate.

Specific examples of the hydrogen phosphate include sodium dihydrogen phosphate, disodium hydrogen phosphate, potassium dihydrogen phosphate, dipotassium hydrogen phosphate, ammonium dihydrogen phosphate, ammonium dihydrogen phosphate, diammonium hydrogen phosphate, magnesium dihydrogen phosphate, dimagnesium hydrogen phosphate, calcium dihydrogenphosphate, and dicalcium hydrogen phosphate.

Specific examples of the bicarbonate include ammonium bicarbonate, potassium bicarbonate, sodium bicarbonate, lithium bicarbonate, lithium bicarbonate, magnesium bicarbonate, and calcium bicarbonate.

Specific examples of the basic salt include calcium hydroxide chloride, and magnesium hydroxide chloride.

One type of the above acid, acid aqueous solution, salt, and salt aqueous solution may be used alone, or two or more types thereof can be mixed and used.

Examples of the salt mixed aqueous solution in which two or more types of salts or salt aqueous solutions are mixed include a mixed aqueous solution of the organic salts, a mixed aqueous solution of the inorganic salts, and a mixed aqueous solution of the organic salt and the inorganic salt. Brackish water and sea water are particularly preferable from the viewpoint of reducing production cost. The brackish water and sea water are known to primarily contain potassium chloride, sodium chloride, magnesium chloride, magnesium sulfate, and calcium sulfate.

Preferably, the coagulation liquid preferably contains a salt aqueous solution, and more preferably, the coagulation liquid is a salt aqueous solution. Inclusion of salt can further improve solvent removal rate. The salt more preferably includes at least one selected from the group consisting of a carboxylate, a sulfate, a chloride, a hydrogen phosphate, and a bicarbonate. The salt still more preferably includes at least one selected from the group consisting of a carboxylate, a sulfate, and a chloride. The salt still more preferably includes at least one selected from the group consisting of a sulfate and a chloride. The salt particularly preferably includes a sulfate. Inclusion of these salts can further improve the fiber-forming property, and thus can further improve elongation of the fiber to be obtained.

The carboxylate is more preferably sodium carboxylate. The sulfate is more preferably ammonium sulfate, sodium sulfate, magnesium sulfate, and calcium sulfate. The chloride is more preferably potassium chloride, sodium chloride, magnesium chloride, and calcium chloride. The bicarbonate is more preferably sodium bicarbonate. The mixed aqueous solution is particularly preferably brackish water and sea water. Use of these salts and mixed aqueous solutions can further reduce production cost, in addition to the effect of improving the fiber-forming property.

The content of the salt may be 0.1 mass % or more, 0.3 mass % or more, 0.5 mass % or more, 0.7 mass % or more, 1 mass % or more, 1.3 mass % or more, 1.5 mass % or more, 1.7 mass % or more, 2 mass % or more, 2.3 mass % or more, 2.5 mass % or more, 2.7 mass % or more, 3 mass % or more, 4 mass % or more, 5 mass % or more, 7 mass % or more, 10 mass % or more, or 15 mass % or more, with respect to total amount of the coagulation liquid. An upper limit thereof may be 30 mass % or less, 25 mass % or less, 20 mass % or less, or equal to or less than the solubility. The content of the salt may be, for example, 0.1 mass % or more and 30 mass % or less, 0.3 mass % or more and 25 mass % or less, 5 mass % or more and 25 mass % or less, 1 mass % or more and 25 mass % or less, 3 mass % or more and 25 mass % or less, 8 mass % or more and 25 mass % or less, 10 mass % or more and 25 mass % or less, 10 mass % or more and 25 mass % or less, 1 mass % or more and 20 mass % or less, 3 mass % or more and 20 mass % or less, 5 mass % or more and 20 mass % or less, 8 mass % or more and 20 mass % or less, 10 mass % or more and 20 mass % or less, 10 mass % or more and 15 mass % or less, 12 mass % or more and 17 mass % or less, 13 mass % or more and 18 mass % or less, 15 mass % or more and 20 mass % or less, or 16 mass % or more and 20 mass % or less, with respect to the total amount of the coagulation liquid. The content of the salt may be, for example, preferably 0.05 mol/L or more, 0.05 mol/L or more and 5.5 mol/L or less, 0.1 mol/L or more and 5.0 mol/L or less, 0.1 mol/L or more and 4.5 mol/L or less, or 0.1 mol/L or more and 4.0 mol/L or less, with respect to the total amount of the coagulation liquid.

The content of the salt in a case of using sodium chloride may be, for example, 0.1 mol/L or more and 5.0 mol/L or less, 0.1 mol/L or more and 4.5 mol/L or less, or 0.1 mol/L or more and 4.0 mol/L or less, with respect to the total amount of the coagulation liquid.

The content of the salt in a case of using a case of using sodium sulfate may be, for example, 0.1 mol/L or more and 3.4 mol/L or less, 0.1 mol/L or more and 3.0 mol/L or less, 0.1 mol/L or more and 2.5 mol/L or less, or 0.1 mol/L or more and 2.0 mol/L or less, with respect to the total amount of the coagulation liquid. In addition, the content may be, for example, 3 mass % or more and 28 mass % or less, 3 mass % or more and 25 mass % or less, 3 mass % or more and 20 mass % or less, 5 mass % or more and 20 mass % or less, or 8 mass % or more and 20 mass % or less, with respect to the total amount of the coagulation liquid.

In addition, the content of the sodium sulfate with respect to the total amount of the coagulation liquid is preferably 10 mass % or more and 20 mass % or less, preferably 11 mass % or more and 19 mass % or less, more preferably 11 mass % or more and 18 mass % or less, still more preferably 12 mass % or more and 18 mass % or less, still more preferably 12 mass % or more and 17 mass % or less, and particularly preferably 13 mass % or more and 16 mass % or less. When the content of the sodium sulfate with respect to the total amount of the coagulation liquid is 10 mass % or more, sufficient coagulation rate can be obtained, thus enabling cost increase due to facility investment to be prevented. When the content of the sodium sulfate with respect to the total amount of the coagulation liquid is 20 mass % or less, the breakage of the yarn can be prevented that occurs at the interface between the dope solution and the coagulated yarn (thread) caused by rapid coagulation of the dope solution.

In addition, the content of water with respect to the total amount of the coagulation liquid in the above case is preferably 50 mass % or more and 80 mass % or less, more preferably 60 mass % or more and 80 mass % or less, and still more preferably 60 mass % or more and 70 mass % or less, from the viewpoint of improving the recovery efficiency of the solvent. In addition, the concentration of the aqueous sodium sulfate solution in a case of using sodium sulfate is preferably 10 mass % or more and 22 mass % or less, preferably 10 mass % or more and 20 mass % or less, more preferably 12 mass % or more and 20 mass % or less, still more preferably 14 mass % or more and 20 mass % or less, and particularly preferably 16 mass % or more and 20 mass % or less. When the concentration of the aqueous sodium sulfate solution is 10 mass % or more, sufficient coagulation rate can be obtained, thus enabling cost increase due to facility investment to be prevented. When the concentration of the aqueous sodium sulfate solution is 22 mass % or less, it is possible to prevent the breakage of the yarn that occurs at the interface between the dope solution and the coagulated yarn (thread) caused by rapid coagulation of the dope solution.

The aqueous solution contained in the coagulation liquid of the present embodiment may be selected from the group consisting of, for example, an aqueous carboxylic acid solution, an aqueous bicarbonate solution, an aqueous formate solution, an aqueous acetate solution, an aqueous chloride solution, an aqueous sulfate solution, an aqueous hydrogen phosphate solution, an aqueous citrate solution, brackish water, sea water, and a mixed solution thereof. In addition, the aqueous solution contained in the coagulation liquid of the present embodiment may be, for example, selected from the group consisting of an aqueous citric acid solution, an aqueous formic acid solution, an aqueous sodium hydrogen carbonate solution, an aqueous sodium formate solution, an aqueous sodium acetate solution, an aqueous sodium chloride solution, an aqueous sodium sulfate solution, an aqueous ammonium sulfate solution, an aqueous potassium hydrogen phosphate solution, an aqueous calcium chloride solution, an aqueous sodium citrate solution, brackish water, seawater, and a mixed solution thereof, may be at least one selected from the group consisting of water, an aqueous formic acid solution, and an aqueous sodium sulfate solution, or may be at least one selected from the group consisting of water and an aqueous sodium sulfate solution.

The coagulation liquid before contact with the spinning raw material solution may or may not contain an organic solvent. In a case where the coagulation liquid contains an organic solvent, the organic solvent may be the same as or different from the organic solvent in the spinning raw material solution, but the organic solvent is preferably the same as the organic solvent in the spinning raw material solution. In addition, even in a case where the coagulation liquid before contact with the spinning raw material solution contains no organic solvent, there may be a case where the organic solvent is dissolved from the spinning raw material solution in contact with the coagulation liquid in the coagulation liquid in a process of bringing the spinning raw material solution into contact with the coagulation liquid. The content of the organic solvent contained in the coagulation liquid (including a case where the organic solvent is dissolved from the spinning raw material solution in contact with the coagulation liquid to the coagulation liquid) may be 0 mass % to 30 mass %, 5 mass % to 30 mass %, 5 mass % to 25 mass %, 0 mass % to 20 mass %, 5 mass % to 20 mass %, 5 mass % to 15 mass %, 10 mass % to 20 mass %, 0 mass % to 10 mass %, 0 mass % to 5 mass %, or 0 mass % to 2 mass %, and is preferably 10 mass % to 30 mass %, more preferably 12 mass % to 28 mass %, still more preferably 14 mass % to 26 mass %, and still more preferably 15 mass % to 25 mass %, with respect to 100 mass % of the total amount of the coagulation liquid (in a case where the organic solvent is dissolved from the spinning raw material solution to the coagulation liquid, the total content of the coagulation liquid before being in contact with the spinning raw material solution and the organic solvent dissolved from the spinning raw material solution to the coagulation liquid). When the content of the organic solvent is within the above-described range, the fiber-forming property of the structural protein is further improved. As the organic solvent, formic acid, DMSO, or HFIP is preferred, formic acid or HFIP is more preferred, and formic acid is still more preferred.

The pH of the aqueous solution contained in the coagulation liquid may be 0.25 to 10.00 or 0.25 to 9.50.

The pH of the acid aqueous solution in the coagulation liquid may be, for example, 0.25 to less than 7.00, 0.50 to less than 7.00, 1.00 to less than 7.00, 1.50 to less than 7.00, 2.00 to less than 7.00, or 3.00 to less than 7.00.

The pH of the salt aqueous solution in the coagulation liquid may be, for example, 0.50 to 10.00, 1.00 to 10.00, 2.00 to 10.00, 3.00 to 10.00, 3.50 to 10.00, 4.00 to 10.00, 4.50 to 10.00, 5.00 to 10.00, 5.50 to 10.00, 6.00 to 10.00, 6.50 to 10.00, or 6.50 to 9.50.

The content of the water or aqueous solution in the coagulation liquid may be 60 mass % or more, 65 mass % or more, or 68 mass % or more, preferably 70 mass % or more, more preferably 71 mass % or more, more preferably 72 mass % or more, more preferably 73 mass % or more, more preferably 74 mass % or more, more preferably 75 mass % or more, more preferably 76 mass % or more, more preferably 77 mass % or more, more preferably 78 mass % or more, more preferably 79 mass % or more, particularly preferably 80 mass % or more, 85 mass % or more, 90 mass % or more, or 95 mass %, with respect to the total amount of the coagulation liquid. When the content of the water or the aqueous solution is within the above-described range, the fiber-forming property of the structural protein is further improved. The content of the water or aqueous solution in the coagulation liquid may be, for example, 60 mass % to 100 mass %, 70 mass % to 100 mass %, 75 mass % to 100 mass %, 80 mass % to 100 mass %, 85 mass % to 100 mass %, 90 mass % to 100 mass %, 95 mass % to 100 mass %, 70 mass % to 90 mass %, 75 mass % to 85 mass %, or 78 mass % to 82 mass %, with respect to the total amount of the coagulation liquid.

The coagulation liquid preferably contains at least one selected from the group consisting of methanol, ethanol, acetone, water, and an aqueous sulfate solution, and a content of the methanol, ethanol, acetone, water, and/or aqueous sulfate solution in the coagulation liquid is preferably 70 mass % or more with respect to 100 mass % of the total amount of the coagulation liquid.

The temperature of the coagulation liquid may be room temperature, 0° C. to 90° C., 0° C. to 80° C., 5° C. to 80° C., 10° C. to 80° C., 15° C. to 80° C., 20° C. to 80° C., 25° C. to 80° C., 30° C. to 80° C., 40° C. to 80° C., 50° C. to 80° C., 60° C. to 80° C., 70° C. to 80° C., 20° C. to 70° C., 30° C. to 70° C., 40° C. to 70° C., 50° C. to 70° C., 20° C. to 60° C., 30° C. to 60° C., 40° C. to 60° C., 30° C. to 50° C., or 50° C. to 60° C. In a case where water or an aqueous solution (an aqueous formic acid solution, an aqueous sodium sulfate solution, or a mixed aqueous solution thereof) having a pH of 0.25 to 10.00 is used in the coagulation liquid, the temperature of the coagulation liquid is preferably 30° C. to 50° C., more preferably 32° C. to 48° C., more preferably 33° C. to 47° C., more preferably 34° C. to 46° C., and still more preferably 35° C. to 45° C., from the viewpoint of more excellent spinning stability. The lower limit of the temperature of the coagulation liquid may be equal to or higher than the melting point of the organic solvent contained in the spinning raw material solution. The upper limit of the temperature may be equal to or lower than the boiling point of the organic solvent contained in the spinning raw material solution. By setting the temperature of the coagulation liquid to a higher temperature, the solvent removal rate of the spinning raw material solution can be increased.

The coagulation liquid may further contain a dope solvent. A content of the dope solvent (for example: formic acid) is preferably 15 to 25 mass %, more preferably 16 to 25 mass %, still more preferably 16 to 24 mass %, and particularly preferably 18 to 24 mass %, with respect to the total amount of the coagulation liquid, from the viewpoint of improving the recovery efficiency of the solvent.

The coagulation liquid may further contain the above-described dissolution promoter that can be added to the spinning raw material solution.

[Method for Producing Recombinant Structural Protein Multifilament]

[Spinning Step]

In a method for producing a multifilament according to the present embodiment, a multifilament can be produced by a known wet spinning method, dry spinning method, dry wet spinning method, or melt spinning method using a spinning nozzle having 100 or more holes, and a multifilament composed of single yarns as many as the number of holes of the spinning nozzle (a multifilament having 100 or more constituent yarns) is obtained. The method for producing the multifilament according to the present embodiment can be performed using, for example, a spinning apparatus illustrated in FIG. 6 or 7. Preferred examples of the spinning method can include wet spinning and dry wet spinning. Hereinafter, a method for producing a modified fibroin multifilament will be described as an example.

Figure 6:
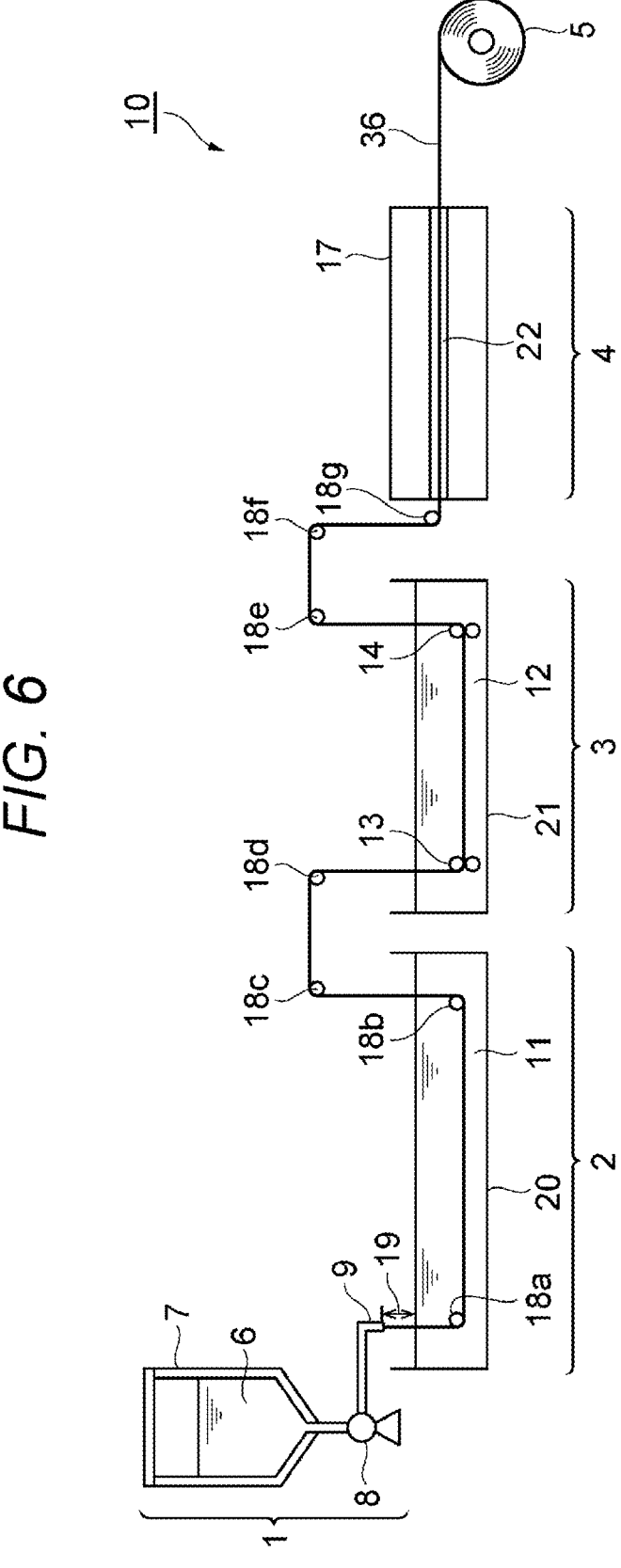
FIG. 6 is an explanation view schematically illustrating an example of a spinning apparatus for producing a modified fibroin multifilament.

FIG. 6 is an explanation view schematically illustrating an example of a spinning apparatus for producing a modified fibroin multifilament. A spinning apparatus 10 illustrated in FIG. 6 is an example of a spinning apparatus for dry wet spinning, and includes an extrusion device 1, a coagulation bath 20, a washing bath (drawing bath) 21, and a drying device 4 in order from an upstream side.

The extrusion apparatus 1 has a storage tank 7 that stores a spinning raw material solution (dope solution) 6. A coagulation liquid 11 is stored in the coagulation bath 20. The spinning raw material solution 6 is extruded from a spinneret (nozzle) 9 by a gear pump 8 attached to a lower end portion of the storage tank 7. The extruded spinning raw material solution 6 is fed (introduced) to the coagulation liquid 11 in the coagulation bath 20 via an air gap 19. In the coagulation liquid 11, the solvent is removed from the spinning raw material solution to coagulate the modified fibroin to form a fibrous coagulated body. Next, the fibrous coagulated body is fed into a washing solution 12 in the washing bath 21 to be drawn. A draw ratio is determined according to a speed ratio of a first nip roller 13 and a second nip roller 14 that are installed in the washing bath 21. Thereafter, the drawn fibrous coagulated body is fed into the drying device 4 to be dried in a yarn path 22, and then the dried fibrous coagulated body is wound around a winder. By doing so, the multifilament is finally obtained as a wound product 5 wound around the winder by the spinning apparatus 10. Note that reference numerals 18a to 18g represent thread guides.

In a case where a syringe pump having a nozzle with a diameter of 0.1 to 0.6 mm is used as the spinneret 9, an extrusion speed is preferably 0.2 to 6.0 ml/hr and more preferably 1.4 to 4.0 ml/hr per hole. A distance in which the coagulated modified fibroin passes through the coagulation liquid 11 (substantially, a distance from the yarn guide 18a to the yarn guide 18b) may be any length that enables efficient desolvation, and is, for example, 200 to 500 mm. A withdrawing speed of an undrawn yarn may be, for example, 1 to 100 m/min, or 1 to 20 m/min, and is preferably 1 to 3 m/min. When the withdrawing speed is 1 m/min or higher, productivity can be sufficiently increased. When the withdrawing speed is 100 m/min or lower, it is possible to remarkably prevent liquid scattering of the solvent. A retention time in the coagulation liquid 11 may be any time as long as the solvent is removed from the spinning raw material solution, and the retention time may be, for example, 0.01 to 3 minutes, and is preferably 0.05 to 0.15 minutes. In addition, the drawing (pre-drawing) may be performed in the coagulation liquid 11. The coagulation bath 20 may be provided in multiple stages, and the drawing may be performed in each stage or in a specific stage, if necessary.

Figure 7:
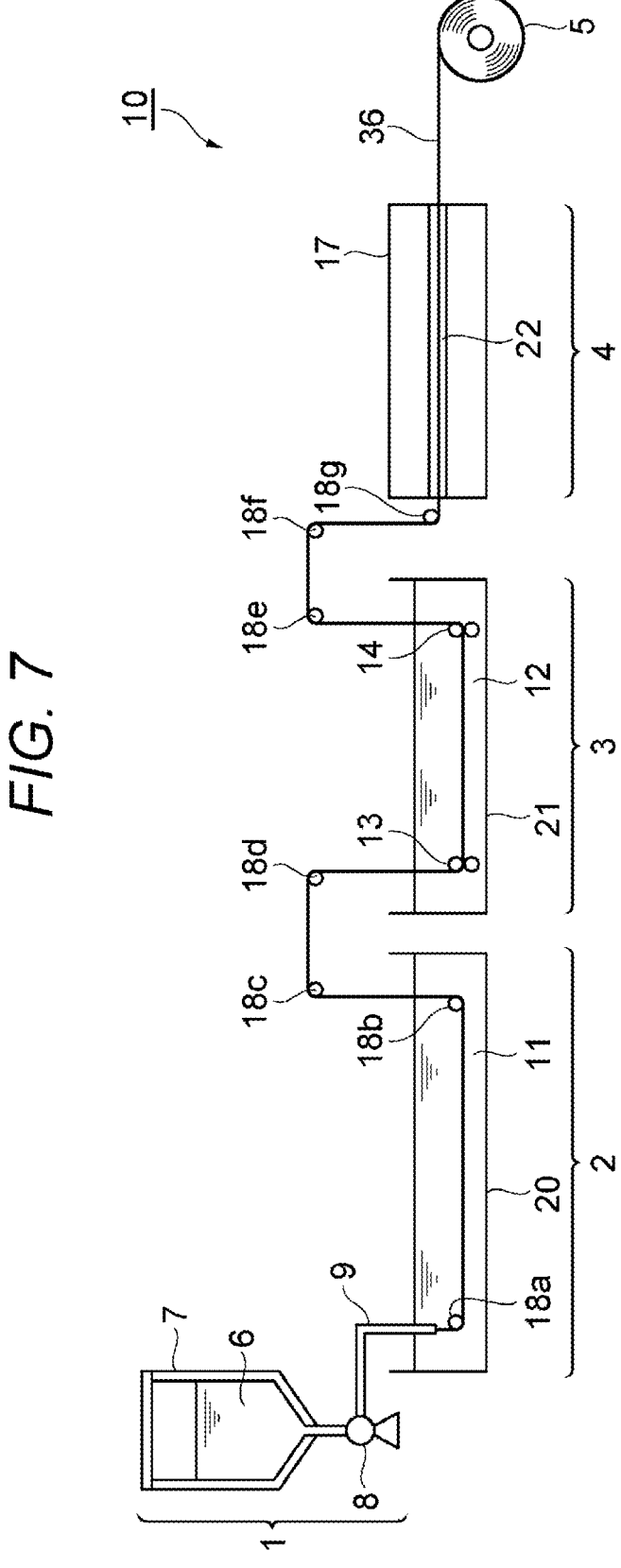
FIG. 7 is an explanation view schematically illustrating an example of a spinning apparatus for producing a modified fibroin multifilament.

FIG. 7 is an explanation view schematically illustrating an example of a spinning apparatus for producing a modified fibroin multifilament. The spinning apparatus 10 illustrated in FIG. 6 is an example of a spinning apparatus for wet spinning, and is the same apparatus of FIG. 6 except that the air gap 19 is not included.

A spinneret shape, a hole shape, the number of holes, or the like of the spinneret is not particularly limited, but can be appropriately selected depending on a desired fiber diameter and the number of single yarns.

In a case where the hole shape of the spinneret is a circular shape, a hole diameter thereof can be 0.01 mm or more and 0.6 mm or less. When the hole diameter is 0.01 mm or more, a pressure loss can be reduced and an equipment cost can thus be saved. When the hole diameter is 0.6 mm or less, it is possible to reduce the necessity of a drawing operation for reducing the fiber diameter, and it is possible to reduce possibility of drawing breakage during the operation from discharging to withdrawing.

A lower limit of the number of holes per weight of the spinning nozzle 1 is 100 or more from the viewpoint of improving productivity, and may be preferably 150 or more, 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1,000 or more, 1,100 or more, 1,200 or more, 1,300 or more, 1,400 or more, 1,500 or more, 1,600 or more, 1,700 or more, 1,800 or more, 1,900 or more, 2,000 or more, 2,100 or more, 2,200 or more, 2,300 or more, 2,400 or more, 2,500 or more, 2,600 or more, 2,700 or more, 2,800 or more, 2,900 or more, 3,000 or more, 3,100 or more, 3,200 or more, 3,300 or more, 3,400 or more, 3,500 or more, 3,600 or more, 3,700 or more, 3,800 or more, 3,900 or more, 4,000 or more, 4,100 or more, 4,200 or more, 4,300 or more, 4,400 or more, 4,500 or more, 4,600 or more, 4,700 or more, 4,800 or more, 4,900 or more, 5,000 or more, 5,100 or more, 5,200 or more, 5,300 or more, 5,400 or more, 5,500 or more, 5,600 or more, 5,700 or more, 5,800 or more, or 5,900 or more, from the viewpoint of further preferably obtaining the effect.

An upper limit of the number of holes per weight of the spinning nozzle 1 is 9,000 or less, and may be 8,900 or less, 8,800 or less, 8,700 or less, 8,600 or less, 8,500 or less, 8,400 or less, 8,300 or less, 8,200 or less, 8,100 or less, 8,000 or less, 7,900 or less, 7,800 or less, 7,700 or less, 7,600 or less, 7,500 or less, 7,400 or less, 7,300 or less, 7,200 or less, 7,100 or less, 7,000 or less, 6,900 or less, 6,800 or less, 6,700 or less, 6,600 or less, 6,500 or less, 6,400 or less, 6,300 or less, 6,200 or less, 6,100 or less, or 6,000 or less, from the viewpoint of improving productivity.

From the viewpoint of sufficiently improving productivity, the number of holes per weight of the spinning nozzle 1 may be 100 to 9,000, 150 to 9,000, 200 to 9,000, 250 to 9,000, 350 to 9,000, 300 to 9,000, 350 to 9,000, 400 to 9,000, 450 to 9,000, 500 to 9,000, 650 to 9,000, 750 to 9,000, 800 to 9,000, 850 to 9,000, 900 to 9,000, 950 to 9,000, or 1,000 to 9,000, for example, the number may be 100 to 8,000, 150 to 8,000, 200 to 8,000, 250 to 8,000, 350 to 8,000, 300 to 8,000, 350 to 8,000, 400 to 8,000, 450 to 8,000, 500 to 8,000, 650 to 8,000, 750 to 8,000, 800 to 8,000, 850 to 8,000, 900 to 8,000, 950 to 8,000, or 1,000 to 8,000, for example, the number may be 100 to 7,000, 150 to 7,000, 200 to 7,000, 250 to 7,000, 350 to 7,000, 300 to 7,000, 350 to 7,000, 400 to 7,000, 450 to 7,000, 500 to 7,000, 650 to 7,000, 750 to 7,000, 800 to 7,000, 850 to 7,000, 900 to 7,000, 950 to 7,000, or 1,000 to 7,000, for example, the number may be 100 to 6,000, 150 to 6,000, 200 to 6,000, 250 to 6,000, 350 to 6,000, 300 to 6,000, 350 to 6,000, 400 to 6,000, 450 to 6,000, 500 to 6,000, 650 to 6,000, 750 to 6,000, 800 to 6,000, 850 to 6,000, 900 to 6,000, 950 to 6,000, 1,000 to 6,000, 100 to 5,500, 150 to 5,500, 200 to 5,500, 250 to 5,500, 350 to 5,000, 300 to 5,500, 350 to 5,500, 400 to 5,500, 450 to 5,500, 500 to 5,000, 650 to 5,500, 750 to 5,500, 800 to 5,500, 850 to 5,500, 900 to 5,500, 950 to 5,500, or 1,000 to 5,500, for example, the number may be 100 to 5,200, 150 to 5,200, 200 to 5,200, 250 to 5,200, 350 to 5,200, 300 to 5,200, 350 to 5,200, 400 to 5,200, 450 to 5,200, 500 to 5,200, 650 to 5,200, 750 to 5,200, 800 to 5,200, 850 to 5,200, 900 to 5,200, 950 to 5,200, or 1,000 to 5,200, for example, the number may be 100 to 4,800, 150 to 4,800, 200 to 4,800, 250 to 4,800, 350 to 4,800, 300 to 4,800, 350 to 4,800, 400 to 4,800, 450 to 4,800, 500 to 4,800, 650 to 4,800, 750 to 4,800, 800 to 4,800, 850 to 4,800, 900 to 4,800, 950 to 4,800, or 1,000 to 4,800, for example, the number may be 100 to 4,500, 150 to 4,500, 200 to 4,500, 250 to 4,500, 350 to 4,500, 300 to 4,500, 350 to 4,500, 400 to 4,500, 450 to 4,500, 500 to 4,500, 650 to 4,500, 750 to 4,500, 800 to 4,500, 850 to 4,500, 900 to 4,500, 950 to 4,500, or 1,000 to 4,500, for example, the number may be 100 to 4,000, 150 to 4,500, 200 to 4,500, 250 to 4,000, 350 to 4,500, 300 to 4,000, 350 to 4,000, 400 to 4,000, 450 to 4,000, 500 to 4,000, 650 to 4,000, 750 to 4,000, 800 to 4,000, 850 to 4,500, 900 to 4,000, 950 to 4,000, or 1,000 to 4,000.

The number of weights of the spinning nozzle is not particularly limited as long as it is appropriately selected depending on the production amount of the target fiber and the like, and may be, for example, 1, 2, 3, 4, 5, 6, 7, 8, 9, 10, 11, 12, 13, 14, 15, 16, 17, 18, 19, 20, 20 or more, 25, 30 or more, 35 or more, 40 or more, 45 or more, 50 or more, 55 or more, 60 or more, 65 or more, 70 or more, 75 or more, 80 or more, 85 or more, 90 or more, 95 or more, or 100 or more. As the spinning nozzle, a plurality of spinning nozzles (a plurality of weights) having the same number of holes may be used in combination (for example, 12 spinning nozzles each having 3,000 holes may be used in combination), or a plurality of spinning nozzles having different numbers of holes may be used in combination.

The temperature of the spinning raw material solution when the spinning raw material solution passes through the spinneret and the temperature of the spinneret are not particularly limited. The temperatures may be appropriately adjusted depending on the concentration and viscosity of the spinning raw material solution to be used, the type of the organic solvent, and the like. The temperature is preferably 30° C. to 100° C., from the viewpoint of preventing a deterioration of the modified fibroin. In addition, an upper limit of the temperature is preferably a temperature lower than a boiling point of the solvent to be used, from the viewpoint of reducing an increase in pressure due to vola- tilization of the solvent and the possibility of blockage in a pipe due to solidification of the spinning raw material solution. This improves process stability.

A temperature of the coagulation liquid 11 is not particu- larly limited, but may be 40° C. or lower, 30° C. or lower, 25° C. or lower, 20° C. or lower, 10° C. or lower, or 5° C. or lower. The temperature of the coagulation liquid 11 is preferably 0° C. or higher, from the viewpoint of workabil- ity, a cooling cost, or the like. Additionally, the temperature of the coagulation liquid 11 can be adjusted by, for example, using the spinning apparatus 10 having the coagulation bath 20 including a heat exchanger inside thereof and a coolant circulation device. For example, a cooled medium, which has been cooled to a predetermined temperature by the coolant circulation device, is allowed to flow through the heat exchanger provided in the coagulation bath. Whereby, the temperature can be adjusted to a temperature within the above range by heat exchange between the coagulation liquid 11 and the heat exchanger. In this case, more efficient cooling can be achieved by circulating, as a medium, a solvent used for the coagulation liquid 11.

A plurality of coagulation baths storing the coagulation liquid may be provided.

The coagulated modified fibroin (fibrous coagulated body) may be wound around the winder as it is after released from the coagulation bath or the washing bath, or may be wound around the winder after passing through the drying device to be dried.

A distance in which the coagulated modified fibroin (fibrous coagulated body) passes through the coagulation liquid may be determined depending on an extrusion speed (discharge speed) of the spinning raw material solution from the nozzle, as long as desolvation is efficiently performed. A retention time of the coagulated modified fibroin (or the spinning raw material solution) in the coagulation liquid may be determined depending on the distance in which the coagulated modified fibroin passes through the coagulation liquid, the extrusion speed of the spinning raw material solution from the nozzle, and the like.

[Drawing Step]

The method for producing the modified fibroin multifila- ment of the present embodiment may further include a step of drawing the coagulated modified fibroin (fibrous coagu- lated body) (drawing step). Examples of the drawing method include wet heat drawing and dry heat drawing. The drawing step may be performed by, for example, in the coagulation bath 20, or in the washing bath 21. The drawing step can also be performed in the air.

The drawing in the washing bath 21 may be drawing in hot water, in a solution in which an organic solvent is added to hot water, or the like, that is, wet heat drawing. A temperature in the wet heat drawing is preferably 50 to 90° C. When the temperature is 50° C. or higher, it is possible to make a pore diameter of the yarn small and stable. In addition, when the temperature is 90° C. or lower, the temperature is easily set, which improves spinning stability. The temperature is more preferably 75 to 85° C.

The wet heat drawing can be performed in hot water, in a solution in which an organic solvent or the like is added to hot water, or in a heated steam. The temperature may be, for example, 40 to 200° C., 50 to 180° C., 50 to 150° C., or 75 to 90° C. The draw ratio in the wet heat drawing may be, for example, 1 to 30 times, 2 to 25 times, 2 to 20 times, 2 to 15 times, 2 to 10 times, 2 to 8 times, 2 to 6 times, or 2 to 4 times, with respect to the undrawn yarn (or pre-drawing yarn). However, the draw ratio is not limited as long as character- istics such as a desired fiber thickness and mechanical properties can be obtained.

The dry heat drawing can be performed in the air using a device provided with a heat source such as a contact type heat plate and a non-contact type furnace, but the present invention is not particularly limited thereto. Any device may be used as long as a fiber can be heated to a predetermined temperature and to be drawn at a predetermined ratio. The temperature for dry heat drawing may be, for example, 100° C. to 270° C., 140° C. to 230° C., 140° C. to 200° C., 160° C. to 200° C., or 160° C. to 180° C.

The draw ratio in the dry heat drawing step may be, for example, 1 to 30 times, may be 2 to 30 times, may be 2 to 20 times, may be 3 to 15 times, preferably 3 to 10 times, more preferably 3 to 8 times, and still more preferably 4 to 8 times, with respect to the undrawn yarn (or pre-drawing yarn). However, the draw ratio is not limited as long as it is within a range in which characteristics such as a desired fiber thickness and mechanical properties can be obtained.

The drawing step may be a step that performs each of wet heat drawing and dry heat drawing separately, or a step that performs these drawings in multiple stages or in combination. That is, as the drawing step, wet heat drawing and dry heat drawing can be appropriately combined and performed as follows: wet heat drawing is performed at a first drawing stage and then dry heat drawing is performed at a second drawing stage, or wet heat drawing is performed at a first drawing stage, then wet heat drawing is performed at a second drawing stage, and further dry heat drawing is performed at a third drawing stage, for example.

A lower limit of the final draw ratio of the multifilament subjected to the drawing step is preferably any of 1 time, 2 times, 3 times, 4 times, 5 times, 6 times, 7 times, 8 times, or 9 times, with respect to the undrawn yarn (or pre-drawn yarn). An upper limit of the final draw ratio of the multifilament subjected to the drawing step is preferably any of 40 times, 30 times, 20 times, 15 times, 14 times, 13 times, 12 times, 11 times, or 10 times. In addition, the final draw ratio may be, for example, 3 to 40 times, 3 to 30 times, 5 to 30 times, 5 to 20 times, 5 to 15 times, or 5 to 13 times. However, the draw ratio is not limited as long as characteristics such as a desired fiber thickness and mechanical properties can be obtained. By adjusting the draw ratio, the fiber diameter of the obtained multifilament can be adjusted to an arbitrary value.

An oil agent may be applied to an undrawn yarn (or pre-drawing yarns) or drawn yarn, as necessary, for the purpose of imparting an antistatic property, convergence and lubricity, or the like before or after drying. The type of the oil agent applied and application amount thereof, and the like are not particularly limited, but can be appropriately adjusted in consideration of use application of the fiber, dealing of the fiber, and the like.

The production method according to the present embodiment may further include a step of filtrating the spinning raw material solution before discharging the spinning raw material solution (filtration step) and/or a step of defoaming the spinning raw material solution before discharging (defoaming step).

The production method according to the present embodiment may further include a shrinking step before or after the drying step. In a case where a shrinking step is performed after the drying step, the shrinking step may be performed by winding the dried multifilament around a bobbin after spinning, and unwinding the multifilament from the bobbin.

[Shrinking Step]

The modified fibroin multifilament according to the present embodiment may further include a shrinking step of irreversibly shrinking the multifilament. In the shrinking step of irreversibly shrinking the multifilament, the multifilament may be irreversibly shrunk by bringing the multifilament into contact with water, or the multifilament may be irreversibly shrunk by heating and relaxing the multifilament. In the case where the multifilament is irreversibly shrunk by bringing the multifilament into contact with water, the irreversibly shrunk multifilament may be dried and further shrunk.

[Shrinking Step by Contact with Water (Contact Step)]

Figure 8:
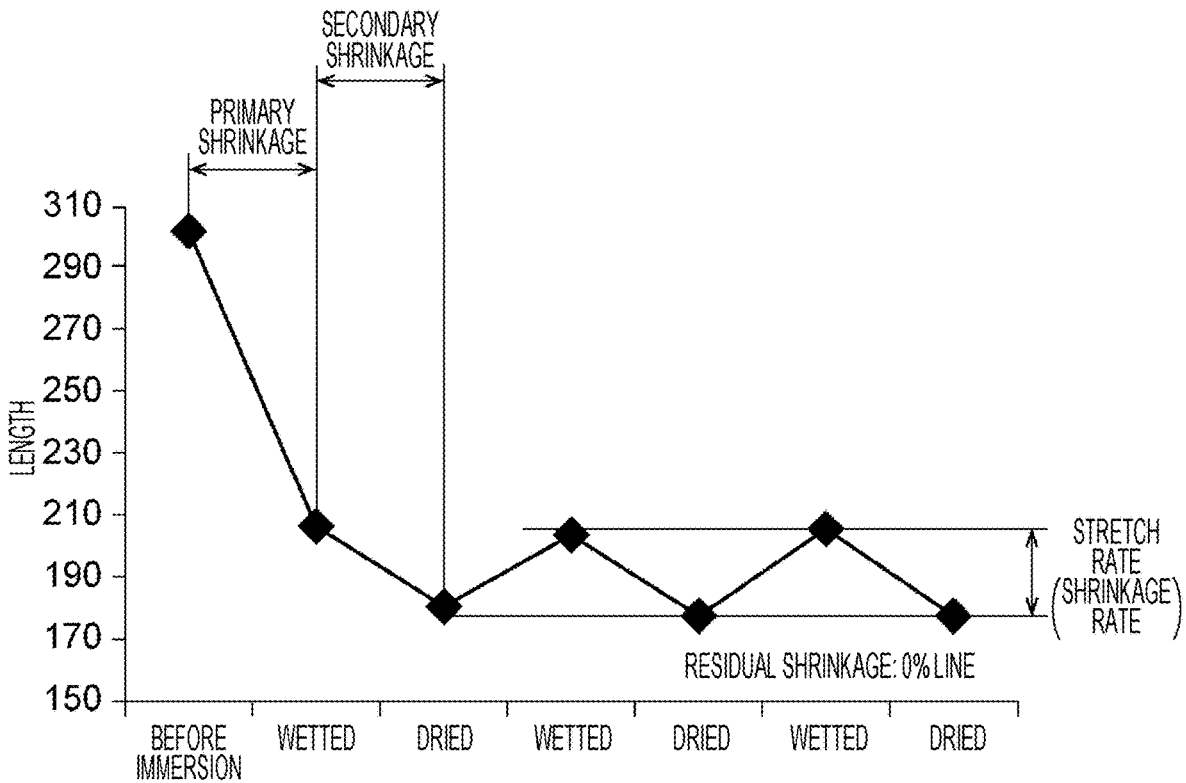
FIG. 8 is a view illustrating an example of a change in length of the multifilament due to contact with water.

FIG. 8 is a view illustrating an example of a change in length of the multifilament (fiber containing the modified fibroin) due to contact with water. The multifilament (fiber containing the modified fibroin) according to the present embodiment has a property of being further shrunk by brining (wetting) the multifilament into contact with water having a temperature lower than a boiling point (primary shrinkage) (in FIG. 8, a change in length indicated by "primary shrinkage"). After the primary shrinkage, the multifilament is further shrunk when dried (in FIG. 8, a change in length indicated by "secondary shrinkage"). After the secondary shrinkage, when the multifilament is brought into contact with water again, the multifilament is stretched to the same as or similar to the length before the secondary shrinkage and then drying and wetting are repeated, the multifilament is repeatedly shrunk and stretched with a width similar to that in the secondary shrinkage (in FIG. 8, a width indicated by "stretch rate (shrinkage rate)"). That is, the primary shrinkage is irreversible shrinkage due to contact of the multifilament with water. Therefore, the modified fibroin multifilament having a shrinkage history of being irreversibly shrunk according to the present embodiment can be obtained by bringing the multifilament into contact with water in the shrinking step. A step of irreversibly shrinking the multifilament by bringing the multifilament into contact with water (primary shrinkage) is hereinafter referred to as a "contact step".

It is considered that the irreversible shrinkage of the multifilament (fiber containing the modified fibroin) in the contact step ("primary shrinkage" in FIG. 8) occurs, for example, for the following reasons. That is, one reason is considered to be due to a primary structure of the multifilament (fiber containing the modified fibroin). Another reason is considered to be that, for example, in the multifilament (fiber containing modified fibroin) having a residual stress due to drawing or the like in the production process, the residual stress is relieved by water entering between fibers or into the fiber.

In the contact step, the multifilament before being brought into contact with water after spinning is brought into contact with water to bring the multifilament into a wet state. The wet state refers to a state in which at least a part of the multifilament is wetted with water. Therefore, the multifilament can be shrunk regardless of an external force. This shrinkage is irreversible (corresponding to the "primary shrinkage" in FIG. 8).

A temperature of the water coming into contact with the multifilament in the contact step may be lower than a boiling point. Therefore, handleability, workability in the shrinking step, and the like are improved. In addition, a lower limit of the temperature of the water is preferably 10° C. or higher, more preferably 40° C. or higher, and still more preferably 70° C. or higher, from the viewpoint of sufficiently shortening the shrinkage time. An upper limit of the temperature of the water is preferably 90° C. or lower.

In the contact step, a method of bringing the multifilament into contact with water is not particularly limited. Examples of the method can include a method of immersing the multifilament in water, a method of spraying water onto the multifilament at room temperature or in a heated steam state, and a method of exposing the multifilament to a high humidity environment in which water vapor is filled. Among these methods, the method of immersing the multifilament in water is preferred in the contact step, because the shrinkage time can be effectively shortened and the processing equipment can be simplified.

When the multifilament is brought into contact with water in a relaxed state in the contact step, the multifilament may be not only shrunk but also be curled to be wavy. In order to prevent the occurrence of curling, for example, the contact step may be performed in a state where the multifilament is not relaxed, for example, in a state where the multifilament is brought into contact with water while being tensioned in an axial direction of the fiber to the extent that a tension is not applied.

(Drying Step)

The method for producing the modified fibroin multifilament according to the present embodiment may further include a drying step. The drying step is a step of drying and further shrinking the multifilament subjected to the contact step (or the modified fibroin multifilament obtained through the contact step) (corresponding to "secondary shrinkage" of FIG. 8). Drying may be, for example, natural drying, or forced drying using drying equipment. As the drying equipment, any known drying equipment of contact type or non-contact type can be used. In addition, a drying temperature is not limited as long as it is lower than a temperature at which the modified fibroin contained in the multifilament is degraded or the multifilament is thermally damaged. In general, the drying temperature is a temperature in a range of 20 to 150° C., and is preferably a temperature in a range of 50 to 100° C. When the temperature is in this range, the fiber is more quickly and efficiently dried without thermal damage to the fiber or degradation of the modified fibroin contained in the fiber. A drying time is appropriately set depending on the drying temperature or the like, and for example, a time during which the influence on the quality and physical properties of the modified fibroin multifilament due to overdrying can be eliminated as much as possible is employed.

Figure 9:
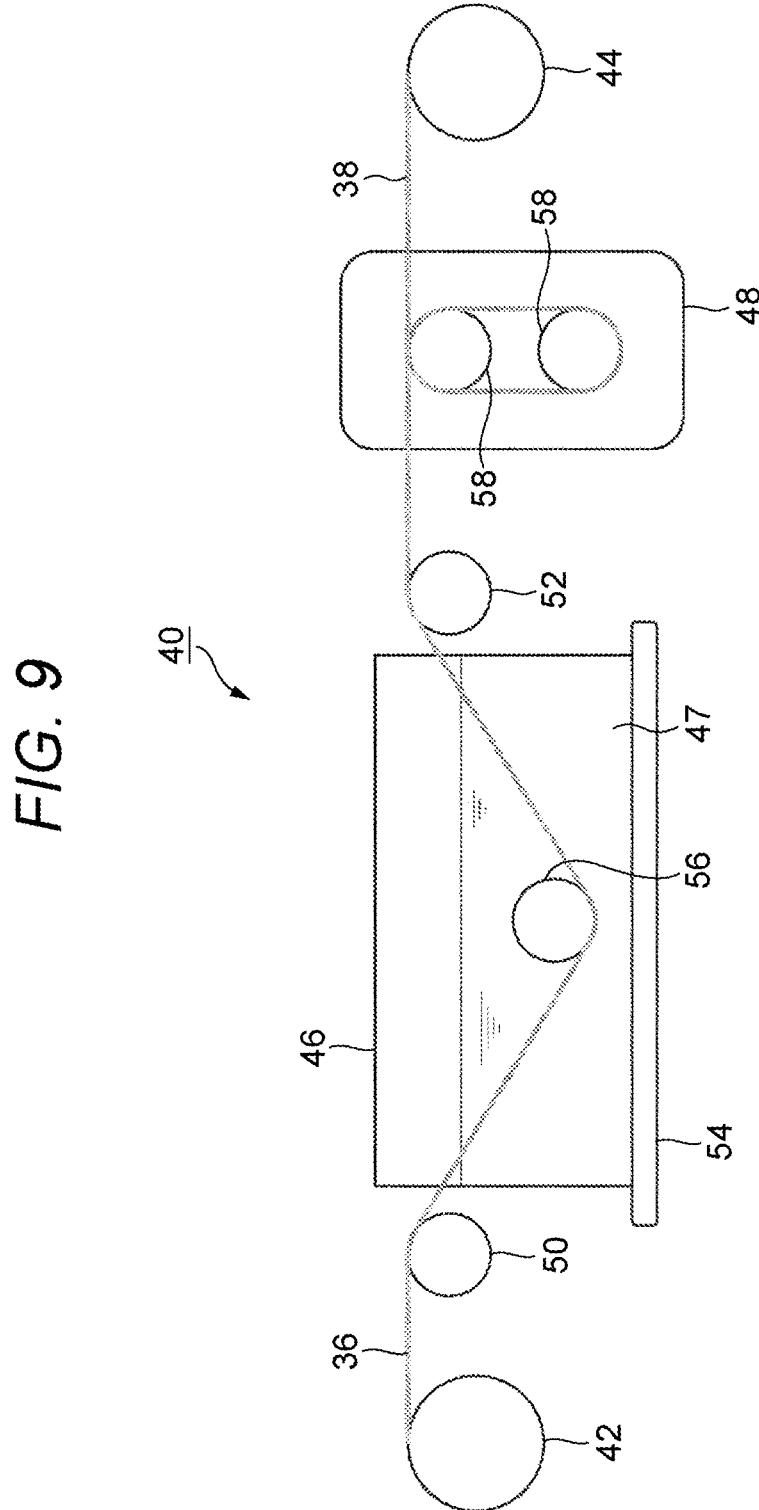
FIG. 9 is an explanation view schematically illustrating an example of a producing apparatus for producing a modified fibroin multifilament.

FIG. 9 is an explanation view schematically illustrating an example of a producing apparatus for producing a modified fibroin multifilament. A producing apparatus 40 illustrated in FIG. 9 includes a feed roller 42 for feeding the multifilament, a winder 44 for winding a modified fibroin multifilament 38, a water bath 46 for performing the contact step, and a dryer 48 for performing the drying step.

More specifically, the feed roller 42 can be loaded with a wound product of a multifilament 36, and the multifilament 36 can be continuously and automatically fed from the wound product of the multifilament 36 by rotation of an electric motor or the like (not illustrated). The winder 44 can continuously and automatically wind the modified fibroin multifilament 38 produced through the contact step and the drying step after being fed out from the feed roller 42 by the rotation of the electric motor (not illustrated). Here, a feed speed of the multifilament 36 by the feed roller 42 and a winding speed of the modified fibroin multifilament 38 by the winder 44 can be controlled independently of each other.

The water bath 46 and the dryer 48 are arranged between the feed roller 42 and the winder 44 on the upstream side and the downstream side in a feed direction of the multifilament 36, respectively. The producing apparatus 40 illustrated in FIG. 9 includes relay rollers 50 and 52 relaying the multifilament 36 before and after the contact step, the multifilament moving from the feed roller 42 toward the winder 44.

The water bath 46 includes a heater 54, and water 47 heated by the heater 54 is accommodated in the water bath 46. In addition, in the water bath 46, a tension roller 56 is installed in a state of being immersed in the water 47. Accordingly, the multifilament 36 fed from the feed roller 42 moves toward the winder 44 while being immersed in the water 47 in a state of being wound around the tension roller 56 in the water bath 46. An immersion time of the multifilament 36 in the water 47 is appropriately controlled according to a moving speed of the multifilament 36.

The dryer 48 has a pair of hot rollers 58. The pair of hot rollers 58 can be wound with the multifilament 36 which is released from the water bath 46 and moves toward the winder 44. Accordingly, the multifilament 36 immersed in the water 47 in the water bath 46 is heated by the pair of hot rollers 58 in the dryer 48, the multifilament 36 is dried, and then the dried multifilament is further fed toward the winder 44.

Figure 11:
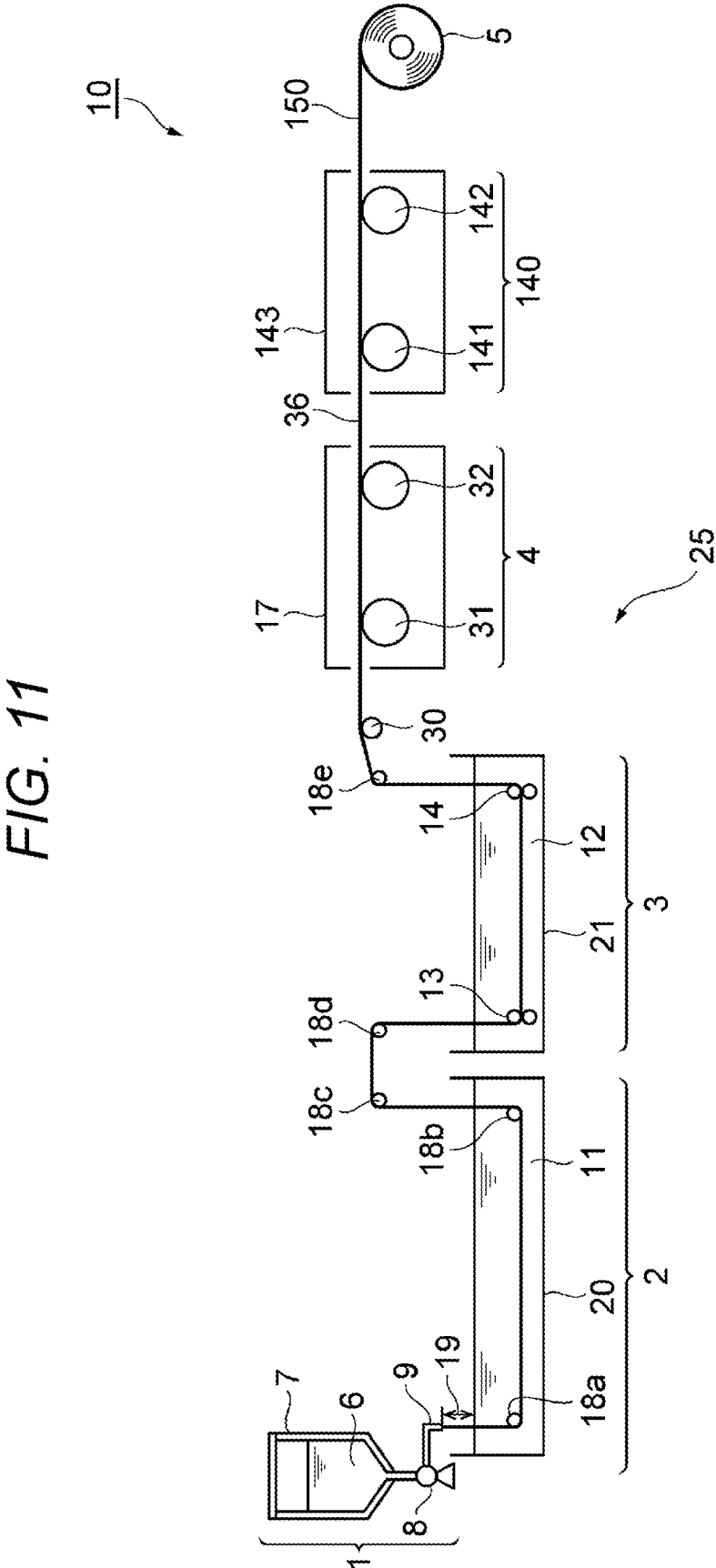
FIG. 11 is an explanation view schematically illustrating an example of a producing apparatus for producing a modified fibroin multifilament.

When the modified fibroin multifilament 38 is produced using the producing apparatus 40 having such a structure, first, for example, the wound product of the multifilament 36 spun using the spinning apparatus 10 illustrated in FIG. 11 is mounted on the feed roller 42. Next, the multifilament 36 is continuously fed from the feed roller 42 and immersed in the water 47 in the water bath 46. In this case, for example, the winding speed of the winder 44 is slower than the feed speed of the feed roller 42. Accordingly, since the multifilament 36 is shrunk due to contact with the water 47 in a state of not being relaxed between the feed roller 42 and the winder 44, the occurrence of curling can be prevented. The multifilament 36 is irreversibly shrunk due to contact with the water 47 (corresponding to "primary shrinkage" of FIG. 8).

Next, the multifilament 36 after being brought into contact with the water 47 (or the modified fibroin multifilament 38 produced through contact with the water 47) is heated by the pair of hot rollers 58 of the dryer 48. Accordingly, the multifilament 36 after being brought into contact with the water 47 (or the modified fibroin multifilament 38 produced through contact with the water 47) can be dried and further shrunk (corresponding to "secondary shrinkage" of FIG. 8). In this case, a ratio of the feed speed of the feed roller 42 to the winding speed of the winder 44 can be controlled so that the length of the modified fibroin multifilament 38 is not changed. Then, the obtained modified fibroin multifilament 38 is wound around the winder 44 to obtain the wound product of the modified fibroin multifilament 38.

Instead of the pair of hot rollers 58, the multifilament 36 obtained after being brought into contact with the water 47 may be dried using drying equipment having only a heat source, such as a dry heat plate 64 as illustrated in FIG. 10(b). Also, in this case, by adjusting a relative speed between the feed speed of the feed roller 42 and the winding speed of the winder 44 in the same manner as in the case of using the pair of hot rollers 58 as the drying equipment, the length of the modified fibroin multifilament cannot be changed. Here, the drying means includes the dry heat plate 64. In addition, the dryer 48 is optional.

As described above, the modified fibroin multifilament 38 to be targeted can be automatically, continuously, and extremely easily produced using the producing apparatus 40.

Figure 10:
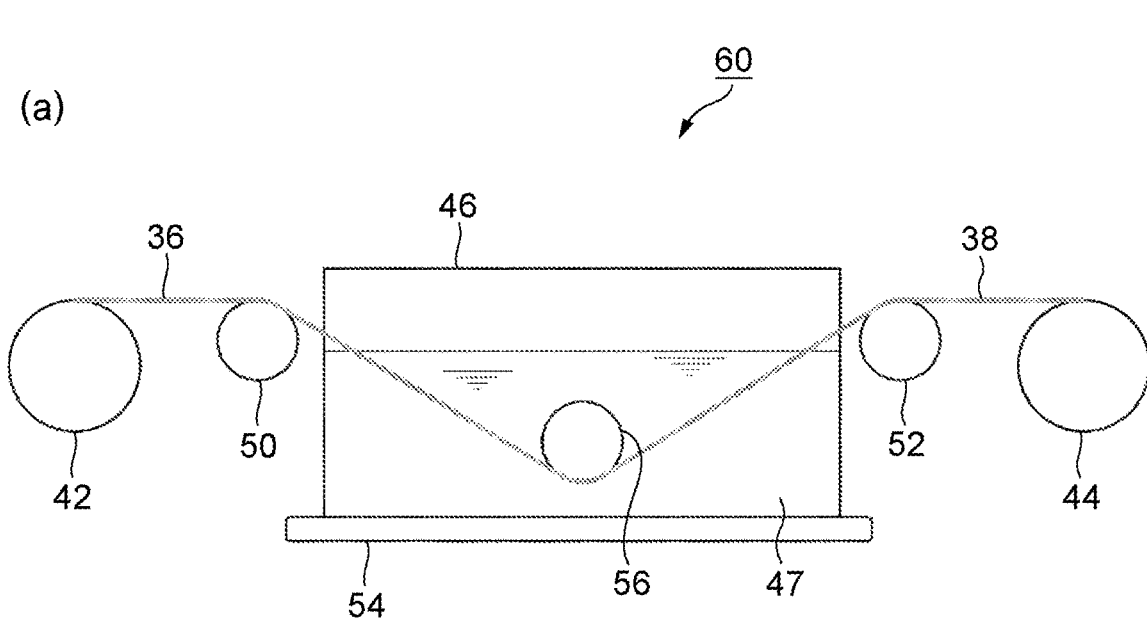
FIG. 10 is an explanation view schematically illustrating an example of a producing apparatus for producing a modified fibroin multifilament.
Figure 10:
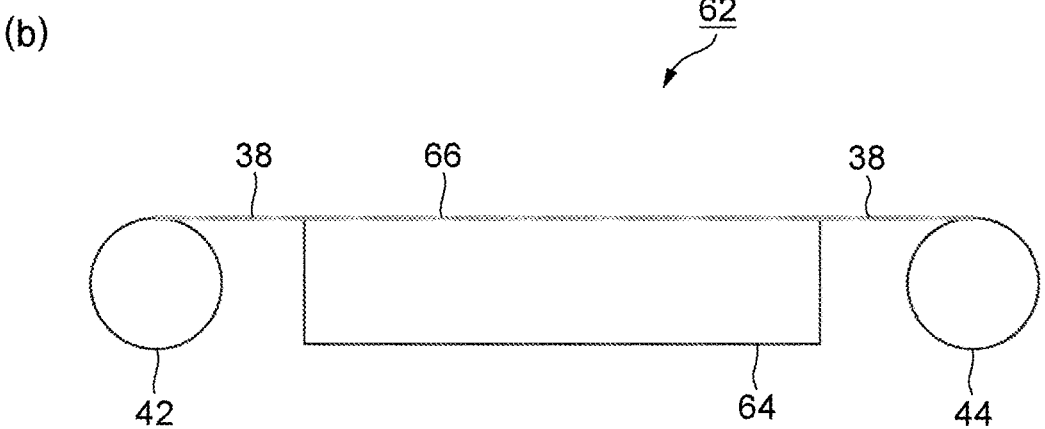

FIG. 10 is an explanation view schematically illustrating another example of a producing apparatus for producing a modified fibroin multifilament. FIG. 10(a) illustrates a processing device that is included in the producing apparatus and that performs the contact step (primary shrinkage). FIG. 10(b) illustrates a drying device that is included in the producing apparatus and that performs the drying step. The producing apparatus illustrated in FIG. 10 includes a processing device 60 for performing the contact step on the multifilament 36, and a drying device 62 for drying the multifilament 36 after the contact step (or the modified fibroin multifilament 38 produced through the contact step), and the producing apparatus has a structure in which these devices are installed independently of each other.

More specifically, the processing device 60 illustrated in FIG. 10(a) has a structure in which the feed roller 42, the water bath 46, and the winder 44 are arranged in order from the upstream side to the downstream side in a moving direction of the multifilament 36. Such a processing device 60 is designed to allow the multifilament 36 fed from the feed roller 42 to be immersed in the water 47 in the water bath 46 and to be shrunk. In addition, the obtained modified fibroin multifilament 38 is wound around the winder 44. In this case, for example, the winding speed of the winder 44 is slower than the feed speed of the feed roller 42. Accordingly, since the multifilament 36 is shrunk due to contact with the water 47 in a state of being relaxed between the feed roller 42 and the winder 44, it is possible to prevent the fiber from being tensioned. The multifilament 36 is irreversibly shrunk due to contact with the water 47 (corresponding to "primary shrinkage" of FIG. 8).

The drying device 62 illustrated in FIG. 10(b) includes a feed roller 42, a winder 44, and a dry heat plate 64. The dry heat plate 64 is arranged between the feed roller 42 and the winder 44 so that a dry heat surface 66 comes into contact with the modified fibroin multifilament 38 and extends along in the moving direction thereof. In the drying device 62, as described above, the length of the modified fibroin multifilament 38 cannot be changed by, for example, controlling a ratio of a feed speed of the feed roller 42 and a winding speed of the winder 44.

By using the producing apparatus having such a structure, the modified fibroin multifilament 38 is obtained by shrinking the multifilament 36 by the processing device 60, and then, the modified fibroin multifilament 38 can be dried by the drying device 62.

The feed roller 42 and the winder 44 may be omitted from the processing device 60 illustrated in FIG. 10(a), and the processing device may include only the water bath 46. In a case where the producing apparatus including such a processing device is used, for example, the modified fibroin multifilament is produced in a so-called batch system. In addition, the drying device 62 illustrated in FIG. 10(b) is optional.

[Shrinking Step by Heating and Relaxation]

Figure 12:
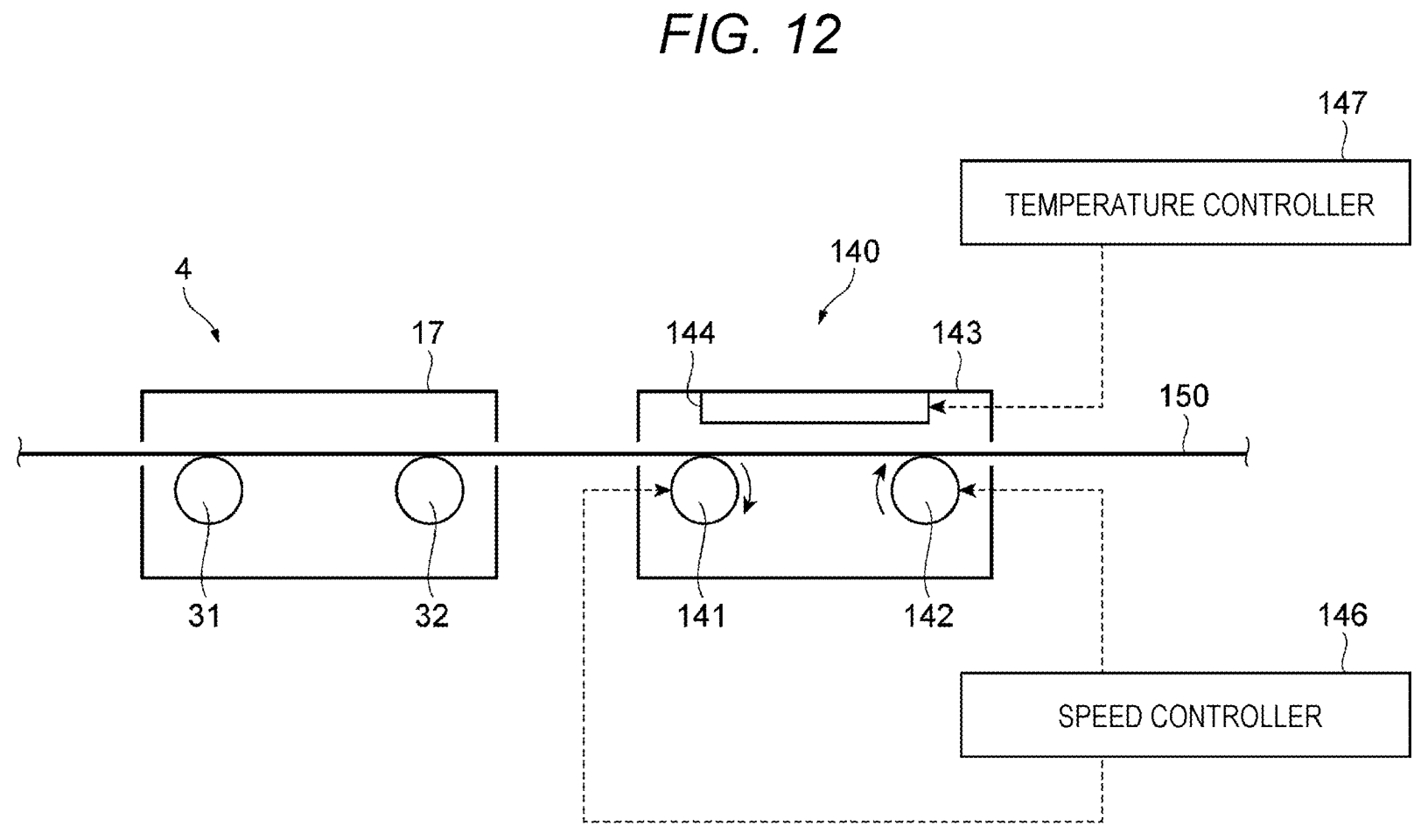

The shrinking step of irreversibly shrinking the multifilament may be performed by heating and relaxing the multifilament. The heating and relaxation of the multifilament can be performed by heating the multifilament and relaxing and shrinking the heated multifilament. Hereinafter, in the shrinkage performed by the heating and relaxation of the multifilament, the step of heating the multifilament is referred to as a "heating step", and the step of relaxing and shrinking the heated multifilament is referred to as a "relaxation and shrinking step". The heating step and the relaxation and shrinking step can be performed by, for example, a high temperature heating relaxation device 140 illustrated in FIG. 11 or 12.

(Heating Step)

In the heating step, the heating temperature of the multifilament 36 is preferably equal to or higher than a softening temperature of the modified fibroin used in the multifilament 36. In the specification, the softening temperature of the modified fibroin is a temperature at which shrinkage is initiated due to stress relaxation of the multifilament 36. In the heating and relaxation shrinking at the temperature equal to or higher than the softening temperature of the modified fibroin, the fiber is shrunk to the extent that it cannot be obtained simply by removing moisture in the fiber. As a result, a residual stress in the fiber generated by drawing in the spinning process can be removed.

An example of a temperature corresponding to the softening temperature includes 180° C. In a case where the heating and relaxation shrinking is performed in a high temperature range of 180° C. or higher, as a relaxation ratio becomes large or the temperature becomes high, the residual stress in the multifilament can be more efficiently removed. Accordingly, the heating temperature of the multifilament 36 is preferably 180° C. or higher, more preferably 180° C. to 280° C., still more preferably 200° C. to 240° C., and particularly preferably 220° C. to 240° C.

A heating time in the heating step, that is, a retention time in a high temperature heating furnace 143 is preferably 60 seconds or shorter, more preferably 30 seconds or shorter, and still more preferably 5 seconds or shorter, from the viewpoint that stretching of the fiber obtained after the heat treatment is not impaired. It is considered that the length of the heating time does not significantly affect the stress. When the heating time at the heating temperature of 200° C. is 5 seconds or shorter, a deterioration of stretching of the fiber obtained by the heat treatment can be prevented.

(Relaxation and Shrinking Step)

In the relaxation and shrinking step, the relaxation ratio preferably exceeds 1 time, more preferably 1.4 times or more, still more preferably 1.7 times or more, and particularly preferably 2 times or more. The relaxation ratio is a ratio of the feed speed to the winding speed of the multifilament 36, and more specifically, a ratio of a feed speed by a feed roller 141 to a winding speed by a winding roller 142.

In the heating and relaxation method performed using the high temperature heating relaxation device 140, the heating step and the relaxation and shrinking step may be separately performed as long as the multifilament 36 can be relaxed in a heated state. That is, the heating device may be a device separated from and independent of a relaxation device. In this case, the relaxation device is provided at a subsequence stage of the heating device (the downstream side in the moving direction of the multifilament 36) so that the relaxation and shrinking step is performed after the heating step.

The heating and relaxation step may be performed on the multifilament separately from the production process of the multifilament. That is, the same device as the high temperature heating relaxation device 140 may be provided as an independent device separated from a spinning apparatus 25. A method in which the multifilaments 36 separately produced are set to the feed roller and the multifilament is fed from the feed roller may be adopted. The heating and relaxation step may be performed on one multifilament or a plurality of bundled multifilaments.

[Crosslinking Step]

A crosslinking step of performing chemical crosslinking between polypeptide molecules in the fiber in the modified fibroin multifilament having a shrinkage history of being irreversibly shrunk, which is obtained as described above, or in the multifilament before being irreversibly shrunk may be further performed. Examples of functional groups that can be crosslinked include an amino group, a carboxyl group, a thiol groups, and a hydroxy group. For example, an amino group of a lysine side chain contained in the polypeptide can be crosslinked through an amide bond by dehydration condensation with a carboxyl group of a glutamic acid or aspartic acid side chain. The crosslinking may be performed by performing a dehydration condensation reaction under vacuum heating, or by a dehydration condensation agent such as carbodiimides.

The crosslinking between polypeptide molecules may be performed using a crosslinking agent such as carbodiimides or glutaraldehyde, or may be performed using an enzyme such as transglutaminase. Carbodiimides are compounds represented by the general formula $R_1N$=$C$=$NR_2$ (where $R_1$ and $R_2$ each independently represent an organic group containing an alkyl group having 1 to 6 carbon atoms or a cycloalkyl group). Specific examples of carbodiimides include 1-ethyl-3-(3-dimethylaminopropyl) carbodiimide hydrochloride (EDC), N,N'-dicyclohexylcarbodiimide (DCC), 1-cyclohexyl-3-(2-morpholinoethyl) carbodiimide, and diisopropyl carbodiimide (DIC). Among these, EDC and DIC are preferable because they have a high ability to form an amide bond between polypeptide molecules and easily perform a crosslinking reaction.

A crosslinking treatment is preferably performed by applying a crosslinking agent to the fiber and performing crosslinking by vacuum heating drying. As the crosslinking agent, a pure product may be applied to the fiber. Alternatively, the crosslinking agent may be applied to the fiber by diluting a pure product with a lower alcohol having 1 to 5 carbon atoms and a buffer or the like to a concentration of 0.005 to 10 mass %. The crosslinking treatment is preferably performed at a temperature of 20 to 45° C. for 3 to 42 hours. By the crosslinking treatment, a higher stress (strength) can be imparted to the fiber.

[Multifilament]

The multifilament according to the present embodiment contains a recombinant structural protein, the multifilament has 100 or more constituent single yarns, and a coefficient of variation in elongation is less than 33%. Here, a constituent single yarn means a single yarn constituting a multifilament (also referred to as a thread), and the number of constituent yarns means the number of single yarns constituting a multifilament. The multifilament according to the present embodiment contains, for example, modified fibroin, the number of constituent yarns of the multifilament is 100 or more, a coefficient of variation in elastic modulus may be 15% or less, a coefficient of variation in strength may be 15% or less, and a coefficient of variation in elongation is less than 33%.

A lower limit of the number of constituent yarns of the multifilament is 100 or more from the viewpoint of improving productivity. From the viewpoint of more preferably obtaining the effect, the lower limit of the number of constituent yarns of the multifilament is preferably 150 or more, and may be 200 or more, 250 or more, 300 or more, 350 or more, 400 or more, 450 or more, 500 or more, 550 or more, 600 or more, 650 or more, 700 or more, 750 or more, 800 or more, 850 or more, 900 or more, 950 or more, 1,000 or more, 1,100 or more, 1,200 or more, 1,300 or more, 1,400 or more, 1,500 or more, 1,600 or more, 1,700 or more, 1,800 or more, 1,900 or more, 2,000 or more, 2,100 or more, 2,200 or more, 2,300 or more, 2,400 or more, 2,500 or more, 2,600 or more, 2,700 or more, 2,800 or more, 2,900 or more, 3,000 or more, 3,100 or more, 3,200 or more, 3,300 or more, 3,400 or more, 3,500 or more, 3,600 or more, 3,700 or more, 3,800 or more, 3,900 or more, 4,000 or more, 4,100 or more, 4,200 or more, 4,300 or more, 4,400 or more, 4,500 or more, 4,600 or more, 4,700 or more, 4,800 or more, 4,900 or more, 5,000 or more, 5,100 or more, 5,200 or more, 5,300 or more, 5,400 or more, 5,500 or more, 5,600 or more, 5,700 or more, 5,800 or more, or 5,900 or more, and the lower limit of the number of constituent yarns of the multifilament is appropriately selected depending on the number of holes of the spinning nozzle to be used and/or the number of weights of the spinning nozzle.

From the viewpoint of sufficiently improving productivity, an upper limit of the number of constituent yarns of the multifilament is 900,000 or less, and may be 800,000 or less, 700,000 or less, 675,000 or less, 600,000 or less, 500,000 or less, 450,000 or less, 400,000 or less, 300,000 or less, 250,000 or less, 200,000 or less, 150,000 or less, 100,000 or less, 98,000 or less, 96,000 or less, 95,000 or less, 90,000 or less, 85,000 or less, 80,000 or less, 78,000 or less, 76,000 or less, 75,000 or less, 72,000 or less, 70,000 or less, 68,000 or less, 66,000 or less, 64,000 or less, 62,000 or less, 60,000 or less, 58,000 or less, 56,000 or less, 54,000 or less, 52,000 or less, 50,000 or less, 48,000 or less, 46,000 or less, 45,000 or less, 42,000 or less, 40,000 or less, 38,000 or less, 36,000 or less, 35,000 or less, 32,000 or less, 30,000 or less, 28,000 or less, 26,000 or less, 25,000 or less, 24,000 or less, 22,000 or less, 20,000 or less, 18,000 or less, 16,000 or less, 14,000 or less, 12,000 or less, 10,000 or less, 9,500 or less, 9,000 or less, 8,900 or less, 8,800 or less, 8,700 or less, 8600 or less, 8500 or less, 8400 or less, 8,300 or less, 8,200 or less, 8,100 or less, 8,000 or less, 7,900 or less, 7800 or less, 7,700 or less, 7,600 or less, 7500 or less, 7,400 or less, 7300 or less, 7,200 or less, 7,100 or less, 7,000 or less, 6,900 or less, 6,800 or less, 6,700 or less, 6,600 or less, 6,500 or less, 6,400 or less, 6,300 or less, 6,200 or less, 6,100 or less, or 6,000 or less.

From the viewpoint of sufficiently improving productivity, the number of constituent yarns of the multifilament is 100 to 900,000, and may be, for example, 100 to 800,000, 100 to 700,000, 100 to 600,000, 100 to 500,000, 100 to 400,000, 100 to 300,000, 100 to 200,000, 100 to 100,000, 1,000 to 90,000, 950 to 90,000, 900 to 90,000, 800 to 90,000, 700 to 90,000, 600 to 90,000, 550 to 90,000, 500 to 90,000, 450 to 90,000, 400 to 90,000, 350 to 90,000, 300 to 90,000, 250 to 90,000, 200 to 90,000, 150 to 90,000, 100 to 90,000, 1,000 to 60,000, 950 to 60,000, 900 to 60,000, 850 to 60,000, 800 to 60,000, 750 to 60,000, 700 to 60,000, 650 to 60,000, 600 to 60,000, 550 to 60,000, 500 to 60,000, 450 to 60,000, 400 to 60,000, 350 to 60,000, 300 to 60,000, 250 to 60,000, 200 to 60,000, 150 to 60,000, or 100 to 60,000, may be 1,000 to 48,000, 950 to 48,000, 900 to 48,000, 850 to 48,000, 800 to 48,000, 750 to 48,000, 700 to 48,000, 650 to 48,000, 600 to 48,000, 550 to 48,000, 500 to 48,000, 450 to 48,000, 400 to 48,000, 350 to 48,000, 300 to 48,000, 250 to 48,000, 200 to 48,000, 150 to 48,000, or 100 to 48,000, may be 1,000 to 39,000, 950 to 39,000, 900 to 39,000, 850 to 39,000, 800 to 39,000, 750 to 39,000, 700 to 39,000, 650 to 39,000, 600 to 39,000, 550 to 39,000, 500 to 39,000, 450 to 39,000, 400 to 39,000, 350 to 39,000, 300 to 39,000, 250 to 39,000, 200 to 39,000, 150 to 39,000, or 100 to 39,000, may be 1,000 to 30,000, 950 to 30,000, 900 to 30,000, 850 to 30,000, 800 to 30,000, 750 to 30,000, 700 to 30,000, 650 to 30,000, 600 to 30,000, 550 to 30,000, 500 to 30,000, 450 to 30,000, 400 to 30,000, 350 to 30,000, 300 to 30,000, 250 to 30,000, 200 to 30,000, 150 to 30,000, or 100 to 30,000, may be 1,000 to 24,000, 950 to 24,000, 900 to 24,000, 850 to 24,000, 800 to 24,000, 750 to 24,000, 700 to 24,000, 650 to 24,000, 600 to 24,000, 550 to 24,000, 500 to 24,000, 450 to 24,000, 400 to 24,000, 350 to 24,000, 300 to 24,000, 250 to 24,000, 200 to 24,000, 150 to 24,000, or 100 to 24,000, may be 1,000 to 18,000, 950 to 18,000, 900 to 18,000, 850 to 18,000, 800 to 18,000, 750 to 18,000, 700 to 18,000, 650 to 18,000, 600 to 18,000, 550 to 18,000, 500 to 18,000, 450 to 18,000, 400 to 18,000, 350 to 18,000, 300 to 18,000, 250 to 18,000, 200 to 18,000, 150 to 18,000, or 100 to 18,000, may be 1,000 to 12,000, 950 to 12,000, 900 to 12,000, 850 to 12,000, 800 to 12,000, 750 to 13,000, 700 to 12,000, 650 to 12,000, 600 to 12,000, 550 to 12,000, 500 to 12,000, 450 to 12,000, 400 to 12,000, 350 to 12,000, 300 to 12,000, 250 to 12,000, 200 to 12,000, 150 to 12,000, or 100 to 12,000, may be 1,000 to 100,000, 950 to 10,000, 900 to 10,000, 850 to 10,000, 800 to 10,000, 750 to 10,000, 700 to 10,000, 650 to 10,000, 600 to 10,000, 550 to 10,000, 500 to 10,000, 450 to 10,000, 400 to 10,000, 350 to 10,000, 300 to 10,000, 250 to 10,000, 200 to 10,000, 150 to 10,000, or 100 to 10,000, may be 1,000 to 9,000, 950 to 9,000, 900 to 9,000, 850 to 9,000, 800 to 9,000, 750 to 9,000, 700 to 9,000, 650 to 9,000, 600 to 9,000, 550 to 9,000, 500 to 4,000, 450 to 9,000, 400 to 9,000, 350 to 9,000, 300 to 9,000, 250 to 9,000, 200 to 9,000, 150 to 9,000, or 100 to 9,000, 1,000 to 6,000, 950 to 6,000, 900 to 6,000, 850 to 6,000, 800 to 6,000, 750 to 6,000, 700 to 6,000, 650 to 6,000, 600 to 6,000, 550 to 6,000, 500 to 6,000, 450 to 6,000, 400 to 6,000, 350 to 6,000, 300 to 6,000, 250 to 6,000, 200 to 6,000, 150 to 6,000, or 100 to 6,000.

Each of the coefficient of variation in elastic modulus, the coefficient of variation in strength, the coefficient of variation in elongation, and the coefficient of variation in fineness of the multifilament can be calculated by measuring an elastic modulus [gf/D] ([gf/den]), a strength [g/D] ([g/den]), an elongation at break [%], and a fineness [D] ([den]), and determining an average value and a standard deviation of each of the physical properties. The coefficients of variation are calculated using the following equations, respectively. The smaller the value of each coefficient of variation, the smaller the variation of each of the physical properties.

Coefficient of variation in elastic modulus (CV) [%]=standard deviation of elastic modulus/average value of elastic modulus×100

Coefficient of variation in strength (CV) [%]=standard deviation of strength/average value of strength×100

Coefficient of variation in elongation (CV) [%]=standard deviation of elongation/average value of elongation×100

Coefficient of variation in fineness (CV) [%]=standard deviation of fineness/average value of fineness×100

The measurement of the elastic modulus [gf/D], the strength [g/D], and the elongation at break [%] of the multifilament and the calculation of each standard deviation thereof can be performed using a 3345 series tensile tester manufactured by Instron corp. based on JIS L1013. The test may be performed under conditions of, for example, a test length of 300 mm and a test speed of 300 mm/min under an environment of a temperature of 20° C. and a relative humidity of 65%, and a load cell capacity may be appropriately selected depending on the fineness of the multifilament (fiber). The measured value may be calculated as, for example, an average value of the number of samples n=5.

An upper limit of the coefficient of variation in elongation of the multifilament is less than 33%. When the coefficient of variation in elongation is less than 33%, process passability in the subsequent processes such as twisting, spinning, weaving, knitting, and cutting can be further improved. In addition, a lower limit of the coefficient of variation in elongation of the multifilament may be 0.01% or more, 0.1% or more, 0.2% or more, 0.3% or more, 0.4% or more, 0.5% or more, 0.6% or more, 0.7% or more, 0.8% or more, 0.9% or more, 1% or more, 1.3% or more, 1.4% or more, 1.5% or more, 1.6% or more, 1.7% or more, 1.8% or more, 1.9% or more, 2% or more, 2.1% or more, 2.2% or more, 2.3% or more, 2.4% or more, or 2.5% or more, and may be appropriately selected in consideration of productivity. The coefficient of variation in elongation of the multifilament 32% or less, 31% or less, 30% or less, 29% or less, 28% or less, 27% or less, 26% or less, 25% or less, 24% or less, or 23% or less, more preferably 22% or less, 21% or less, 20% or less, 19% or less, 18% or less, 17% or less, 16% or less, 15% or less, 14% or less, 13% or less, 12% or less, or 11% or less, and still more preferably 10% or less, 9.5% or less, 9% or less, 8.5% or less, 8% or less, 7.5% or less, 7% or less, 6.5% or less, 6% or less, 5.5% or less, or 5% or less.

In addition, the coefficient of variation in elongation of the multifilament is preferably 0.01% to less than 0.1%, more than 0.1% to less than 1%, more than 1% to less than 5%, more than 5% to less than 10%, more than 10% to less than 15%, more than 15% to less than 20%, or more than 20% to less than 30%, more preferably 0.01% to less than 0.1%, more than 0.1% to less than 1%, more than 1% to less than 5%, more than 5% to less than 10%, more than 10% to less than 15%, more than 15% to less than 20%, or more than 20% to less than 25%, more preferably 0.01% to less than 0.1%, more than 0.1% to less than 1%, more than 1% to less than 5%, more than 5% to less than 10%, more than 10% to less than 15%, or more than 15% to less than 20%, more preferably 0.01% to less than 0.1%, more than 0.1% to less than 1%, more than 1% to less than 5%, more than 5% to less than 10%, or more than 10% to less than 15%, still more preferably 0.01% to less than 0.1%, more than 0.1% to less than 1%, more than 1% to less than 5%, or more than 5% to less than 10%, and particularly preferably 0.01% to less than 0.1%, more than 0.1% to less than 1%, or more than 1% to less than 5%.

In addition, the coefficient of variation in elongation of the multifilament is preferably 0.01% to less than 33%, 0.01% to 30%, 0.01% to 29%, 0.01% to 28%, 0.01% to 27%, 0.01% to 26%, 0.01% to 25%, 0.01% to 24%, 0.01% to 23%, 0.01% to 22%, 0.01% to 21%, 0.01% to 20%, 0.01% to 19%, 0.01% to 18%, 0.01% to 17%, 0.01% to 16%, 0.01% to 15%, 0.01% to 14%, 0.01% to 13%, 0.01% to 12%, 0.01% to 11%, 0.01% to 10%, 0.01% to 9.5%, 0.01% to 9%, 0.01% to 8.5%, 0.01% to 8%, 0.01% to 7.5%, 0.01% to 7%, 0.01% to 6.5%, 0.01% to 6%, 0.01% to 5.5%, 0.01% to 5%, 0.01% to 4.5%, 0.01% to 4%, 0.01% to 3.5%, 0.01% to 3%, or 0.01% to 2.5%.

In addition, the coefficient of variation in elongation of the multifilament may be 0.1% to 32%, 0.1% to 31%, 0.1% to 30%, 0.1% to 29%, 0.1% to 28%, 0.1% to 27%, 0.1% to 26%, 0.1% to 25%, 0.1% to 24%, 0.1% to 23%, 0.1% to 22%, 0.1% to 21%, 0.1% to 20%, 0.1% to 19%, 0.1% to 18%, 0.1% to 17%, 0.1% to 16%, 0.1% to 15%, 0.1% to 14.5%, 0.1% to 14%, 0.1% to 13.5%, 0.1% to 13%, 0.1% to 12.5%, 0.1% to 12%, 0.1% to 11.5%, 0.1% to 11%, 0.1% to 10.5%, 0.1% to 10%, 0.1% to 9.5%, 0.1% to 9%, 0.1% to 8.5%, 0.1% to 8%, 0.1% to 7.5%, 0.1% to 7%, 0.1% to 6.5%, 0.1% to 6%, 0.1% to 5.5%, 0.1% to 5%, 0.1% to 4.5%, 0.1% to 4%, 0.1% to 3.5%, 0.1% to 3%, 0.1% to 2.5%, 0.5% to less than 33%, 0.5% to 32%, 0.5% to 31%, 0.5% to 30%, 0.5% to 29%, 0.5% to 28%, 0.5% to 27%, 0.5% to 26%, 0.5% to 25%, 0.5% to 24%, 0.5% to 23%, 0.5% to 22%, 0.5% to 21%, 0.5% to 20%, 0.5% to 19%, 0.5% to 18%, 0.5% to 17%, 0.5% to 16%, 0.5% to 15%, 0.5% to 14.5%, 0.5% to 14%, 0.5% to 13.5%, 0.5% to 13%, 0.5% to 12.5%, 0.5% to 12%, 0.5% to 11.5%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 0.5% to 3.5%, 0.5% to 3%, 0.5% to 2.5%, 0.8% to less than 33%, 0.8% to 32%, 0.8% to 31%, 0.8% to 30%, 0.8% to 29%, 0.8% to 28%, 0.8% to 27%, 0.8% to 26%, 0.8% to 25%, 0.8% to 24%, 0.8% to 23%, 0.8% to 22%, 0.8% to 21%, 0.8% to 20%, 0.8% to 19%, 0.8% to 18%, 0.8% to 17%, 0.8% to 16%, 0.8% to 15%, 0.8% to 14.5%, 0.8% to 14%, 0.8% to 13.5%, 0.8% to 13%, 0.8% to 12.5%, 0.8% to 12%, 0.8% to 11.5%, 0.8% to 10%, 0.8% to 9.5%, 0.8% to 9%, 0.8% to 8.5%, 0.8% to 8%, 0.8% to 7.5%, 0.8% to 7%, 0.8% to 6.5%, 0.8% to 6%, 0.8% to 5.5%, 1% to less than 33%, 1% to 32%, 1% to 31%, 1% to 30%, 1% to 29%, 1% to 28%, 1% to 27%, 1% to 26%1% to 25%, 1% to 24%, 1% to 23%, 1% to 22%, 1% to 21%, 1% to 20%, 1% to 19%, 1% to 18%, 1% to 17%, 1% to 16%, 1% to 15%, 1% to 14.5%, 1% to 14%, 1% to 13.5%, 1% to 13%, 1% to 12%, 1% to 12%, 1% to 11.5%, 1% to 10%, 1% to 9%, 1% to 8%, 1% to 7%, 1% to 6.5%, 1% to 6%, 1% to 5.5%, 1% to 5%, 1% to 4%, 1.5% to less than 33%, 1.5% to 32%, 1.5% to 31%, 1.5% to 30%, 1.5% to 29%, 1.5% to 28%, 1.5% to 27%, 1.5% to 26%, 1.5% to 25%, 1.5% to 24%, 1.5% to 23%, 1.5% to 22%, 1.5% to 21%, 1.5% to 20%, 1.5% to 19%, 1.5% to 18%, 1.5% to 17%, 1.5% to 16%, 1.5% to 15%, 1.5% to 14.5%, 1.5% to 14%, 1.5% to 13.5%, 1.5% to 13%, 1.5% to 12%, 1.5% to 12%, 1.5% to 11.5%, 1.5% to 10%, 1.5% to 9%, 1.5% to 8%, 1.5% to 7%, 1.5% to 6.5%, 1.5% to 6%, 1.5% to 5.5%, 1.5% to 5%, 2% to less than 33%, 2% to 32%, 2% to 31%, 2% to 30%, 2% to 29%, 2% to 28%, 2% to 27%, 2% to 26%, 2% to 25%, 2% to 24%, 2% to 23%, 2% to 22%, 2% to 21%, 2% to 20%, 2% to 19%, 2% to 18%, 2% to 17%, 2% to 16%, 2% to 15%, 2% to 14.5%, 2% to 14%, 2% to 13.5%, 2% to 13%, 2% to 12%, 2% to 12%, 2% to 11.5%, 2% to 10%, 2% to 9%, 2% to 8%, 2% to 7%, 2% to 6.5%, 2% to 6%, 2% to 5.5%, 2% to 5%, 2% to 4%, 2.5% to 10%, 2.5% to 9%, 2.5% to 8%, 2.5% to 7%, 2.5% to 6%, 2.5% to 5.5%, 2.5% to 5%, 2.5% to 4.5%, or 2.5% to 4%.

The value of the elongation of the multifilament may be appropriately selected depending on use, and may be, for example, 1% to 100%, 3% to 100%, 5% to 100%, 5% to 95%, 5% to 90%, 5% to 85%, 5% to 80%, 5% to 70%, 5% to 65%, 5% to 60%, 5% to 55%, 5% to 50%, 8% to 100%, 8% to 95%, 8% to 90%, 8% to 85%, 8% to 80%, 8% to 75%, 8% to 70%, 8% to 65%, 8% to 60%, 8% to 55%, 8% to 50%, 10% to 100%, 10% to 95%, 10% to 90%, 10% to 85%, 10% to 80%, 10% to 75%, 10% to 70%, 10% to 65%, 10% to 60%, 10% to 55%, or 10% to 50%.

An upper limit of the coefficient of variation in strength of the multifilament is more preferably 20% or less. When the coefficient of variation in strength of the multifilament is 20% or less, process passability in the subsequent processes such as twisting, spinning, weaving, knitting, and cutting can be further improved. In addition, a lower limit of the coefficient of variation in strength may be 0.01% or more, 0.1% or more, 0.2% or more, 0.3% or more, 0.4% or more, 0.5% or more, or 0.6% or more, and may be appropriately selected in consideration of productivity. The coefficient of variation in strength of the multifilament is preferably 19% or less, 18% or less, 17% or less, 16% or less, 15% or less, 14.5% or less, 14% or less, 13.5% or less, 13% or less, 12.5% or less, 12% or less, 11.5% or less, or 11% or less, and more preferably 10.5% or less, 10% or less, 9.5% or less, 9% or less, 8.5% or less, 8% or less, 7.5% or less, 7% or less, 6.5% or less, 6% or less, 5.5% or less, 5% or less, 4.5% or less, 4% or less, 3.5% or less, 3% or less, or 2.5% or less.

In addition, the coefficient of variation in strength of the multifilament is preferably 0.01% to less than 0.1%, more than 0.1% to less than 1%, more than 1% to less than 5%, more than 5% to less than 10%, or more than 10% to less than 15%, more preferably 0.01% to less than 0.1%, more than 0.1% to less than 1%, more than 1% to less than 5%, or more than 5% to less than 10%, more preferably 0.01% to less than 0.1%, more than 0.1% to less than 1%, or more than 1% to less than 5%, still more preferably 0.01% to less than 0.1%, more than 0.1% to less than 1%, or more than 1% to 3.8%, and particularly preferably 0.01% to less than 0.1%, more than 0.1% to less than 1%, or more than 1% to less than 3.5%. In addition, the coefficient of variation in strength of the multifilament is preferably 0.01% to 20%, 0.01% to 19%, 0.01% to 18%, 0.01% to 17%, 0.01% to 16%, 0.01% to 15%, 0.01% to 14.5%, 0.01% to 14%, 0.01% to 13.5%, 0.01% to 13%, 0.01% to 12.5%, 0.01% to 12%, 0.01% to 11.5%, 0.01% to 11%, 0.01% to 10.5%, 0.01% to 10%, 0.01% to 9.5%, 0.01% to 9%, 0.01% to 8.5%, 0.01% to 8%, 0.01% to 7.5%, 0.01% to 7%, 0.01% to 6.5%, 0.01% to 6%, 0.01% to 5.5%, 0.01% to 5%, 0.01% to 4.5%, 0.01% to 4%, 0.01% to 3.8%, 0.01% to 3.5%, 0.01% to 3%, 0.01% to 2.5%, 0.01% to 2%, 0.01% to 1.5%, or 0.01% to 1%, and may be 0.1% to 20%, 0.1% to 19%, 0.1% to 18%, 0.1% to 17%, 0.0.1% to 16%, 0.1% to 15%, 0.1% to 14.5%, 0.1% to 14%, 0.1% to 13.5%, 0.1% to 13%, 0.1% to 12.5%, 0.1% to 12%, 0.1% to 11.5%, 0.1% to 11%, 0.1% to 10.5%, 0.1% to 10%, 0.1% to 9.5%, 0.1% to 9%, 0.1% to 8.5%, 0.1% to 8%, 0.1% to 7.5%, 0.1% to 7%, 0.1% to 6.5%, 0.1% to 6%, 0.1% to 5.5%, 0.1% to 5%, 0.1% to 4.5%, 0.1% to 4%, 0.1% to 3.5%, 0.1% to 3%, 0.1% to 2.5%, 0.1% to 2%, 0.1% to 1.5%, or 0.1% to 1%, or, 0.2% to 20%, 0.2% to 19%, 0.2% to 18%, 0.2% to 17%, 0.0.2% to 16%, 0.2% to 15%, 0.2% to 14.5%, 0.2% to 14%, 0.2% to 13.5%, 0.2% to 13%, 0.2% to 12.5%, 0.2% to 12%, 0.2% to 11.5%, 0.2% to 11%, 0.2% to 10.5%, 0.2% to 10%, 0.2% to 9.5%, 0.2% to 9%, 0.2% to 8.5%, 0.2% to 8%, 0.2% to 7.5%, 0.2% to 7%, 0.2% to 6.5%, 0.2% to 6%, 0.2% to 5.5%, 0.2% to 5%, 0.2% to 4.5%, 0.2% to 4%, 0.2% to 3.5%, 0.2% to 3%, or 0.2% to 2.5%, or, 0.3% to 20%, 0.3% to 19%, 0.3% to 18%, 0.3% to 17%, 0.0.3% to 16%, 0.3% to 15%, 0.3% to 14.5%, 0.3% to 14%, 0.3% to 13.5%, 0.3% to 13%, 0.3% to 12.5%, 0.3% to 12%, 0.3% to 11.5%, 0.3% to 11%, 0.3% to 10.5%, 0.3% to 10%, 0.3% to 9.5%, 0.3% to 9%, 0.3% to 8.5%, 0.3% to 8%, 0.3% to 7.5%, 0.3% to 7%, 0.3% to 6.5%, 0.3% to 6%, 0.3% to 5.5%, 0.3% to 5%, 0.3% to 4.5%, 0.3% to 4%, 0.3% to 3.5%, 0.3% to 3%, or 0.3% to 2.5%, or, 0.4% to 20%, 0.4% to 19%, 0.4% to 18%, 0.4% to 17%, 0.0.4% to 16%, 0.4% to 15%, 0.4% to 14.5%, 0.4% to 14%, 0.4% to 13.5%, 0.4% to 13%, 0.4% to 12.5%, 0.4% to 12%, 0.4% to 11.5%, 0.4% to 11%, 0.4% to 10.5%, 0.4% to 10%, 0.4% to 9.5%, 0.4% to 9%, 0.4% to 8.5%, 0.4% to 8%, 0.4% to 7.5%, 0.4% to 7%, 0.4% to 6.5%, 0.4% to 6%, 0.4% to 5.5%, 0.4% to 5%, 0.4% to 4.5%, 0.4% to 4%, 0.4% to 3.5%, 0.4% to 3%, or 0.4% to 2.5%, or, 0.5% to 20%, 0.5% to 19%, 0.5% to 18%, 0.5% to 17%, 0.0.5% to 16%, 0.5% to 15%, 0.5% to 14.5%, 0.5% to 14%, 0.5% to 13.5%, 0.5% to 13%, 0.5% to 12.5%, 0.5% to 12%, 0.5% to 11.5%, 0.5% to 11%, 0.5% to 10.5%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 0.5% to 3.5%, 0.5% to 3%, or 0.5% to 2.5%.

An upper limit of the coefficient of variation in elastic modulus of the modified fibroin multifilament is more preferably 20% or less. When the coefficient of variation in elastic modulus is 20% or less, process passability in the subsequent processes such as twisting, spinning, weaving, knitting, and cutting can be further improved. In addition, a lower limit of the coefficient of variation in elastic modulus of the multifilament may be 0.01% or more, 0.1% or more, 0.2% or more, 0.3% or more, 0.4% or more, 0.5% or more, 0.6% or more, 0.7% or more, 0.8% or more, 0.9% or more, or 1% or more, and may be appropriately selected in consideration of productivity. The coefficient of variation in elastic modulus of the multifilament is more preferably 19% or less, 18% or less, 17% or less, 16% or less, 15% or less, 14.5% or less, 14% or less, 13.5% or less, 13% or less, 12.5% or less, 12% or less, 11.5% or less, or 11% or less, and still more preferably 10.5% or less, 10% or less, less than 10%, 9.5% or less, 9% or less, 8.5% or less, 8% or less, 7.5% or less, 7% or less, 6.5% or less, 6% or less, 5.5% or less, or 5% or less.

In addition, the coefficient of variation in elastic modulus of the multifilament is preferably 0.01% to less than 0.1%, more than 0.1% to less than 1%, more than 1% to less than 5%, more than 5% to less than 10%, or more than 10% to less than 15%, more preferably 0.01% to less than 0.1%, more than 0.1% to less than 1%, more than 1% to less than 5%, or more than 5% to less than 10%, and still more preferably 0.01% to less than 0.1%, more than 0.1% to less than 1%, or more than 1% to less than 5%. In addition, the coefficient of variation in elastic modulus of the multifilament is preferably 0.01% to 20%, 0.01% to 19%, 0.01% to 18%, 0.01% to 17%, 0.01% to 16%, 0.01% to 15%, 0.01% to 14.5%, 0.01% to 14%, 0.01% to 13.5%, 0.01% to 13%, 0.01% to 12.5%, 0.01% to 12%, 0.01% to 11.5%, 0.01% to 11%, 0.01% to 10.5%, 0.01% to 10%, 0.01% to 9.5%, 0.01% to 9%, 0.01% to 8.5%, 0.01% to 8%, 0.01% to 7.5%, 0.01% to 7%, 0.01% to 6.5%, 0.01% to 6%, 0.01% to 5.5%, 0.01% to 5%, 0.01% to 4.5%, 0.01% to 4%, 0.01% to 3.5%, 0.01% to 3%, 0.01% to 2.5%, 0.01% to 2%, 0.1% to 20%, 0.1% to 19%, 0.1% to 18%, 0.1% to 17%, 0.01% to 16%, 0.1% to 15%, 0.1% to 14.5%, 0.1% to 14%, 0.1% to 13.5%, 0.1% to 13%, 0.1% to 12.5%, 0.1% to 12%, 0.1% to 11.5%, 0.1% to 11%, 0.1% to 10.5%, 0.1% to 10%, 0.1% to 9.5%, 0.1% to 9%, 0.1% to 8.5%, 0.1% to 8%, 0.1% to 7.5%, 0.1% to 7%, 0.1% to 6.5%, 0.1% to 6%, 0.1% to 5.5%, 0.1% to 5%, 0.1% to 4.5%, 0.1% to 4%, 0.1% to 3.5%, 0.1% to 3%, 0.1% to 2.5%, 0.1% to 2%, 0.2% to 20%, 0.2% to 19%, 0.2% to 18%, 0.2% to 17%, 0.2% to 16%, 0.2% to 15%, 0.2% to 14.5%, 0.2% to 14%, 0.2% to 13.5%, 0.2% to 13%, 0.2% to 12.5%, 0.2% to 12%, 0.2% to 11.5%, 0.2% to 11%, 0.2% to 10.5, 0.2% to 10%, 0.2% to 9.5%, 0.2% to 9%, 0.2% to 8.5%, 0.2% to 8%, 0.2% to 7.5%, 0.2% to 7%, 0.2% to 6.5%, 0.2% to 6%, 0.2% to 5.5%, 0.2% to 5%, 0.2% to 4.5%, 0.2% to 4%, 0.2% to 3.5%, 0.2% to 3%, 0.2% to 2.5%, 0.3% to 20%, 0.3% to 19%, 0.3% to 18%, 0.3% to 17%, 0.3% to 16%, 0.3% to 15%, 0.3% to 14.5%, 0.3% to 14%, 0.3% to 13.5%, 0.3% to 13%, 0.3% to 12.5%, 0.3% to 12%, 0.3% to 11.5%, 0.3% to 11%, 0.3% to 10.5%, 0.3% to 10%, 0.3% to 9.5%, 0.3% to 9%, 0.3% to 8.5%, 0.3% to 8%, 0.3% to 7.5%, 0.3% to 7%, 0.3% to 6.5%, 0.3% to 6%, 0.3% to 5.5%, 0.3% to 5%, 0.3% to 4.5%, 0.3% to 4%, 0.3% to 3.5%, 0.3% to 3%, 0.3% to 2.5%, 0.4% to 20%, 0.4% to 19%, 0.4% to 18%, 0.4% to 17%, 0.4% to 16%, 0.4% to 15%, 0.4% to 14.5%, 0.4% to 14%, 0.4% to 13.5%, 0.4% to 13%, 0.4% to 12.5%, 0.4% to 12%, 0.4% to 11.5%, 0.4% to 11%, 0.4% to 10.5%, 0.4% to 10%, 0.4% to 9.5%, 0.4% to 9%, 0.4% to 8.5%, 0.4% to 8%, 0.4% to 7.5%, 0.4% to 7%, 0.4% to 6.5%, 0.4% to 6%, 0.4% to 5.5%, 0.4% to 5%, 0.4% to 4.5%, 0.4% to 4%, 0.4% to 3.5%, 0.4% to 3%, 0.4% to 2.5%, 0.5% to 20%, 0.5% to 19%, 0.5% to 18%, 0.5% to 17%, 0.05% to 16%, 0.5% to 15%, 0.5% to 14.5%, 0.5% to 14%, 0.5% to 13.5%, 0.5% to 13%, 0.5% to 12.5%, 0.5% to 12%, 0.5% to 11.5%, 0.5% to 11%, 0.5% to 10.5%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 1% to 10%, 1% to 9%, 1% to 8%, 1% to 7%, 1% to 6%, 1% to 5%, or 1% to 4%.

An upper limit of the coefficient of variation in fineness of the multifilament is preferably 20% or less. When the coefficient of variation in fineness is 20% or less, process passability in the subsequent processes such as twisting, spinning, weaving, knitting, and cutting can be further improved. In addition, a lower limit of the coefficient of variation in fineness of the multifilament may be 0.01% or more, 0.1% or more, 0.2% or more, 0.3% or more, or 0.4% or more, and may be appropriately selected in consideration of productivity. The coefficient of variation in fineness of the multifilament is preferably 19% or less, 18% or less, 17% or less, 16% or less, 15% or less, 14% or less, 13% or less, 12% or less, or 11% or less, and more preferably 10% or less, 9% or less, 8% or less, 7% or less, 6% or less, or 5% or less. In addition, the coefficient of variation in fineness of the multifilament is preferably 0.01% to less than 0.1%, more than 0.1% to less than 1%, more than 1% to less than 5%, more than 5% to less than 10%, more than 10% to less than 15%, or more than 15% to less than 20%, more preferably 0.01% to less than 0.1%, more than 0.1% to less than 1%, more than 1% to less than 5%, more than 5% to less than 10%, or more than 10% to less than 15%, more preferably 0.01% to less than 0.1%, more than 0.1% to less than 1%, more than 1% to less than 5%, or more than 5% to less than 10%, more preferably 0.01% to less than 0.1%, more than 0.1% to less than 1%, more than 1% to less than 5%, or more than 5% to 6.7%, still more preferably 0.01% to less than 0.1%, more than 0.1% to less than 1%, or more than 1% to less than 5%, and particularly preferably 0.01% to less than 0.1%, more than 0.1% to less than 1%, or more than 1% to less than 3.5%.

In addition, the coefficient of variation in fineness of the multifilament is preferably 0.01% to 15%, 0.01% to 14%, 0.01% to 13%, 0.01% to 12%, 0.01% to 11%, 0.01% to 10%, 0.01% to 9.5%, 0.01% to 9%, 0.01% to 8.5%, 0.01% to 8%, 0.01% to 7.5%, 0.01% to 7%, 0.01% to 6.7%, 0.01% to 6.5%, 0.01% to 6%, 0.01% to 5.5%, 0.01% to 5%, 0.01% to 4.5%, 0.01% to 4%, 0.01% to 3.5%, 0.01% to 3%, 0.01% to 2.5%, 0.01% to 2%, 0.01% to 1.5%, or 0.01% to 1%. In addition, the coefficient of variation in fineness of the multifilament may be 0.1% to 20%, 0.1% to 19%, 0.1% to 18%, 0.1% to 17%, 0.1% to 16%, 0.1% to 15%, 0.1% to 14%, 0.1% to 13%, 0.1% to 12%, 0.1% to 11%, 0.1% to 10%, 0.1% to 9.5%, 0.1% to 9%, 0.1% to 8.5%, 0.1% to 8%, 0.1% to 7.5%, 0.1% to 7%, 0.1% to 6.5%, 0.1% to 6%, 0.1% to 5.5%, 0.1% to 5%, 0.1% to 4.5%, 0.1% to 4%, 0.1% to 3.5%, 0.1% to 3%, 0.1% to 2.5%, 0.1% to 2%, 0.1% to 1.5%, or 0.1% to 1%, 0.2% to 20%, 0.2% to 19%, 0.2% to 18%, 0.2% to 17%, 0.2% to 16%, 0.2% to 15%, 0.2% to 14%, 0.2% to 13%, 0.2% to 12%, 0.2% to 11%, 0.2% to 10%, 0.2% to 9.5%, 0.2% to 9%, 0.2% to 8.5%, 0.2% to 8%, 0.2% to 7.5%, 0.2% to 7%, 0.2% to 6.5%, 0.2% to 6%, 0.2% to 5.5%, 0.2% to 5%, 0.2% to 4.5%, 0.2% to 4%, 0.2% to 3.5%, 0.2% to 3%, or 0.2% to 2.5%, 0.3% to 20%, 0.3% to 19%, 0.3% to 18%, 0.3% to 17%, 0.3% to 16%, 0.3% to 15%, 0.3% to 14%, 0.3% to 13%, 0.3% to 12%, 0.3% to 11%, 0.3% to 10%, 0.3% to 9.5%, 0.3% to 9%, 0.3% to 8.5%, 0.3% to 8%, 0.3% to 7.5%, 0.3% to 7%, 0.3% to 6.5%, 0.3% to 6%, 0.3% to 5.5%, 0.3% to 5%, 0.3% to 4.5%, 0.3% to 4%, 0.3% to 3.5%, 0.3% to 3%, or 0.3% to 2.5%, 0.4% to 20%, 0.4% to 19%, 0.4% to 18%, 0.4% to 17%, 0.4% to 16%, 0.4% to 15%, 0.5% to 14%, 0.4% to 13%, 0.4% to 12%, 0.4% to 11%, 0.4% to 10%, 0.4% to 9.5%, 0.4% to 9%, 0.4% to 8.5%, 0.4% to 8%, 0.4% to 7.5%, 0.4% to 7%, 0.4% to 6.5%, 0.4% to 6%, 0.4% to 5.5%, 0.4% to 5%, 0.4% to 4.5%, 0.4% to 4%, 0.4% to 3.5%, 0.4% to 3%, or 0.4% to 2.5%, 0.5% to 20%, 0.5% to 19%, 0.5% to 18%, 0.5% to 17%, 0.5% to 16%, 0.5% to 15%, 0.5% to 14%, 0.5% to 13%, 0.5% to 12%, 0.5% to 11%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 0.5% to 3.5%, 0.5% to 3%, 0.5% to 2.5%, 0.3% to 3%, or 0.3% to 2.8%.

The value of the fineness [D] ([den]) of the multifilament may be appropriately selected depending on use, and the fineness [D] per single yarn ([D/filament]) may be, for example, 0.7 to 150 D, 0.7 to 140, 0.7 to 130 D, 0.7 to 120

D, 0.7 to 110 D, 0.8 to 100 D, 0.7 to 100 D, 0.7 to 90 D, 0.7 to 80 D, 0.7 to 70 D, 0.7 to 60 D, 0.7 to 50 D, 0.7 to 40 D, 0.7 to 30 D, 0.7 to 20 D, 0.7 to 15 D, 0.7 to 10 D, 0.7 to 9 D, 0.7 to 8 D, 0.7 to 7 D, 0.7 to 6 D, 0.7 to 5 D, 0.7 to 4 D, 0.7 to 3 D, 0.7 to 2.5 D, 0.7 to 2.2 D, 0.7 to 2 D, 0.7 to 1.8 D, 0.7 to 1.6 D, 0.7 to 1.5 D, 0.7 to 1.4 D, 0.7 to 1.3 D, 0.7 to 1.2 D, 0.7 to 1.1 D, 0.7 to 1 D, 0.8 to 3 D, 0.8 to 2.5 D, 0.8 to 2.2 D, 0.8 to 2 D, 0.8 to 1.8 D, 0.8 to 1.6 D, 0.8 to 1.5 D, 0.8 to 1.4 D, 0.8 to 1.3 D, 0.8 to 1.2 D, 0.8 to 1.1 D, 0.8 to 1 D, 1 to 3 D, 1 to 2.5 D, 1 to 2.2 D, 1 to 2 D, 1 to 1.9 D, 1 to 1.8 D, 1 to 1.7 D, or 1 to 1.6 D. A density of the recombinant structural protein may be, for example, 1.3 to 1.4 [g/cm$^3$], 1.35 [g/cm$^3$], or 1.34 [g/cm$^3$].

The multifilament according to the present embodiment may have a shrinkage history of being irreversibly shrunk after spinning. The shrinkage history is a shrinkage history of being irreversibly shrunk by bringing the multifilament into contact with water or a shrinkage history of being irreversibly shrunk by heating and relaxing the multifilament. Since the multifilament according to the present embodiment is obtained by, for example, the production method described above, there is substantially no residual stress generated by drawing during a spinning process.

<Shrinkage Rate>

In the multifilament having a shrinkage history of being irreversibly shrunk after spinning according to the present embodiment, a shrinkage rate defined by the following equation is preferably 5% or less. The multifilament in the following equation is a multifilament having a shrinkage history of being irreversibly shrunk after spinning.

$$\text{Shrinkage rate [\%]}=(1-(\text{length of multifilament when dried from wet state/length of multifilament when in wet state}))\times100$$

Shrinkability by contact of the fiber with water can be evaluated using, for example, the shrinkage rate determined by the above equation as an index. "Length of multifilament when in wet state" and "length of multifilament when dried from wet state" can be measured by, for example, the following method.

The multifilament is cut out to obtain a fiber bundle having a length of about 30 cm. The fiber bundle is immersed (wetted) in water at 40° C. for 15 minutes, and the immersed fiber bundle is dried at room temperature for 2 hours. After drying, a length of the fiber bundle is measured. Wetting and drying are performed again at least 3 times, an average length during wetting can be used as "length of multifilament when in wet state", and an average length during drying can be used as "length of multifilament when dried from wet state".

In the multifilament, it is preferable that such shrinkage is small, and it is particularly preferable that shrinkage of a product such as a fabric formed of a multifilament is small.

The shrinkage rate defined by the above equation is preferably 5.0% or less, and may be 4.5% or less, 4% or less, 3.5% or less, 3.2% or less, 3.1% or less, 3.0% or less, 2.9% or less, 2.8% or less, 2.7% or less, 2.6% or less, 2.5% or less, 2.4% or less, 2.3% or less, 2.2% or less, 2.1% or less, 2.0% or less, 1.9% or less, 1.8% or less, 1.7% or less, 1.6% or less, 1.5% or less, 1.4% or less, 1.3% or less, 1.2% or less, 1.1% or less, 1.0% or less, 0.9% or less, 0.8% or less, 0.7% or less, 0.6% or less, 0.5% or less, 0.4% or less, or 0.3% or less.

[Product]

The modified fibroin fiber multifilament according to the present embodiment can be applied to a fabric, a knitted fabric, a braided fabric, or a non-woven fabric, and a paper or cotton, as a fiber or a yarn (a spun yarn, a twisted yarn, a false twisted yarn, a processed yarn, a blended yarn, a blended spun yarn, or the like). In addition, this protein fiber can also be applied to high strength applications such as a rope, a surgical suture, a flexible stop for electrical components, and a physiologically active material for implantation (for example, artificial ligament and aortic band). These fibers can be produced based on a known method.

A limited oxygen index (LOI) value of the modified fibroin fiber may be 18 or more, 20 or more, 22 or more, 24 or more, 26 or more, 28 or more, 29 or more, or 30 or more. The LOI value is a value measured in accordance with the test method of a particulate or low-melting point synthetic resin specified in Notice No. 50 of the Office of Hazardous Materials Regulation (May 31, 1995).

A maximum hygroscopic and exothermic degree of the modified fibroin fiber may be more than 0.025° C./g, 0.026° C./g or more, 0.027° C./g or more, 0.028° C./g or more, 0.029° C./g or more, 0.030° C./g or more, 0.035° C./g or more, or 0.040° C./g or more, when determined according to the following Equation A. An upper limit of the maximum hygroscopic and exothermic degree is not particularly limited, but is usually 0.060° C./g or less.

$$\begin{aligned}\text{maximum hygroscopic and exothermic degree}=\{&\\ (\text{maximum value of sample temperature when}&\\ \text{sample is placed under low humidity environ-}&\\ \text{ment until sample temperature reaches equilib-}&\\ \text{rium and then transferred to high humidity}&\\ \text{environment})-(\text{sample temperature when}&\\ \text{sample is placed under low humidity environ-}&\\ \text{ment until sample temperature reaches equilib-}&\\ \text{rium and then transferred to high humidity}&\\ \text{environment})\}(° \text{ C.})/\text{sample weight (g)}&\end{aligned}$$
Equation A:

The modified fibroin fiber preferably has excellent heat retaining properties, and the heat retention index determined according to the following Equation C may be 0.20 or more.

$$\text{heat retention index}=\text{heat retention rate (\%)/basis weight (g/m}^2)\text{ of sample}$$
Equation C:

The heat retention index of the modified fibroin fiber may be 0.22 or more, 0.24 or more, 0.26 or more, 0.28 or more, 0.30 or more, or 0.32 or more. An upper limit of the heat retention index is not particularly limited, but may be, for example, 0.60 or less or 0.40 or less.

EXAMPLES

[Production of Modified Fibroin]
(1) Production of Expression Vector

Modified spider silk fibroin having SEQ ID NO: 40 (hereinafter, referred to as "PRT966") and modified spider silk fibroin having SEQ ID NO: 15 (hereinafter, referred to as "PRT799") were designed based on a base sequence and an amino acid sequence of fibroin derived from *Nephila clavipes* (GenBank Accession No.: P46804.1, GI: 1174415). The amino acid sequence set forth in SEQ ID NO: 40 has a sequence obtained by substituting, with VF, all QQs in a sequence obtained by repeating a region of 20 domain sequences present in an amino acid sequence set forth in SEQ ID NO: 7 two times and substituting the remaining Q with I, for the purpose of improving hydrophobicity, and is obtained by adding an amino acid sequence (tag sequence and hinge sequence) set forth in SEQ ID NO: 11 to the N-terminus. In addition, the amino acid sequence set forth in SEQ ID NO: 15 has an amino acid sequence in which substitution, insertion, and deletion of an amino acid residue for the purpose of improving productivity are performed on the amino acid sequence of the fibroin derived from *Nephila*

61

*clavipes*, and is obtained by adding an amino acid sequence (a tag sequence and a hinge sequence) set forth in SEQ ID NO: 11 to the N-terminus.

Subsequently, a nucleic acid encoding the designed artificial structural proteins (modified fibroins) PRT966 and PRT799 having amino acid sequences set forth in SEQ ID NO: 40 and SEQ ID NO: 15, respectively, was synthesized. In the nucleic acids, an NdeI site was added to the 5'-terminus and an EcoRI site was added to a termination codon downstream. The nucleic acid was each cloned into a cloning vector (pUC118). Then, the nucleic acid was excised by restriction enzyme treatment with NdeI and EcoRI, and then recombined into a protein expression vector pET-22b (+), thus obtaining an expression vector.

(2) Expression of Modified Fibroin

*E. coli* BLR (DE3) was transformed with the expression vector obtained in (1). The transformed *E. coli* was cultured in a 2 mL LB medium containing ampicillin for 15 hours. The culture solution was added to a 100 mL seed culture medium containing ampicillin (Table 4) so that $OD_{600}$ was 0.005. While maintaining the temperature of the culture solution at 30° C., flask culture was carried out (for about 15 hours) until the $OD_{600}$ reached 5, thereby obtaining a seed culture solution.

TABLE 4

| Reagent | Concentration (g/L) |
|---|---|
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which a 500 mL production medium (Table 5) was added so that $OD_{600}$ was 0.05. The culture was performed while maintaining the culture solution temperature at 37° C. and constantly controlling the pH to 6.9. Further, the dissolved oxygen concentration in the culture solution was maintained at 20% of the dissolved oxygen saturation concentration.

TABLE 5

| Reagent | Concentration (g/L) |
|---|---|
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |
| $CaCl_2 \cdot 2H_2O$ | 0.04 |
| GD-113 | 0.1 |
| (Antifoaming agent) | (mL/L) |

Immediately after glucose in the production medium was completely consumed, a feed solution (455 g/1 L of glucose and 120 g/1 L of Yeast Extract) was added at a rate of 1 mL/min. The culture was performed while maintaining the culture solution temperature at 37° C. and constantly controlling the pH to 6.9. Further, the dissolved oxygen concentration in the culture solution was maintained at 20% of the dissolved oxygen saturation concentration, and the culture was carried out for 20 hours. Thereafter, 1 M isopropyl-β-thiogalactopyranoside (IPTG) was added to the culture solution to a final concentration of 1 mM to induce the expression of the modified fibroin. 20 hours after addition of IPTG, the culture solution was centrifuged to recover the bacterial cell pellet. SDS-PAGE was carried out using bacterial cell pellets prepared from the culture solution before the addition of IPTG and after the addition of IPTG, and the expression of the target modified fibroin was checked by the IPTG addition-dependent appearance of a band equivalent to a target modified fibroin size.

(3) Purification of Modified Fibroin 2 hours after the addition of IPTG, the collected fungus bodies were washed with a 20 mM Tris-HCl buffer (pH 7.4). The bacterial cell pellet after washing were suspended in 20 mM Tris-HCl buffer solution (pH 7.4) containing about 1 mM PMSF, and the cell suspension was disrupted with a high-pressure homogenizer (manufactured by GEA Niro Soavi SpA). The disrupted cells were centrifuged to obtain a precipitate. The obtained precipitate was washed with 20 mM Tris-HCl buffer solution (pH 7.4) until the obtained precipitate became highly pure. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so that the concentration of the suspension was 100 mg/mL, and dissolved by stirring with a stirrer at 60° C. for 30 minutes. After dissolution, dialysis was carried out in water using a dialysis tube (cellulose tube 36/32 manufactured by Sanko Junyaku Co., Ltd.). A white coagulation protein obtained after dialysis was collected by centrifugation, and water was removed in a freeze dryer to recover freeze-dried powder, thereby obtaining modified fibroins (PRT966 and PRT799).

Production of Modified Fibroin Multifilament (1) Preparation of Spinning Raw Material Solution (Dope Solution)

26 mass % of the modified fibroin (PRT966) obtained in the production process of the modified fibroin was mixed with 74 mass % of formic acid (manufactured by Asahi Chemical Co., Ltd., purity: 98%) as a dissolving solution, and the mixture was dissolved by heating the mixture by an aluminum block heater at 40° C. while being stirred for 1 hour. Filtration was performed with a metal filter having an opening of 1 μm and defoaming was performed, thereby preparing a spinning raw material solution.

(2) Dry Wet Spinning

Example 1

The spinning was performed using the spinning apparatus illustrated in FIG. 6. The prepared spinning raw material solution was filled in a reserve tank (storage tank), and the spinning raw material solution was discharged into the coagulation bath through an air gap from the spinning nozzle (spinneret) having 100 holes using a gear pump, thereby forming a raw yarn. Then, the coagulated raw yarn was drawn in a water washing bath. After washing and drawing in the water washing bath, drying was performed using a dry heat plate, and the obtained modified fibroin multifilament was wound around a winder. The number of constituent yarns of the multifilament was 100. Conditions of dry wet spinning were as follows.

Hole diameter of spinneret: 0.08 mm
Number of holes of spinning nozzle: 100
Coagulation liquid: 100% methanol
Temperature of coagulation liquid: 10° C.

Temperature of water washing bath: 40° C.
Temperature of drawing bath: 40° C.
Total draw ratio: 4.4 times
Dry temperature: 70° C.

Example 2

A modified fibroin multifilament was produced by performing dry wet spinning in the same manner as that of Example 1, except that a spinning nozzle having a hole diameter of 0.1 mm and 360 holes was used and the total draw ratio was 5.3 times. The number of constituent yarns of the multifilament was 360.

(3) Wet Spinning

Example 3

The spinning was performed using the spinning apparatus illustrated in FIG. 7. The prepared spinning raw material solution was filled in a reserve tank, and the spinning raw material solution was discharged into the coagulation bath from the spinning nozzle having 200 holes using a gear pump, thereby forming a raw yarn (thread). Then, the coagulated raw yarn was drawn in a water washing bath. After washing and drawing in the water washing bath, drying was performed using a dry heat plate, and the obtained modified fibroin multifilament was wound around a winder. The number of constituent yarns of the multifilament was 200. In addition, in the obtained multifilament, a recess extending in an axial direction of the filament was formed on a surface. Conditions of wet spinning were as follows.

Hole diameter of spinning nozzle: 0.05 mm
Number of holes of spinning nozzle: 200
Coagulation liquid: mixed solution of 14.4 mass % of sodium sulfate, 65.6 mass % of water (80 mass % of 18 mass % aqueous sodium sulfate solution), and 20 mass % of formic acid
Temperature of coagulation liquid: 40° C.
Temperature of water washing bath: 40° C.
Temperature of drawing bath: 60° C.
Total draw ratio: 4.3 times
Dry temperature: 60° C.

Example 4

Figure 13:
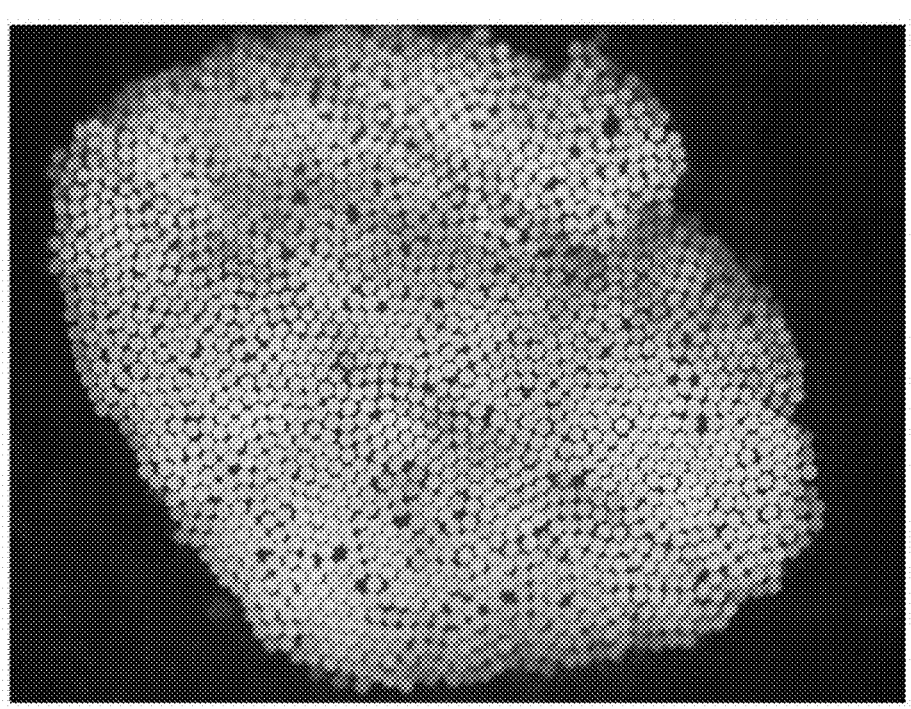
FIG. 13 is a photograph showing a cross section of the modified fibroin multifilament (the number of constituent single yarns of the multifilament: 1,000) produced using a spinning nozzle having 1,000 holes.

A modified fibroin multifilament was produced by performing wet spinning in the same manner as that of Example 3, except that a spinning nozzle having a hole diameter of 0.1 mm and 1,000 holes was used and the total draw ratio was 6.2 times. The number of constituent yarns of the obtained multifilament was 1,000. In addition, in the obtained multifilament, a recess extending in an axial direction of the filament was formed on a surface (FIG. 13).

Example 9

A modified fibroin multifilament was produced by performing wet spinning in the same manner as that of Example 3, except that the concentration of the spinning raw material solution (dope solution) was 31 mass %, a spinning nozzle having a hole diameter of 0.08 mm and 1,664 holes was used, and the total draw ratio was 5.7 times. The number of constituent yarns of the obtained multifilament was 1,664.

Example 10

A modified fibroin multifilament was produced by performing wet spinning in the same manner as that of Example 3, except that the concentration of the spinning raw material solution (dope solution) was 31 mass %, a spinning nozzle having a hole diameter of 0.1 mm and 2,328 holes was used, and the total draw ratio was 5.7 times. The number of constituent yarns of the obtained multifilament was 2,328.

Example 11

Figure 14:
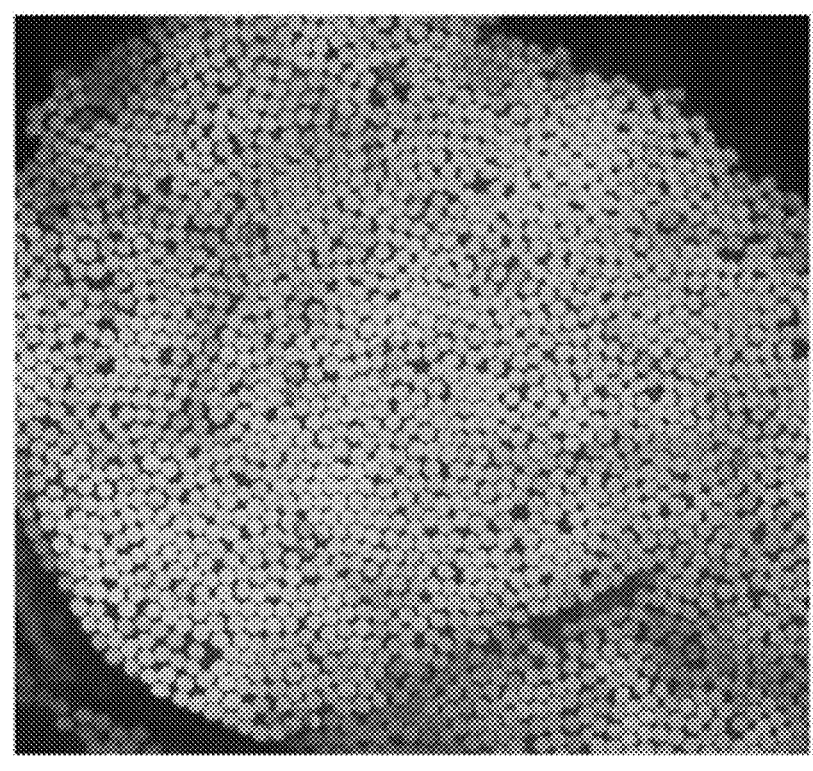
FIG. 14 is a photograph showing a cross section of the modified fibroin multifilament (the number of constituent single yarns of the multifilament: 3,000) produced using a spinning nozzle having 3,000 holes.

A modified fibroin multifilament was produced by performing wet spinning in the same manner as that of Example 3, except that the concentration of the spinning raw material solution (dope solution) was 31 mass %, a spinning nozzle having a hole diameter of 0.08 mm and 3,000 holes was used, and the total draw ratio was 5.7 times. The number of constituent yarns of the obtained multifilament was 3,000. A cross-sectional view of the multifilament was illustrated in FIG. 14.

[Evaluation of Modified Fibroin Multifilament]

The elastic modulus [gf/D], the strength [g/D], the elongation at break [%], and the fineness [D] of the modified fibroin multifilament obtained in each of Examples 1 to 4 and Examples 9 to 11 were measured. The coefficient of variation in elastic modulus, the coefficient of variation in strength, the coefficient of variation in elongation at break, and the coefficient of variation in fineness were calculated using the following equations, respectively.

Coefficient of variation in elastic modulus (CV) [%]=standard deviation of elastic modulus/average value of elastic modulus×100

Coefficient of variation in strength (CV) [%]=standard deviation of strength/average value of strength×100

Coefficient of variation in elongation (CV) [%]=standard deviation of elongation/average value of elongation×100

Coefficient of variation in fineness (CV) [%]=standard deviation of fineness/average value of fineness×100

A density [g/cm$^3$] of the used modified fibroin was 1.34 [g/cm$^3$].

The measurement of the elastic modulus [gf/D], the strength [g/D], and the elongation at break [%] of the modified fibroin multifilament and the calculation of each standard deviation thereof was performed using a 3345 series tensile tester manufactured by Instron corp. based on JIS L1013. The test was performed under conditions in which a test length was 300 mm and a test speed was 300 mm/min under an environment of a temperature of 20° C. and a relative humidity of 65%, and a load cell capacity of 10 N was used in each of Examples 1 and 3, and a load cell capacity of 50 N was used in each of Examples 2 and 4 and Examples 9 to 11. The fineness [D] of the modified fibroin multifilament was calculated by measuring the mass of the multifilament cut into a length of 3 m under an environment of a temperature of 20° C. and a relative humidity of 65% and converting the mass into a mass per 9,000 m. The average value of each of the physical properties of the modified fibroin multifilament of each of Examples 1 to 4 was calculated as an average value of the number of samples n=5. The average value of each of the physical properties of the multifilament of Example 9 was calculated as an average value of the number of samples n=10. The average value of each of the physical properties of the multifilament of Example 10 was calculated as an average value of the number of samples n=15. The average value of each of the physical properties of the multifilament of Example 11 was calculated as an average value of the number of samples n=30. The value of each coefficient of variation was calculated by each of the above equations using each of the average values (the average value of the elastic modulus, the average value of the strength, the average value of the elongation, and the average value of the fineness) of the physical properties of the measured multifilament. Evaluation results of each coefficient of variation are shown in Table 6. In addition, the average values of the standard deviation of the elongation at break [%] and the fineness [D] of each of Examples 1 to 4 and 9 to 11 are shown in Table 7.

TABLE 6

| | Number of constituent yarns of multifilament | Coefficient of variation in elastic modulus (CV) [%] | Coefficient of variation in strength (CV) [%] | Coefficient of variation in elongation (CV) [%] | Coefficient of variation in fineness (CV) [%] |
|---|---|---|---|---|---|
| Example 1 | 100 | 4.7 | 2.2 | 3.6 | 0.5 |
| Example 2 | 360 | 1.7 | 1.5 | 3.2 | 0.8 |
| Example 3 | 200 | 1.5 | 1.0 | 3.6 | 2.6 |
| Example 4 | 1,000 | 1.2 | 0.8 | 2.6 | 0.9 |
| Example 9 | 1,664 | 1.4 | 1.0 | 2.6 | 0.04 |
| Example 10 | 2,328 | 1.6 | 1.2 | 3.6 | 1.2 |
| Example 11 | 3,000 | 2.2 | 1.0 | 5.3 | 2.1 |

As shown in Table 6, the productivity was dramatically improved using the spinning nozzle having 100 to 3,000 holes. Further, in the obtained multifilaments (Examples 1 to 4 and Examples 9 to 11), the coefficient of variation (CV) in elastic modulus was 1.2 to 4.7, the coefficient of variation (CV) in strength was 0.8 to 2.2, the coefficient of variation (CV) in elongation was 2.6 to 5.3, and the coefficient of variation (CV) in fineness was 0.04 to 2.6, and the variation of the physical property value of the multifilament was extremely small, which showed that quality stability was significantly excellent.

TABLE 7

| | Number of constituent yarns of multifilament | Average value of elongation [%] | Standard deviation of elongation [%] | Average value of fineness [D] | Standard deviation of fineness [D] |
|---|---|---|---|---|---|
| Example 1 | 100 | 23.5 | 0.85 | 183 | 1.68 |
| Example 2 | 360 | 48.6 | 1.74 | 170 | 4.39 |
| Example 3 | 200 | 15.3 | 0.49 | 466 | 3.74 |
| Example 4 | 1,000 | 10.8 | 0.28 | 953 | 4.38 |
| Example 9 | 1,664 | 20.3 | 0.46 | 1729 | 0.70 |
| Example 10 | 2,328 | 14.1 | 0.51 | 2389 | 27.7 |
| Example 11 | 3,000 | 18.3 | 0.98 | 3359 | 69.2 |

Examples 5 to 8

(4) Shrinking Step and Drying Step

Each of the modified fibroin multifilaments obtained in Examples 1 to 4 was cut into a length of about 30 cm, and each multifilament bundle was immersed in water at 40° C. for 90 seconds to be shrunk. Thereafter, each multifilament bundle was taken out from the water and dried, and the length of each dried multifilament was measured.

(5) Evaluation of Shrinkability of Multifilament Having Irreversible Shrinkage History The shrinkability of the modified fibroin multifilament obtained in (4) was evaluated by using the shrinkage rate determined by the following method as an index. The number of samples was set to n=3 and was calculated according to the following equation. The calculation results are shown in Table 8.

Shrinkage rate [%]=(1−(length of multifilament when dried from wet state/length of multifilament when in wet state))×100

TABLE 8

| | Number of constituent yarns of multifilament | Shrinkage rate [%] |
|---|---|---|
| Example 5 | 100 | −0.2 |
| Example 6 | 360 | 0.4 |
| Example 7 | 200 | 0 |
| Example 8 | 1,000 | 0.2 |

As shown in Table 8, the shrinkage rate of the modified fibroin multifilament after the shrinking treatment was within ±0.4% (Examples 5 to 8), which showed that dimensional stability against moisture was excellent. As described above, the multifilament having an irreversible shrinkage history was excellent in dimensional stability against moisture, and the variation of the physical property value of the multifilament was relatively extremely small, which showed that quality stability was significantly excellent.

Test Examples 1 to 3: Peelability Test of Dope Solution (1) Preparation of Dope Solution 31 mass % of the modified fibroin (PRT966) obtained in the production process of the modified fibroin was mixed with 69 mass % of formic acid (manufactured by Asahi Chemical Co., Ltd., purity: 99%) as a dissolving solution, and the mixture was dissolved by heating the mixture by an aluminum block heater at 40° C. while being stirred for 1 hour. Filtration was performed with a metal filter having an opening of 1 μm and defoaming was performed, thereby preparing a dope solution.

(2) Peelability Test

The peelability of the dope solution from the material of the spinning nozzle (spinneret) was evaluated. The dope solution was added dropwise within a range of about φ 15 mm onto a surface of each of circular test pieces formed of different materials. These test pieces were immersed in a coagulation liquid, and after 5 seconds, the dope solution (semi-coagulated body) was peeled off from the surface of each of the test pieces in the coagulation liquid. The peelability of the dope solution from the spinning nozzle material was evaluated by the degree of force required to peel off the dope solution (semi-coagulated body). The materials used for the spinning nozzle and the evaluation results are shown in Table 9. As the coagulation liquid, a mixed solution obtained by mixing an aqueous sodium sulfate solution having a concentration of 18 mass % and formic acid in a ratio of 80 mass %:20 mass % was used. The evaluation indices of the peelability were as follows.

◯: Good peelability (the dope solution (semi-coagulated body) can be peeled off with a light force)

△: Poor peelability (a large force was required to peel off the dope solution (semi-coagulated body) as compared with the material evaluated as ◯)

TABLE 9

|  | Material of spinning nozzle | Evaluation of peelability of dope |
|---|---|---|
| Test Example 1 | Pt/Au | △ |
| Test Example 2 | Hastelloy | ◯ |
| Test Example 3 | SUS316L | ◯ |

As shown in Table 9, it was confirmed that in the case where the material of the spinning nozzle was Hastelloy or SUS 316L, the dope solution (semi-coagulated body) was peeled off from the surface of the test piece with a light force and the peelability of the dope solution was more excellent, as compared to the case where the material of the spinning nozzle was Pt/Au. As described above, the recombinant structural protein has a property of easily adhering (adsorbing) to Pt/Au. In particular, in the case of using a dope solution containing modified fibroin, a material (Hastelloy, SUS 316L, or the like) from which modified fibroin is easily peeled off is used as the material of the spinning nozzle, such that clogging of the spinning nozzle, which may occur when the dope solution adheres to the spinning nozzle, can be further prevented, thereby further improving the spinning stability. In particular, it is preferable that the spinning is performed in a large scale using a spinning nozzle having more than 100 holes.

Reference Example 1: Combustion Test of Modified Fibroin

A freeze-dried powder of the modified fibroin (PRT799) was added to a dimethyl sulfoxide solution of lithium chloride (concentration: 4.0 mass %) so that the concentration was 24 mass %, and then dissolved by mixing using a shaker for 3 hours. Thereafter, insoluble matters and foams were removed to obtain a modified fibroin solution (spinning raw material solution).

The obtained spinning raw material solution was heated to 90° C., and filtrated with a metal filter having an opening of 5 μm. Thereafter, the filtrate was allowed to stand in a 30 mL-stainless steel syringe to remove foams. The resulting spinning raw material solution was discharged from a solid nozzle having a needle diameter of 0.2 mm into a 100 mass % methanol coagulation bath. The discharge temperature was 90° C. After completion of the coagulation, the obtained raw yarn was wound up, and naturally dried to obtain a modified fibroin fiber (raw material fiber).

A knitted fabric (thickness: 180 denier, gauge number: 18) was produced by circular knitting a twisted yarn obtained by twisting the raw material fibers by using a circular knitting machine. 20 g of the obtained knitted fabric was cut out, and used as a test piece.

The combustion test was performed in accordance with the "test method of a particulate or low-melting point synthetic resin" specified in "Notice No. 50 of the Office of Hazardous Materials Regulation (May 31, 1995). The test was performed under conditions of a temperature of 22° C., a relative humidity of 45%, and an atmospheric pressure of 1,021 hPa. The measurement results (oxygen concentration (%), combustion rate (%), and converted combustion rate (%)) are shown in Table 10.

TABLE 10

| Oxygen concentration (%) | Combustion rate (%) | Converted combustion rate (%) |
|---|---|---|
| 20.0 | 39.1 | 40.1 |
| 27.0 | 48.1 | 49.3 |
| 28.0 | 51.9 | 53.2 |
| 30.0 | 53.6 | 54.9 |
| 50.0 | 61.2 | 62.7 |
| 70.0 | 91.1 | 93.3 |
| 100.0 | 97.6 | 100.0 |

As a result of the combustion test, the limited oxygen index (LOI) value of the knitted fabric obtained by knitting the modified fibroin (PRT799) fibers was 27.2. An LOI value of 26 or more is generally known to be flame retardant. The results show that the modified fibroin is excellent in flame retardancy.

Reference Example 2: Evaluation of Hygroscopic and Exothermic Properties of Modified Fibroin A freeze-dried powder of a modified fibroin was added to a dimethyl sulfoxide solution of lithium chloride (concentration: 4.0 mass %) so that the concentration was 24 mass %, and then dissolved by mixing using a shaker for 3 hours. Thereafter, insoluble matters and foams were removed to obtain a modified fibroin solution (spinning raw material solution).

The obtained spinning raw material solution was heated to 60° C., and filtrated with a metal filter having an opening of 5 μm. Thereafter, the filtrate was allowed to stand in a 30 mL-stainless steel syringe to remove foams. The resulting spinning raw material solution was discharged from a solid nozzle having a needle diameter of 0.2 mm into a 100 mass % methanol coagulation bath. The discharge temperature was 60° C. After completion of the coagulation, the obtained raw yarn was wound up, and naturally dried to obtain a modified fibroin fiber (raw material fiber).

For comparison, commercially available wool fibers, cotton fibers, tencel fibers, rayon fibers, and polyester fibers were prepared as a raw material fiber.

A knitted fabric was produced by weft-knitting each of the raw material fibers by using a weft-knitting machine. The thickness and gauge number of the knitted fabric formed by using PRT918 fibers or PRT799 fibers are as shown in Table 11. The thickness and gauge number of each of the knitted fabrics formed by using other raw material fibers were adjusted so as to have a cover factor approximately the same as that of the knitted fabric of the modified fibroin fiber. Details are as follows.

TABLE 11

| Raw material fiber | Thickness [N] | Gauge number [GG] |
|---|---|---|
| PRT918 | 1/30 (metrical count of single yarn) | 18 |
| PRT799 | 1/30 (metrical count of single yarn) | 16 |

TABLE 11-continued

| Raw material fiber | Thickness [N] | Gauge number [GG] |
|---|---|---|
| Wool | 2/30 (double yarn) | 14 |
| Cotton | 2/34 (double yarn) | 14 |
| Tencel | 2/30 (double yarn) | 15 |
| Rayon | 1/38 (single yarn) | 14 |
| Polyester | 1/60 (single yarn) | 14 |

Two pieces of knitted fabrics each cut with a size of 10 cm×10 cm were faced to each other, and four sides thereof were sewn to each other to prepare a test piece (sample). The test piece was left to stand in a low humidity environment (temperature: 20±2° C., relative humidity: 40±5%) for 4 hours or longer, and then transferred to a high humidity environment (temperature: 20±2° C., relative humidity: 90±5%). Then, measurement of the temperature was performed with a temperature sensor attached to the center of inside of the test piece for 30 minutes at 1 minute intervals.

Figure 15:
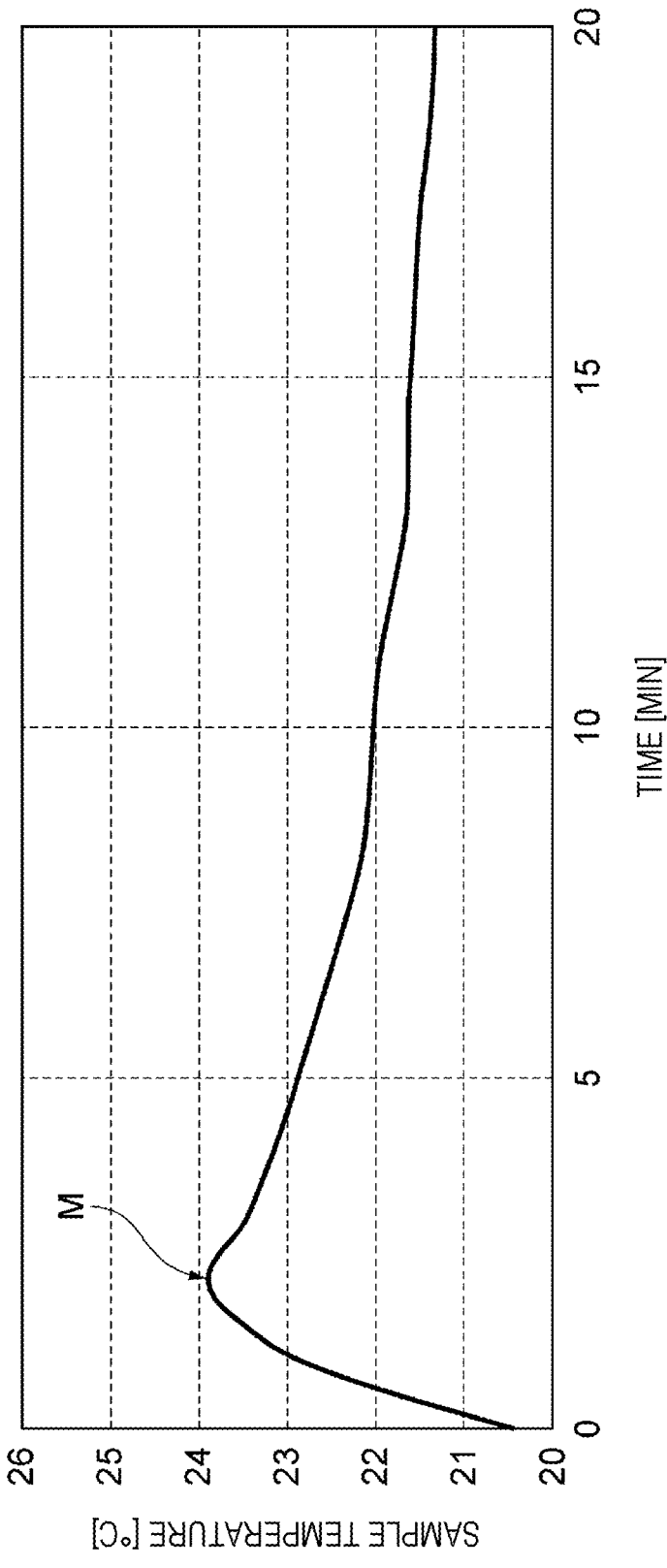
FIG. 15 is a graph showing an example of results of a hygroscopic and exothermic test.

From the measurement results, the maximum hygroscopic and exothermic degree was determined according to the following Equation A.

$$\text{maximum hygroscopic and exothermic degree}=\{$$
(maximum value of sample temperature when sample is placed under low humidity environment until sample temperature reaches equilibrium and then transferred to high humidity environment)−(sample temperature when sample is placed under low humidity environment until sample temperature reaches equilibrium and then transferred to high humidity environment)}(° C.)/sample weight (g)   Equation A:

FIG. 15 is a graph showing an example of results of a hygroscopic and exothermic test. In the horizontal axis of the graph, a time point at which the sample is transferred from a low humidity environment to a high humidity environment is defined as 0, and the horizontal axis represents a period of time during which the sample is left to stand in a high humidity environment (min). The vertical axis of the graph represents a temperature measured with a temperature sensor (sample temperature). In the graph illustrated in FIG. 15, the point indicated by M corresponds to the maximum value of the sample temperature.

The calculation results of the maximum hygroscopic and exothermic degree of each of the knitted fabrics are shown in Table 12.

TABLE 12

| Raw material fiber | Maximum hygroscopic and exothermic degree (° C./g) |
|---|---|
| PRT918 | 0.040 |
| PRT799 | 0.031 |
| Wool | 0.020 |
| Cotton | 0.021 |
| Tencel | 0.018 |
| Rayon | 0.025 |
| Polyester | 0.010 |

Table 12 shows that the modified fibroins (PRT918 and PRT799) have a high maximum hygroscopic and exothermic degree compared to existing materials, and thus are excellent in the hygroscopic and exothermic properties.

Reference Example 3: Evaluation of Heat Retaining Properties of Modified Fibroin A freeze-dried powder of a modified fibroin was added to a dimethyl sulfoxide solution of lithium chloride (concentration: 4.0 mass %) so that the concentration was 24 mass %, and then dissolved by mixing using a shaker for 3 hours. Thereafter, insoluble matters and foams were removed to obtain a modified fibroin solution (spinning raw material solution).

The obtained spinning raw material solution was heated to 60° C., and filtrated with a metal filter having an opening of 5 μm. Thereafter, the filtrate was allowed to stand in a 30 mL-stainless steel syringe to remove foams. The resulting spinning raw material solution was discharged from a solid nozzle having a needle diameter of 0.2 mm into a 100 mass % methanol coagulation bath. The discharge temperature was 60° C. After completion of the coagulation, the obtained raw yarn was wound up, and naturally dried to obtain a modified fibroin fiber (raw material fiber).

For comparison, commercially available wool fibers, silk fibers, cotton fibers, rayon fibers, and polyester fibers were prepared as a raw material fiber.

A knitted fabric was produced by weft-knitting each of the raw material fibers by using a weft-knitting machine. The count, the number of twisted yarns, the gauge number, and the basis weight of the knitted fabric formed by using PRT966 fibers or PRT799 fibers are as shown in Table 13. Each of the knitted fabrics formed by using other raw material fibers was adjusted so as to have a cover factor approximately the same as that of the knitted fabric of the modified fibroin fiber. Details are as follows.

TABLE 13

| Raw material fiber | Count [Nm] | Number of twists | Gauge number [GG] | Basis weight [g/m²] |
|---|---|---|---|---|
| PRT966 | 30 | 1 | 18 | 90.1 |
| PRT799 | 30 | 1 | 16 | 111.0 |
| Wool | 30 | 2 | 14 | 242.6 |
| Silk | 60 | 2 | 14 | 225.2 |
| Cotton | 34 | 2 | 14 | 194.1 |
| Rayon | 38 | 1 | 14 | 181.8 |
| Polyester | 60 | 1 | 14 | 184.7 |

The heat retaining properties were evaluated by using a KES-F7 THERMO LABO II tester, manufactured by Kato Tech Co., Ltd., according to a dry contact method (a method based on an assumption that the skin and clothing are in direct contact in a dried state). One piece of square knitted fabric cut with a size of 20 cm×20 cm was used as a test piece (sample). The test piece was set on a hot plate set at a predetermined temperature (30° C.), and the amount of heat (a) dissipated via the test piece was measured under a condition of a wind speed of 30 cm/sec in a wind tunnel. The amount of heat (b) dissipated in a state in which the test piece was not set was determined under the same condition as described above. Then, the heat retention ratio (%) was calculated according to the following Equation B.

$$\text{Heat Retention Ratio (\%)}=(1-a/b)\times100 \quad \text{Equation B:}$$

From the measurement results, the heat retention index was determined according to the following Equation C.

$$\text{heat retention index}=\text{heat retention rate (\%)/basis weight (g/m}^2\text{) of sample} \quad \text{Equation C:}$$

The calculation results of the heat retention index are shown in Table 14. A higher heat retention index can be evaluated as being a material having excellent heat retaining properties.

TABLE 14

| Raw material fiber | Heat retention index |
| --- | --- |
| PRT966 | 0.33 |
| PRT799 | 0.22 |
| Wool | 0.16 |
| Silk | 0.11 |
| Cotton | 0.13 |
| Rayon | 0.02 |
| Polyester | 0.18 |

Table 14 shows that the modified fibroins (PRT966 and PRT799) have a high heat retention index compared to existing materials, and thus are excellent in the heat retaining properties.

As shown in Reference Examples 1 to 3, when the modified fibroin is a modified spider silk fibroin, the heat retaining properties, hygroscopic and exothermic properties, and/or flame retardancy can be made even better. When the modified spider silk fibroin is used to form a multifilament, it is possible to obtain a multifilament having more excellent heat retaining properties, hygroscopic and exothermic properties, and/or flame retardancy and having extremely excellent quality stability.

REFERENCE SIGNS LIST

1 Extrusion device
2 Undrawn yarn producing apparatus
3 Wet heat drawing device
4 Drying device
6 Dope solution
10 Spinning apparatus
20 Coagulation bath
21 Drawing bath
25 Spinning apparatus
36 Multifilament
38 Modified fibroin multifilament
40 Producing apparatus
42 Feed roller
44 Winder
46 Water bath
48 Dryer
54 Heater
56 Tension roller
58 Hot roller
60 Processing device
62 Drying device
64 Dry heat plate
140 Relaxation shrinking means (heating means)
141 Feed means
142 Winding means
146 Speed control means
147 Temperature control means

The invention claimed is:

1. A multifilament comprising modified fibroin, wherein the multifilament has 1,000 or more and 300,000 or less constituent single yarns, a coefficient of variation in elastic modulus of the multifilament is 15% or less, a coefficient of variation in strength of the multifilament is 15% or less, and a coefficient of variation in elongation of the multifilament is 2.6 to 10%.

2. The multifilament according to claim 1, wherein a coefficient of variation in fineness of the multifilament is 20% or less.

3. The multifilament according to claim 1, wherein the coefficient of variation in strength of the multifilament is 10% or less, and the coefficient of variation in elastic modulus of the multifilament is 10% or less.

4. The multifilament according to claim 1, wherein an average hydropathy index of the modified fibroin is more than −0.8.

5. The multifilament according to claim 1, wherein the modified fibroin is modified spider silk fibroin.

6. The multifilament according to claim 1, wherein the multifilament has a shrinkage history of being irreversibly shrunk after spinning.

7. The multifilament according to claim 6, wherein the shrinkage history is a shrinkage history of being irreversibly shrunk by bringing the multifilament into contact with water or a shrinkage history of being irreversibly shrunk by heating and relaxing the multifilament.

8. The multifilament according to claim 6, wherein a shrinkage rate of the multifilament having a shrinkage history of being irreversibly shrunk after spinning is 5% or less, the shrinkage rate being defined by the following equation:

Shrinkage rate [%]=(1−(length of multifilament when dried from wet state/length of multifilament when in wet state))×100.

9. The multifilament according to claim 1, wherein a coefficient of variation in fineness of the multifilament is 0.01% to 6.5%.

10. The multifilament according to claim 1, wherein the coefficient of variation in strength of the multifilament is 0.01% to 3.8%.

11. A multifilament comprising a recombinant structural protein, wherein the multifilament has 100 or more constituent single yarns, and a coefficient of variation in elongation is 2.6 to 10%.

12. A method for producing the multifilament of claim 1, comprising a step of discharging a spinning raw material solution containing modified fibroin and a solvent from a spinning nozzle having 100 or more holes, and bringing the spinning raw material solution into contact with a coagulation liquid to coagulate the modified fibroin.

13. A method for producing the multifilament of claim 1, comprising a step of discharging a spinning raw material solution containing a recombinant structural protein and a solvent from a spinning nozzle having 100 or more holes, and bringing the spinning raw material solution into contact with a coagulation liquid to coagulate the recombinant structural protein.

14. A method for producing the multifilament of claim 11, comprising a step of discharging a spinning raw material solution containing modified fibroin and a solvent from a spinning nozzle having 100 or more holes, and bringing the spinning raw material solution into contact with a coagulation liquid to coagulate the modified fibroin.

15. A method for producing the multifilament of claim 11, comprising a step of discharging a spinning raw material solution containing a recombinant structural protein and a solvent from a spinning nozzle having 100 or more holes, and bringing the spinning raw material solution into contact with a coagulation liquid to coagulate the recombinant structural protein.

* * * * *

SEQUENCE LISTING

```
<160> NUMBER OF SEQ ID NOS: 49

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 3
<211> LENGTH: 21
<212> TYPE: PRT
<213> ORGANISM: Araneus diadematus
```

-continued

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 4

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
            245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gly Gln
305                 310                 315                 320

-continued

```
Gly Pro Tyr Gly Pro Gly Ala Ser Ala Ala Ala Ala Ala Gly Gly
            325             330             335

Tyr Gly Pro Gly Ser Gly Gln Gln Gly Pro Gly Gln Gln Gly Pro Gly
            340             345             350

Gln Gln Gly Pro Gly Gln Gln Gly Pro Gly Gly Gln Gly Pro Tyr Gly
            355             360             365

Pro Gly Ala Ser Ala Ala Ala Ala Ala Ala Gly Gly Tyr Gly Pro Gly
    370             375             380

Ser Gly Gln Gln Gly Pro Gly Gln Gln Gly Pro Gly Gln Gln Gly Pro
385             390             395             400

Gly Gln Gln Gly Pro Gly Gln Gln Gly Pro Gly Gln Gln Gly Pro Gly
            405             410             415

Gln Gln Gly Pro Gly Gln Gln Gly Pro Gly Gln Gln Gly Pro Gly Gly
            420             425             430

Gln Gly Ala Tyr Gly Pro Gly Ala Ser Ala Ala Ala Gly Ala Ala Gly
            435             440             445

Gly Tyr Gly Pro Gly Ser Gly Gln Gln Gly Pro Gly Gln Gln Gly Pro
    450             455             460

Gly Gln Gln Gly Pro Gly Gln Gln Gly Pro Gly Gln Gln Gly Pro Gly
465             470             475             480

Gln Gln Gly Pro Gly Gln Gln Gly Pro Gly Gln Gln Gly Pro Tyr Gly
            485             490             495

Pro Gly Ala Ser Ala Ala Ala Ala Ala Ala Gly Gly Tyr Gly Pro Gly
            500             505             510

Ser Gly Gln Gln Gly Pro Gly Gln Gln Gly Pro Gly Gln Gln Gly Pro
    515             520             525

Gly Gly Gln Gly Pro Tyr Gly Pro Gly Ala Ala Ser Ala Ala Val Ser
    530             535             540

Val Ser Arg Ala Arg Ala Gly Ser Gly Gln Gln Gly Pro Gly Gln Gln
545             550             555             560

Gly Pro Gly Gln Gln Gly Pro Gly Gln Gln Gly Pro Tyr Gly Pro Gly
            565             570             575

Ala Ser Ala Ala Ala Ala Ala Ala Gly Gly Tyr Gly Pro Gly Ser Gly
            580             585             590

Gln Gln Gly Pro Ser Gln Gln Gly Pro Gly Gln Gln Gly Pro Gly Gly
    595             600             605

Gln Gly Pro Tyr Gly Pro Gly Ala Ser Ala Ala Ala Ala Ala Ala Gly
    610             615             620

Gly Tyr Gly Pro Gly Ser Gly Gln Gln Gly Pro Gly Gly Gln Gly Pro
625             630             635             640

Tyr Gly Pro Gly Ser Ser Ala Ala Ala Ala Ala Ala Gly Gly Asn Gly
            645             650             655

Pro Gly Ser Gly Gln Gln Gly Ala Gly Gln Gln Gly Pro Gly Gln Gln
            660             665             670

Gly Pro Gly Ala Ser Ala Ala Ala Ala Ala Ala Gly Gly Tyr Gly Pro
    675             680             685

Gly Ser Gly Gln Gln Gly Pro Gly Gln Gln Gly Pro Gly Gly Gln Gly
    690             695             700

Pro Tyr Gly Pro Gly Ala Ser Ala Ala Ala Ala Ala Ala Gly Gly Tyr
705             710             715             720

Gly Pro Gly Ser Gly Gln Gly Pro Gly Gln Gln Gly Pro Gly Gly Gln
            725             730             735
```

```
Gly Pro Tyr Gly Pro Gly Ala Ser Ala Ala Ala Ala Ala Gly Gly
        740             745             750

Tyr Gly Pro Gly Ser Gly Gln Gln Gly Pro Gly Gln Gln Gly Pro Gly
        755             760             765

Gln Gln Gly Pro Gly Gly Gln Gly Pro Tyr Gly Pro Gly Ala Ser Ala
        770             775             780

Ala Ala Ala Ala Ala Gly Gly Tyr Gly Pro Gly Tyr Gly Gln Gln Gly
785             790             795             800

Pro Gly Gln Gln Gly Pro Gly Gly Gln Gly Pro Tyr Gly Pro Gly Ala
            805             810             815

Ser Ala Ala Ser Ala Ala Ser Gly Gly Tyr Gly Pro Gly Ser Gly Gln
            820             825             830

Gln Gly Pro Gly Gln Gln Gly Pro Gly Gly Gln Gly Pro Tyr Gly Pro
            835             840             845

Gly Ala Ser Ala Ala Ala Ala Ala Gly Gly Tyr Gly Pro Gly Ser
        850             855             860

Gly Gln Gln Gly Pro Gly Gln Gln Gly Pro Gly Gln Gln Gly Pro Gly
865             870             875             880

Gln Gln Gly Pro Gly Gly Gln Gly Pro Tyr Gly Pro Gly Ala Ser Ala
            885             890             895

Ala Ala Ala Ala Gly Gly Tyr Gly Pro Gly Ser Gly Gln Gln Gly
            900             905             910

Pro Gly Gln Gln Gly Pro Gly Gln Gln Gly Pro Gly Gln Gln Gly Pro
            915             920             925

Gly Gln Gln Gly Pro Gly Gln Gln Gly Pro Gly Gln Gln Gly Pro Gly
        930             935             940

Gln Gln Gly Pro Gly Gln Gln Gly Pro Gly Gly Gln Gly Ala Tyr Gly
945             950             955             960

Pro Gly Ala Ser Ala Ala Ala Gly Ala Ala Gly Gly Tyr Gly Pro Gly
            965             970             975

Ser Gly Gln Gln Gly Pro Gly Gln Gln Gly Pro Gly Gln Gln Gly Pro
            980             985             990

Gly Gln Gln Gly Pro Gly Gln Gln  Gly Pro Gly Gln Gln  Gly Pro Gly
            995             1000                1005

Gln Gln  Gly Pro Gly Gln Gln  Gly Pro Tyr Gly Pro  Gly Ala Ser
    1010            1015                1020

Ala Ala  Ala Ala Ala Ala Gly  Gly Tyr Gly Pro Gly  Ser Gly Gln
    1025            1030                1035

Gln Gly  Pro Gly Gln Gln Gly  Pro Gly Gln Gln Gly  Pro Gly Gly
    1040            1045                1050

Gln Gly  Pro Tyr Gly Pro Gly  Ala Ala Ser Ala Ala  Val Ser Val
    1055            1060                1065

Gly Gly  Tyr Gly Pro Gln Ser  Ser Ser Val Pro Val  Ala Ser Ala
    1070            1075                1080

Val Ala  Ser Arg Leu Ser Ser  Pro Ala Ala Ser Ser  Arg Val Ser
    1085            1090                1095

Ser Ala  Val Ser Ser Leu Val  Ser Ser Gly Pro Thr  Lys His Ala
    1100            1105                1110

Ala Leu  Ser Asn Thr Ile Ser  Ser Val Val Ser Gln  Val Ser Ala
    1115            1120                1125

Ser Asn  Pro Gly Leu Ser Gly  Cys Asp Val Leu Val  Gln Ala Leu
    1130            1135                1140

Leu Glu  Val Val Ser Ala Leu  Val Ser Ile Leu
```

```
     1145                 1150

<210> SEQ ID NO 5
<211> LENGTH: 24
<212> TYPE: PRT
<213> ORGANISM: Artificial Sequence
<220> FEATURE:
<223> OTHER INFORMATION: His tag and start codon

<400> SEQUENCE: 5

Met His His His His His His His His His His Ser Ser Gly Ser Ser
1               5                   10                  15

Leu Glu Val Leu Phe Gln Gly Pro
            20

<210> SEQ ID NO 6
<211> LENGTH: 597
<212> TYPE: PRT
<213> ORGANISM: Artificial Sequence
<220> FEATURE:
<223> OTHER INFORMATION: Met-PRT380

<400> SEQUENCE: 6

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Ala Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Ala Gly Pro
    50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gln Tyr Gly Pro Gly Gln Gln Gly Pro Gly Gln Gln
            100                 105                 110

Gly Pro Gly Ser Ser Ala Ala Ala Ala Ala Gly Gln Tyr Gly Ser Gly
            115                 120                 125

Pro Gly Gln Gln Gly Pro Tyr Gly Ser Ala Ala Ala Ala Ala Gly Pro
    130                 135                 140

Gly Ser Gly Gln Tyr Gly Gln Gly Pro Tyr Gly Pro Gly Ala Ser Ala
145                 150                 155                 160

Ala Ala Ala Gly Pro Gly Gln Tyr Gly Pro Gly Gln Gln Gly Pro
                165                 170                 175

Ser Ala Ser Ala Ala Ala Ala Ala Gly Ser Gly Gln Gln Gly Pro Gly
            180                 185                 190

Gln Tyr Gly Pro Tyr Ala Ser Ala Ala Ala Ala Ala Gly Gln Tyr Gly
        195                 200                 205

Ser Gly Pro Gly Gln Gln Gly Pro Tyr Gly Pro Gly Gln Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Ala Gly Pro Gly Gln Gln Gly Pro Tyr Gly
                245                 250                 255

Pro Gly Ser Ser Ala Ala Ala Ala Ala Gly Gln Tyr Gly Tyr Gly Pro
            260                 265                 270
```

```
Gly Gln Gln Gly Pro Tyr Gly Pro Gly Ala Ser Ala Ala Ala Ala
        275                 280                 285

Gly Gln Asn Gly Pro Gly Ser Gly Gln Tyr Gly Pro Gly Gln Gln Gly
        290                 295                 300

Pro Gly Gln Ser Ala Ala Ala Ala Ala Gly Pro Gly Gln Gln Gly Pro
305                 310                 315                 320

Tyr Gly Pro Gly Ala Ser Ala Ala Ala Ala Gly Gln Tyr Gly Pro
                325                 330                 335

Gly Gln Gln Gly Pro Gly Gln Tyr Gly Pro Gly Ser Ser Ala Ala
        340                 345                 350

Ala Ala Gly Pro Gly Gln Gln Gly Pro Tyr Gly Pro Gly Ser Ser Ala
        355                 360                 365

Ala Ala Ala Ala Gly Gln Tyr Gly Pro Gly Gln Gln Gly Pro Tyr Gly
        370                 375                 380

Pro Gly Gln Ser Ala Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala Ala
        405                 410                 415

Gly Pro Gly Gln Gln Gly Pro Tyr Gly Pro Gly Ala Ser Ala Ala Ala
        420                 425                 430

Ala Ala Gly Pro Gly Gln Tyr Gly Pro Gly Gln Gln Gly Pro Ser Ala
        435                 440                 445

Ser Ala Ala Ala Ala Ala Gly Gln Tyr Gly Ser Gly Pro Gly Gln Tyr
        450                 455                 460

Gly Pro Tyr Gly Pro Gly Gln Ser Ala Ala Ala Ala Ala Gly Pro Gly
465                 470                 475                 480

Ser Gly Gln Gln Gly Gln Gly Pro Tyr Gly Pro Gly Ala Ser Ala Ala
        485                 490                 495

Ala Ala Ala Gly Gln Tyr Gly Pro Gly Gln Gln Gly Pro Tyr Gly Pro
        500                 505                 510

Gly Gln Ser Ala Ala Ala Ala Ala Gly Pro Gly Ser Gly Gln Tyr Gly
        515                 520                 525

Pro Gly Ala Ser Ala Ala Ala Ala Ala Gly Gln Asn Gly Pro Gly Ser
        530                 535                 540

Gly Gln Tyr Gly Pro Gly Gln Gly Pro Gly Gln Ser Ala Ala Ala
545                 550                 555                 560

Ala Ala Gly Gln Tyr Gln Gln Gly Pro Gly Gln Gln Gly Pro Tyr Gly
        565                 570                 575

Pro Gly Ala Ser Ala Ala Ala Ala Ala Gly Pro Gly Ser Gly Gln Gln
        580                 585                 590

Gly Pro Gly Ala Ser
        595

<210> SEQ ID NO 7
<211> LENGTH: 590
<212> TYPE: PRT
<213> ORGANISM: Artificial Sequence
<220> FEATURE:
<223> OTHER INFORMATION: Met-PRT410

<400> SEQUENCE: 7

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
        20                  25                  30
```

-continued

```
Gln Ser Gly Gln Tyr Gly Pro Gly Gln Gln Gly Pro Gly Gln Gln Gly
        35              40              45

Pro Gly Ser Ser Ala Ala Ala Ala Ala Gly Pro Gly Gln Tyr Gly Pro
    50              55              60

Gly Gln Gln Gly Pro Ser Ala Ser Ala Ala Ala Ala Gly Pro Gly
65              70              75              80

Ser Gly Gln Gln Gly Pro Gly Ala Ser Gly Gln Tyr Gly Pro Gly Gln
                85              90              95

Gln Gly Pro Gly Gln Gln Gly Pro Gly Ser Ser Ala Ala Ala Ala Ala
            100             105             110

Gly Gln Tyr Gly Ser Gly Pro Gly Gln Gln Gly Pro Tyr Gly Ser Ala
        115             120             125

Ala Ala Ala Ala Gly Pro Gly Ser Gly Gln Tyr Gly Gln Gly Pro Tyr
    130             135             140

Gly Pro Gly Ala Ser Gly Pro Gly Gln Tyr Gly Pro Gly Gln Gln Gly
145             150             155             160

Pro Ser Ala Ser Ala Ala Ala Ala Gly Ser Gly Gln Gln Gly Pro
            165             170             175

Gly Gln Tyr Gly Pro Tyr Ala Ser Ala Ala Ala Ala Gly Gln Tyr
        180             185             190

Gly Ser Gly Pro Gly Gln Gln Gly Pro Tyr Gly Pro Gly Gln Ser Gly
        195             200             205

Ser Gly Gln Gln Gly Pro Gly Gln Gln Gly Pro Tyr Ala Ser Ala Ala
    210             215             220

Ala Ala Ala Gly Pro Gly Gln Gln Gly Pro Tyr Gly Pro Gly Ser Ser
225             230             235             240

Ala Ala Ala Ala Ala Gly Gln Tyr Gly Tyr Gly Pro Gly Gln Gln Gly
            245             250             255

Pro Tyr Gly Pro Gly Ala Ser Gly Gln Asn Gly Pro Gly Ser Gly Gln
        260             265             270

Tyr Gly Pro Gly Gln Gln Gly Pro Gly Gln Ser Ala Ala Ala Ala Ala
        275             280             285

Gly Pro Gly Gln Gln Gly Pro Tyr Gly Pro Gly Ala Ser Ala Ala Ala
    290             295             300

Ala Ala Gly Gln Tyr Gly Pro Gly Gln Gln Gly Pro Gly Gln Tyr Gly
305             310             315             320

Pro Gly Ser Ser Gly Pro Gly Gln Gln Gly Pro Tyr Gly Pro Gly Ser
            325             330             335

Ser Ala Ala Ala Ala Ala Gly Gln Tyr Gly Pro Gly Gln Gln Gly Pro
            340             345             350

Tyr Gly Pro Gly Gln Ser Ala Ala Ala Ala Gly Gln Tyr Gln Gln
        355             360             365

Gly Pro Gly Gln Gln Gly Pro Tyr Gly Pro Gly Ala Ser Gly Pro Gly
    370             375             380

Gln Gln Gly Pro Tyr Gly Pro Gly Ala Ser Ala Ala Ala Ala Gly
385             390             395             400

Pro Gly Gln Tyr Gly Pro Gly Gln Gln Gly Pro Ser Ala Ser Ala Ala
            405             410             415

Ala Ala Ala Gly Gln Tyr Gly Ser Gly Pro Gly Gln Tyr Gly Pro Tyr
            420             425             430

Gly Pro Gly Gln Ser Gly Pro Gly Ser Gly Gln Gln Gly Gln Gly Pro
    435             440             445

Tyr Gly Pro Gly Ala Ser Ala Ala Ala Ala Ala Gly Gln Tyr Gly Pro
```

-continued

```
            450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
            530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
                580                 585                 590
```

```
<210> SEQ ID NO 8
<211> LENGTH: 565
<212> TYPE: PRT
<213> ORGANISM: Artificial Sequence
<220> FEATURE:
<223> OTHER INFORMATION: Met-PRT525

<400> SEQUENCE: 8

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
        50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
            100                 105                 110

Ser Ala Ala Ala Ala Ala Ala Ala Gly Ser Tyr Gly Ser Gly Pro Gly
        115                 120                 125

Gln Gln Gly Pro Tyr Gly Ser Ala Ala Ala Ala Ala Ala Gly Pro
        130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Gln Gln Gly Pro Ser Ala Ser Ala Ala
                165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Gly Ser Tyr Gly Ser
            195                 200                 205

Gly Pro Gly Gln Gln Gly Pro Tyr Gly Pro Gly Gln Ser Gly Ser Gly
        210                 215                 220

Gln Gln Gly Pro Gly Gln Gln Gly Pro Tyr Ala Ser Ala Ala Ala Ala
```

-continued

```
225                 230                 235                 240

Ala Ala Ala Gly Pro Gly Gln Gln Gly Pro Tyr Gly Pro Gly Ser Ser
                245                 250                 255

Ala Ala Ala Ala Ala Ala Ala Gly Ser Tyr Gly Tyr Gly Pro Gly Gln
                260                 265                 270

Gln Gly Pro Tyr Gly Pro Gly Ala Ser Gly Gln Asn Gly Pro Gly Ser
                275                 280                 285

Gly Gln Tyr Gly Pro Gly Gln Gln Gly Pro Gly Pro Ser Ala Ala Ala
                290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Ala Gly Ser Tyr Gly Pro Gly Gln Gln
                325                 330                 335

Gly Pro Gly Gln Tyr Gly Pro Gly Ser Ser Gly Pro Gly Gln Gln Gly
                340                 345                 350

Pro Tyr Gly Pro Gly Ser Ser Ala Ala Ala Ala Ala Ala Ala Gly Ser
                355                 360                 365

Tyr Gly Pro Gly Gln Gln Gly Pro Tyr Gly Pro Gly Pro Ser Ala Ala
                370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
                405                 410                 415

Pro Gly Ala Ser Ala Ala Ala Ala Ala Ala Gly Pro Gly Gln Tyr
                420                 425                 430

Gly Pro Gly Gln Gln Gly Pro Ser Ala Ser Ala Ala Ala Ala Ala
                435                 440                 445

Ala Gly Ser Tyr Gly Ser Gly Pro Gly Gln Tyr Gly Pro Tyr Gly Pro
                450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Gly Ser Tyr Gly Pro
                485                 490                 495

Gly Gln Gln Gly Pro Tyr Gly Pro Gly Pro Ser Ala Ala Ala Ala Ala
                500                 505                 510

Ala Ala Gly Pro Gly Ser Gly Gln Tyr Gly Pro Gly Ala Ser Gly Gln
                515                 520                 525

Asn Gly Pro Gly Ser Gly Gln Tyr Gly Pro Gly Gln Gln Gly Pro Gly
                530                 535                 540

Pro Ser Ala Ala Ala Ala Ala Ala Ala Gly Pro Gly Ser Gly Gln Gln
545                 550                 555                 560

Gly Pro Gly Ala Ser
                565
```

```
<210> SEQ ID NO 9
<211> LENGTH: 2364
<212> TYPE: PRT
<213> ORGANISM: Artificial Sequence
<220> FEATURE:
<223> OTHER INFORMATION: Met-PRT799

<400> SEQUENCE: 9

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
```

```
              20              25              30

Gln Ser Gly Gln Tyr Gly Pro Gly Gln Gln Gly Pro Gly Gln Gln Gly
         35              40              45

Pro Gly Ser Ser Ala Ala Ala Ala Ala Gly Pro Gly Gln Tyr Gly Pro
    50              55              60

Gly Gln Gln Gly Pro Ser Ala Ser Ala Ala Ala Ala Gly Pro Gly
65              70              75              80

Ser Gly Gln Gln Gly Pro Gly Ala Ser Gly Gln Tyr Gly Pro Gly Gln
             85              90              95

Gln Gly Pro Gly Gln Gln Gly Pro Gly Ser Ser Ala Ala Ala Ala Ala
         100             105             110

Gly Gln Tyr Gly Ser Gly Pro Gly Gln Gln Gly Pro Tyr Gly Ser Ala
         115             120             125

Ala Ala Ala Ala Gly Pro Gly Ser Gly Gln Tyr Gly Gln Gly Pro Tyr
         130             135             140

Gly Pro Gly Ala Ser Gly Pro Gly Gln Tyr Gly Pro Gly Gln Gln Gly
145             150             155             160

Pro Ser Ala Ser Ala Ala Ala Ala Ala Gly Ser Gly Gln Gln Gly Pro
         165             170             175

Gly Gln Tyr Gly Pro Tyr Ala Ser Ala Ala Ala Ala Ala Gly Gln Tyr
         180             185             190

Gly Ser Gly Pro Gly Gln Gln Gly Pro Tyr Gly Pro Gly Gln Ser Gly
         195             200             205

Ser Gly Gln Gln Gly Pro Gly Gln Gln Gly Pro Tyr Ala Ser Ala Ala
    210             215             220

Ala Ala Ala Gly Pro Gly Gln Gln Gly Pro Tyr Gly Pro Gly Ser Ser
225             230             235             240

Ala Ala Ala Ala Ala Gly Gln Tyr Gly Tyr Gly Pro Gly Gln Gln Gly
         245             250             255

Pro Tyr Gly Pro Gly Ala Ser Gly Gln Asn Gly Pro Gly Ser Gly Gln
         260             265             270

Tyr Gly Pro Gly Gln Gln Gly Pro Gly Gln Ser Ala Ala Ala Ala Ala
         275             280             285

Gly Pro Gly Gln Gln Gly Pro Tyr Gly Pro Gly Ala Ser Ala Ala Ala
    290             295             300

Ala Ala Gly Gln Tyr Gly Pro Gly Gln Gln Gly Pro Gly Gln Tyr Gly
305             310             315             320

Pro Gly Ser Ser Gly Pro Gly Gln Gln Gly Pro Tyr Gly Pro Gly Ser
         325             330             335

Ser Ala Ala Ala Ala Ala Gly Gln Tyr Gly Pro Gly Gln Gln Gly Pro
         340             345             350

Tyr Gly Pro Gly Gln Ser Ala Ala Ala Ala Gly Gln Tyr Gln Gln
         355             360             365

Gly Pro Gly Gln Gln Gly Pro Tyr Gly Pro Gly Ala Ser Gly Pro Gly
    370             375             380

Gln Gln Gly Pro Tyr Gly Pro Gly Ala Ser Ala Ala Ala Ala Gly
385             390             395             400

Pro Gly Gln Tyr Gly Pro Gly Gln Gln Gly Pro Ser Ala Ser Ala Ala
         405             410             415

Ala Ala Ala Gly Gln Tyr Gly Ser Gly Pro Gly Gln Tyr Gly Pro Tyr
         420             425             430

Gly Pro Gly Gln Ser Gly Pro Gly Ser Gly Gln Gln Gly Gln Gly Pro
         435             440             445
```

-continued

```
Tyr Gly Pro Gly Ala Ser Ala Ala Ala Ala Gly Gln Tyr Gly Pro
    450             455             460

Gly Gln Gln Gly Pro Tyr Gly Pro Gly Gln Ser Ala Ala Ala Ala
465             470             475             480

Gly Pro Gly Ser Gly Gln Tyr Gly Pro Gly Ala Ser Gly Gln Asn Gly
                485             490             495

Pro Gly Ser Gly Gln Tyr Gly Pro Gly Gln Gln Gly Pro Gly Gln Ser
            500             505             510

Ala Ala Ala Ala Ala Gly Gln Tyr Gln Gln Gly Pro Gly Gln Gln Gly
            515             520             525

Pro Tyr Gly Pro Gly Ala Ser Ala Ala Ala Ala Gly Gln Tyr Gly
    530             535             540

Ser Gly Pro Gly Gln Gln Gly Pro Tyr Gly Pro Gly Gln Ser Gly Ser
545             550             555             560

Gly Gln Gln Gly Pro Gly Gln Gly Pro Tyr Ala Ser Ala Ala Ala
            565             570             575

Ala Ala Gly Pro Gly Ser Gly Gln Gln Gly Pro Gly Ala Ser Gly Gln
            580             585             590

Gln Gly Pro Tyr Gly Pro Gly Ala Ser Ala Ala Ala Ala Gly Gln
    595             600             605

Asn Gly Pro Gly Ser Gly Gln Gln Gly Pro Gly Gln Ser Gly Gln Tyr
    610             615             620

Gly Pro Gly Gln Gln Gly Pro Gly Gln Gly Pro Gly Ser Ser Ala
625             630             635             640

Ala Ala Ala Ala Gly Pro Gly Gln Tyr Gly Pro Gly Gln Gln Gly Pro
            645             650             655

Ser Ala Ser Ala Ala Ala Ala Ala Gly Pro Gly Ser Gly Gln Gln Gly
            660             665             670

Pro Gly Ala Ser Gly Gln Tyr Gly Pro Gly Gln Gln Gly Pro Gly Gln
    675             680             685

Gln Gly Pro Gly Ser Ser Ala Ala Ala Ala Gly Gln Tyr Gly Ser
    690             695             700

Gly Pro Gly Gln Gln Gly Pro Tyr Gly Ser Ala Ala Ala Ala Gly
705             710             715             720

Pro Gly Ser Gly Gln Tyr Gly Gln Gly Pro Tyr Gly Pro Gly Ala Ser
            725             730             735

Gly Pro Gly Gln Tyr Gly Pro Gly Gln Gly Pro Ser Ala Ser Ala
            740             745             750

Ala Ala Ala Ala Gly Ser Gly Gln Gln Gly Pro Gly Gln Tyr Gly Pro
            755             760             765

Tyr Ala Ser Ala Ala Ala Ala Ala Gly Gln Tyr Gly Ser Gly Pro Gly
    770             775             780

Gln Gln Gly Pro Tyr Gly Pro Gly Gln Ser Gly Ser Gly Gln Gln Gly
785             790             795             800

Pro Gly Gln Gln Gly Pro Tyr Ala Ser Ala Ala Ala Ala Gly Pro
            805             810             815

Gly Gln Gln Gly Pro Tyr Gly Pro Gly Ser Ser Ala Ala Ala Ala Ala
            820             825             830

Gly Gln Tyr Gly Tyr Gly Pro Gly Gln Gln Gly Pro Tyr Gly Pro Gly
    835             840             845

Ala Ser Gly Gln Asn Gly Pro Gly Ser Gly Gln Tyr Gly Pro Gly Gln
    850             855             860
```

-continued

```
Gln Gly Pro Gly Gln Ser Ala Ala Ala Ala Gly Pro Gly Gln Gln
865                 870                 875                 880

Gly Pro Tyr Gly Pro Gly Ala Ser Ala Ala Ala Ala Gly Gln Tyr
                885                 890                 895

Gly Pro Gly Gln Gln Gly Pro Gly Gln Tyr Gly Pro Gly Ser Ser Gly
                900                 905                 910

Pro Gly Gln Gln Gly Pro Tyr Gly Pro Gly Ser Ser Ala Ala Ala Ala
        915                 920                 925

Ala Gly Gln Tyr Gly Pro Gly Gln Gln Gly Pro Tyr Gly Pro Gly Gln
        930                 935                 940

Ser Ala Ala Ala Ala Ala Gly Gln Tyr Gln Gln Gly Pro Gly Gln Gln
945                 950                 955                 960

Gly Pro Tyr Gly Pro Gly Ala Ser Gly Pro Gly Gln Gln Gly Pro Tyr
                965                 970                 975

Gly Pro Gly Ala Ser Ala Ala Ala Ala Ala Gly Pro Gly Gln Tyr Gly
                980                 985                 990

Pro Gly Gln Gln Gly Pro Ser Ala  Ser Ala Ala Ala Ala  Ala Gly Gln
        995                 1000                 1005

Tyr Gly  Ser Gly Pro Gly Gln  Tyr Gly Pro Tyr Gly  Pro Gly Gln
    1010                 1015                 1020

Ser Gly  Pro Gly Ser Gly Gln  Gln Gly Gln Gly Pro  Tyr Gly Pro
    1025                 1030                 1035

Gly Ala  Ser Ala Ala Ala Ala  Ala Gly Gln Tyr Gly  Pro Gly Gln
    1040                 1045                 1050

Gln Gly  Pro Tyr Gly Pro Gly  Gln Ser Ala Ala Ala  Ala Ala Gly
    1055                 1060                 1065

Pro Gly  Ser Gly Gln Tyr Gly  Pro Gly Ala Ser Gly  Gln Asn Gly
    1070                 1075                 1080

Pro Gly  Ser Gly Gln Tyr Gly  Pro Gly Gln Gln Gly  Pro Gly Gln
    1085                 1090                 1095

Ser Ala  Ala Ala Ala Ala Gly  Gln Tyr Gln Gln Gly  Pro Gly Gln
    1100                 1105                 1110

Gln Gly  Pro Tyr Gly Pro Gly  Ala Ser Ala Ala Ala  Ala Ala Gly
    1115                 1120                 1125

Gln Tyr  Gly Ser Gly Pro Gly  Gln Gln Gly Pro Tyr  Gly Pro Gly
    1130                 1135                 1140

Gln Ser  Gly Ser Gly Gln Gln  Gly Pro Gly Gln Gln  Gly Pro Tyr
    1145                 1150                 1155

Ala Ser  Ala Ala Ala Ala Ala  Gly Pro Gly Ser Gly  Gln Gln Gly
    1160                 1165                 1170

Pro Gly  Ala Ser Gly Gln Gln  Gly Pro Tyr Gly Pro  Gly Ala Ser
    1175                 1180                 1185

Ala Ala  Ala Ala Ala Gly Gln  Asn Gly Pro Gly Ser  Gly Gln Gln
    1190                 1195                 1200

Gly Pro  Gly Gln Ser Gly Gln  Tyr Gly Pro Gly Gln  Gln Gly Pro
    1205                 1210                 1215

Gly Gln  Gln Gly Pro Gly Ser  Ser Ala Ala Ala Ala  Ala Gly Pro
    1220                 1225                 1230

Gly Gln  Tyr Gly Pro Gly Gln  Gln Gly Pro Ser Ala  Ser Ala Ala
    1235                 1240                 1245

Ala Ala  Ala Gly Pro Gly Ser  Gly Gln Gln Gly Pro  Gly Ala Ser
    1250                 1255                 1260

Gly Gln  Tyr Gly Pro Gly Gln  Gln Gly Pro Gly Gln  Gln Gly Pro
```

-continued

```
            1265               1270               1275

Gly Ser  Ser Ala Ala Ala Ala  Ala Gly Gln Tyr Gly  Ser Gly Pro
    1280               1285               1290

Gly Gln  Gln Gly Pro Tyr Gly  Ser Ala Ala Ala Ala  Gly Pro
    1295               1300               1305

Gly Ser  Gly Gln Tyr Gly Gln  Gly Pro Tyr Gly Pro  Gly Ala Ser
    1310               1315               1320

Gly Pro  Gly Gln Tyr Gly Pro  Gly Gln Gln Gly Pro  Ser Ala Ser
    1325               1330               1335

Ala Ala  Ala Ala Ala Gly Ser  Gly Gln Gln Gly Pro  Gly Gln Tyr
    1340               1345               1350

Gly Pro  Tyr Ala Ser Ala Ala  Ala Ala Ala Gly Gln  Tyr Gly Ser
    1355               1360               1365

Gly Pro  Gly Gln Gln Gly Pro  Tyr Gly Pro Gly Gln  Ser Gly Ser
    1370               1375               1380

Gly Gln  Gln Gly Pro Gly Gln  Gln Gly Pro Tyr Ala  Ser Ala Ala
    1385               1390               1395

Ala Ala  Ala Gly Pro Gly Gln  Gln Gly Pro Tyr Gly  Pro Gly Ser
    1400               1405               1410

Ser Ala  Ala Ala Ala Ala Gly  Gln Tyr Gly Tyr Gly  Pro Gly Gln
    1415               1420               1425

Gln Gly  Pro Tyr Gly Pro Gly  Ala Ser Gly Gln Asn  Gly Pro Gly
    1430               1435               1440

Ser Gly  Gln Tyr Gly Pro Gly  Gln Gln Gly Pro Gly  Gln Ser Ala
    1445               1450               1455

Ala Ala  Ala Ala Gly Pro Gly  Gln Gln Gly Pro Tyr  Gly Pro Gly
    1460               1465               1470

Ala Ser  Ala Ala Ala Ala Ala  Gly Gln Tyr Gly Pro  Gly Gln Gln
    1475               1480               1485

Gly Pro  Gly Gln Tyr Gly Pro  Gly Ser Ser Gly Pro  Gly Gln Gln
    1490               1495               1500

Gly Pro  Tyr Gly Pro Gly Ser  Ser Ala Ala Ala Ala  Gly Gln
    1505               1510               1515

Tyr Gly  Pro Gly Gln Gln Gly  Pro Tyr Gly Pro Gly  Gln Ser Ala
    1520               1525               1530

Ala Ala  Ala Ala Gly Gln Tyr  Gln Gln Gly Pro Gly  Gln Gln Gly
    1535               1540               1545

Pro Tyr  Gly Pro Gly Ala Ser  Gly Pro Gly Gln Gln  Gly Pro Tyr
    1550               1555               1560

Gly Pro  Gly Ala Ser Ala Ala  Ala Ala Ala Gly Pro  Gly Gln Tyr
    1565               1570               1575

Gly Pro  Gly Gln Gln Gly Pro  Ser Ala Ser Ala Ala  Ala Ala Ala
    1580               1585               1590

Gly Gln  Tyr Gly Ser Gly Pro  Gly Gln Tyr Gly Pro  Tyr Gly Pro
    1595               1600               1605

Gly Gln  Ser Gly Pro Gly Ser  Gly Gln Gln Gly Gln  Gly Pro Tyr
    1610               1615               1620

Gly Pro  Gly Ala Ser Ala Ala  Ala Ala Ala Gly Gln  Tyr Gly Pro
    1625               1630               1635

Gly Gln  Gln Gly Pro Tyr Gly  Pro Gly Gln Ser Ala  Ala Ala Ala
    1640               1645               1650

Ala Gly  Pro Gly Ser Gly Gln  Tyr Gly Pro Gly Ala  Ser Gly Gln
    1655               1660               1665
```

-continued

```
Asn Gly  Pro Gly Ser Gly Gln  Tyr Gly Pro Gly Gln  Gln Gly Pro
    1670             1675             1680

Gly Gln  Ser Ala Ala Ala Ala  Ala Gly Gln Tyr Gln  Gln Gly Pro
    1685             1690             1695

Gly Gln  Gln Gly Pro Tyr Gly  Pro Gly Ala Ser Ala  Ala Ala Ala
    1700             1705             1710

Ala Gly  Gln Tyr Gly Ser Gly  Pro Gly Gln Gln Gly  Pro Tyr Gly
    1715             1720             1725

Pro Gly  Gln Ser Gly Ser Gly  Gln Gln Gly Pro Gly  Gln Gln Gly
    1730             1735             1740

Pro Tyr  Ala Ser Ala Ala Ala  Ala Ala Gly Pro Gly  Ser Gly Gln
    1745             1750             1755

Gln Gly  Pro Gly Ala Ser Gly  Gln Gln Gly Pro Tyr  Gly Pro Gly
    1760             1765             1770

Ala Ser  Ala Ala Ala Ala Ala  Gly Gln Asn Gly Pro  Gly Ser Gly
    1775             1780             1785

Gln Gln  Gly Pro Gly Gln Ser  Gly Gln Tyr Gly Pro  Gly Gln Gln
    1790             1795             1800

Gly Pro  Gly Gln Gln Gly Pro  Gly Ser Ser Ala Ala  Ala Ala Ala
    1805             1810             1815

Gly Pro  Gly Gln Tyr Gly Pro  Gly Gln Gln Gly Pro  Ser Ala Ser
    1820             1825             1830

Ala Ala  Ala Ala Ala Gly Pro  Gly Ser Gly Gln Gln  Gly Pro Gly
    1835             1840             1845

Ala Ser  Gly Gln Tyr Gly Pro  Gly Gln Gln Gly Pro  Gly Gln Gln
    1850             1855             1860

Gly Pro  Gly Ser Ser Ala Ala  Ala Ala Ala Gly Gln  Tyr Gly Ser
    1865             1870             1875

Gly Pro  Gly Gln Gln Gly Pro  Tyr Gly Ser Ala Ala  Ala Ala Ala
    1880             1885             1890

Gly Pro  Gly Ser Gly Gln Tyr  Gly Gln Gly Pro Tyr  Gly Pro Gly
    1895             1900             1905

Ala Ser  Gly Pro Gly Gln Tyr  Gly Pro Gly Gln Gln  Gly Pro Ser
    1910             1915             1920

Ala Ser  Ala Ala Ala Ala Ala  Gly Ser Gly Gln Gln  Gly Pro Gly
    1925             1930             1935

Gln Tyr  Gly Pro Tyr Ala Ser  Ala Ala Ala Ala Ala  Gly Gln Tyr
    1940             1945             1950

Gly Ser  Gly Pro Gly Gln Gln  Gly Pro Tyr Gly Pro  Gly Gln Ser
    1955             1960             1965

Gly Ser  Gly Gln Gln Gly Pro  Gly Gln Gln Gly Pro  Tyr Ala Ser
    1970             1975             1980

Ala Ala  Ala Ala Ala Gly Pro  Gly Gln Gln Gly Pro  Tyr Gly Pro
    1985             1990             1995

Gly Ser  Ser Ala Ala Ala Ala  Ala Gly Gln Tyr Gly  Tyr Gly Pro
    2000             2005             2010

Gly Gln  Gln Gly Pro Tyr Gly  Pro Gly Ala Ser Gly  Gln Asn Gly
    2015             2020             2025

Pro Gly  Ser Gly Gln Tyr Gly  Pro Gly Gln Gln Gly  Pro Gly Gln
    2030             2035             2040

Ser Ala  Ala Ala Ala Ala Gly  Pro Gly Gln Gln Gly  Pro Tyr Gly
    2045             2050             2055
```

-continued

```
Pro Gly  Ala Ser Ala Ala Ala  Ala Ala Gly Gln Tyr  Gly Pro Gly
    2060             2065              2070

Gln Gln  Gly Pro Gly Gln Tyr  Gly Pro Gly Ser Ser  Gly Pro Gly
    2075             2080              2085

Gln Gln  Gly Pro Tyr Gly Pro  Gly Ser Ser Ala Ala  Ala Ala Ala
    2090             2095              2100

Gly Gln  Tyr Gly Pro Gly Gln  Gln Gly Pro Tyr Gly  Pro Gly Gln
    2105             2110              2115

Ser Ala  Ala Ala Ala Ala Gly  Gln Tyr Gln Gln Gly  Pro Gly Gln
    2120             2125              2130

Gln Gly  Pro Tyr Gly Pro Gly  Ala Ser Gly Pro Gly  Gln Gln Gly
    2135             2140              2145

Pro Tyr  Gly Pro Gly Ala Ser  Ala Ala Ala Ala Ala  Gly Pro Gly
    2150             2155              2160

Gln Tyr  Gly Pro Gly Gln Gln  Gly Pro Ser Ala Ser  Ala Ala Ala
    2165             2170              2175

Ala Ala  Gly Gln Tyr Gly Ser  Gly Pro Gly Gln Tyr  Gly Pro Tyr
    2180             2185              2190

Gly Pro  Gly Gln Ser Gly Pro  Gly Ser Gly Gln Gln  Gly Gln Gly
    2195             2200              2205

Pro Tyr  Gly Pro Gly Ala Ser  Ala Ala Ala Ala Ala  Gly Gln Tyr
    2210             2215              2220

Gly Pro  Gly Gln Gln Gly Pro  Tyr Gly Pro Gly Gln  Ser Ala Ala
    2225             2230              2235

Ala Ala  Ala Gly Pro Gly Ser  Gly Gln Tyr Gly Pro  Gly Ala Ser
    2240             2245              2250

Gly Gln  Asn Gly Pro Gly Ser  Gly Gln Tyr Gly Pro  Gly Gln Gln
    2255             2260              2265

Gly Pro  Gly Gln Ser Ala Ala  Ala Ala Ala Gly Gln  Tyr Gln Gln
    2270             2275              2280

Gly Pro  Gly Gln Gln Gly Pro  Tyr Gly Pro Gly Ala  Ser Ala Ala
    2285             2290              2295

Ala Ala  Ala Gly Gln Tyr Gly  Ser Gly Pro Gly Gln  Gln Gly Pro
    2300             2305              2310

Tyr Gly  Pro Gly Gln Ser Gly  Ser Gly Gln Gln Gly  Pro Gly Gln
    2315             2320              2325

Gln Gly  Pro Tyr Ala Ser Ala  Ala Ala Ala Gly  Pro Gly Ser
    2330             2335              2340

Gly Gln  Gln Gly Ser Ser Val  Asp Lys Leu Ala Ala  Ala Leu Glu
    2345             2350              2355

His His  His His His His
    2360
```

```
<210> SEQ ID NO 10
<211> LENGTH: 597
<212> TYPE: PRT
<213> ORGANISM: Artificial Sequence
<220> FEATURE:
<223> OTHER INFORMATION: Met-PRT313

<400> SEQUENCE: 10

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30
```

-continued

```
Gly Ser Ala Ala Ala Ala Ala Gly Gly Tyr Gly Pro Gly Gly Gln Gly
        35                  40              45

Pro Gly Gln Gln Gly Pro Gly Ser Ser Ala Ala Ala Ala Gly Ala Gly Pro
    50                  55              60

Gly Gly Tyr Gly Pro Gly Gly Gln Gly Pro Ser Ala Ser Ala Ala Ala
65                  70              75              80

Ala Ala Gly Pro Gly Ser Gly Gln Gln Gly Pro Gly Ala Ser Ala Ala
            85              90              95

Ala Ala Ala Gly Gly Tyr Gly Pro Gly Gln Gly Pro Gly Gln Gln
            100             105             110

Gly Pro Gly Ser Ser Ala Ala Ala Ala Ala Gly Gly Tyr Gly Ser Gly
        115             120             125

Pro Gly Gln Gln Gly Pro Tyr Gly Ser Ala Ala Ala Ala Gly Pro
    130             135             140

Gly Ser Gly Gly Tyr Gly Gln Gly Pro Tyr Gly Pro Gly Ala Ser Ala
145             150             155             160

Ala Ala Ala Gly Pro Gly Gly Tyr Gly Pro Gly Gly Gln Gly Pro
            165             170             175

Ser Ala Ser Ala Ala Ala Ala Ala Gly Ser Gly Gln Gln Gly Pro Gly
        180             185             190

Gly Tyr Gly Pro Tyr Ala Ser Ala Ala Ala Ala Gly Gly Tyr Gly
    195             200             205

Ser Gly Pro Gly Gln Gln Gly Pro Tyr Gly Pro Gly Gly Ser Ala Ala
    210             215             220

Ala Ala Ala Gly Ser Gly Gln Gln Gly Pro Gly Gln Gln Gly Pro Tyr
225             230             235             240

Ala Ser Ala Ala Ala Ala Ala Gly Pro Gly Gly Gln Gly Pro Tyr Gly
            245             250             255

Pro Gly Ser Ser Ala Ala Ala Ala Ala Gly Gly Tyr Gly Tyr Gly Pro
        260             265             270

Gly Gly Gln Gly Pro Tyr Gly Pro Gly Ala Ser Ala Ala Ala Ala Ala
        275             280             285

Gly Gly Asn Gly Pro Gly Ser Gly Gly Tyr Gly Pro Gly Gln Gln Gly
    290             295             300

Pro Gly Gly Ser Ala Ala Ala Ala Ala Gly Pro Gly Gly Gln Gly Pro
305             310             315             320

Tyr Gly Pro Gly Ala Ser Ala Ala Ala Ala Gly Gly Tyr Gly Pro
        325             330             335

Gly Gly Gln Gly Pro Gly Gly Tyr Gly Pro Gly Ser Ser Ala Ala Ala
        340             345             350

Ala Ala Gly Pro Gly Gly Gln Gly Pro Tyr Gly Pro Gly Ser Ser Ala
        355             360             365

Ala Ala Ala Ala Gly Gly Tyr Gly Pro Gly Gln Gln Gly Pro Tyr Gly
    370             375             380

Pro Gly Gly Ser Ala Ala Ala Ala Ala Gly Gly Tyr Gln Gln Gly Pro
385             390             395             400

Gly Gly Gln Gly Pro Tyr Gly Pro Gly Ala Ser Ala Ala Ala Ala Ala
            405             410             415

Gly Pro Gly Gly Gln Gly Pro Tyr Gly Pro Gly Ala Ser Ala Ala Ala
        420             425             430

Ala Ala Gly Pro Gly Gly Tyr Gly Pro Gly Gly Gln Gly Pro Ser Ala
        435             440             445

Ser Ala Ala Ala Ala Ala Gly Gly Tyr Gly Ser Gly Pro Gly Gly Tyr
```

```
        450             455             460

Gly Pro Tyr Gly Pro Gly Gly Ser Ala Ala Ala Ala Ala Gly Pro Gly
465             470             475             480

Ser Gly Gln Gln Gly Gln Gly Pro Tyr Gly Pro Gly Ala Ser Ala Ala
                485             490             495

Ala Ala Ala Gly Gly Tyr Gly Pro Gly Gln Gln Gly Pro Tyr Gly Pro
                500             505             510

Gly Gly Ser Ala Ala Ala Ala Ala Gly Pro Gly Ser Gly Gly Tyr Gly
                515             520             525

Pro Gly Ala Ser Ala Ala Ala Ala Gly Gly Asn Gly Pro Gly Ser
        530             535             540

Gly Gly Tyr Gly Pro Gly Gln Gln Gly Pro Gly Gly Ser Ala Ala Ala
545             550             555             560

Ala Ala Gly Gly Tyr Gln Gln Gly Pro Gly Gly Gln Gly Pro Tyr Gly
                565             570             575

Pro Gly Ala Ser Ala Ala Ala Ala Gly Pro Gly Ser Gly Gln Gln
        580             585             590

Gly Pro Gly Ala Ser
        595
```

```
<210> SEQ ID NO 11
<211> LENGTH: 12
<212> TYPE: PRT
<213> ORGANISM: Artificial Sequence
<220> FEATURE:
<223> OTHER INFORMATION: HisTag

<400> SEQUENCE: 11

Met His His His His His His Ser Ser Gly Ser Ser
1               5               10
```

```
<210> SEQ ID NO 12
<211> LENGTH: 608
<212> TYPE: PRT
<213> ORGANISM: Artificial Sequence
<220> FEATURE:
<223> OTHER INFORMATION: PRT380

<400> SEQUENCE: 12

Met His His His His His His Ser Ser Gly Ser Ser Gly Pro Gly Gln
1               5               10              15

Gln Gly Pro Tyr Gly Pro Gly Ala Ser Ala Ala Ala Ala Gly Gln
                20              25              30

Asn Gly Pro Gly Ser Gly Gln Gln Gly Pro Gly Gln Ser Ala Ala Ala
        35              40              45

Ala Ala Gly Gln Tyr Gly Pro Gly Gln Gln Gly Pro Gly Gln Gln Gly
        50              55              60

Pro Gly Ser Ser Ala Ala Ala Ala Ala Gly Pro Gly Gln Tyr Gly Pro
65              70              75              80

Gly Gln Gln Gly Pro Ser Ala Ser Ala Ala Ala Ala Gly Pro Gly
                85              90              95

Ser Gly Gln Gln Gly Pro Gly Ala Ser Ala Ala Ala Ala Gly Gln
        100             105             110

Tyr Gly Pro Gly Gln Gln Gly Pro Gly Gln Gln Gly Pro Gly Ser Ser
        115             120             125

Ala Ala Ala Ala Ala Gly Gln Tyr Gly Ser Gly Pro Gly Gln Gln Gly
        130             135             140
```

```
Pro Tyr Gly Ser Ala Ala Ala Ala Ala Gly Pro Gly Ser Gly Gln Tyr
145             150                 155                 160

Gly Gln Gly Pro Tyr Gly Pro Gly Ala Ser Ala Ala Ala Ala Ala Gly
                165             170             175

Pro Gly Gln Tyr Gly Pro Gly Gln Gln Gly Pro Ser Ala Ser Ala Ala
            180             185             190

Ala Ala Ala Gly Ser Gly Gln Gln Gly Pro Gly Gln Tyr Gly Pro Tyr
        195             200             205

Ala Ser Ala Ala Ala Ala Ala Gly Gln Tyr Gly Ser Gly Pro Gly Gln
    210             215             220

Gln Gly Pro Tyr Gly Pro Gly Gln Ser Ala Ala Ala Ala Ala Gly Ser
225             230             235             240

Gly Gln Gln Gly Pro Gly Gln Gly Pro Tyr Ala Ser Ala Ala Ala
        245             250             255

Ala Ala Gly Pro Gly Gln Gln Gly Pro Tyr Gly Pro Gly Ser Ser Ala
        260             265             270

Ala Ala Ala Gly Gln Tyr Gly Tyr Gly Pro Gly Gln Gln Gly Pro
        275             280             285

Tyr Gly Pro Gly Ala Ser Ala Ala Ala Ala Gly Gln Asn Gly Pro
    290             295             300

Gly Ser Gly Gln Tyr Gly Pro Gly Gln Gln Gly Pro Gly Gln Ser Ala
305             310             315             320

Ala Ala Ala Ala Gly Pro Gly Gln Gln Gly Pro Tyr Gly Pro Gly Ala
        325             330             335

Ser Ala Ala Ala Ala Ala Gly Gln Tyr Gly Pro Gly Gln Gln Gly Pro
        340             345             350

Gly Gln Tyr Gly Pro Gly Ser Ser Ala Ala Ala Ala Gly Pro Gly
        355             360             365

Gln Gln Gly Pro Tyr Gly Pro Gly Ser Ser Ala Ala Ala Ala Ala Gly
    370             375             380

Gln Tyr Gly Pro Gly Gln Gln Gly Pro Tyr Gly Pro Gly Gln Ser Ala
385             390             395             400

Ala Ala Ala Gly Gln Tyr Gln Gln Gly Pro Gly Gln Gln Gly Pro
        405             410             415

Tyr Gly Pro Gly Ala Ser Ala Ala Ala Ala Gly Pro Gly Gln Gln
    420             425             430

Gly Pro Tyr Gly Pro Gly Ala Ser Ala Ala Ala Ala Gly Pro Gly
    435             440             445

Gln Tyr Gly Pro Gly Gln Gln Gly Pro Ser Ala Ser Ala Ala Ala Ala
    450             455             460

Ala Gly Gln Tyr Gly Ser Gly Pro Gly Gln Tyr Gly Pro Tyr Gly Pro
465             470             475             480

Gly Gln Ser Ala Ala Ala Ala Ala Gly Pro Gly Ser Gly Gln Gln Gly
            485             490             495

Gln Gly Pro Tyr Gly Pro Gly Ala Ser Ala Ala Ala Ala Gly Gln
        500             505             510

Tyr Gly Pro Gly Gln Gln Gly Pro Tyr Gly Pro Gly Gln Ser Ala Ala
    515             520             525

Ala Ala Ala Gly Pro Gly Ser Gly Gln Tyr Gly Pro Gly Ala Ser Ala
    530             535             540

Ala Ala Ala Gly Gln Asn Gly Pro Gly Ser Gly Gln Tyr Gly Pro
545             550             555             560

Gly Gln Gln Gly Pro Gly Gln Ser Ala Ala Ala Ala Ala Gly Gln Tyr
```

```
                  565                 570                 575
Gln Gln Gly Pro Gly Gln Gln Gly Pro Tyr Gly Pro Gly Ala Ser Ala
            580                 585                 590

Ala Ala Ala Ala Gly Pro Gly Ser Gly Gln Gln Gly Pro Gly Ala Ser
        595                 600                 605

<210> SEQ ID NO 13
<211> LENGTH: 601
<212> TYPE: PRT
<213> ORGANISM: Artificial Sequence
<220> FEATURE:
<223> OTHER INFORMATION: PRT410

<400> SEQUENCE: 13

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
            100                 105                 110

Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Gly
    130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
            180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
    210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala Ala
                245                 250                 255

Gly Gln Tyr Gly Tyr Gly Pro Gly Gln Gln Gly Pro Tyr Gly Pro Gly
            260                 265                 270

Ala Ser Gly Gln Asn Gly Pro Gly Ser Gly Gln Tyr Gly Pro Gly Gln
        275                 280                 285

Gln Gly Pro Gly Gln Ser Ala Ala Ala Ala Gly Pro Gly Gln Gln
    290                 295                 300

Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
```

-continued

```
                325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
            435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
            515                 520                 525

Gly Gln Tyr Gln Gln Gly Pro Gly Gln Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
            595                 600
```

```
<210> SEQ ID NO 14
<211> LENGTH: 576
<212> TYPE: PRT
<213> ORGANISM: Artificial Sequence
<220> FEATURE:
<223> OTHER INFORMATION: PRT525

<400> SEQUENCE: 14

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Ala Gly Pro
```

-continued

```
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
            115                 120                 125

Ala Ala Ala Gly Ser Tyr Gly Ser Gly Pro Gly Gln Gln Gly Pro Tyr
            130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
            165                 170                 175

Pro Gly Gln Gln Gly Pro Ser Ala Ser Ala Ala Ala Ala Ala Ala Ala
            180                 185                 190

Gly Ser Gly Gln Gln Gly Pro Gly Gln Tyr Gly Pro Tyr Ala Ser Ala
            195                 200                 205

Ala Ala Ala Ala Ala Ala Gly Ser Tyr Gly Ser Gly Pro Gly Gln Gln
            210                 215                 220

Gly Pro Tyr Gly Pro Gly Gln Ser Gly Ser Gly Gln Gln Gly Pro Gly
225                 230                 235                 240

Gln Gln Gly Pro Tyr Ala Ser Ala Ala Ala Ala Ala Ala Ala Gly Pro
            245                 250                 255

Gly Gln Gln Gly Pro Tyr Gly Pro Gly Ser Ser Ala Ala Ala Ala Ala
            260                 265                 270

Ala Ala Gly Ser Tyr Gly Tyr Gly Pro Gly Gln Gln Gly Pro Tyr Gly
            275                 280                 285

Pro Gly Ala Ser Gly Gln Asn Gly Pro Gly Ser Gly Gln Tyr Gly Pro
            290                 295                 300

Gly Gln Gln Gly Pro Gly Pro Ser Ala Ala Ala Ala Ala Ala Ala Gly
305                 310                 315                 320

Pro Gly Gln Gln Gly Pro Tyr Gly Pro Gly Ala Ser Ala Ala Ala Ala
            325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
            355                 360                 365

Ser Ser Ala Ala Ala Ala Ala Ala Ala Gly Ser Tyr Gly Pro Gly Gln
            370                 375                 380

Gln Gly Pro Tyr Gly Pro Gly Pro Ser Ala Ala Ala Ala Ala Ala Ala
385                 390                 395                 400

Gly Ser Tyr Gln Gln Gly Pro Gly Gln Gln Gly Pro Tyr Gly Pro Gly
            405                 410                 415

Ala Ser Gly Pro Gly Gln Gln Gly Pro Tyr Gly Pro Gly Ala Ser Ala
            420                 425                 430

Ala Ala Ala Ala Ala Ala Gly Pro Gly Gln Tyr Gly Pro Gly Gln Gln
            435                 440                 445

Gly Pro Ser Ala Ser Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
            485                 490                 495

Ala Ala Ala Ala Ala Gly Ser Tyr Gly Pro Gly Gln Gln Gly Pro
    500                 505                 510
```

```
Tyr Gly Pro Gly Pro Ser Ala Ala Ala Ala Ala Ala Gly Pro Gly
        515             520             525

Ser Gly Gln Tyr Gly Pro Gly Ala Ser Gly Gln Asn Gly Pro Gly Ser
    530             535             540

Gly Gln Tyr Gly Pro Gly Gln Gln Gly Pro Gly Pro Ser Ala Ala Ala
545             550             555             560

Ala Ala Ala Ala Gly Pro Gly Ser Gly Gln Gln Gly Pro Gly Ala Ser
        565             570             575
```

```
<210> SEQ ID NO 15
<211> LENGTH: 2375
<212> TYPE: PRT
<213> ORGANISM: Artificial Sequence
<220> FEATURE:
<223> OTHER INFORMATION: PRT799

<400> SEQUENCE: 15

Met His His His His His Ser Ser Gly Ser Ser Gly Pro Gly Gln
1               5               10              15

Gln Gly Pro Tyr Gly Pro Gly Ala Ser Ala Ala Ala Ala Gly Gln
            20              25              30

Asn Gly Pro Gly Ser Gly Gln Gln Gly Pro Gly Gln Ser Gly Gln Tyr
        35              40              45

Gly Pro Gly Gln Gln Gly Pro Gly Gln Gln Gly Pro Gly Ser Ser Ala
    50              55              60

Ala Ala Ala Ala Gly Pro Gly Gln Tyr Gly Pro Gly Gln Gln Gly Pro
65              70              75              80

Ser Ala Ser Ala Ala Ala Ala Ala Gly Pro Gly Ser Gly Gln Gln Gly
            85              90              95

Pro Gly Ala Ser Gly Gln Tyr Gly Pro Gly Gln Gln Gly Pro Gly Gln
            100             105             110

Gln Gly Pro Gly Ser Ser Ala Ala Ala Ala Gly Gln Tyr Gly Ser
        115             120             125

Gly Pro Gly Gln Gln Gly Pro Tyr Gly Ser Ala Ala Ala Ala Ala Gly
    130             135             140

Pro Gly Ser Gly Gln Tyr Gly Gln Gly Pro Tyr Gly Pro Gly Ala Ser
145             150             155             160

Gly Pro Gly Gln Tyr Gly Pro Gly Gln Gln Gly Pro Ser Ala Ser Ala
            165             170             175

Ala Ala Ala Gly Ser Gly Gln Gln Gly Pro Gly Gln Tyr Gly Pro
        180             185             190

Tyr Ala Ser Ala Ala Ala Ala Ala Gly Gln Tyr Gly Ser Gly Pro Gly
        195             200             205

Gln Gln Gly Pro Tyr Gly Pro Gly Gln Ser Gly Ser Gly Gln Gln Gly
    210             215             220

Pro Gly Gln Gln Gly Pro Tyr Ala Ser Ala Ala Ala Ala Gly Pro
225             230             235             240

Gly Gln Gln Gly Pro Tyr Gly Pro Gly Ser Ser Ala Ala Ala Ala Ala
            245             250             255

Gly Gln Tyr Gly Tyr Gly Pro Gly Gln Gln Gly Pro Tyr Gly Pro Gly
            260             265             270

Ala Ser Gly Gln Asn Gly Pro Gly Ser Gly Gln Tyr Gly Pro Gly Gln
        275             280             285

Gln Gly Pro Gly Gln Ser Ala Ala Ala Ala Gly Pro Gly Gln Gln
    290             295             300
```

```
Gly Pro Tyr Gly Pro Gly Ala Ser Ala Ala Ala Ala Ala Gly Gln Tyr
305                 310                 315                 320

Gly Pro Gly Gln Gln Gly Pro Gly Gln Tyr Gly Pro Gly Ser Ser Gly
            325                 330                 335

Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
            355                 360                 365

Ser Ala Ala Ala Ala Ala Gly Gln Tyr Gln Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Ala Gly Pro Gly Gln Tyr Gly
            405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
            485                 490                 495

Gln Tyr Gly Pro Gly Ala Ser Gly Gln Asn Gly Pro Gly Ser Gly Gln
            500                 505                 510

Tyr Gly Pro Gly Gln Gln Gly Pro Gly Gln Ser Ala Ala Ala Ala Ala
        515                 520                 525

Gly Gln Tyr Gln Gln Gly Pro Gly Gln Gly Pro Tyr Gly Pro Gly
    530                 535                 540

Ala Ser Ala Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
        595                 600                 605

Pro Gly Ala Ser Ala Ala Ala Ala Gly Gln Asn Gly Pro Gly Ser
        610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Ala Gly
            645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
        675                 680                 685

Gln Tyr Gly Pro Gly Gln Gln Gly Pro Gly Gln Gln Gly Pro Gly Ser
        690                 695                 700

Ser Ala Ala Ala Ala Ala Gly Gln Tyr Gly Ser Gly Pro Gly Gln Gln
705                 710                 715                 720
```

```
Gly Pro Tyr Gly Ser Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Gly
            755                 760                 765

Ser Gly Gln Gln Gly Pro Gly Gln Tyr Gly Pro Tyr Ala Ser Ala Ala
        770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Ala Gly Pro Gly Gln Gln Gly Pro
            820                 825                 830

Tyr Gly Pro Gly Ser Ser Ala Ala Ala Ala Gly Gln Tyr Gly Tyr
            835                 840                 845

Gly Pro Gly Gln Gln Gly Pro Tyr Gly Pro Gly Ala Ser Gly Gln Asn
    850                 855                 860

Gly Pro Gly Ser Gly Gln Tyr Gly Pro Gly Gln Gln Gly Pro Gly Gln
865                 870                 875                 880

Ser Ala Ala Ala Ala Ala Gly Pro Gly Gln Gln Gly Pro Tyr Gly Pro
            885                 890                 895

Gly Ala Ser Ala Ala Ala Ala Gly Gln Tyr Gly Pro Gly Gln Gln
            900                 905                 910

Gly Pro Gly Gln Tyr Gly Pro Gly Ser Ser Gly Pro Gly Gln Gln Gly
    915                 920                 925

Pro Tyr Gly Pro Gly Ser Ser Ala Ala Ala Ala Gly Gln Tyr Gly
    930                 935                 940

Pro Gly Gln Gln Gly Pro Tyr Gly Pro Gly Gln Ser Ala Ala Ala Ala
945                 950                 955                 960

Ala Gly Gln Tyr Gln Gln Gly Pro Gly Gln Gln Gly Pro Tyr Gly Pro
            965                 970                 975

Gly Ala Ser Gly Pro Gly Gln Gln Gly Pro Tyr Gly Pro Gly Ala Ser
            980                 985                 990

Ala Ala Ala Ala Ala Gly Pro Gly  Gln Tyr Gly Pro Gly  Gln Gln Gly
        995                 1000                 1005

Pro Ser  Ala Ser Ala Ala Ala  Ala Ala Gly Gln Tyr  Gly Ser Gly
    1010                 1015                 1020

Pro Gly  Gln Tyr Gly Pro Tyr  Gly Pro Gly Gln Ser  Gly Pro Gly
    1025                 1030                 1035

Ser Gly  Gln Gln Gly Gln Gly  Pro Tyr Gly Pro Gly  Ala Ser Ala
    1040                 1045                 1050

Ala Ala  Ala Ala Gly Gln Tyr  Gly Pro Gly Gln Gln  Gly Pro Tyr
    1055                 1060                 1065

Gly Pro  Gly Gln Ser Ala Ala  Ala Ala Ala Gly Pro  Gly Ser Gly
    1070                 1075                 1080

Gln Tyr  Gly Pro Gly Ala Ser  Gly Gln Asn Gly Pro  Gly Ser Gly
    1085                 1090                 1095

Gln Tyr  Gly Pro Gly Gln Gln  Gly Pro Gly Gln Ser  Ala Ala Ala
    1100                 1105                 1110

Ala Ala  Gly Gln Tyr Gln Gln  Gly Pro Gly Gln Gln  Gly Pro Tyr
    1115                 1120                 1125

Gly Pro  Gly Ala Ser Ala Ala  Ala Ala Ala Gly Gln  Tyr Gly Ser
```

-continued

```
        1130              1135              1140

Gly Pro Gly Gln Gln Gly Pro Tyr Gly Pro Gly Gln Ser Gly Ser
    1145              1150              1155

Gly Gln Gln Gly Pro Gly Gln Gln Gly Pro Tyr Ala Ser Ala Ala
    1160              1165              1170

Ala Ala Ala Gly Pro Gly Ser Gly Gln Gln Gly Pro Gly Ala Ser
    1175              1180              1185

Gly Gln Gln Gly Pro Tyr Gly Pro Gly Ala Ser Ala Ala Ala Ala
    1190              1195              1200

Ala Gly Gln Asn Gly Pro Gly Ser Gly Gln Gln Gly Pro Gly Gln
    1205              1210              1215

Ser Gly Gln Tyr Gly Pro Gly Gln Gln Gly Pro Gly Gln Gln Gly
    1220              1225              1230

Pro Gly Ser Ser Ala Ala Ala Ala Ala Gly Pro Gly Gln Tyr Gly
    1235              1240              1245

Pro Gly Gln Gln Gly Pro Ser Ala Ser Ala Ala Ala Ala Ala Gly
    1250              1255              1260

Pro Gly Ser Gly Gln Gln Gly Pro Gly Ala Ser Gly Gln Tyr Gly
    1265              1270              1275

Pro Gly Gln Gln Gly Pro Gly Gln Gln Gly Pro Gly Ser Ser Ala
    1280              1285              1290

Ala Ala Ala Ala Gly Gln Tyr Gly Ser Gly Pro Gly Gln Gln Gly
    1295              1300              1305

Pro Tyr Gly Ser Ala Ala Ala Ala Ala Gly Pro Gly Ser Gly Gln
    1310              1315              1320

Tyr Gly Gln Gly Pro Tyr Gly Pro Gly Ala Ser Gly Pro Gly Gln
    1325              1330              1335

Tyr Gly Pro Gly Gln Gln Gly Pro Ser Ala Ser Ala Ala Ala Ala
    1340              1345              1350

Ala Gly Ser Gly Gln Gln Gly Pro Gly Gln Tyr Gly Pro Tyr Ala
    1355              1360              1365

Ser Ala Ala Ala Ala Gly Gln Tyr Gly Ser Gly Pro Gly Gln
    1370              1375              1380

Gln Gly Pro Tyr Gly Pro Gly Gln Ser Gly Ser Gly Gln Gln Gly
    1385              1390              1395

Pro Gly Gln Gln Gly Pro Tyr Ala Ser Ala Ala Ala Ala Ala Gly
    1400              1405              1410

Pro Gly Gln Gln Gly Pro Tyr Gly Pro Gly Ser Ser Ala Ala Ala
    1415              1420              1425

Ala Ala Gly Gln Tyr Gly Tyr Gly Pro Gly Gln Gln Gly Pro Tyr
    1430              1435              1440

Gly Pro Gly Ala Ser Gly Gln Asn Gly Pro Gly Ser Gly Gln Tyr
    1445              1450              1455

Gly Pro Gly Gln Gln Gly Pro Gly Gln Ser Ala Ala Ala Ala Ala
    1460              1465              1470

Gly Pro Gly Gln Gln Gly Pro Tyr Gly Pro Gly Ala Ser Ala Ala
    1475              1480              1485

Ala Ala Ala Gly Gln Tyr Gly Pro Gly Gln Gln Gly Pro Gly Gln
    1490              1495              1500

Tyr Gly Pro Gly Ser Ser Gly Pro Gly Gln Gln Gly Pro Tyr Gly
    1505              1510              1515

Pro Gly Ser Ser Ala Ala Ala Ala Ala Gly Gln Tyr Gly Pro Gly
    1520              1525              1530
```

```
Gln Gln  Gly Pro Tyr Gly Pro  Gly Gln Ser Ala Ala  Ala Ala Ala
    1535                 1540                 1545

Gly Gln  Tyr Gln Gln Gly Pro  Gly Gln Gln Gly Pro  Tyr Gly Pro
    1550                 1555                 1560

Gly Ala  Ser Gly Pro Gly Gln  Gln Gly Pro Tyr Gly  Pro Gly Ala
    1565                 1570                 1575

Ser Ala  Ala Ala Ala Ala Gly  Pro Gly Gln Tyr Gly  Pro Gly Gln
    1580                 1585                 1590

Gln Gly  Pro Ser Ala Ser Ala  Ala Ala Ala Gly  Gln Tyr Gly
    1595                 1600                 1605

Ser Gly  Pro Gly Gln Tyr Gly  Pro Tyr Gly Pro Gly  Gln Ser Gly
    1610                 1615                 1620

Pro Gly  Ser Gly Gln Gln Gly  Gln Gly Pro Tyr Gly  Pro Gly Ala
    1625                 1630                 1635

Ser Ala  Ala Ala Ala Ala Gly  Gln Tyr Gly Pro Gly  Gln Gln Gly
    1640                 1645                 1650

Pro Tyr  Gly Pro Gly Gln Ser  Ala Ala Ala Ala Ala  Gly Pro Gly
    1655                 1660                 1665

Ser Gly  Gln Tyr Gly Pro Gly  Ala Ser Gly Gln Asn  Gly Pro Gly
    1670                 1675                 1680

Ser Gly  Gln Tyr Gly Pro Gly  Gln Gln Gly Pro Gly  Gln Ser Ala
    1685                 1690                 1695

Ala Ala  Ala Ala Gly Gln Tyr  Gln Gln Gly Pro Gly  Gln Gln Gly
    1700                 1705                 1710

Pro Tyr  Gly Pro Gly Ala Ser  Ala Ala Ala Ala Ala  Gly Gln Tyr
    1715                 1720                 1725

Gly Ser  Gly Pro Gly Gln Gln  Gly Pro Tyr Gly Pro  Gly Gln Ser
    1730                 1735                 1740

Gly Ser  Gly Gln Gln Gly Pro  Gly Gln Gln Gly Pro  Tyr Ala Ser
    1745                 1750                 1755

Ala Ala  Ala Ala Ala Gly Pro  Gly Ser Gly Gln Gln  Gly Pro Gly
    1760                 1765                 1770

Ala Ser  Gly Gln Gln Gly Pro  Tyr Gly Pro Gly Ala  Ser Ala Ala
    1775                 1780                 1785

Ala Ala  Ala Gly Gln Asn Gly  Pro Gly Ser Gly Gln  Gln Gly Pro
    1790                 1795                 1800

Gly Gln  Ser Gly Gln Tyr Gly  Pro Gly Gln Gln Gly  Pro Gly Gln
    1805                 1810                 1815

Gln Gly  Pro Gly Ser Ser Ala  Ala Ala Ala Gly  Pro Gly Gln
    1820                 1825                 1830

Tyr Gly  Pro Gly Gln Gln Gly  Pro Ser Ala Ser Ala  Ala Ala Ala
    1835                 1840                 1845

Ala Gly  Pro Gly Ser Gly Gln  Gln Gly Pro Gly Ala  Ser Gly Gln
    1850                 1855                 1860

Tyr Gly  Pro Gly Gln Gln Gly  Pro Gly Gln Gln Gly  Pro Gly Ser
    1865                 1870                 1875

Ser Ala  Ala Ala Ala Ala Gly  Gln Tyr Gly Ser Gly  Pro Gly Gln
    1880                 1885                 1890

Gln Gly  Pro Tyr Gly Ser Ala  Ala Ala Ala Ala Gly  Pro Gly Ser
    1895                 1900                 1905

Gly Gln  Tyr Gly Gln Gly Pro  Tyr Gly Pro Gly Ala  Ser Gly Pro
    1910                 1915                 1920
```

-continued

```
Gly Gln Tyr Gly Pro Gly Gln Gln Gly Pro Ser Ala Ser Ala Ala
    1925              1930              1935

Ala Ala Ala Gly Ser Gly Gln Gln Gly Pro Gly Gln Tyr Gly Pro
    1940              1945              1950

Tyr Ala Ser Ala Ala Ala Ala Ala Gly Gln Tyr Gly Ser Gly Pro
    1955              1960              1965

Gly Gln Gln Gly Pro Tyr Gly Pro Gly Gln Ser Gly Ser Gly Gln
    1970              1975              1980

Gln Gly Pro Gly Gln Gln Gly Pro Tyr Ala Ser Ala Ala Ala Ala
    1985              1990              1995

Ala Gly Pro Gly Gln Gln Gly Pro Tyr Gly Pro Gly Ser Ser Ala
    2000              2005              2010

Ala Ala Ala Ala Gly Gln Tyr Gly Tyr Gly Pro Gly Gln Gln Gly
    2015              2020              2025

Pro Tyr Gly Pro Gly Ala Ser Gly Gln Asn Gly Pro Gly Ser Gly
    2030              2035              2040

Gln Tyr Gly Pro Gly Gln Gln Gly Pro Gly Gln Ser Ala Ala Ala
    2045              2050              2055

Ala Ala Gly Pro Gly Gln Gln Gly Pro Tyr Gly Pro Gly Ala Ser
    2060              2065              2070

Ala Ala Ala Ala Gly Gln Tyr Gly Pro Gly Gln Gln Gly Pro
    2075              2080              2085

Gly Gln Tyr Gly Pro Gly Ser Ser Gly Pro Gly Gln Gln Gly Pro
    2090              2095              2100

Tyr Gly Pro Gly Ser Ser Ala Ala Ala Ala Ala Gly Gln Tyr Gly
    2105              2110              2115

Pro Gly Gln Gln Gly Pro Tyr Gly Pro Gly Gln Ser Ala Ala Ala
    2120              2125              2130

Ala Ala Gly Gln Tyr Gln Gln Gly Pro Gly Gln Gln Gly Pro Tyr
    2135              2140              2145

Gly Pro Gly Ala Ser Gly Pro Gly Gln Gln Gly Pro Tyr Gly Pro
    2150              2155              2160

Gly Ala Ser Ala Ala Ala Ala Ala Gly Pro Gly Gln Tyr Gly Pro
    2165              2170              2175

Gly Gln Gln Gly Pro Ser Ala Ser Ala Ala Ala Ala Gly Gln
    2180              2185              2190

Tyr Gly Ser Gly Pro Gly Gln Tyr Gly Pro Tyr Gly Pro Gly Gln
    2195              2200              2205

Ser Gly Pro Gly Ser Gly Gln Gln Gly Gln Gly Pro Tyr Gly Pro
    2210              2215              2220

Gly Ala Ser Ala Ala Ala Ala Ala Gly Gln Tyr Gly Pro Gly Gln
    2225              2230              2235

Gln Gly Pro Tyr Gly Pro Gly Gln Ser Ala Ala Ala Ala Ala Gly
    2240              2245              2250

Pro Gly Ser Gly Gln Tyr Gly Pro Gly Ala Ser Gly Gln Asn Gly
    2255              2260              2265

Pro Gly Ser Gly Gln Tyr Gly Pro Gly Gln Gln Gly Pro Gly Gln
    2270              2275              2280

Ser Ala Ala Ala Ala Ala Gly Gln Tyr Gln Gln Gly Pro Gly Gln
    2285              2290              2295

Gln Gly Pro Tyr Gly Pro Gly Ala Ser Ala Ala Ala Ala Ala Gly
    2300              2305              2310

Gln Tyr Gly Ser Gly Pro Gly Gln Gln Gly Pro Tyr Gly Pro Gly
```

```
        2315              2320              2325

Gln Ser  Gly Ser Gly Gln Gln  Gly Pro Gly Gln Gln  Gly Pro Tyr
     2330              2335              2340

Ala Ser  Ala Ala Ala Ala Ala  Gly Pro Gly Ser Gly  Gln Gln Gly
     2345              2350              2355

Ser Ser  Val Asp Lys Leu Ala  Ala Ala Leu Glu His  His His His
     2360              2365              2370

His His
     2375

<210> SEQ ID NO 16
<211> LENGTH: 608
<212> TYPE: PRT
<213> ORGANISM: Artificial Sequence
<220> FEATURE:
<223> OTHER INFORMATION: PRT313

<400> SEQUENCE: 16

Met His His His His His His Ser Ser Gly Ser Ser Gly Pro Gly Gly
1               5                  10                  15

Gln Gly Pro Tyr Gly Pro Gly Ala Ser Ala Ala Ala Ala Gly Gly
             20                  25                  30

Asn Gly Pro Gly Ser Gly Gln Gln Gly Pro Gly Gly Ser Ala Ala Ala
         35                  40                  45

Ala Ala Gly Gly Tyr Gly Pro Gly Gly Gln Gly Pro Gly Gln Gln Gly
     50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Gly Pro Gly
             85                  90                  95

Ser Gly Gln Gln Gly Pro Gly Ala Ser Ala Ala Ala Ala Gly Gly
         100                 105                 110

Tyr Gly Pro Gly Gly Gln Gly Pro Gly Gln Gln Gly Pro Gly Ser Ser
         115                 120                 125

Ala Ala Ala Ala Ala Gly Gly Tyr Gly Ser Gly Pro Gly Gln Gln Gly
     130                 135                 140

Pro Tyr Gly Ser Ala Ala Ala Ala Ala Gly Pro Gly Ser Gly Gly Tyr
145                 150                 155                 160

Gly Gln Gly Pro Tyr Gly Pro Gly Ala Ser Ala Ala Ala Ala Gly
             165                 170                 175

Pro Gly Gly Tyr Gly Pro Gly Gly Gln Gly Pro Ser Ala Ser Ala Ala
         180                 185                 190

Ala Ala Ala Gly Ser Gly Gln Gln Gly Pro Gly Gly Tyr Gly Pro Tyr
         195                 200                 205

Ala Ser Ala Ala Ala Ala Ala Gly Gly Tyr Gly Ser Gly Pro Gly Gln
     210                 215                 220

Gln Gly Pro Tyr Gly Pro Gly Gly Ser Ala Ala Ala Ala Ala Gly Ser
225                 230                 235                 240

Gly Gln Gln Gly Pro Gly Gln Gln Gly Pro Tyr Ala Ser Ala Ala Ala
             245                 250                 255

Ala Ala Gly Pro Gly Gly Gln Gly Pro Tyr Gly Pro Gly Ser Ser Ala
         260                 265                 270

Ala Ala Ala Gly Gly Tyr Gly Tyr Gly Pro Gly Gly Gln Gly Pro
         275                 280                 285

Tyr Gly Pro Gly Ala Ser Ala Ala Ala Ala Ala Gly Gly Asn Gly Pro
```

```
        290                 295                 300
Gly Ser Gly Gly Tyr Gly Pro Gly Gln Gln Gly Pro Gly Gly Ser Ala
305                 310                 315                 320

Ala Ala Ala Ala Gly Pro Gly Gly Gln Gly Pro Tyr Gly Pro Gly Ala
                325                 330                 335

Ser Ala Ala Ala Ala Ala Gly Gly Tyr Gly Pro Gly Gly Gln Gly Pro
            340                 345                 350

Gly Gly Tyr Gly Pro Gly Ser Ser Ala Ala Ala Ala Gly Pro Gly
            355                 360                 365

Gly Gln Gly Pro Tyr Gly Pro Gly Ser Ser Ala Ala Ala Ala Gly
        370                 375                 380

Gly Tyr Gly Pro Gly Gln Gln Gly Pro Tyr Gly Pro Gly Gly Ser Ala
385                 390                 395                 400

Ala Ala Ala Gly Gly Tyr Gln Gln Gly Pro Gly Gly Gln Gly Pro
                405                 410                 415

Tyr Gly Pro Gly Ala Ser Ala Ala Ala Ala Gly Pro Gly Gly Gln
            420                 425                 430

Gly Pro Tyr Gly Pro Gly Ala Ser Ala Ala Ala Ala Gly Pro Gly
        435                 440                 445

Gly Tyr Gly Pro Gly Gly Gln Gly Pro Ser Ala Ser Ala Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
        500                 505                 510

Tyr Gly Pro Gly Gln Gln Gly Pro Tyr Gly Pro Gly Gly Ser Ala Ala
        515                 520                 525

Ala Ala Ala Gly Pro Gly Ser Gly Gly Tyr Gly Pro Gly Ala Ser Ala
    530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Ala Gly Gly Tyr
            565                 570                 575

Gln Gln Gly Pro Gly Gly Gln Gly Pro Tyr Gly Pro Gly Ala Ser Ala
            580                 585                 590

Ala Ala Ala Gly Pro Gly Ser Gly Gln Gln Gly Pro Gly Ala Ser
        595                 600                 605
```

<210> SEQ ID NO 17
<211> LENGTH: 590
<212> TYPE: PRT
<213> ORGANISM: Artificial Sequence
<220> FEATURE:
<223> OTHER INFORMATION: Met-PRT399

<400> SEQUENCE: 17

```
Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gly Gln Gly Pro Gly Gln Gln Gly
        35                  40                  45

Pro Gly Ser Ser Ala Ala Ala Ala Ala Gly Pro Gly Gly Tyr Gly Pro
```

```
            50                  55                  60

Gly Gly Gln Gly Pro Ser Ala Ser Ala Ala Ala Ala Ala Gly Pro Gly
65                  70                  75                  80

Ser Gly Gln Gln Gly Pro Gly Ala Ser Gly Gly Tyr Gly Pro Gly Gly
                    85                  90                  95

Gln Gly Pro Gly Gln Gln Gly Pro Gly Ser Ser Ala Ala Ala Ala Ala
                100                 105                 110

Gly Gly Tyr Gly Ser Gly Pro Gly Gln Gln Gly Pro Tyr Gly Ser Ala
                115                 120                 125

Ala Ala Ala Ala Gly Pro Gly Ser Gly Gly Tyr Gly Gln Gly Pro Tyr
        130                 135                 140

Gly Pro Gly Ala Ser Gly Pro Gly Gly Tyr Gly Pro Gly Gly Gln Gly
145                 150                 155                 160

Pro Ser Ala Ser Ala Ala Ala Ala Gly Ser Gly Gln Gln Gly Pro
                165                 170                 175

Gly Gly Tyr Gly Pro Tyr Ala Ser Ala Ala Ala Ala Gly Gly Tyr
                180                 185                 190

Gly Ser Gly Pro Gly Gln Gln Gly Pro Tyr Gly Pro Gly Gly Ser Gly
                195                 200                 205

Ser Gly Gln Gln Gly Pro Gly Gln Gln Gly Pro Tyr Ala Ser Ala Ala
        210                 215                 220

Ala Ala Ala Gly Pro Gly Gly Gln Gly Pro Tyr Gly Pro Gly Ser Ser
225                 230                 235                 240

Ala Ala Ala Ala Ala Gly Gly Tyr Gly Tyr Gly Pro Gly Gly Gln Gly
                245                 250                 255

Pro Tyr Gly Pro Gly Ala Ser Gly Gly Asn Gly Pro Gly Ser Gly Gly
                260                 265                 270

Tyr Gly Pro Gly Gln Gln Gly Pro Gly Gly Ser Ala Ala Ala Ala Ala
                275                 280                 285

Gly Pro Gly Gly Gln Gly Pro Tyr Gly Pro Gly Ala Ser Ala Ala Ala
        290                 295                 300

Ala Ala Gly Gly Tyr Gly Pro Gly Gly Gln Gly Pro Gly Gly Tyr Gly
305                 310                 315                 320

Pro Gly Ser Ser Gly Pro Gly Gly Gln Gly Pro Tyr Gly Pro Gly Ser
                325                 330                 335

Ser Ala Ala Ala Ala Ala Gly Gly Tyr Gly Pro Gly Gln Gln Gly Pro
        340                 345                 350

Tyr Gly Pro Gly Gly Ser Ala Ala Ala Ala Ala Gly Gly Tyr Gln Gln
        355                 360                 365

Gly Pro Gly Gly Gln Gly Pro Tyr Gly Pro Gly Ala Ser Gly Pro Gly
        370                 375                 380

Gly Gln Gly Pro Tyr Gly Pro Gly Ala Ser Ala Ala Ala Ala Gly
385                 390                 395                 400

Pro Gly Gly Tyr Gly Pro Gly Gly Gln Gly Pro Ser Ala Ser Ala Ala
                405                 410                 415

Ala Ala Ala Gly Gly Tyr Gly Ser Gly Pro Gly Gly Tyr Gly Pro Tyr
                420                 425                 430

Gly Pro Gly Gly Ser Gly Pro Gly Ser Gly Gln Gln Gly Gln Gly Pro
        435                 440                 445

Tyr Gly Pro Gly Ala Ser Ala Ala Ala Ala Gly Gly Tyr Gly Pro
        450                 455                 460

Gly Gln Gln Gly Pro Tyr Gly Pro Gly Gly Ser Ala Ala Ala Ala Ala
465                 470                 475                 480
```

```
Gly Pro Gly Ser Gly Gly Tyr Gly Pro Gly Ala Ser Gly Gly Asn Gly
            485                 490                 495

Pro Gly Ser Gly Gly Tyr Gly Pro Gly Gln Gln Gly Pro Gly Gly Ser
            500                 505                 510

Ala Ala Ala Ala Ala Gly Gly Tyr Gln Gln Gly Pro Gly Gly Gln Gly
            515                 520                 525

Pro Tyr Gly Pro Gly Ala Ser Ala Ala Ala Ala Gly Gly Tyr Gly
    530                 535                 540

Ser Gly Pro Gly Gln Gln Gly Pro Tyr Gly Pro Gly Ser Gly Ser
545                 550                 555                 560

Gly Gln Gln Gly Pro Gly Gln Gln Gly Pro Tyr Ala Ser Ala Ala Ala
            565                 570                 575

Ala Ala Gly Pro Gly Ser Gly Gln Gln Gly Pro Gly Ala Ser
            580                 585                 590

<210> SEQ ID NO 18
<211> LENGTH: 601
<212> TYPE: PRT
<213> ORGANISM: Artificial Sequence
<220> FEATURE:
<223> OTHER INFORMATION: PRT399

<400> SEQUENCE: 18

Met His His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Gly Gly Tyr
            35                  40                  45

Gly Pro Gly Gly Gln Gly Pro Gly Gln Gln Gly Pro Gly Ser Ser Ala
    50                  55                  60

Ala Ala Ala Ala Gly Pro Gly Gly Tyr Gly Pro Gly Gly Gln Gly Pro
65                  70                  75                  80

Ser Ala Ser Ala Ala Ala Ala Ala Gly Pro Gly Ser Gly Gln Gln Gly
            85                  90                  95

Pro Gly Ala Ser Gly Gly Tyr Gly Pro Gly Gly Gln Gly Pro Gly Gln
            100                 105                 110

Gln Gly Pro Gly Ser Ser Ala Ala Ala Ala Ala Gly Gly Tyr Gly Ser
            115                 120                 125

Gly Pro Gly Gln Gln Gly Pro Tyr Gly Ser Ala Ala Ala Ala Ala Gly
    130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Gly Pro Ser Ala Ser Ala
            165                 170                 175

Ala Ala Ala Gly Ser Gly Gln Gln Gly Pro Gly Gly Tyr Gly Pro
            180                 185                 190

Tyr Ala Ser Ala Ala Ala Ala Ala Gly Gly Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Ala Ser Ala Ala Ala Ala Gly Pro
225                 230                 235                 240

Gly Gly Gln Gly Pro Tyr Gly Pro Gly Ser Ser Ala Ala Ala Ala Ala
            245                 250                 255
```

-continued

```
Gly Gly Tyr Gly Tyr Gly Pro Gly Gly Gln Gly Pro Tyr Gly Pro Gly
            260                 265                 270

Ala Ser Gly Gly Asn Gly Pro Gly Ser Gly Gly Tyr Gly Pro Gly Gln
            275                 280                 285

Gln Gly Pro Gly Gly Ser Ala Ala Ala Ala Gly Pro Gly Gly Gln
            290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
            325                 330                 335

Pro Gly Gly Gln Gly Pro Tyr Gly Pro Gly Ser Ser Ala Ala Ala
            340                 345                 350

Ala Gly Gly Tyr Gly Pro Gly Gln Gln Gly Pro Tyr Gly Pro Gly Gly
            355                 360                 365

Ser Ala Ala Ala Ala Ala Gly Gly Tyr Gln Gln Gly Pro Gly Gly Gln
    370                 375                 380

Gly Pro Tyr Gly Pro Gly Ala Ser Gly Pro Gly Gly Gln Gly Pro Tyr
385                 390                 395                 400

Gly Pro Gly Ala Ser Ala Ala Ala Ala Gly Pro Gly Gly Tyr Gly
            405                 410                 415

Pro Gly Gly Gln Gly Pro Ser Ala Ser Ala Ala Ala Ala Gly Gly
            420                 425                 430

Tyr Gly Ser Gly Pro Gly Gly Tyr Gly Pro Tyr Gly Pro Gly Gly Ser
            435                 440                 445

Gly Pro Gly Ser Gly Gln Gln Gly Gln Gly Pro Tyr Gly Pro Gly Ala
    450                 455                 460

Ser Ala Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
            485                 490                 495

Gly Tyr Gly Pro Gly Ala Ser Gly Gly Asn Gly Pro Gly Ser Gly Gly
            500                 505                 510

Tyr Gly Pro Gly Gln Gln Gly Pro Gly Gly Ser Ala Ala Ala Ala Ala
            515                 520                 525

Gly Gly Tyr Gln Gln Gly Pro Gly Gly Gln Gly Pro Tyr Gly Pro Gly
    530                 535                 540

Ala Ser Ala Ala Ala Ala Ala Gly Gly Tyr Gly Ser Gly Pro Gly Gln
545                 550                 555                 560

Gln Gly Pro Tyr Gly Pro Gly Gly Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
        595                 600
```

```
<210> SEQ ID NO 19
<211> LENGTH: 612
<212> TYPE: PRT
<213> ORGANISM: Artificial Sequence
<220> FEATURE:
<223> OTHER INFORMATION: Met-PRT720

<400> SEQUENCE: 19
```

```
Met Gly Pro Gly Gln Gln Gly Pro Tyr Gly Pro Gly Ala Ser Ala Ala
1               5                   10                  15
```

```
Ala Ala Ala Gly Gln Asn Gly Pro Gly Ser Gly Gln Gln Gly Pro Gly
         20                  25                  30

Gln Ser Gly Gln Tyr Gly Pro Gly Gln Gln Gly Pro Gly Gln Gln Gly
         35                  40                  45

Pro Gly Ser Ser Ala Ala Ala Ala Ala Gly Pro Gly Gln Tyr Val Leu
    50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gln Gly Pro Gly Gln Gln Gly Pro Gly Ser
         100                 105                 110

Ser Ala Ala Ala Ala Ala Gly Ser Tyr Gly Ser Val Leu Ile Gly Pro
         115                 120                 125

Gly Gln Gln Val Leu Ile Gly Pro Tyr Gly Ser Ala Ala Ala Ala Ala
    130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
         165                 170                 175

Ala Ala Ala Ala Ala Gly Ser Gly Gln Gln Val Leu Ile Gly Pro Gly
         180                 185                 190

Gln Tyr Val Leu Ile Gly Pro Tyr Ala Ser Ala Ala Ala Ala Ala Gly
         195                 200                 205

Gln Tyr Gly Ser Gly Pro Gly Gln Gln Gly Pro Tyr Gly Pro Gly Gln
    210                 215                 220

Ser Gly Ser Gly Gln Gln Gly Pro Gly Gln Gln Gly Pro Tyr Ala Ser
225                 230                 235                 240

Ala Ala Ala Ala Ala Gly Pro Gly Gln Gln Val Leu Ile Gly Pro Tyr
         245                 250                 255

Val Leu Ile Gly Pro Gly Ser Ser Ala Ala Ala Ala Ala Gly Gln Tyr
         260                 265                 270

Gly Tyr Gly Pro Gly Gln Gln Gly Pro Tyr Gly Pro Gly Ala Ser Gly
         275                 280                 285

Gln Asn Gly Pro Gly Ser Gly Gln Tyr Gly Pro Gly Gln Gln Gly Pro
    290                 295                 300

Gly Gln Ser Ala Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala Ala
         325                 330                 335

Gly Gln Tyr Gly Pro Gly Gln Gln Gly Pro Gly Gln Tyr Gly Pro Gly
         340                 345                 350

Ser Ser Gly Pro Gly Gln Gln Gly Pro Tyr Gly Pro Gly Ser Ser Ala
         355                 360                 365

Ala Ala Ala Gly Ser Tyr Gly Pro Gly Gln Gln Val Leu Ile Gly
    370                 375                 380

Pro Tyr Val Leu Ile Gly Pro Gly Pro Ser Ala Ala Ala Ala Ala Gly
385                 390                 395                 400

Gln Tyr Gln Gln Gly Pro Gly Gln Gln Gly Pro Tyr Gly Pro Gly Ala
         405                 410                 415

Ser Gly Pro Gly Gln Gln Gly Pro Tyr Gly Pro Gly Ala Ser Ala Ala
         420                 425                 430
```

-continued

```
Ala Ala Ala Gly Pro Gly Gln Tyr Val Leu Ile Gly Pro Gly Gln Gln
        435                 440                 445

Val Leu Ile Gly Pro Ser Ala Ser Ala Ala Ala Ala Gly Gln Tyr
    450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
            485                 490                 495

Ala Ala Ala Ala Ala Gly Ser Tyr Gly Pro Gly Gln Gln Val Leu Ile
        500                 505                 510

Gly Pro Tyr Val Leu Ile Gly Pro Gly Pro Ser Ala Ala Ala Ala Ala
        515                 520                 525

Gly Pro Gly Ser Gly Gln Tyr Gly Pro Gly Ala Ser Gly Gln Asn Gly
    530                 535                 540

Pro Gly Ser Gly Gln Tyr Gly Pro Gly Gln Gln Gly Pro Gly Gln Ser
545                 550                 555                 560

Ala Ala Ala Ala Ala Gly Gln Tyr Gln Gln Val Leu Ile Gly Pro Gly
            565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
        595                 600                 605

Ser Val Leu Ile
        610

<210> SEQ ID NO 20
<211> LENGTH: 592
<212> TYPE: PRT
<213> ORGANISM: Artificial Sequence
<220> FEATURE:
<223> OTHER INFORMATION: Met-PRT665

<400> SEQUENCE: 20

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
        20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Gly Pro Gly
    50                  55                  60

Gln Tyr Val Leu Ile Gly Pro Gly Gln Gln Gly Pro Ser Ala Ser Ala
65                  70                  75                  80

Ala Ala Ala Ala Ala Gly Pro Gly Ser Gly Gln Gln Gly Pro Gly
            85                  90                  95

Ala Ser Gly Gln Tyr Gly Pro Gly Gln Gln Gly Pro Gly Gln Gln Gly
        100                 105                 110

Pro Gly Ser Ser Ala Ala Ala Ala Ala Ala Gly Ser Tyr Gly Ser
        115                 120                 125

Val Leu Ile Gly Pro Gly Gln Gln Gly Pro Tyr Gly Ser Ala Ala Ala
    130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
            165                 170                 175
```

-continued

```
Pro Ser Ala Ser Ala Ala Ala Ala Ala Ala Gly Ser Gly Gln Gln
        180             185             190

Val Leu Ile Gly Pro Gly Gln Tyr Gly Pro Tyr Ala Ser Ala Ala Ala
        195             200             205

Ala Ala Ala Ala Gly Ser Tyr Gly Ser Gly Pro Gly Gln Gln Gly Pro
        210             215             220

Tyr Gly Pro Gly Gln Ser Gly Ser Gly Gln Gln Gly Pro Gly Gln Gln
225             230             235             240

Gly Pro Tyr Ala Ser Ala Ala Ala Ala Ala Ala Gly Pro Gly Gln
        245             250             255

Gln Val Leu Ile Gly Pro Tyr Gly Pro Gly Ser Ser Ala Ala Ala Ala
        260             265             270

Ala Ala Ala Gly Ser Tyr Gly Tyr Gly Pro Gly Gln Gln Gly Pro Tyr
        275             280             285

Gly Pro Gly Ala Ser Gly Gln Asn Gly Pro Gly Ser Gly Gln Tyr Gly
        290             295             300

Pro Gly Gln Gln Gly Pro Gly Pro Ser Ala Ala Ala Ala Ala Ala Ala
305             310             315             320

Gly Pro Gly Gln Gln Val Leu Ile Gly Pro Tyr Gly Pro Gly Ala Ser
        325             330             335

Ala Ala Ala Ala Ala Ala Ala Gly Ser Tyr Gly Pro Gly Gln Gln Gly
        340             345             350

Pro Gly Gln Tyr Gly Pro Gly Ser Ser Gly Pro Gly Gln Gln Gly Pro
        355             360             365

Tyr Gly Pro Gly Ser Ser Ala Ala Ala Ala Ala Ala Gly Ser Tyr
        370             375             380

Gly Pro Gly Gln Gln Val Leu Ile Gly Pro Tyr Gly Pro Gly Pro Ser
385             390             395             400

Ala Ala Ala Ala Ala Ala Ala Gly Ser Tyr Gln Gln Gly Pro Gly Gln
        405             410             415

Gln Gly Pro Tyr Gly Pro Gly Ala Ser Gly Pro Gly Gln Gln Gly Pro
        420             425             430

Tyr Gly Pro Gly Ala Ser Ala Ala Ala Ala Ala Ala Gly Pro Gly
        435             440             445

Gln Tyr Val Leu Ile Gly Pro Gly Gln Gln Gly Pro Ser Ala Ser Ala
        450             455             460

Ala Ala Ala Ala Ala Gly Ser Tyr Gly Ser Gly Pro Gly Gln Tyr
465             470             475             480

Gly Pro Tyr Gly Pro Gly Gln Ser Gly Pro Gly Ser Gly Gln Gln Gly
        485             490             495

Gln Gly Pro Tyr Gly Pro Gly Ala Ser Ala Ala Ala Ala Ala Ala
        500             505             510

Gly Ser Tyr Gly Pro Gly Gln Gln Val Leu Ile Gly Pro Tyr Gly Pro
        515             520             525

Gly Pro Ser Ala Ala Ala Ala Ala Ala Gly Pro Gly Ser Gly Gln
        530             535             540

Tyr Gly Pro Gly Ala Ser Gly Gln Asn Gly Pro Gly Ser Gly Gln Tyr
545             550             555             560

Gly Pro Gly Gln Gln Gly Pro Gly Pro Ser Ala Ala Ala Ala Ala Ala
        565             570             575

Ala Gly Pro Gly Ser Gly Gln Gln Gly Pro Gly Ala Ser Val Leu Ile
        580             585             590
```

```
<210> SEQ ID NO 21
<211> LENGTH: 619
<212> TYPE: PRT
<213> ORGANISM: Artificial Sequence
<220> FEATURE:
<223> OTHER INFORMATION: Met-PRT666

<400> SEQUENCE: 21

Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Gly Pro Gly
    50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
            100                 105                 110

Gln Gln Gly Pro Gly Ser Ser Ala Ala Ala Ala Ala Ala Gly Ser
        115                 120                 125

Tyr Gly Ser Val Leu Ile Gly Pro Gly Gln Gln Val Leu Ile Gly Pro
    130                 135                 140

Tyr Gly Ser Ala Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
                165                 170                 175

Gly Pro Gly Gln Gln Gly Pro Ser Ala Ser Ala Ala Ala Ala Ala Ala
            180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Ala Gly Ser Tyr
    210                 215                 220

Gly Ser Gly Pro Gly Gln Gln Gly Pro Tyr Gly Pro Gly Gln Ser Gly
225                 230                 235                 240

Ser Gly Gln Gln Gly Pro Gly Gln Gln Gly Pro Tyr Ala Ser Ala Ala
                245                 250                 255

Ala Ala Ala Ala Ala Gly Pro Gly Gln Gln Val Leu Ile Gly Pro Tyr
            260                 265                 270

Val Leu Ile Gly Pro Gly Ser Ser Ala Ala Ala Ala Ala Ala Gly
        275                 280                 285

Ser Tyr Gly Tyr Gly Pro Gly Gln Gln Gly Pro Tyr Gly Pro Gly Ala
    290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Gly Pro Gly Gln
            325                 330                 335

Gln Val Leu Ile Gly Pro Tyr Val Leu Ile Gly Pro Gly Ala Ser Ala
        340                 345                 350

Ala Ala Ala Ala Ala Gly Ser Tyr Gly Pro Gly Gln Gln Gly Pro
    355                 360                 365

Gly Gln Tyr Gly Pro Gly Ser Ser Gly Pro Gly Gln Gln Gly Pro Tyr
```

-continued

```
          370                375                380

Gly Pro Gly Ser Ser Ala Ala Ala Ala Ala Ala Gly Ser Tyr Gly
385                 390                395                400

Pro Gly Gln Gln Val Leu Ile Gly Pro Tyr Val Leu Ile Gly Pro Gly
                405                410                415

Pro Ser Ala Ala Ala Ala Ala Ala Ala Gly Ser Tyr Gln Gln Gly Pro
                420                425                430

Gly Gln Gln Gly Pro Tyr Gly Pro Gly Ala Ser Gly Pro Gly Gln Gln
            435                440                445

Gly Pro Tyr Gly Pro Gly Ala Ser Ala Ala Ala Ala Ala Ala Gly
    450                455                460

Pro Gly Gln Tyr Val Leu Ile Gly Pro Gly Gln Gln Val Leu Ile Gly
465                470                475                480

Pro Ser Ala Ser Ala Ala Ala Ala Ala Ala Gly Ser Tyr Gly Ser
                485                490                495

Gly Pro Gly Gln Tyr Gly Pro Tyr Gly Pro Gly Gln Ser Gly Pro Gly
                500                505                510

Ser Gly Gln Gln Gly Gln Gly Pro Tyr Gly Pro Gly Ala Ser Ala Ala
            515                520                525

Ala Ala Ala Ala Ala Gly Ser Tyr Gly Pro Gly Gln Gln Val Leu Ile
    530                535                540

Gly Pro Tyr Val Leu Ile Gly Pro Gly Pro Ser Ala Ala Ala Ala Ala
545                550                555                560

Ala Ala Gly Pro Gly Ser Gly Gln Tyr Gly Pro Gly Ala Ser Gly Gln
                565                570                575

Asn Gly Pro Gly Ser Gly Gln Tyr Gly Pro Gly Gln Gln Gly Pro Gly
                580                585                590

Pro Ser Ala Ala Ala Ala Ala Ala Ala Gly Pro Gly Ser Gly Gln Gln
            595                600                605

Val Leu Ile Gly Pro Gly Ala Ser Val Leu Ile
    610                615
```

```
<210> SEQ ID NO 22
<211> LENGTH: 623
<212> TYPE: PRT
<213> ORGANISM: Artificial Sequence
<220> FEATURE:
<223> OTHER INFORMATION: PRT720

<400> SEQUENCE: 22

Met His His His His His His Ser Ser Gly Ser Ser Gly Pro Gly Gln
1                5                10                15

Gln Gly Pro Tyr Gly Pro Gly Ala Ser Ala Ala Ala Ala Gly Gln
                20                25                30

Asn Gly Pro Gly Ser Gly Gln Gln Gly Pro Gly Gln Ser Gly Gln Tyr
            35                40                45

Gly Pro Gly Gln Gln Gly Pro Gly Gln Gln Gly Pro Gly Ser Ser Ala
    50                55                60

Ala Ala Ala Gly Pro Gly Gln Tyr Val Leu Ile Gly Pro Gly Gln
65                70                75                80

Gln Val Leu Ile Gly Pro Ser Ala Ser Ala Ala Ala Ala Gly Pro
                85                90                95

Gly Ser Gly Gln Gln Gly Pro Gly Ala Ser Gly Gln Tyr Gly Pro Gly
                100                105                110

Gln Gln Gly Pro Gly Gln Gln Gly Pro Gly Ser Ser Ala Ala Ala Ala
```

-continued

```
            115              120              125
Ala Gly Ser Tyr Gly Ser Val Leu Ile Gly Pro Gly Gln Gln Val Leu
    130              135              140
Ile Gly Pro Tyr Gly Ser Ala Ala Ala Ala Gly Pro Gly Ser Gly
145              150              155              160
Gln Tyr Gly Gln Gly Pro Tyr Gly Pro Gly Ala Ser Gly Pro Gly Gln
                 165              170              175
Tyr Gly Pro Gly Gln Gln Gly Pro Ser Ala Ser Ala Ala Ala Ala
                 180              185              190
Gly Ser Gly Gln Gln Val Leu Ile Gly Pro Gly Gln Tyr Val Leu Ile
                 195              200              205
Gly Pro Tyr Ala Ser Ala Ala Ala Ala Gly Gln Tyr Gly Ser Gly
    210              215              220
Pro Gly Gln Gln Gly Pro Tyr Gly Pro Gly Gln Ser Gly Ser Gly Gln
225              230              235              240
Gln Gly Pro Gly Gln Gln Gly Pro Tyr Ala Ser Ala Ala Ala Ala Ala
             245              250              255
Gly Pro Gly Gln Gln Val Leu Ile Gly Pro Tyr Val Leu Ile Gly Pro
             260              265              270
Gly Ser Ser Ala Ala Ala Ala Ala Gly Gln Tyr Gly Tyr Gly Pro Gly
         275              280              285
Gln Gln Gly Pro Tyr Gly Pro Gly Ala Ser Gly Gln Asn Gly Pro Gly
    290              295              300
Ser Gly Gln Tyr Gly Pro Gly Gln Gln Gly Pro Gly Gln Ser Ala Ala
305              310              315              320
Ala Ala Ala Gly Pro Gly Gln Gln Val Leu Ile Gly Pro Tyr Val Leu
             325              330              335
Ile Gly Pro Gly Ala Ser Ala Ala Ala Ala Gly Gln Tyr Gly Pro
             340              345              350
Gly Gln Gln Gly Pro Gly Gln Tyr Gly Pro Gly Ser Ser Gly Pro Gly
         355              360              365
Gln Gln Gly Pro Tyr Gly Pro Gly Ser Ser Ala Ala Ala Ala Gly
    370              375              380
Ser Tyr Gly Pro Gly Gln Gln Val Leu Ile Gly Pro Tyr Val Leu Ile
385              390              395              400
Gly Pro Gly Pro Ser Ala Ala Ala Ala Gly Gln Tyr Gln Gln Gly
             405              410              415
Pro Gly Gln Gln Gly Pro Tyr Gly Pro Gly Ala Ser Gly Pro Gly Gln
         420              425              430
Gln Gly Pro Tyr Gly Pro Gly Ala Ser Ala Ala Ala Ala Gly Pro
         435              440              445
Gly Gln Tyr Val Leu Ile Gly Pro Gly Gln Gln Val Leu Ile Gly Pro
    450              455              460
Ser Ala Ser Ala Ala Ala Ala Ala Gly Gln Tyr Gly Ser Gly Pro Gly
465              470              475              480
Gln Tyr Gly Pro Tyr Gly Pro Gly Gln Ser Gly Pro Gly Ser Gly Gln
             485              490              495
Gln Gly Gln Gly Pro Tyr Gly Pro Gly Ala Ser Ala Ala Ala Ala Ala
         500              505              510
Gly Ser Tyr Gly Pro Gly Gln Gln Val Leu Ile Gly Pro Tyr Val Leu
         515              520              525
Ile Gly Pro Gly Pro Ser Ala Ala Ala Ala Ala Gly Pro Gly Ser Gly
    530              535              540
```

```
Gln Tyr Gly Pro Gly Ala Ser Gly Gln Asn Gly Pro Gly Ser Gly Gln
545                 550                 555                 560

Tyr Gly Pro Gly Gln Gln Gly Pro Gly Gln Ser Ala Ala Ala Ala Ala
                565                 570                 575

Gly Gln Tyr Gln Gln Val Leu Ile Gly Pro Gly Gln Gln Gly Pro Tyr
            580                 585                 590

Val Leu Ile Gly Pro Gly Ala Ser Ala Ala Ala Ala Gly Pro Gly
        595                 600                 605

Ser Gly Gln Gln Val Leu Ile Gly Pro Gly Ala Ser Val Leu Ile
        610                 615                 620

<210> SEQ ID NO 23
<211> LENGTH: 603
<212> TYPE: PRT
<213> ORGANISM: Artificial Sequence
<220> FEATURE:
<223> OTHER INFORMATION: PRT665

<400> SEQUENCE: 23

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
            20                  25                  30

Gly Ser Asn Gly Pro Gly Ser Gly Gln Gln Gly Pro Gly Gln Ser Gly
        35                  40                  45

Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Gly Pro Ser Ala Ser Ala Ala Ala Ala Ala
                85                  90                  95

Ala Gly Pro Gly Ser Gly Gln Gln Gly Pro Gly Ala Ser Gly Gln Tyr
        100                 105                 110

Gly Pro Gly Gln Gln Gly Pro Gly Gln Gln Gly Pro Gly Ser Ser Ala
        115                 120                 125

Ala Ala Ala Ala Ala Gly Ser Tyr Gly Ser Val Leu Ile Gly Pro
    130                 135                 140

Gly Gln Gln Gly Pro Tyr Gly Ser Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
            180                 185                 190

Ala Ala Ala Ala Ala Gly Ser Gly Gln Gln Val Leu Ile Gly Pro
        195                 200                 205

Gly Gln Tyr Gly Pro Tyr Ala Ser Ala Ala Ala Ala Ala Ala Gly
    210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
                245                 250                 255

Ala Ala Ala Ala Ala Ala Gly Pro Gly Gln Gln Val Leu Ile Gly
            260                 265                 270

Pro Tyr Gly Pro Gly Ser Ser Ala Ala Ala Ala Ala Ala Gly Ser
    275                 280                 285
```

-continued

```
Tyr Gly Tyr Gly Pro Gly Gln Gln Gly Pro Tyr Gly Pro Gly Ala Ser
    290             295             300

Gly Gln Asn Gly Pro Gly Ser Gly Gln Tyr Gly Pro Gly Gln Gln Gly
305             310             315             320

Pro Gly Pro Ser Ala Ala Ala Ala Ala Ala Ala Gly Pro Gly Gln Gln
                325             330             335

Val Leu Ile Gly Pro Tyr Gly Pro Gly Ala Ser Ala Ala Ala Ala Ala
            340             345             350

Ala Ala Gly Ser Tyr Gly Pro Gly Gln Gln Gly Pro Gly Gln Tyr Gly
        355             360             365

Pro Gly Ser Ser Gly Pro Gly Gln Gln Gly Pro Tyr Gly Pro Gly Ser
    370             375             380

Ser Ala Ala Ala Ala Ala Ala Ala Gly Ser Tyr Gly Pro Gly Gln Gln
385             390             395             400

Val Leu Ile Gly Pro Tyr Gly Pro Gly Pro Ser Ala Ala Ala Ala Ala
            405             410             415

Ala Ala Gly Ser Tyr Gln Gln Gly Pro Gly Gln Gln Gly Pro Tyr Gly
        420             425             430

Pro Gly Ala Ser Gly Pro Gly Gln Gln Gly Pro Tyr Gly Pro Gly Ala
    435             440             445

Ser Ala Ala Ala Ala Ala Ala Ala Gly Pro Gly Gln Tyr Val Leu Ile
    450             455             460

Gly Pro Gly Gln Gln Gly Pro Ser Ala Ser Ala Ala Ala Ala Ala Ala
465             470             475             480

Ala Gly Ser Tyr Gly Ser Gly Pro Gly Gln Tyr Gly Pro Tyr Gly Pro
        485             490             495

Gly Gln Ser Gly Pro Gly Ser Gly Gln Gln Gly Gln Gly Pro Tyr Gly
        500             505             510

Pro Gly Ala Ser Ala Ala Ala Ala Ala Ala Gly Ser Tyr Gly Pro
        515             520             525

Gly Gln Gln Val Leu Ile Gly Pro Tyr Gly Pro Gly Pro Ser Ala Ala
    530             535             540

Ala Ala Ala Ala Gly Pro Gly Ser Gly Gln Tyr Gly Pro Gly Ala
545             550             555             560

Ser Gly Gln Asn Gly Pro Gly Ser Gly Gln Tyr Gly Pro Gly Gln Gln
        565             570             575

Gly Pro Gly Pro Ser Ala Ala Ala Ala Ala Ala Gly Pro Gly Ser
        580             585             590

Gly Gln Gln Gly Pro Gly Ala Ser Val Leu Ile
    595             600
```

```
<210> SEQ ID NO 24
<211> LENGTH: 630
<212> TYPE: PRT
<213> ORGANISM: Artificial Sequence
<220> FEATURE:
<223> OTHER INFORMATION: PRT666

<400> SEQUENCE: 24

Met His His His His His His Ser Ser Gly Ser Ser Gly Pro Gly Gln
1               5               10              15

Gln Gly Pro Tyr Gly Pro Gly Ala Ser Ala Ala Ala Ala Ala Ala
            20              25              30

Gly Ser Asn Gly Pro Gly Ser Gly Gln Gln Gly Pro Gly Gln Ser Gly
        35              40              45
```

-continued

```
Gln Tyr Gly Pro Gly Gln Gln Gly Pro Gly Gln Gln Gly Pro Gly Ser
    50                  55                  60

Ser Ala Ala Ala Ala Ala Ala Gly Pro Gly Gln Tyr Val Leu Ile
65                  70                  75                  80

Gly Pro Gly Gln Gln Val Leu Ile Gly Pro Ser Ala Ser Ala Ala Ala
                85                  90                  95

Ala Ala Ala Ala Gly Pro Gly Ser Gly Gln Gln Gly Pro Gly Ala Ser
                100                 105                 110

Gly Gln Tyr Gly Pro Gly Gln Gln Gly Pro Gly Gln Gln Gly Pro Gly
        115                 120                 125

Ser Ser Ala Ala Ala Ala Ala Ala Gly Ser Tyr Gly Ser Val Leu
    130                 135                 140

Ile Gly Pro Gly Gln Gln Val Leu Ile Gly Pro Tyr Gly Ser Ala Ala
145                 150                 155                 160

Ala Ala Ala Ala Ala Gly Pro Gly Ser Gly Gln Tyr Gly Gln Gly Pro
                165                 170                 175

Tyr Gly Pro Gly Ala Ser Gly Pro Gly Gln Tyr Gly Pro Gly Gln Gln
        180                 185                 190

Gly Pro Ser Ala Ser Ala Ala Ala Ala Ala Ala Gly Ser Gly Gln
        195                 200                 205

Gln Val Leu Ile Gly Pro Gly Gln Tyr Val Leu Ile Gly Pro Tyr Ala
    210                 215                 220

Ser Ala Ala Ala Ala Ala Ala Ala Gly Ser Tyr Gly Ser Gly Pro Gly
225                 230                 235                 240

Gln Gln Gly Pro Tyr Gly Pro Gly Gln Ser Gly Ser Gly Gln Gln Gly
                245                 250                 255

Pro Gly Gln Gln Gly Pro Tyr Ala Ser Ala Ala Ala Ala Ala Ala Ala
        260                 265                 270

Gly Pro Gly Gln Gln Val Leu Ile Gly Pro Tyr Val Leu Ile Gly Pro
        275                 280                 285

Gly Ser Ser Ala Ala Ala Ala Ala Ala Gly Ser Tyr Gly Tyr Gly
    290                 295                 300

Pro Gly Gln Gln Gly Pro Tyr Gly Pro Gly Ala Ser Gly Gln Asn Gly
305                 310                 315                 320

Pro Gly Ser Gly Gln Tyr Gly Pro Gly Gln Gln Gly Pro Gly Pro Ser
                325                 330                 335

Ala Ala Ala Ala Ala Ala Ala Gly Pro Gly Gln Gln Val Leu Ile Gly
        340                 345                 350

Pro Tyr Val Leu Ile Gly Pro Gly Ala Ser Ala Ala Ala Ala Ala Ala
        355                 360                 365

Ala Gly Ser Tyr Gly Pro Gly Gln Gln Gly Pro Gly Gln Tyr Gly Pro
    370                 375                 380

Gly Ser Ser Gly Pro Gly Gln Gln Gly Pro Tyr Gly Pro Gly Ser Ser
385                 390                 395                 400

Ala Ala Ala Ala Ala Ala Ala Gly Ser Tyr Gly Pro Gly Gln Gln Val
                405                 410                 415

Leu Ile Gly Pro Tyr Val Leu Ile Gly Pro Gly Pro Ser Ala Ala Ala
        420                 425                 430

Ala Ala Ala Ala Gly Ser Tyr Gln Gln Gly Pro Gly Gln Gln Gly Pro
        435                 440                 445

Tyr Gly Pro Gly Ala Ser Gly Pro Gly Gln Gln Gly Pro Tyr Gly Pro
    450                 455                 460
```

```
Gly Ala Ser Ala Ala Ala Ala Ala Ala Gly Pro Gly Gln Tyr Val
465             470             475             480

Leu Ile Gly Pro Gly Gln Gln Val Leu Ile Gly Pro Ser Ala Ser Ala
                485             490             495

Ala Ala Ala Ala Ala Ala Gly Ser Tyr Gly Ser Gly Pro Gly Gln Tyr
                500             505             510

Gly Pro Tyr Gly Pro Gly Gln Ser Gly Pro Gly Ser Gly Gln Gln Gly
                515             520             525

Gln Gly Pro Tyr Gly Pro Gly Ala Ser Ala Ala Ala Ala Ala Ala
            530             535             540

Gly Ser Tyr Gly Pro Gly Gln Gln Val Leu Ile Gly Pro Tyr Val Leu
545             550             555             560

Ile Gly Pro Gly Pro Ser Ala Ala Ala Ala Ala Ala Gly Pro Gly
                565             570             575

Ser Gly Gln Tyr Gly Pro Gly Ala Ser Gly Gln Asn Gly Pro Gly Ser
                580             585             590

Gly Gln Tyr Gly Pro Gly Gln Gln Gly Pro Gly Pro Ser Ala Ala Ala
            595             600             605

Ala Ala Ala Ala Gly Pro Gly Ser Gly Gln Gln Val Leu Ile Gly Pro
    610             615             620

Gly Ala Ser Val Leu Ile
625             630

<210> SEQ ID NO 25
<211> LENGTH: 593
<212> TYPE: PRT
<213> ORGANISM: Artificial Sequence
<220> FEATURE:
<223> OTHER INFORMATION: Met-PRT888

<400> SEQUENCE: 25

Met Gly Ser Ser Gly Pro Gly Val Leu Gly Pro Tyr Gly Pro Gly Ala
1               5               10              15

Ser Ala Ala Ala Ala Ala Gly Gln Asn Gly Pro Gly Ser Gly Val Leu
                20              25              30

Gly Pro Gly Gln Ser Gly Gln Tyr Gly Pro Gly Val Leu Gly Pro Gly
            35              40              45

Val Leu Gly Pro Gly Ser Ser Ala Ala Ala Ala Gly Pro Gly Gln
    50              55              60

Tyr Gly Pro Gly Val Leu Gly Pro Ser Ala Ser Ala Ala Ala Ala
65              70              75              80

Gly Pro Gly Ser Gly Val Leu Gly Pro Gly Ala Ser Gly Gln Tyr Gly
            85              90              95

Pro Gly Val Leu Gly Pro Gly Val Leu Gly Pro Gly Ser Ser Ala Ala
            100             105             110

Ala Ala Ala Gly Gln Tyr Gly Ser Gly Pro Gly Val Leu Gly Pro Tyr
        115             120             125

Gly Ser Ala Ala Ala Ala Ala Gly Pro Gly Ser Gly Gln Tyr Gly Gln
        130             135             140

Gly Pro Tyr Gly Pro Gly Ala Ser Gly Pro Gly Gln Tyr Gly Pro Gly
145             150             155             160

Val Leu Gly Pro Ser Ala Ser Ala Ala Ala Ala Gly Ser Gly Val
            165             170             175

Leu Gly Pro Gly Gln Tyr Gly Pro Tyr Ala Ser Ala Ala Ala Ala Ala
            180             185             190
```

```
Gly Gln Tyr Gly Ser Gly Pro Gly Val Leu Gly Pro Tyr Gly Pro Gly
        195             200             205

Gln Ser Gly Ser Gly Val Leu Gly Pro Gly Val Leu Gly Pro Tyr Ala
    210             215             220

Ser Ala Ala Ala Ala Ala Gly Pro Gly Val Leu Gly Pro Tyr Gly Pro
225             230             235             240

Gly Ser Ser Ala Ala Ala Ala Ala Gly Gln Tyr Gly Tyr Gly Pro Gly
            245             250             255

Val Leu Gly Pro Tyr Gly Pro Gly Ala Ser Gly Gln Asn Gly Pro Gly
            260             265             270

Ser Gly Gln Tyr Gly Pro Gly Val Leu Gly Pro Gly Gln Ser Ala Ala
        275             280             285

Ala Ala Ala Gly Pro Gly Val Leu Gly Pro Tyr Gly Pro Gly Ala Ser
    290             295             300

Ala Ala Ala Ala Ala Gly Gln Tyr Gly Pro Gly Val Leu Gly Pro Gly
305             310             315             320

Gln Tyr Gly Pro Gly Ser Ser Gly Pro Gly Val Leu Gly Pro Tyr Gly
        325             330             335

Pro Gly Ser Ser Ala Ala Ala Ala Ala Gly Gln Tyr Gly Pro Gly Val
            340             345             350

Leu Gly Pro Tyr Gly Pro Gly Gln Ser Ala Ala Ala Ala Ala Gly Gln
        355             360             365

Tyr Val Leu Gly Pro Gly Val Leu Gly Pro Tyr Gly Pro Gly Ala Ser
    370             375             380

Gly Pro Gly Val Leu Gly Pro Tyr Gly Pro Gly Ala Ser Ala Ala Ala
385             390             395             400

Ala Ala Gly Pro Gly Gln Tyr Gly Pro Gly Val Leu Gly Pro Ser Ala
            405             410             415

Ser Ala Ala Ala Ala Ala Gly Gln Tyr Gly Ser Gly Pro Gly Gln Tyr
            420             425             430

Gly Pro Tyr Gly Pro Gly Gln Ser Gly Pro Gly Ser Gly Val Leu Gly
        435             440             445

Gln Gly Pro Tyr Gly Pro Gly Ala Ser Ala Ala Ala Ala Gly Gln
    450             455             460

Tyr Gly Pro Gly Val Leu Gly Pro Tyr Gly Pro Gly Gln Ser Ala Ala
465             470             475             480

Ala Ala Ala Gly Pro Gly Ser Gly Gln Tyr Gly Pro Gly Ala Ser Gly
            485             490             495

Gln Asn Gly Pro Gly Ser Gly Gln Tyr Gly Pro Gly Val Leu Gly Pro
            500             505             510

Gly Gln Ser Ala Ala Ala Ala Ala Gly Gln Tyr Val Leu Gly Pro Gly
        515             520             525

Val Leu Gly Pro Tyr Gly Pro Gly Ala Ser Ala Ala Ala Ala Ala Gly
        530             535             540

Gln Tyr Gly Ser Gly Pro Gly Val Leu Gly Pro Tyr Gly Pro Gly Gln
545             550             555             560

Ser Gly Ser Gly Val Leu Gly Pro Gly Val Leu Gly Pro Tyr Ala Ser
            565             570             575

Ala Ala Ala Ala Ala Gly Pro Gly Ser Gly Val Leu Gly Pro Gly Ala
            580             585             590

Ser
```

<210> SEQ ID NO 26

-continued

```
<211> LENGTH: 590
<212> TYPE: PRT
<213> ORGANISM: Artificial Sequence
<220> FEATURE:
<223> OTHER INFORMATION: Met-PRT965

<400> SEQUENCE: 26

Met Gly Pro Gly Thr Ser Gly Pro Tyr Gly Pro Gly Ala Ser Ala Ala
1               5                   10                  15

Ala Ala Ala Gly Ala Asn Gly Pro Gly Ser Gly Thr Ser Gly Pro Gly
            20                  25                  30

Ala Ser Gly Ala Tyr Gly Pro Gly Thr Ser Gly Pro Gly Thr Ser Gly
        35                  40                  45

Pro Gly Ser Ser Ala Ala Ala Ala Ala Gly Pro Gly Ala Tyr Gly Pro
    50                  55                  60

Gly Thr Ser Gly Pro Ser Ala Ser Ala Ala Ala Ala Gly Pro Gly
65                  70                  75                  80

Ser Gly Thr Ser Gly Pro Gly Ala Ser Gly Ala Tyr Gly Pro Gly Thr
                85                  90                  95

Ser Gly Pro Gly Thr Ser Gly Pro Gly Ser Ser Ala Ala Ala Ala Ala
            100                 105                 110

Gly Ala Tyr Gly Ser Gly Pro Gly Thr Ser Gly Pro Tyr Gly Ser Ala
        115                 120                 125

Ala Ala Ala Ala Gly Pro Gly Ser Gly Ala Tyr Gly Ala Gly Pro Tyr
    130                 135                 140

Gly Pro Gly Ala Ser Gly Pro Gly Ala Tyr Gly Pro Gly Thr Ser Gly
145                 150                 155                 160

Pro Ser Ala Ser Ala Ala Ala Ala Ala Gly Ser Gly Thr Ser Gly Pro
                165                 170                 175

Gly Ala Tyr Gly Pro Tyr Ala Ser Ala Ala Ala Ala Gly Ala Tyr
        180                 185                 190

Gly Ser Gly Pro Gly Thr Ser Gly Pro Tyr Gly Pro Gly Ala Ser Gly
        195                 200                 205

Ser Gly Thr Ser Gly Pro Gly Thr Ser Gly Pro Tyr Ala Ser Ala Ala
    210                 215                 220

Ala Ala Ala Gly Pro Gly Thr Ser Gly Pro Tyr Gly Pro Gly Ser Ser
225                 230                 235                 240

Ala Ala Ala Ala Ala Gly Ala Tyr Gly Tyr Gly Pro Gly Thr Ser Gly
            245                 250                 255

Pro Tyr Gly Pro Gly Ala Ser Gly Ala Asn Gly Pro Gly Ser Gly Ala
        260                 265                 270

Tyr Gly Pro Gly Thr Ser Gly Pro Gly Ala Ser Ala Ala Ala Ala Ala
    275                 280                 285

Gly Pro Gly Thr Ser Gly Pro Tyr Gly Pro Gly Ala Ser Ala Ala Ala
    290                 295                 300

Ala Ala Gly Ala Tyr Gly Pro Gly Thr Ser Gly Pro Gly Ala Tyr Gly
305                 310                 315                 320

Pro Gly Ser Ser Gly Pro Gly Thr Ser Gly Pro Tyr Gly Pro Gly Ser
            325                 330                 335

Ser Ala Ala Ala Ala Ala Gly Ala Tyr Gly Pro Gly Thr Ser Gly Pro
        340                 345                 350

Tyr Gly Pro Gly Ala Ser Ala Ala Ala Ala Gly Ala Tyr Thr Ser
        355                 360                 365

Gly Pro Gly Thr Ser Gly Pro Tyr Gly Pro Gly Ala Ser Gly Pro Gly
    370                 375                 380
```

```
Thr Ser Gly Pro Tyr Gly Pro Gly Ala Ser Ala Ala Ala Ala Ala Gly
385                 390                 395                 400

Pro Gly Ala Tyr Gly Pro Gly Thr Ser Gly Pro Ser Ala Ser Ala Ala
                405                 410                 415

Ala Ala Ala Gly Ala Tyr Gly Ser Gly Pro Gly Ala Tyr Gly Pro Tyr
            420                 425                 430

Gly Pro Gly Ala Ser Gly Pro Gly Ser Gly Thr Ser Gly Ala Gly Pro
        435                 440                 445

Tyr Gly Pro Gly Ala Ser Ala Ala Ala Ala Gly Ala Tyr Gly Pro
    450                 455                 460

Gly Thr Ser Gly Pro Tyr Gly Pro Gly Ala Ser Ala Ala Ala Ala Ala
465                 470                 475                 480

Gly Pro Gly Ser Gly Ala Tyr Gly Pro Gly Ala Ser Gly Ala Asn Gly
            485                 490                 495

Pro Gly Ser Gly Ala Tyr Gly Pro Gly Thr Ser Gly Pro Gly Ala Ser
        500                 505                 510

Ala Ala Ala Ala Ala Gly Ala Tyr Thr Ser Gly Pro Gly Thr Ser Gly
        515                 520                 525

Pro Tyr Gly Pro Gly Ala Ser Ala Ala Ala Ala Ala Gly Ala Tyr Gly
    530                 535                 540

Ser Gly Pro Gly Thr Ser Gly Pro Tyr Gly Pro Gly Ala Ser Gly Ser
545                 550                 555                 560

Gly Thr Ser Gly Pro Gly Thr Ser Gly Pro Tyr Ala Ser Ala Ala Ala
            565                 570                 575

Ala Ala Gly Pro Gly Ser Gly Thr Ser Gly Pro Gly Ala Ser
            580                 585                 590

<210> SEQ ID NO 27
<211> LENGTH: 593
<212> TYPE: PRT
<213> ORGANISM: Artificial Sequence
<220> FEATURE:
<223> OTHER INFORMATION: Met-PRT889

<400> SEQUENCE: 27

Met Gly Ser Ser Gly Pro Gly Val Leu Gly Pro Tyr Gly Pro Gly Ala
1               5                   10                  15

Ser Ala Ala Ala Ala Ala Gly Ile Asn Gly Pro Gly Ser Gly Val Leu
            20                  25                  30

Gly Pro Gly Ile Ser Gly Ile Tyr Gly Pro Gly Val Leu Gly Pro Gly
        35                  40                  45

Val Leu Gly Pro Gly Ser Ser Ala Ala Ala Ala Gly Pro Gly Ile
    50                  55                  60

Tyr Gly Pro Gly Val Leu Gly Pro Ser Ala Ser Ala Ala Ala Ala Ala
65                  70                  75                  80

Gly Pro Gly Ser Gly Val Leu Gly Pro Gly Ala Ser Gly Ile Tyr Gly
            85                  90                  95

Pro Gly Val Leu Gly Pro Gly Val Leu Gly Pro Gly Ser Ser Ala Ala
            100                 105                 110

Ala Ala Ala Gly Ile Tyr Gly Ser Gly Pro Gly Val Leu Gly Pro Tyr
        115                 120                 125

Gly Ser Ala Ala Ala Ala Ala Gly Pro Gly Ser Gly Ile Tyr Gly Ile
    130                 135                 140

Gly Pro Tyr Gly Pro Gly Ala Ser Gly Pro Gly Ile Tyr Gly Pro Gly
145                 150                 155                 160
```

-continued

```
Val Leu Gly Pro Ser Ala Ser Ala Ala Ala Ala Gly Ser Gly Val
             165                 170                 175

Leu Gly Pro Gly Ile Tyr Gly Pro Tyr Ala Ser Ala Ala Ala Ala
             180                 185                 190

Gly Ile Tyr Gly Ser Gly Pro Gly Val Leu Gly Pro Tyr Gly Pro Gly
             195                 200                 205

Ile Ser Gly Ser Gly Val Leu Gly Pro Gly Val Leu Gly Pro Tyr Ala
         210                 215                 220

Ser Ala Ala Ala Ala Ala Gly Pro Gly Val Leu Gly Pro Tyr Gly Pro
225                 230                 235                 240

Gly Ser Ser Ala Ala Ala Ala Gly Ile Tyr Gly Tyr Gly Pro Gly
             245                 250                 255

Val Leu Gly Pro Tyr Gly Pro Gly Ala Ser Gly Ile Asn Gly Pro Gly
             260                 265                 270

Ser Gly Ile Tyr Gly Pro Gly Val Leu Gly Pro Gly Ile Ser Ala Ala
             275                 280                 285

Ala Ala Ala Gly Pro Gly Val Leu Gly Pro Tyr Gly Pro Gly Ala Ser
         290                 295                 300

Ala Ala Ala Ala Ala Gly Ile Tyr Gly Pro Gly Val Leu Gly Pro Gly
305                 310                 315                 320

Ile Tyr Gly Pro Gly Ser Ser Gly Pro Gly Val Leu Gly Pro Tyr Gly
             325                 330                 335

Pro Gly Ser Ser Ala Ala Ala Ala Gly Ile Tyr Gly Pro Gly Val
             340                 345                 350

Leu Gly Pro Tyr Gly Pro Gly Ile Ser Ala Ala Ala Ala Gly Ile
             355                 360                 365

Tyr Val Leu Gly Pro Gly Val Leu Gly Pro Tyr Gly Pro Gly Ala Ser
         370                 375                 380

Gly Pro Gly Val Leu Gly Pro Tyr Gly Pro Gly Ala Ser Ala Ala Ala
385                 390                 395                 400

Ala Ala Gly Pro Gly Ile Tyr Gly Pro Gly Val Leu Gly Pro Ser Ala
             405                 410                 415

Ser Ala Ala Ala Ala Gly Ile Tyr Gly Ser Gly Pro Gly Ile Tyr
         420                 425                 430

Gly Pro Tyr Gly Pro Gly Ile Ser Gly Pro Gly Ser Gly Val Leu Gly
             435                 440                 445

Ile Gly Pro Tyr Gly Pro Gly Ala Ser Ala Ala Ala Ala Gly Ile
         450                 455                 460

Tyr Gly Pro Gly Val Leu Gly Pro Tyr Gly Pro Gly Ile Ser Ala Ala
465                 470                 475                 480

Ala Ala Ala Gly Pro Gly Ser Gly Ile Tyr Gly Pro Gly Ala Ser Gly
             485                 490                 495

Ile Asn Gly Pro Gly Ser Gly Ile Tyr Gly Pro Gly Val Leu Gly Pro
             500                 505                 510

Gly Ile Ser Ala Ala Ala Ala Ala Gly Ile Tyr Val Leu Gly Pro Gly
             515                 520                 525

Val Leu Gly Pro Tyr Gly Pro Gly Ala Ser Ala Ala Ala Ala Ala Gly
         530                 535                 540

Ile Tyr Gly Ser Gly Pro Gly Val Leu Gly Pro Tyr Gly Pro Gly Ile
545                 550                 555                 560

Ser Gly Ser Gly Val Leu Gly Pro Gly Val Leu Gly Pro Tyr Ala Ser
             565                 570                 575
```

```
Ala Ala Ala Ala Ala Gly Pro Gly Ser Gly Val Leu Gly Pro Gly Ala
        580                 585                 590

Ser

<210> SEQ ID NO 28
<211> LENGTH: 590
<212> TYPE: PRT
<213> ORGANISM: Artificial Sequence
<220> FEATURE:
<223> OTHER INFORMATION: Met-PRT916

<400> SEQUENCE: 28

Met Gly Pro Gly Val Ile Gly Pro Tyr Gly Pro Gly Ala Ser Ala Ala
1               5                   10                  15

Ala Ala Ala Gly Leu Asn Gly Pro Gly Ser Gly Val Ile Gly Pro Gly
            20                  25                  30

Leu Ser Gly Leu Tyr Gly Pro Gly Val Ile Gly Pro Gly Val Ile Gly
        35                  40                  45

Pro Gly Ser Ser Ala Ala Ala Ala Ala Gly Pro Gly Leu Tyr Gly Pro
    50                  55                  60

Gly Val Ile Gly Pro Ser Ala Ser Ala Ala Ala Ala Gly Pro Gly
65                  70                  75                  80

Ser Gly Val Ile Gly Pro Gly Ala Ser Gly Leu Tyr Gly Pro Gly Val
                85                  90                  95

Ile Gly Pro Gly Val Ile Gly Pro Gly Ser Ser Ala Ala Ala Ala Ala
            100                 105                 110

Gly Leu Tyr Gly Ser Gly Pro Gly Val Ile Gly Pro Tyr Gly Ser Ala
        115                 120                 125

Ala Ala Ala Gly Pro Gly Ser Gly Leu Tyr Gly Leu Gly Pro Tyr
    130                 135                 140

Gly Pro Gly Ala Ser Gly Pro Gly Leu Tyr Gly Pro Gly Val Ile Gly
145                 150                 155                 160

Pro Ser Ala Ser Ala Ala Ala Ala Gly Ser Gly Val Ile Gly Pro
                165                 170                 175

Gly Leu Tyr Gly Pro Tyr Ala Ser Ala Ala Ala Ala Gly Leu Tyr
        180                 185                 190

Gly Ser Gly Pro Gly Val Ile Gly Pro Tyr Gly Pro Gly Leu Ser Gly
        195                 200                 205

Ser Gly Val Ile Gly Pro Gly Val Ile Gly Pro Tyr Ala Ser Ala Ala
    210                 215                 220

Ala Ala Ala Gly Pro Gly Val Ile Gly Pro Tyr Gly Pro Gly Ser Ser
225                 230                 235                 240

Ala Ala Ala Ala Ala Gly Leu Tyr Gly Tyr Gly Pro Gly Val Ile Gly
            245                 250                 255

Pro Tyr Gly Pro Gly Ala Ser Gly Leu Asn Gly Pro Gly Ser Gly Leu
        260                 265                 270

Tyr Gly Pro Gly Val Ile Gly Pro Gly Leu Ser Ala Ala Ala Ala Ala
        275                 280                 285

Gly Pro Gly Val Ile Gly Pro Tyr Gly Pro Gly Ala Ser Ala Ala Ala
    290                 295                 300

Ala Ala Gly Leu Tyr Gly Pro Gly Val Ile Gly Pro Gly Leu Tyr Gly
305                 310                 315                 320

Pro Gly Ser Ser Gly Pro Gly Val Ile Gly Pro Tyr Gly Pro Gly Ser
            325                 330                 335

Ser Ala Ala Ala Ala Ala Gly Leu Tyr Gly Pro Gly Val Ile Gly Pro
```

```
                340                 345                 350

Tyr Gly Pro Gly Leu Ser Ala Ala Ala Ala Gly Leu Tyr Val Ile
        355                 360                 365

Gly Pro Gly Val Ile Gly Pro Tyr Gly Pro Gly Ala Ser Gly Pro Gly
        370                 375                 380

Val Ile Gly Pro Tyr Gly Pro Gly Ala Ser Ala Ala Ala Ala Gly
385                 390                 395                 400

Pro Gly Leu Tyr Gly Pro Gly Val Ile Gly Pro Ser Ala Ser Ala Ala
                405                 410                 415

Ala Ala Ala Gly Leu Tyr Gly Ser Gly Pro Gly Leu Tyr Gly Pro Tyr
                420                 425                 430

Gly Pro Gly Leu Ser Gly Pro Gly Ser Gly Val Ile Gly Leu Gly Pro
                435                 440                 445

Tyr Gly Pro Gly Ala Ser Ala Ala Ala Ala Gly Leu Tyr Gly Pro
        450                 455                 460

Gly Val Ile Gly Pro Tyr Gly Pro Gly Leu Ser Ala Ala Ala Ala Ala
465                 470                 475                 480

Gly Pro Gly Ser Gly Leu Tyr Gly Pro Gly Ala Ser Gly Leu Asn Gly
                485                 490                 495

Pro Gly Ser Gly Leu Tyr Gly Pro Gly Val Ile Gly Pro Gly Leu Ser
                500                 505                 510

Ala Ala Ala Ala Ala Gly Leu Tyr Val Ile Gly Pro Gly Val Ile Gly
                515                 520                 525

Pro Tyr Gly Pro Gly Ala Ser Ala Ala Ala Ala Gly Leu Tyr Gly
        530                 535                 540

Ser Gly Pro Gly Val Ile Gly Pro Tyr Gly Pro Gly Leu Ser Gly Ser
545                 550                 555                 560

Gly Val Ile Gly Pro Gly Val Ile Gly Pro Tyr Ala Ser Ala Ala Ala
                565                 570                 575

Ala Ala Gly Pro Gly Ser Gly Val Ile Gly Pro Gly Ala Ser
        580                 585                 590
```

```
<210> SEQ ID NO 29
<211> LENGTH: 590
<212> TYPE: PRT
<213> ORGANISM: Artificial Sequence
<220> FEATURE:
<223> OTHER INFORMATION: Met-PRT918

<400> SEQUENCE: 29

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
                20                  25                  30

Ile Ser Gly Ile Tyr Gly Pro Gly Val Phe Gly Pro Gly Val Phe Gly
        35                  40                  45

Pro Gly Ser Ser Ala Ala Ala Ala Gly Pro Gly Ile Tyr Gly Pro
        50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
                100                 105                 110

Gly Ile Tyr Gly Ser Gly Pro Gly Val Phe Gly Pro Tyr Gly Ser Ala
```

```
                115                 120                 125

Ala Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
                165                 170                 175

Gly Ile Tyr Gly Pro Tyr Ala Ser Ala Ala Ala Ala Gly Ile Tyr
                180                 185                 190

Gly Ser Gly Pro Gly Val Phe Gly Pro Tyr Gly Pro Gly Ile Ser Gly
                195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
                260                 265                 270

Tyr Gly Pro Gly Val Phe Gly Pro Gly Ile Ser Ala Ala Ala Ala Ala
    275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320

Pro Gly Ser Ser Gly Pro Gly Val Phe Gly Pro Tyr Gly Pro Gly Ser
                325                 330                 335

Ser Ala Ala Ala Ala Ala Gly Ile Tyr Gly Pro Gly Val Phe Gly Pro
                340                 345                 350

Tyr Gly Pro Gly Ile Ser Ala Ala Ala Ala Gly Ile Tyr Val Phe
    355                 360                 365

Gly Pro Gly Val Phe Gly Pro Tyr Gly Pro Gly Ala Ser Gly Pro Gly
    370                 375                 380

Val Phe Gly Pro Tyr Gly Pro Gly Ala Ser Ala Ala Ala Ala Ala Gly
385                 390                 395                 400

Pro Gly Ile Tyr Gly Pro Gly Val Phe Gly Pro Ser Ala Ser Ala Ala
                405                 410                 415

Ala Ala Ala Gly Ile Tyr Gly Ser Gly Pro Gly Ile Tyr Gly Pro Tyr
                420                 425                 430

Gly Pro Gly Ile Ser Gly Pro Gly Ser Gly Val Phe Gly Ile Gly Pro
    435                 440                 445

Tyr Gly Pro Gly Ala Ser Ala Ala Ala Ala Gly Ile Tyr Gly Pro
    450                 455                 460

Gly Val Phe Gly Pro Tyr Gly Pro Gly Ile Ser Ala Ala Ala Ala Ala
465                 470                 475                 480

Gly Pro Gly Ser Gly Ile Tyr Gly Pro Gly Ala Ser Gly Ile Asn Gly
                485                 490                 495

Pro Gly Ser Gly Ile Tyr Gly Pro Gly Val Phe Gly Pro Gly Ile Ser
                500                 505                 510

Ala Ala Ala Ala Ala Gly Ile Tyr Val Phe Gly Pro Gly Val Phe Gly
    515                 520                 525

Pro Tyr Gly Pro Gly Ala Ser Ala Ala Ala Ala Gly Ile Tyr Gly
    530                 535                 540
```

```
Ser Gly Pro Gly Val Phe Gly Pro Tyr Gly Pro Gly Ile Ser Gly Ser
545                 550                 555                 560

Gly Val Phe Gly Pro Gly Val Phe Gly Pro Tyr Ala Ser Ala Ala Ala
                565                 570                 575

Ala Ala Gly Pro Gly Ser Gly Val Phe Gly Pro Gly Ala Ser
            580                 585                 590

<210> SEQ ID NO 30
<211> LENGTH: 565
<212> TYPE: PRT
<213> ORGANISM: Artificial Sequence
<220> FEATURE:
<223> OTHER INFORMATION: Met-PRT699

<400> SEQUENCE: 30

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Gln Ser Gly Gln Tyr Gly Pro Gly Val Leu Gly Pro Gly Val
        35                  40                  45

Leu Gly Pro Gly Ser Ser Ala Ala Ala Ala Ala Ala Gly Pro Gly
    50                  55                  60

Gln Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
                85                  90                  95

Gln Tyr Gly Pro Gly Val Leu Gly Pro Gly Val Leu Gly Pro Gly Ser
            100                 105                 110

Ser Ala Ala Ala Ala Ala Ala Gly Ser Tyr Gly Ser Gly Pro Gly
            115                 120                 125

Val Leu Gly Pro Tyr Gly Ser Ala Ala Ala Ala Ala Ala Gly Pro
    130                 135                 140

Gly Ser Gly Gln Tyr Gly Gln Gly Pro Tyr Gly Pro Gly Ala Ser Gly
145                 150                 155                 160

Pro Gly Gln Tyr Gly Pro Gly Val Leu Gly Pro Ser Ala Ser Ala Ala
                165                 170                 175

Ala Ala Ala Ala Gly Ser Gly Val Leu Gly Pro Gly Gln Tyr Gly
            180                 185                 190

Pro Tyr Ala Ser Ala Ala Ala Ala Ala Ala Gly Ser Tyr Gly Ser
        195                 200                 205

Gly Pro Gly Val Leu Gly Pro Tyr Gly Pro Gly Gln Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
            245                 250                 255

Ala Ala Ala Ala Ala Ala Ala Gly Ser Tyr Gly Tyr Gly Pro Gly Val
            260                 265                 270

Leu Gly Pro Tyr Gly Pro Gly Ala Ser Gly Gln Asn Gly Pro Gly Ser
        275                 280                 285

Gly Gln Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320
```

```
Ser Ala Ala Ala Ala Ala Ala Ala Gly Ser Tyr Gly Pro Gly Val Leu
            325                 330                 335

Gly Pro Gly Gln Tyr Gly Pro Gly Ser Ser Gly Pro Gly Val Leu Gly
            340                 345                 350

Pro Tyr Gly Pro Gly Ser Ser Ala Ala Ala Ala Ala Ala Gly Ser
            355                 360                 365

Tyr Gly Pro Gly Val Leu Gly Pro Tyr Gly Pro Gly Pro Ser Ala Ala
            370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
            405                 410                 415

Pro Gly Ala Ser Ala Ala Ala Ala Ala Ala Ala Gly Pro Gly Gln Tyr
            420                 425                 430

Gly Pro Gly Val Leu Gly Pro Ser Ala Ser Ala Ala Ala Ala Ala
            435                 440                 445

Ala Gly Ser Tyr Gly Ser Gly Pro Gly Gln Tyr Gly Pro Tyr Gly Pro
    450                 455                 460

Gly Gln Ser Gly Pro Gly Ser Gly Val Leu Gly Gln Gly Pro Tyr Gly
465                 470                 475                 480

Pro Gly Ala Ser Ala Ala Ala Ala Ala Ala Gly Ser Tyr Gly Pro
            485                 490                 495

Gly Val Leu Gly Pro Tyr Gly Pro Gly Pro Ser Ala Ala Ala Ala Ala
            500                 505                 510

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Val Leu Gly Pro Gly
            530                 535                 540

Pro Ser Ala Ala Ala Ala Ala Ala Ala Gly Pro Gly Ser Gly Val Leu
545                 550                 555                 560

Gly Pro Gly Ala Ser
            565

<210> SEQ ID NO 31
<211> LENGTH: 565
<212> TYPE: PRT
<213> ORGANISM: Artificial Sequence
<220> FEATURE:
<223> OTHER INFORMATION: Met-PRT698

<400> SEQUENCE: 31

Met Gly Pro Gly Val Leu Gly Pro Tyr Gly Pro Gly Ala Ser Ala Ala
1               5                   10                  15

Ala Ala Ala Ala Ala Gly Ser Asn Gly Pro Gly Ser Gly Val Leu Gly
            20                  25                  30

Pro Gly Ile Ser Gly Ile Tyr Gly Pro Gly Val Leu Gly Pro Gly Val
            35                  40                  45

Leu Gly Pro Gly Ser Ser Ala Ala Ala Ala Ala Ala Gly Pro Gly
    50                  55                  60

Ile Tyr Gly Pro Gly Val Leu Gly Pro Ser Ala Ser Ala Ala Ala Ala
65                  70                  75                  80

Ala Ala Ala Gly Pro Gly Ser Gly Val Leu Gly Pro Gly Ala Ser Gly
            85                  90                  95

Ile Tyr Gly Pro Gly Val Leu Gly Pro Gly Val Leu Gly Pro Gly Ser
            100                 105                 110
```

```
Ser Ala Ala Ala Ala Ala Ala Ala Gly Ser Tyr Gly Ser Gly Pro Gly
        115                 120                 125

Val Leu Gly Pro Tyr Gly Ser Ala Ala Ala Ala Ala Ala Gly Pro
    130                 135                 140

Gly Ser Gly Ile Tyr Gly Ile Gly Pro Tyr Gly Pro Gly Ala Ser Gly
145                 150                 155                 160

Pro Gly Ile Tyr Gly Pro Gly Val Leu Gly Pro Ser Ala Ser Ala Ala
                165                 170                 175

Ala Ala Ala Ala Ala Gly Ser Gly Val Leu Gly Pro Gly Ile Tyr Gly
                180                 185                 190

Pro Tyr Ala Ser Ala Ala Ala Ala Ala Ala Gly Ser Tyr Gly Ser
    195                 200                 205

Gly Pro Gly Val Leu Gly Pro Tyr Gly Pro Gly Ile Ser Gly Ser Gly
    210                 215                 220

Val Leu Gly Pro Gly Val Leu Gly Pro Tyr Ala Ser Ala Ala Ala Ala
225                 230                 235                 240

Ala Ala Ala Gly Pro Gly Val Leu Gly Pro Tyr Gly Pro Gly Ser Ser
                245                 250                 255

Ala Ala Ala Ala Ala Ala Ala Gly Ser Tyr Gly Tyr Gly Pro Gly Val
                260                 265                 270

Leu Gly Pro Tyr Gly Pro Gly Ala Ser Gly Ile Asn Gly Pro Gly Ser
    275                 280                 285

Gly Ile Tyr Gly Pro Gly Val Leu Gly Pro Gly Pro Ser Ala Ala Ala
    290                 295                 300

Ala Ala Ala Ala Gly Pro Gly Val Leu Gly Pro Tyr Gly Pro Gly Ala
305                 310                 315                 320

Ser Ala Ala Ala Ala Ala Ala Ala Gly Ser Tyr Gly Pro Gly Val Leu
                325                 330                 335

Gly Pro Gly Ile Tyr Gly Pro Gly Ser Ser Gly Pro Gly Val Leu Gly
                340                 345                 350

Pro Tyr Gly Pro Gly Ser Ser Ala Ala Ala Ala Ala Ala Ala Gly Ser
    355                 360                 365

Tyr Gly Pro Gly Val Leu Gly Pro Tyr Gly Pro Gly Pro Ser Ala Ala
    370                 375                 380

Ala Ala Ala Ala Ala Gly Ser Tyr Val Leu Gly Pro Gly Val Leu Gly
385                 390                 395                 400

Pro Tyr Gly Pro Gly Ala Ser Gly Pro Gly Val Leu Gly Pro Tyr Gly
                405                 410                 415

Pro Gly Ala Ser Ala Ala Ala Ala Ala Ala Gly Pro Gly Ile Tyr
                420                 425                 430

Gly Pro Gly Val Leu Gly Pro Ser Ala Ser Ala Ala Ala Ala Ala
    435                 440                 445

Ala Gly Ser Tyr Gly Ser Gly Pro Gly Ile Tyr Gly Pro Tyr Gly Pro
    450                 455                 460

Gly Ile Ser Gly Pro Gly Ser Gly Val Leu Gly Ile Gly Pro Tyr Gly
465                 470                 475                 480

Pro Gly Ala Ser Ala Ala Ala Ala Ala Ala Ala Gly Ser Tyr Gly Pro
                485                 490                 495

Gly Val Leu Gly Pro Tyr Gly Pro Gly Pro Ser Ala Ala Ala Ala Ala
                500                 505                 510

Ala Ala Gly Pro Gly Ser Gly Ile Tyr Gly Pro Gly Ala Ser Gly Ile
        515                 520                 525
```

```
Asn Gly Pro Gly Ser Gly Ile Tyr Gly Pro Gly Val Leu Gly Pro Gly
    530                 535                 540

Pro Ser Ala Ala Ala Ala Ala Ala Ala Gly Pro Gly Ser Gly Val Leu
545                 550                 555                 560

Gly Pro Gly Ala Ser
                565

<210> SEQ ID NO 32
<211> LENGTH: 1179
<212> TYPE: PRT
<213> ORGANISM: Artificial Sequence
<220> FEATURE:
<223> OTHER INFORMATION: Met-PRT966

<400> SEQUENCE: 32

Met Gly Pro Gly Val Phe Gly Pro Tyr Gly Pro Gly Ala Ser Ala Ala
1               5                   10                  15

Ala Ala Ala Gly Ile Asn Gly Pro Gly Ser Gly Val Phe Gly Pro Gly
                20                  25                  30

Ile Ser Gly Ile Tyr Gly Pro Gly Val Phe Gly Pro Gly Val Phe Gly
            35                  40                  45

Pro Gly Ser Ser Ala Ala Ala Ala Ala Gly Pro Gly Ile Tyr Gly Pro
    50                  55                  60

Gly Val Phe Gly Pro Ser Ala Ser Ala Ala Ala Ala Gly Pro Gly
65                  70                  75                  80

Ser Gly Val Phe Gly Pro Gly Ala Ser Gly Ile Tyr Gly Pro Gly Val
                85                  90                  95

Phe Gly Pro Gly Val Phe Gly Pro Gly Ser Ser Ala Ala Ala Ala Ala
                100                 105                 110

Gly Ile Tyr Gly Ser Gly Pro Gly Val Phe Gly Pro Tyr Gly Ser Ala
            115                 120                 125

Ala Ala Ala Gly Pro Gly Ser Gly Ile Tyr Gly Ile Gly Pro Tyr
    130                 135                 140

Gly Pro Gly Ala Ser Gly Pro Gly Ile Tyr Gly Pro Gly Val Phe Gly
145                 150                 155                 160

Pro Ser Ala Ser Ala Ala Ala Ala Gly Ser Gly Val Phe Gly Pro
                165                 170                 175

Gly Ile Tyr Gly Pro Tyr Ala Ser Ala Ala Ala Ala Gly Ile Tyr
            180                 185                 190

Gly Ser Gly Pro Gly Val Phe Gly Pro Tyr Gly Pro Gly Ile Ser Gly
            195                 200                 205

Ser Gly Val Phe Gly Pro Gly Val Phe Gly Pro Tyr Ala Ser Ala Ala
    210                 215                 220

Ala Ala Ala Gly Pro Gly Val Phe Gly Pro Tyr Gly Pro Gly Ser Ser
225                 230                 235                 240

Ala Ala Ala Ala Ala Gly Ile Tyr Gly Tyr Gly Pro Gly Val Phe Gly
                245                 250                 255

Pro Tyr Gly Pro Gly Ala Ser Gly Ile Asn Gly Pro Gly Ser Gly Ile
        260                 265                 270

Tyr Gly Pro Gly Val Phe Gly Pro Gly Ile Ser Ala Ala Ala Ala Ala
        275                 280                 285

Gly Pro Gly Val Phe Gly Pro Tyr Gly Pro Gly Ala Ser Ala Ala Ala
    290                 295                 300

Ala Ala Gly Ile Tyr Gly Pro Gly Val Phe Gly Pro Gly Ile Tyr Gly
305                 310                 315                 320
```

-continued

```
Pro Gly Ser Ser Gly Pro Gly Val Phe Gly Pro Tyr Gly Pro Gly Ser
                325             330             335

Ser Ala Ala Ala Ala Ala Gly Ile Tyr Gly Pro Gly Val Phe Gly Pro
            340             345             350

Tyr Gly Pro Gly Ile Ser Ala Ala Ala Ala Gly Ile Tyr Val Phe
        355             360             365

Gly Pro Gly Val Phe Gly Pro Tyr Gly Pro Gly Ala Ser Gly Pro Gly
    370             375             380

Val Phe Gly Pro Tyr Gly Pro Gly Ala Ser Ala Ala Ala Ala Gly
385             390             395             400

Pro Gly Ile Tyr Gly Pro Gly Val Phe Gly Pro Ser Ala Ser Ala Ala
            405             410             415

Ala Ala Ala Gly Ile Tyr Gly Ser Gly Pro Gly Ile Tyr Gly Pro Tyr
        420             425             430

Gly Pro Gly Ile Ser Gly Pro Gly Ser Gly Val Phe Gly Ile Gly Pro
    435             440             445

Tyr Gly Pro Gly Ala Ser Ala Ala Ala Ala Gly Ile Tyr Gly Pro
    450             455             460

Gly Val Phe Gly Pro Tyr Gly Pro Gly Ile Ser Ala Ala Ala Ala Ala
465             470             475             480

Gly Pro Gly Ser Gly Ile Tyr Gly Pro Gly Ala Ser Gly Ile Asn Gly
        485             490             495

Pro Gly Ser Gly Ile Tyr Gly Pro Gly Val Phe Gly Pro Gly Ile Ser
        500             505             510

Ala Ala Ala Ala Ala Gly Ile Tyr Val Phe Gly Pro Gly Val Phe Gly
        515             520             525

Pro Tyr Gly Pro Gly Ala Ser Ala Ala Ala Ala Gly Ile Tyr Gly
    530             535             540

Ser Gly Pro Gly Val Phe Gly Pro Tyr Gly Pro Gly Ile Ser Gly Ser
545             550             555             560

Gly Val Phe Gly Pro Gly Val Phe Gly Pro Tyr Ala Ser Ala Ala Ala
            565             570             575

Ala Ala Gly Pro Gly Ser Gly Val Phe Gly Pro Gly Ala Ser Gly Pro
        580             585             590

Gly Val Phe Gly Pro Tyr Gly Pro Gly Ala Ser Ala Ala Ala Ala Ala
    595             600             605

Gly Ile Asn Gly Pro Gly Ser Gly Val Phe Gly Pro Gly Ile Ser Gly
    610             615             620

Ile Tyr Gly Pro Gly Val Phe Gly Pro Gly Val Phe Gly Pro Gly Ser
625             630             635             640

Ser Ala Ala Ala Ala Ala Gly Pro Gly Ile Tyr Gly Pro Gly Val Phe
            645             650             655

Gly Pro Ser Ala Ser Ala Ala Ala Ala Gly Pro Gly Ser Gly Val
        660             665             670

Phe Gly Pro Gly Ala Ser Gly Ile Tyr Gly Pro Gly Val Phe Gly Pro
        675             680             685

Gly Val Phe Gly Pro Gly Ser Ser Ala Ala Ala Ala Gly Ile Tyr
    690             695             700

Gly Ser Gly Pro Gly Val Phe Gly Pro Tyr Gly Ser Ala Ala Ala Ala
705             710             715             720

Ala Gly Pro Gly Ser Gly Ile Tyr Gly Ile Gly Pro Tyr Gly Pro Gly
            725             730             735

Ala Ser Gly Pro Gly Ile Tyr Gly Pro Gly Val Phe Gly Pro Ser Ala
```

179                                                                              180

-continued

|     |     | 740 |     |     |     | 745 |     |     |     | 750 |     |     |     |
|-----|-----|-----|-----|-----|-----|-----|-----|-----|-----|-----|-----|-----|-----|

Ser Ala Ala Ala Ala Ala Gly Ser Gly Val Phe Gly Pro Gly Ile Tyr
        755                 760                 765

Gly Pro Tyr Ala Ser Ala Ala Ala Ala Gly Ile Tyr Gly Ser Gly
    770             775             780

Pro Gly Val Phe Gly Pro Tyr Gly Pro Gly Ile Ser Gly Ser Gly Val
785                 790                 795                 800

Phe Gly Pro Gly Val Phe Gly Pro Tyr Ala Ser Ala Ala Ala Ala Ala
                805             810             815

Gly Pro Gly Val Phe Gly Pro Tyr Gly Pro Gly Ser Ser Ala Ala Ala
            820             825             830

Ala Ala Gly Ile Tyr Gly Tyr Gly Pro Gly Val Phe Gly Pro Tyr Gly
        835             840             845

Pro Gly Ala Ser Gly Ile Asn Gly Pro Gly Ser Gly Ile Tyr Gly Pro
    850             855             860

Gly Val Phe Gly Pro Gly Ile Ser Ala Ala Ala Ala Ala Gly Pro Gly
865                 870             875                 880

Val Phe Gly Pro Tyr Gly Pro Gly Ala Ser Ala Ala Ala Ala Ala Gly
                885             890             895

Ile Tyr Gly Pro Gly Val Phe Gly Pro Gly Ile Tyr Gly Pro Gly Ser
            900             905             910

Ser Gly Pro Gly Val Phe Gly Pro Tyr Gly Pro Gly Ser Ser Ala Ala
            915             920             925

Ala Ala Ala Gly Ile Tyr Gly Pro Gly Val Phe Gly Pro Tyr Gly Pro
    930             935             940

Gly Ile Ser Ala Ala Ala Ala Ala Gly Ile Tyr Val Phe Gly Pro Gly
945             950             955                 960

Val Phe Gly Pro Tyr Gly Pro Gly Ala Ser Gly Pro Gly Val Phe Gly
            965             970             975

Pro Tyr Gly Pro Gly Ala Ser Ala Ala Ala Ala Gly Pro Gly Ile
        980             985             990

Tyr Gly Pro Gly Val Phe Gly Pro  Ser Ala Ser Ala Ala  Ala Ala Ala
        995             1000                1005

Gly Ile  Tyr Gly Ser Gly Pro  Gly Ile Tyr Gly Pro  Tyr Gly Pro
    1010                1015                1020

Gly Ile  Ser Gly Pro Gly Ser  Gly Val Phe Gly Ile  Gly Pro Tyr
    1025                1030                1035

Gly Pro  Gly Ala Ser Ala Ala  Ala Ala Ala Gly Ile  Tyr Gly Pro
    1040                1045                1050

Gly Val  Phe Gly Pro Tyr Gly  Pro Gly Ile Ser Ala  Ala Ala Ala
    1055                1060                1065

Ala Gly  Pro Gly Ser Gly Ile  Tyr Gly Pro Gly Ala  Ser Gly Ile
    1070                1075                1080

Asn Gly  Pro Gly Ser Gly Ile  Tyr Gly Pro Gly Val  Phe Gly Pro
    1085                1090                1095

Gly Ile  Ser Ala Ala Ala Ala  Ala Gly Ile Tyr Val  Phe Gly Pro
    1100                1105                1110

Gly Val  Phe Gly Pro Tyr Gly  Pro Gly Ala Ser Ala  Ala Ala Ala
    1115                1120                1125

Ala Gly  Ile Tyr Gly Ser Gly  Pro Gly Val Phe Gly  Pro Tyr Gly
    1130                1135                1140

Pro Gly  Ile Ser Gly Ser Gly  Val Phe Gly Pro Gly  Val Phe Gly
    1145                1150                1155

```
Pro Tyr  Ala Ser Ala Ala Ala  Ala Ala Gly Pro Gly  Ser Gly Val
    1160             1165              1170

Phe Gly  Pro Gly Ala Ser
    1175

<210> SEQ ID NO 33
<211> LENGTH: 601
<212> TYPE: PRT
<213> ORGANISM: Artificial Sequence
<220> FEATURE:
<223> OTHER INFORMATION: PRT888

<400> SEQUENCE: 33

Met His His His His His Ser Ser Gly Ser Ser Gly Pro Gly Val
1             5                  10                 15

Leu Gly Pro Tyr Gly Pro Gly Ala Ser Ala Ala Ala Ala Gly Gln
            20              25              30

Asn Gly Pro Gly Ser Gly Val Leu Gly Pro Gly Gln Ser Gly Gln Tyr
        35              40                  45

Gly Pro Gly Val Leu Gly Pro Gly Val Leu Gly Pro Gly Ser Ser Ala
    50              55              60

Ala Ala Ala Ala Gly Pro Gly Gln Tyr Gly Pro Gly Val Leu Gly Pro
65              70              75              80

Ser Ala Ser Ala Ala Ala Ala Ala Gly Pro Gly Ser Gly Val Leu Gly
            85              90              95

Pro Gly Ala Ser Gly Gln Tyr Gly Pro Gly Val Leu Gly Pro Gly Val
            100             105             110

Leu Gly Pro Gly Ser Ser Ala Ala Ala Ala Ala Gly Gln Tyr Gly Ser
    115             120             125

Gly Pro Gly Val Leu Gly Pro Tyr Gly Ser Ala Ala Ala Ala Ala Gly
    130             135             140

Pro Gly Ser Gly Gln Tyr Gly Gln Gly Pro Tyr Gly Pro Gly Ala Ser
145             150             155             160

Gly Pro Gly Gln Tyr Gly Pro Gly Val Leu Gly Pro Ser Ala Ser Ala
            165             170             175

Ala Ala Ala Ala Gly Ser Gly Val Leu Gly Pro Gly Gln Tyr Gly Pro
            180             185             190

Tyr Ala Ser Ala Ala Ala Ala Ala Gly Gln Tyr Gly Ser Gly Pro Gly
            195             200             205

Val Leu Gly Pro Tyr Gly Pro Gly Gln Ser Gly Ser Gly Val Leu Gly
    210             215             220

Pro Gly Val Leu Gly Pro Tyr Ala Ser Ala Ala Ala Ala Gly Pro
225             230             235             240

Gly Val Leu Gly Pro Tyr Gly Pro Gly Ser Ser Ala Ala Ala Ala Ala
            245             250             255

Gly Gln Tyr Gly Tyr Gly Pro Gly Val Leu Gly Pro Tyr Gly Pro Gly
            260             265             270

Ala Ser Gly Gln Asn Gly Pro Gly Ser Gly Gln Tyr Gly Pro Gly Val
        275             280             285

Leu Gly Pro Gly Gln Ser Ala Ala Ala Ala Ala Gly Pro Gly Val Leu
    290             295             300

Gly Pro Tyr Gly Pro Gly Ala Ser Ala Ala Ala Ala Ala Gly Gln Tyr
305             310             315             320

Gly Pro Gly Val Leu Gly Pro Gly Gln Tyr Gly Pro Gly Ser Ser Gly
            325             330             335
```

-continued

```
Pro Gly Val Leu Gly Pro Tyr Gly Pro Gly Ser Ser Ala Ala Ala Ala
            340                 345                 350

Ala Gly Gln Tyr Gly Pro Gly Val Leu Gly Pro Tyr Gly Pro Gly Gln
            355                 360                 365

Ser Ala Ala Ala Ala Ala Gly Gln Tyr Val Leu Gly Pro Gly Val Leu
            370                 375                 380

Gly Pro Tyr Gly Pro Gly Ala Ser Gly Pro Gly Val Leu Gly Pro Tyr
385                 390                 395                 400

Gly Pro Gly Ala Ser Ala Ala Ala Ala Gly Pro Gly Gln Tyr Gly
                405                 410                 415

Pro Gly Val Leu Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
            435                 440                 445

Gly Pro Gly Ser Gly Val Leu Gly Gln Gly Pro Tyr Gly Pro Gly Ala
            450                 455                 460

Ser Ala Ala Ala Ala Ala Gly Gln Tyr Gly Pro Gly Val Leu Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
            500                 505                 510

Tyr Gly Pro Gly Val Leu Gly Pro Gly Gln Ser Ala Ala Ala Ala
            515                 520                 525

Gly Gln Tyr Val Leu Gly Pro Gly Val Leu Gly Pro Tyr Gly Pro Gly
            530                 535                 540

Ala Ser Ala Ala Ala Ala Ala Gly Gln Tyr Gly Ser Gly Pro Gly Val
545                 550                 555                 560

Leu Gly Pro Tyr Gly Pro Gly Gln Ser Gly Ser Gly Val Leu Gly Pro
                565                 570                 575

Gly Val Leu Gly Pro Tyr Ala Ser Ala Ala Ala Ala Gly Pro Gly
            580                 585                 590

Ser Gly Val Leu Gly Pro Gly Ala Ser
        595                 600
```

```
<210> SEQ ID NO 34
<211> LENGTH: 601
<212> TYPE: PRT
<213> ORGANISM: Artificial Sequence
<220> FEATURE:
<223> OTHER INFORMATION: PRT965

<400> SEQUENCE: 34
```

```
Met His His His His His His Ser Ser Gly Ser Ser Gly Pro Gly Thr
1               5                   10                  15

Ser Gly Pro Tyr Gly Pro Gly Ala Ser Ala Ala Ala Ala Gly Ala
            20                  25                  30

Asn Gly Pro Gly Ser Gly Thr Ser Gly Pro Gly Ala Ser Gly Ala Tyr
            35                  40                  45

Gly Pro Gly Thr Ser Gly Pro Gly Thr Ser Gly Pro Gly Ser Ser Ala
        50                  55                  60

Ala Ala Ala Ala Gly Pro Gly Ala Tyr Gly Pro Gly Thr Ser Gly Pro
65                  70                  75                  80

Ser Ala Ser Ala Ala Ala Ala Ala Gly Pro Gly Ser Gly Thr Ser Gly
                85                  90                  95
```

```
Pro Gly Ala Ser Gly Ala Tyr Gly Pro Gly Thr Ser Gly Pro Gly Thr
        100                 105                 110

Ser Gly Pro Gly Ser Ser Ala Ala Ala Ala Gly Ala Tyr Gly Ser
        115                 120                 125

Gly Pro Gly Thr Ser Gly Pro Tyr Gly Ser Ala Ala Ala Ala Ala Gly
        130                 135                 140

Pro Gly Ser Gly Ala Tyr Gly Ala Gly Pro Tyr Gly Pro Gly Ala Ser
145                 150                 155                 160

Gly Pro Gly Ala Tyr Gly Pro Gly Thr Ser Gly Pro Ser Ala Ser Ala
                165                 170                 175

Ala Ala Ala Ala Gly Ser Gly Thr Ser Gly Pro Gly Ala Tyr Gly Pro
            180                 185                 190

Tyr Ala Ser Ala Ala Ala Ala Ala Gly Ala Tyr Gly Ser Gly Pro Gly
            195                 200                 205

Thr Ser Gly Pro Tyr Gly Pro Gly Ala Ser Gly Ser Gly Thr Ser Gly
        210                 215                 220

Pro Gly Thr Ser Gly Pro Tyr Ala Ser Ala Ala Ala Ala Ala Gly Pro
225                 230                 235                 240

Gly Thr Ser Gly Pro Tyr Gly Pro Gly Ser Ser Ala Ala Ala Ala Ala
                245                 250                 255

Gly Ala Tyr Gly Tyr Gly Pro Gly Thr Ser Gly Pro Tyr Gly Pro Gly
                260                 265                 270

Ala Ser Gly Ala Asn Gly Pro Gly Ser Gly Ala Tyr Gly Pro Gly Thr
            275                 280                 285

Ser Gly Pro Gly Ala Ser Ala Ala Ala Ala Gly Pro Gly Thr Ser
        290                 295                 300

Gly Pro Tyr Gly Pro Gly Ala Ser Ala Ala Ala Ala Gly Ala Tyr
305                 310                 315                 320

Gly Pro Gly Thr Ser Gly Pro Gly Ala Tyr Gly Pro Gly Ser Ser Gly
                325                 330                 335

Pro Gly Thr Ser Gly Pro Tyr Gly Pro Gly Ser Ser Ala Ala Ala Ala
                340                 345                 350

Ala Gly Ala Tyr Gly Pro Gly Thr Ser Gly Pro Tyr Gly Pro Gly Ala
            355                 360                 365

Ser Ala Ala Ala Ala Ala Gly Ala Tyr Thr Ser Gly Pro Gly Thr Ser
    370                 375                 380

Gly Pro Tyr Gly Pro Gly Ala Ser Gly Pro Gly Thr Ser Gly Pro Tyr
385                 390                 395                 400

Gly Pro Gly Ala Ser Ala Ala Ala Ala Gly Pro Gly Ala Tyr Gly
                405                 410                 415

Pro Gly Thr Ser Gly Pro Ser Ala Ser Ala Ala Ala Ala Gly Ala
                420                 425                 430

Tyr Gly Ser Gly Pro Gly Ala Tyr Gly Pro Tyr Gly Pro Gly Ala Ser
        435                 440                 445

Gly Pro Gly Ser Gly Thr Ser Gly Ala Gly Pro Tyr Gly Pro Gly Ala
        450                 455                 460

Ser Ala Ala Ala Ala Ala Gly Ala Tyr Gly Pro Gly Thr Ser Gly Pro
465                 470                 475                 480

Tyr Gly Pro Gly Ala Ser Ala Ala Ala Ala Gly Pro Gly Ser Gly
            485                 490                 495

Ala Tyr Gly Pro Gly Ala Ser Gly Ala Asn Gly Pro Gly Ser Gly Ala
        500                 505                 510
```

-continued

```
Tyr Gly Pro Gly Thr Ser Gly Pro Gly Ala Ser Ala Ala Ala Ala Ala
        515             520             525

Gly Ala Tyr Thr Ser Gly Pro Gly Thr Ser Gly Pro Tyr Gly Pro Gly
    530             535             540

Ala Ser Ala Ala Ala Ala Ala Gly Ala Tyr Gly Ser Gly Pro Gly Thr
545             550             555             560

Ser Gly Pro Tyr Gly Pro Gly Ala Ser Gly Ser Gly Thr Ser Gly Pro
            565             570             575

Gly Thr Ser Gly Pro Tyr Ala Ser Ala Ala Ala Ala Gly Pro Gly
            580             585             590

Ser Gly Thr Ser Gly Pro Gly Ala Ser
        595             600

<210> SEQ ID NO 35
<211> LENGTH: 601
<212> TYPE: PRT
<213> ORGANISM: Artificial Sequence
<220> FEATURE:
<223> OTHER INFORMATION: PRT889

<400> SEQUENCE: 35

Met His His His His His His Ser Ser Gly Ser Ser Gly Pro Gly Val
1               5               10              15

Leu Gly Pro Tyr Gly Pro Gly Ala Ser Ala Ala Ala Ala Gly Ile
            20              25              30

Asn Gly Pro Gly Ser Gly Val Leu Gly Pro Gly Ile Ser Gly Ile Tyr
        35              40              45

Gly Pro Gly Val Leu Gly Pro Gly Val Leu Gly Pro Gly Ser Ser Ala
    50              55              60

Ala Ala Ala Ala Gly Pro Gly Ile Tyr Gly Pro Gly Val Leu Gly Pro
65              70              75              80

Ser Ala Ser Ala Ala Ala Ala Gly Pro Gly Ser Gly Val Leu Gly
            85              90              95

Pro Gly Ala Ser Gly Ile Tyr Gly Pro Gly Val Leu Gly Pro Gly Val
            100             105             110

Leu Gly Pro Gly Ser Ser Ala Ala Ala Ala Gly Ile Tyr Gly Ser
        115             120             125

Gly Pro Gly Val Leu Gly Pro Tyr Gly Ser Ala Ala Ala Ala Gly
    130             135             140

Pro Gly Ser Gly Ile Tyr Gly Ile Gly Pro Tyr Gly Pro Gly Ala Ser
145             150             155             160

Gly Pro Gly Ile Tyr Gly Pro Gly Val Leu Gly Pro Ser Ala Ser Ala
            165             170             175

Ala Ala Ala Gly Ser Gly Val Leu Gly Pro Gly Ile Tyr Gly Pro
        180             185             190

Tyr Ala Ser Ala Ala Ala Ala Gly Ile Tyr Gly Ser Gly Pro Gly
        195             200             205

Val Leu Gly Pro Tyr Gly Pro Gly Ile Ser Gly Ser Gly Val Leu Gly
    210             215             220

Pro Gly Val Leu Gly Pro Tyr Ala Ser Ala Ala Ala Ala Gly Pro
225             230             235             240

Gly Val Leu Gly Pro Tyr Gly Pro Gly Ser Ser Ala Ala Ala Ala
            245             250             255

Gly Ile Tyr Gly Tyr Gly Pro Gly Val Leu Gly Pro Tyr Gly Pro Gly
        260             265             270
```

```
Ala Ser Gly Ile Asn Gly Pro Gly Ser Gly Ile Tyr Gly Pro Gly Val
        275             280             285

Leu Gly Pro Gly Ile Ser Ala Ala Ala Ala Gly Pro Gly Val Leu
        290             295             300

Gly Pro Tyr Gly Pro Gly Ala Ser Ala Ala Ala Ala Gly Ile Tyr
305             310             315             320

Gly Pro Gly Val Leu Gly Pro Gly Ile Tyr Gly Pro Gly Ser Ser Gly
                325             330             335

Pro Gly Val Leu Gly Pro Tyr Gly Pro Gly Ser Ser Ala Ala Ala
        340             345             350

Ala Gly Ile Tyr Gly Pro Gly Val Leu Gly Pro Tyr Gly Pro Gly Ile
        355             360             365

Ser Ala Ala Ala Ala Ala Gly Ile Tyr Val Leu Gly Pro Gly Val Leu
        370             375             380

Gly Pro Tyr Gly Pro Gly Ala Ser Gly Pro Gly Val Leu Gly Pro Tyr
385             390             395             400

Gly Pro Gly Ala Ser Ala Ala Ala Ala Gly Pro Gly Ile Tyr Gly
                405             410             415

Pro Gly Val Leu Gly Pro Ser Ala Ser Ala Ala Ala Ala Gly Ile
        420             425             430

Tyr Gly Ser Gly Pro Gly Ile Tyr Gly Pro Tyr Gly Pro Gly Ile Ser
        435             440             445

Gly Pro Gly Ser Gly Val Leu Gly Ile Gly Pro Tyr Gly Pro Gly Ala
        450             455             460

Ser Ala Ala Ala Ala Gly Ile Tyr Gly Pro Gly Val Leu Gly Pro
465             470             475             480

Tyr Gly Pro Gly Ile Ser Ala Ala Ala Ala Gly Pro Gly Ser Gly
                485             490             495

Ile Tyr Gly Pro Gly Ala Ser Gly Ile Asn Gly Pro Gly Ser Gly Ile
        500             505             510

Tyr Gly Pro Gly Val Leu Gly Pro Gly Ile Ser Ala Ala Ala Ala Ala
        515             520             525

Gly Ile Tyr Val Leu Gly Pro Gly Val Leu Gly Pro Tyr Gly Pro Gly
        530             535             540

Ala Ser Ala Ala Ala Ala Ala Gly Ile Tyr Gly Ser Gly Pro Gly Val
545             550             555             560

Leu Gly Pro Tyr Gly Pro Gly Ile Ser Gly Ser Gly Val Leu Gly Pro
                565             570             575

Gly Val Leu Gly Pro Tyr Ala Ser Ala Ala Ala Ala Gly Pro Gly
        580             585             590

Ser Gly Val Leu Gly Pro Gly Ala Ser
        595             600
```

```
<210> SEQ ID NO 36
<211> LENGTH: 601
<212> TYPE: PRT
<213> ORGANISM: Artificial Sequence
<220> FEATURE:
<223> OTHER INFORMATION: PRT916

<400> SEQUENCE: 36

Met His His His His His Ser Ser Gly Ser Ser Gly Pro Gly Val
1               5               10              15

Ile Gly Pro Tyr Gly Pro Gly Ala Ser Ala Ala Ala Ala Ala Gly Leu
        20              25              30
```

-continued

```
Asn Gly Pro Gly Ser Gly Val Ile Gly Pro Gly Leu Ser Gly Leu Tyr
        35              40              45

Gly Pro Gly Val Ile Gly Pro Gly Val Ile Gly Pro Gly Ser Ser Ala
    50              55              60

Ala Ala Ala Ala Gly Pro Gly Leu Tyr Gly Pro Gly Val Ile Gly Pro
65              70              75              80

Ser Ala Ser Ala Ala Ala Ala Ala Gly Pro Gly Ser Gly Val Ile Gly
            85              90              95

Pro Gly Ala Ser Gly Leu Tyr Gly Pro Gly Val Ile Gly Pro Gly Val
            100             105             110

Ile Gly Pro Gly Ser Ser Ala Ala Ala Ala Gly Leu Tyr Gly Ser
            115             120             125

Gly Pro Gly Val Ile Gly Pro Tyr Gly Ser Ala Ala Ala Ala Gly
    130             135             140

Pro Gly Ser Gly Leu Tyr Gly Leu Gly Pro Tyr Gly Pro Gly Ala Ser
145             150             155             160

Gly Pro Gly Leu Tyr Gly Pro Gly Val Ile Gly Pro Ser Ala Ser Ala
            165             170             175

Ala Ala Ala Gly Ser Gly Val Ile Gly Pro Gly Leu Tyr Gly Pro
            180             185             190

Tyr Ala Ser Ala Ala Ala Ala Gly Leu Tyr Gly Ser Gly Pro Gly
    195             200             205

Val Ile Gly Pro Tyr Gly Pro Gly Leu Ser Gly Ser Gly Val Ile Gly
    210             215             220

Pro Gly Val Ile Gly Pro Tyr Ala Ser Ala Ala Ala Ala Gly Pro
225             230             235             240

Gly Val Ile Gly Pro Tyr Gly Pro Gly Ser Ser Ala Ala Ala Ala
            245             250             255

Gly Leu Tyr Gly Tyr Gly Pro Gly Val Ile Gly Pro Tyr Gly Pro Gly
            260             265             270

Ala Ser Gly Leu Asn Gly Pro Gly Ser Gly Leu Tyr Gly Pro Gly Val
            275             280             285

Ile Gly Pro Gly Leu Ser Ala Ala Ala Ala Gly Pro Gly Val Ile
    290             295             300

Gly Pro Tyr Gly Pro Gly Ala Ser Ala Ala Ala Ala Gly Leu Tyr
305             310             315             320

Gly Pro Gly Val Ile Gly Pro Gly Leu Tyr Gly Pro Gly Ser Ser Gly
            325             330             335

Pro Gly Val Ile Gly Pro Tyr Gly Pro Gly Ser Ser Ala Ala Ala Ala
            340             345             350

Ala Gly Leu Tyr Gly Pro Gly Val Ile Gly Pro Tyr Gly Pro Gly Leu
            355             360             365

Ser Ala Ala Ala Ala Gly Leu Tyr Val Ile Gly Pro Gly Val Ile
    370             375             380

Gly Pro Tyr Gly Pro Gly Ala Ser Gly Pro Gly Val Ile Gly Pro Tyr
385             390             395             400

Gly Pro Gly Ala Ser Ala Ala Ala Ala Gly Pro Gly Leu Tyr Gly
            405             410             415

Pro Gly Val Ile Gly Pro Ser Ala Ser Ala Ala Ala Ala Gly Leu
            420             425             430

Tyr Gly Ser Gly Pro Gly Leu Tyr Gly Pro Tyr Gly Pro Gly Leu Ser
            435             440             445

Gly Pro Gly Ser Gly Val Ile Gly Leu Gly Pro Tyr Gly Pro Gly Ala
```

-continued

```
            450                 455                 460

Ser Ala Ala Ala Ala Ala Gly Leu Tyr Gly Pro Gly Val Ile Gly Pro
465                 470                 475                 480

Tyr Gly Pro Gly Leu Ser Ala Ala Ala Ala Gly Pro Gly Ser Gly
                485                 490                 495

Leu Tyr Gly Pro Gly Ala Ser Gly Leu Asn Gly Pro Gly Ser Gly Leu
                500                 505                 510

Tyr Gly Pro Gly Val Ile Gly Pro Gly Leu Ser Ala Ala Ala Ala Ala
                515                 520                 525

Gly Leu Tyr Val Ile Gly Pro Gly Val Ile Gly Pro Tyr Gly Pro Gly
            530                 535                 540

Ala Ser Ala Ala Ala Ala Ala Gly Leu Tyr Gly Ser Gly Pro Gly Val
545                 550                 555                 560

Ile Gly Pro Tyr Gly Pro Gly Leu Ser Gly Ser Gly Val Ile Gly Pro
                565                 570                 575

Gly Val Ile Gly Pro Tyr Ala Ser Ala Ala Ala Ala Gly Pro Gly
                580                 585                 590

Ser Gly Val Ile Gly Pro Gly Ala Ser
            595                 600

<210> SEQ ID NO 37
<211> LENGTH: 601
<212> TYPE: PRT
<213> ORGANISM: Artificial Sequence
<220> FEATURE:
<223> OTHER INFORMATION: PRT918

<400> SEQUENCE: 37

Met His His His His His Ser Ser Gly Ser Ser Gly Pro Gly Val
1               5                   10                  15

Phe Gly Pro Tyr Gly Pro Gly Ala Ser Ala Ala Ala Ala Gly Ile
                20                  25                  30

Asn Gly Pro Gly Ser Gly Val Phe Gly Pro Gly Ile Ser Gly Ile Tyr
            35                  40                  45

Gly Pro Gly Val Phe Gly Pro Gly Val Phe Gly Pro Gly Ser Ser Ala
    50                  55                  60

Ala Ala Ala Ala Gly Pro Gly Ile Tyr Gly Pro Gly Val Phe Gly Pro
65                  70                  75                  80

Ser Ala Ser Ala Ala Ala Ala Gly Pro Gly Ser Gly Val Phe Gly
                85                  90                  95

Pro Gly Ala Ser Gly Ile Tyr Gly Pro Gly Val Phe Gly Pro Gly Val
                100                 105                 110

Phe Gly Pro Gly Ser Ser Ala Ala Ala Ala Gly Ile Tyr Gly Ser
            115                 120                 125

Gly Pro Gly Val Phe Gly Pro Tyr Gly Ser Ala Ala Ala Ala Gly
    130                 135                 140

Pro Gly Ser Gly Ile Tyr Gly Ile Gly Pro Tyr Gly Pro Gly Ala Ser
145                 150                 155                 160

Gly Pro Gly Ile Tyr Gly Pro Gly Val Phe Gly Pro Ser Ala Ser Ala
                165                 170                 175

Ala Ala Ala Gly Ser Gly Val Phe Gly Pro Gly Ile Tyr Gly Pro
            180                 185                 190

Tyr Ala Ser Ala Ala Ala Ala Gly Ile Tyr Gly Ser Gly Pro Gly
            195                 200                 205

Val Phe Gly Pro Tyr Gly Pro Gly Ile Ser Gly Ser Gly Val Phe Gly
```

-continued

```
       210              215              220

Pro Gly Val Phe Gly Pro Tyr Ala Ser Ala Ala Ala Ala Ala Gly Pro
225              230              235              240

Gly Val Phe Gly Pro Tyr Gly Pro Gly Ser Ser Ala Ala Ala Ala
                 245              250              255

Gly Ile Tyr Gly Tyr Gly Pro Gly Val Phe Gly Pro Tyr Gly Pro Gly
                 260              265              270

Ala Ser Gly Ile Asn Gly Pro Gly Ser Gly Ile Tyr Gly Pro Gly Val
            275              280              285

Phe Gly Pro Gly Ile Ser Ala Ala Ala Ala Gly Pro Gly Val Phe
            290              295              300

Gly Pro Tyr Gly Pro Gly Ala Ser Ala Ala Ala Ala Gly Ile Tyr
305              310              315              320

Gly Pro Gly Val Phe Gly Pro Gly Ile Tyr Gly Pro Gly Ser Ser Gly
                 325              330              335

Pro Gly Val Phe Gly Pro Tyr Gly Pro Gly Ser Ser Ala Ala Ala Ala
                 340              345              350

Ala Gly Ile Tyr Gly Pro Gly Val Phe Gly Pro Tyr Gly Pro Gly Ile
            355              360              365

Ser Ala Ala Ala Ala Ala Gly Ile Tyr Val Phe Gly Pro Gly Val Phe
            370              375              380

Gly Pro Tyr Gly Pro Gly Ala Ser Gly Pro Gly Val Phe Gly Pro Tyr
385              390              395              400

Gly Pro Gly Ala Ser Ala Ala Ala Ala Gly Pro Gly Ile Tyr Gly
                 405              410              415

Pro Gly Val Phe Gly Pro Ser Ala Ser Ala Ala Ala Ala Gly Ile
                 420              425              430

Tyr Gly Ser Gly Pro Gly Ile Tyr Gly Pro Tyr Gly Pro Gly Ile Ser
            435              440              445

Gly Pro Gly Ser Gly Val Phe Gly Ile Gly Pro Tyr Gly Pro Gly Ala
            450              455              460

Ser Ala Ala Ala Ala Ala Gly Ile Tyr Gly Pro Gly Val Phe Gly Pro
465              470              475              480

Tyr Gly Pro Gly Ile Ser Ala Ala Ala Ala Gly Pro Gly Ser Gly
            485              490              495

Ile Tyr Gly Pro Gly Ala Ser Gly Ile Asn Gly Pro Gly Ser Gly Ile
            500              505              510

Tyr Gly Pro Gly Val Phe Gly Pro Gly Ile Ser Ala Ala Ala Ala Ala
            515              520              525

Gly Ile Tyr Val Phe Gly Pro Gly Val Phe Gly Pro Tyr Gly Pro Gly
            530              535              540

Ala Ser Ala Ala Ala Ala Ala Gly Ile Tyr Gly Ser Gly Pro Gly Val
545              550              555              560

Phe Gly Pro Tyr Gly Pro Gly Ile Ser Gly Ser Gly Val Phe Gly Pro
                 565              570              575

Gly Val Phe Gly Pro Tyr Ala Ser Ala Ala Ala Ala Gly Pro Gly
                 580              585              590

Ser Gly Val Phe Gly Pro Gly Ala Ser
            595              600

<210> SEQ ID NO 38
<211> LENGTH: 576
<212> TYPE: PRT
<213> ORGANISM: Artificial Sequence
```

-continued

```
<220> FEATURE:
<223> OTHER INFORMATION: PRT699

<400> SEQUENCE: 38

Met His His His His His Ser Ser Gly Ser Ser Gly Pro Gly Val
1               5                   10                  15

Leu Gly Pro Tyr Gly Pro Gly Ala Ser Ala Ala Ala Ala Ala Ala
                20                  25                  30

Gly Ser Asn Gly Pro Gly Ser Gly Val Leu Gly Pro Gly Gln Ser Gly
        35                  40                  45

Gln Tyr Gly Pro Gly Val Leu Gly Pro Gly Val Leu Gly Pro Gly Ser
    50                  55                  60

Ser Ala Ala Ala Ala Ala Ala Gly Pro Gly Gln Tyr Gly Pro Gly
65                  70                  75                  80

Val Leu Gly Pro Ser Ala Ser Ala Ala Ala Ala Ala Ala Gly Pro
                85                  90                  95

Gly Ser Gly Val Leu Gly Pro Gly Ala Ser Gly Gln Tyr Gly Pro Gly
            100                 105                 110

Val Leu Gly Pro Gly Val Leu Gly Pro Gly Ser Ser Ala Ala Ala
        115                 120                 125

Ala Ala Ala Gly Ser Tyr Gly Ser Gly Pro Gly Val Leu Gly Pro Tyr
        130                 135                 140

Gly Ser Ala Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
            165                 170                 175

Pro Gly Val Leu Gly Pro Ser Ala Ser Ala Ala Ala Ala Ala Ala
            180                 185                 190

Gly Ser Gly Val Leu Gly Pro Gly Gln Tyr Gly Pro Tyr Ala Ser Ala
            195                 200                 205

Ala Ala Ala Ala Ala Gly Ser Tyr Gly Ser Gly Pro Gly Val Leu
    210                 215                 220

Gly Pro Tyr Gly Pro Gly Gln Ser Gly Ser Gly Val Leu Gly Pro Gly
225                 230                 235                 240

Val Leu Gly Pro Tyr Ala Ser Ala Ala Ala Ala Ala Ala Gly Pro
            245                 250                 255

Gly Val Leu Gly Pro Tyr Gly Pro Gly Ser Ser Ala Ala Ala Ala
            260                 265                 270

Ala Ala Gly Ser Tyr Gly Tyr Gly Pro Gly Val Leu Gly Pro Tyr Gly
    275                 280                 285

Pro Gly Ala Ser Gly Gln Asn Gly Pro Gly Ser Gly Gln Tyr Gly Pro
    290                 295                 300

Gly Val Leu Gly Pro Gly Pro Ser Ala Ala Ala Ala Ala Ala Gly
305                 310                 315                 320

Pro Gly Val Leu Gly Pro Tyr Gly Pro Gly Ala Ser Ala Ala Ala Ala
            325                 330                 335

Ala Ala Ala Gly Ser Tyr Gly Pro Gly Val Leu Gly Pro Gly Gln Tyr
            340                 345                 350

Gly Pro Gly Ser Ser Gly Pro Gly Val Leu Gly Pro Tyr Gly Pro Gly
        355                 360                 365

Ser Ser Ala Ala Ala Ala Ala Ala Ala Gly Ser Tyr Gly Pro Gly Val
    370                 375                 380

Leu Gly Pro Tyr Gly Pro Gly Pro Ser Ala Ala Ala Ala Ala Ala Ala
385                 390                 395                 400
```

```
Gly Ser Tyr Val Leu Gly Pro Gly Val Leu Gly Pro Tyr Gly Pro Gly
            405                 410                 415

Ala Ser Gly Pro Gly Val Leu Gly Pro Tyr Gly Pro Gly Ala Ser Ala
            420                 425                 430

Ala Ala Ala Ala Ala Ala Gly Pro Gly Gln Tyr Gly Pro Gly Val Leu
            435                 440                 445

Gly Pro Ser Ala Ser Ala Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Val Leu Gly Gln Gly Pro Tyr Gly Pro Gly Ala Ser Ala
            485                 490                 495

Ala Ala Ala Ala Ala Gly Ser Tyr Gly Pro Gly Val Leu Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
    530                 535                 540

Gly Gln Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
            565                 570                 575
```

<210> SEQ ID NO 39
<211> LENGTH: 576
<212> TYPE: PRT
<213> ORGANISM: Artificial Sequence
<220> FEATURE:
<223> OTHER INFORMATION: PRT698

<400> SEQUENCE: 39

```
Met His His His His His His Ser Ser Gly Ser Ser Gly Pro Gly Val
1               5                   10                  15

Leu Gly Pro Tyr Gly Pro Gly Ala Ser Ala Ala Ala Ala Ala Ala Ala
            20                  25                  30

Gly Ser Asn Gly Pro Gly Ser Gly Val Leu Gly Pro Gly Ile Ser Gly
            35                  40                  45

Ile Tyr Gly Pro Gly Val Leu Gly Pro Gly Val Leu Gly Pro Gly Ser
    50                  55                  60

Ser Ala Ala Ala Ala Ala Ala Gly Pro Gly Ile Tyr Gly Pro Gly
65                  70                  75                  80

Val Leu Gly Pro Ser Ala Ser Ala Ala Ala Ala Ala Ala Gly Pro
            85                  90                  95

Gly Ser Gly Val Leu Gly Pro Gly Ala Ser Gly Ile Tyr Gly Pro Gly
            100                 105                 110

Val Leu Gly Pro Gly Val Leu Gly Pro Gly Ser Ser Ala Ala Ala Ala
            115                 120                 125

Ala Ala Ala Gly Ser Tyr Gly Ser Gly Pro Gly Val Leu Gly Pro Tyr
    130                 135                 140

Gly Ser Ala Ala Ala Ala Ala Ala Ala Gly Pro Gly Ser Gly Ile Tyr
145                 150                 155                 160

Gly Ile Gly Pro Tyr Gly Pro Gly Ala Ser Gly Pro Gly Ile Tyr Gly
            165                 170                 175

Pro Gly Val Leu Gly Pro Ser Ala Ser Ala Ala Ala Ala Ala Ala Ala
            180                 185                 190
```

```
Gly Ser Gly Val Leu Gly Pro Gly Ile Tyr Gly Pro Tyr Ala Ser Ala
        195                 200                 205

Ala Ala Ala Ala Ala Ala Gly Ser Tyr Gly Ser Gly Pro Gly Val Leu
        210                 215                 220

Gly Pro Tyr Gly Pro Gly Ile Ser Gly Ser Gly Val Leu Gly Pro Gly
225                 230                 235                 240

Val Leu Gly Pro Tyr Ala Ser Ala Ala Ala Ala Ala Ala Ala Gly Pro
                245                 250                 255

Gly Val Leu Gly Pro Tyr Gly Pro Gly Ser Ser Ala Ala Ala Ala Ala
                260                 265                 270

Ala Ala Gly Ser Tyr Gly Tyr Gly Pro Gly Val Leu Gly Pro Tyr Gly
                275                 280                 285

Pro Gly Ala Ser Gly Ile Asn Gly Pro Gly Ser Gly Ile Tyr Gly Pro
        290                 295                 300

Gly Val Leu Gly Pro Gly Pro Ser Ala Ala Ala Ala Ala Ala Ala Gly
305                 310                 315                 320

Pro Gly Val Leu Gly Pro Tyr Gly Pro Gly Ala Ser Ala Ala Ala Ala
                325                 330                 335

Ala Ala Ala Gly Ser Tyr Gly Pro Gly Val Leu Gly Pro Gly Ile Tyr
                340                 345                 350

Gly Pro Gly Ser Ser Gly Pro Gly Val Leu Gly Pro Tyr Gly Pro Gly
                355                 360                 365

Ser Ser Ala Ala Ala Ala Ala Ala Gly Ser Tyr Gly Pro Gly Val
        370                 375                 380

Leu Gly Pro Tyr Gly Pro Gly Pro Ser Ala Ala Ala Ala Ala Ala Ala
385                 390                 395                 400

Gly Ser Tyr Val Leu Gly Pro Gly Val Leu Gly Pro Tyr Gly Pro Gly
                405                 410                 415

Ala Ser Gly Pro Gly Val Leu Gly Pro Tyr Gly Pro Gly Ala Ser Ala
                420                 425                 430

Ala Ala Ala Ala Ala Gly Pro Gly Ile Tyr Gly Pro Gly Val Leu
        435                 440                 445

Gly Pro Ser Ala Ser Ala Ala Ala Ala Ala Ala Gly Ser Tyr Gly
        450                 455                 460

Ser Gly Pro Gly Ile Tyr Gly Pro Tyr Gly Pro Gly Ile Ser Gly Pro
465                 470                 475                 480

Gly Ser Gly Val Leu Gly Ile Gly Pro Tyr Gly Pro Gly Ala Ser Ala
                485                 490                 495

Ala Ala Ala Ala Ala Gly Ser Tyr Gly Pro Gly Val Leu Gly Pro
                500                 505                 510

Tyr Gly Pro Gly Pro Ser Ala Ala Ala Ala Ala Ala Gly Pro Gly
        515                 520                 525

Ser Gly Ile Tyr Gly Pro Gly Ala Ser Gly Ile Asn Gly Pro Gly Ser
        530                 535                 540

Gly Ile Tyr Gly Pro Gly Val Leu Gly Pro Gly Pro Ser Ala Ala Ala
545                 550                 555                 560

Ala Ala Ala Ala Gly Pro Gly Ser Gly Val Leu Gly Pro Gly Ala Ser
                565                 570                 575
```

<210> SEQ ID NO 40
<211> LENGTH: 1190
<212> TYPE: PRT
<213> ORGANISM: Artificial Sequence
<220> FEATURE:

<223> OTHER INFORMATION: PRT966

<400> SEQUENCE: 40

```
Met His His His His His Ser Ser Gly Ser Ser Gly Pro Gly Val
1               5               10              15

Phe Gly Pro Tyr Gly Pro Gly Ala Ser Ala Ala Ala Ala Gly Ile
            20              25              30

Asn Gly Pro Gly Ser Gly Val Phe Gly Pro Gly Ile Ser Gly Ile Tyr
        35              40              45

Gly Pro Gly Val Phe Gly Pro Gly Val Phe Gly Pro Gly Ser Ser Ala
    50              55              60

Ala Ala Ala Ala Gly Pro Gly Ile Tyr Gly Pro Gly Val Phe Gly Pro
65              70              75              80

Ser Ala Ser Ala Ala Ala Ala Ala Gly Pro Gly Ser Gly Val Phe Gly
            85              90              95

Pro Gly Ala Ser Gly Ile Tyr Gly Pro Gly Val Phe Gly Pro Gly Val
            100             105             110

Phe Gly Pro Gly Ser Ser Ala Ala Ala Ala Ala Gly Ile Tyr Gly Ser
            115             120             125

Gly Pro Gly Val Phe Gly Pro Tyr Gly Ser Ala Ala Ala Ala Ala Gly
    130             135             140

Pro Gly Ser Gly Ile Tyr Gly Ile Gly Pro Tyr Gly Pro Gly Ala Ser
145             150             155             160

Gly Pro Gly Ile Tyr Gly Pro Gly Val Phe Gly Pro Ser Ala Ser Ala
            165             170             175

Ala Ala Ala Ala Gly Ser Gly Val Phe Gly Pro Gly Ile Tyr Gly Pro
            180             185             190

Tyr Ala Ser Ala Ala Ala Ala Ala Gly Ile Tyr Gly Ser Gly Pro Gly
            195             200             205

Val Phe Gly Pro Tyr Gly Pro Gly Ile Ser Gly Ser Gly Val Phe Gly
    210             215             220

Pro Gly Val Phe Gly Pro Tyr Ala Ser Ala Ala Ala Ala Gly Pro
225             230             235             240

Gly Val Phe Gly Pro Tyr Gly Pro Gly Ser Ser Ala Ala Ala Ala Ala
            245             250             255

Gly Ile Tyr Gly Tyr Gly Pro Gly Val Phe Gly Pro Tyr Gly Pro Gly
            260             265             270

Ala Ser Gly Ile Asn Gly Pro Gly Ser Gly Ile Tyr Gly Pro Gly Val
            275             280             285

Phe Gly Pro Gly Ile Ser Ala Ala Ala Ala Ala Gly Pro Gly Val Phe
    290             295             300

Gly Pro Tyr Gly Pro Gly Ala Ser Ala Ala Ala Ala Ala Gly Ile Tyr
305             310             315             320

Gly Pro Gly Val Phe Gly Pro Gly Ile Tyr Gly Pro Gly Ser Ser Gly
            325             330             335

Pro Gly Val Phe Gly Pro Tyr Gly Pro Gly Ser Ser Ala Ala Ala Ala
            340             345             350

Ala Gly Ile Tyr Gly Pro Gly Val Phe Gly Pro Tyr Gly Pro Gly Ile
    355             360             365

Ser Ala Ala Ala Ala Ala Gly Ile Tyr Val Phe Gly Pro Gly Val Phe
    370             375             380

Gly Pro Tyr Gly Pro Gly Ala Ser Gly Pro Gly Val Phe Gly Pro Tyr
385             390             395             400
```

-continued

Gly Pro Gly Ala Ser Ala Ala Ala Ala Gly Pro Gly Ile Tyr Gly
            405                 410                 415

Pro Gly Val Phe Gly Pro Ser Ala Ser Ala Ala Ala Ala Gly Ile
            420                 425                 430

Tyr Gly Ser Gly Pro Gly Ile Tyr Gly Pro Tyr Gly Pro Gly Ile Ser
            435                 440                 445

Gly Pro Gly Ser Gly Val Phe Gly Ile Gly Pro Tyr Gly Pro Gly Ala
    450                 455                 460

Ser Ala Ala Ala Ala Ala Gly Ile Tyr Gly Pro Gly Val Phe Gly Pro
465                 470                 475                 480

Tyr Gly Pro Gly Ile Ser Ala Ala Ala Ala Gly Pro Gly Ser Gly
            485                 490                 495

Ile Tyr Gly Pro Gly Ala Ser Gly Ile Asn Gly Pro Gly Ser Gly Ile
            500                 505                 510

Tyr Gly Pro Gly Val Phe Gly Pro Gly Ile Ser Ala Ala Ala Ala Ala
            515                 520                 525

Gly Ile Tyr Val Phe Gly Pro Gly Val Phe Gly Pro Tyr Gly Pro Gly
    530                 535                 540

Ala Ser Ala Ala Ala Ala Ala Gly Ile Tyr Gly Ser Gly Pro Gly Val
545                 550                 555                 560

Phe Gly Pro Tyr Gly Pro Gly Ile Ser Gly Ser Gly Val Phe Gly Pro
            565                 570                 575

Gly Val Phe Gly Pro Tyr Ala Ser Ala Ala Ala Ala Gly Pro Gly
            580                 585                 590

Ser Gly Val Phe Gly Pro Gly Ala Ser Gly Pro Gly Val Phe Gly Pro
            595                 600                 605

Tyr Gly Pro Gly Ala Ser Ala Ala Ala Ala Gly Ile Asn Gly Pro
    610                 615                 620

Gly Ser Gly Val Phe Gly Pro Gly Ile Ser Gly Ile Tyr Gly Pro Gly
625                 630                 635                 640

Val Phe Gly Pro Gly Val Phe Gly Pro Gly Ser Ser Ala Ala Ala Ala
            645                 650                 655

Ala Gly Pro Gly Ile Tyr Gly Pro Gly Val Phe Gly Pro Ser Ala Ser
            660                 665                 670

Ala Ala Ala Ala Ala Gly Pro Gly Ser Gly Val Phe Gly Pro Gly Ala
            675                 680                 685

Ser Gly Ile Tyr Gly Pro Gly Val Phe Gly Pro Gly Val Phe Gly Pro
    690                 695                 700

Gly Ser Ser Ala Ala Ala Ala Ala Gly Ile Tyr Gly Ser Gly Pro Gly
705                 710                 715                 720

Val Phe Gly Pro Tyr Gly Ser Ala Ala Ala Ala Gly Pro Gly Ser
            725                 730                 735

Gly Ile Tyr Gly Ile Gly Pro Tyr Gly Pro Gly Ala Ser Gly Pro Gly
            740                 745                 750

Ile Tyr Gly Pro Gly Val Phe Gly Pro Ser Ala Ser Ala Ala Ala Ala
            755                 760                 765

Ala Gly Ser Gly Val Phe Gly Pro Gly Ile Tyr Gly Pro Tyr Ala Ser
    770                 775                 780

Ala Ala Ala Ala Gly Ile Tyr Gly Ser Gly Pro Gly Val Phe Gly
785                 790                 795                 800

Pro Tyr Gly Pro Gly Ile Ser Gly Ser Gly Val Phe Gly Pro Gly Val
            805                 810                 815

Phe Gly Pro Tyr Ala Ser Ala Ala Ala Ala Ala Gly Pro Gly Val Phe

-continued

```
                820                 825                 830

Gly Pro Tyr Gly Pro Gly Ser Ser Ala Ala Ala Ala Ala Gly Ile Tyr
        835                 840                 845

Gly Tyr Gly Pro Gly Val Phe Gly Pro Tyr Gly Pro Gly Ala Ser Gly
    850                 855                 860

Ile Asn Gly Pro Gly Ser Gly Ile Tyr Gly Pro Gly Val Phe Gly Pro
865                 870                 875                 880

Gly Ile Ser Ala Ala Ala Ala Ala Gly Pro Gly Val Phe Gly Pro Tyr
            885                 890                 895

Gly Pro Gly Ala Ser Ala Ala Ala Ala Gly Ile Tyr Gly Pro Gly
        900                 905                 910

Val Phe Gly Pro Gly Ile Tyr Gly Pro Gly Ser Ser Gly Pro Gly Val
        915                 920                 925

Phe Gly Pro Tyr Gly Pro Gly Ser Ser Ala Ala Ala Ala Ala Gly Ile
    930                 935                 940

Tyr Gly Pro Gly Val Phe Gly Pro Tyr Gly Pro Gly Ile Ser Ala Ala
945                 950                 955                 960

Ala Ala Ala Gly Ile Tyr Val Phe Gly Pro Gly Val Phe Gly Pro Tyr
            965                 970                 975

Gly Pro Gly Ala Ser Gly Pro Gly Val Phe Gly Pro Tyr Gly Pro Gly
            980                 985                 990

Ala Ser Ala Ala Ala Ala Ala Gly  Pro Gly Ile Tyr Gly  Pro Gly Val
        995                 1000                 1005

Phe Gly  Pro Ser Ala Ser Ala  Ala Ala Ala Ala Gly  Ile Tyr Gly
    1010                 1015                 1020

Ser Gly  Pro Gly Ile Tyr Gly  Pro Tyr Gly Pro Gly  Ile Ser Gly
    1025                 1030                 1035

Pro Gly  Ser Gly Val Phe Gly  Ile Gly Pro Tyr Gly  Pro Gly Ala
    1040                 1045                 1050

Ser Ala  Ala Ala Ala Ala Gly  Ile Tyr Gly Pro Gly  Val Phe Gly
    1055                 1060                 1065

Pro Tyr  Gly Pro Gly Ile Ser  Ala Ala Ala Ala Ala  Gly Pro Gly
    1070                 1075                 1080

Ser Gly  Ile Tyr Gly Pro Gly  Ala Ser Gly Ile Asn  Gly Pro Gly
    1085                 1090                 1095

Ser Gly  Ile Tyr Gly Pro Gly  Val Phe Gly Pro Gly  Ile Ser Ala
    1100                 1105                 1110

Ala Ala  Ala Ala Gly Ile Tyr  Val Phe Gly Pro Gly  Val Phe Gly
    1115                 1120                 1125

Pro Tyr  Gly Pro Gly Ala Ser  Ala Ala Ala Ala Ala  Gly Ile Tyr
    1130                 1135                 1140

Gly Ser  Gly Pro Gly Val Phe  Gly Pro Tyr Gly Pro  Gly Ile Ser
    1145                 1150                 1155

Gly Ser  Gly Val Phe Gly Pro  Gly Val Phe Gly Pro  Tyr Ala Ser
    1160                 1165                 1170

Ala Ala  Ala Ala Ala Gly Pro  Gly Ser Gly Val Phe  Gly Pro Gly
    1175                 1180                 1185

Ala Ser
    1190
```

<210> SEQ ID NO 41
<211> LENGTH: 590
<212> TYPE: PRT
<213> ORGANISM: Artificial Sequence
<220> FEATURE:
<223> OTHER INFORMATION: Met-PRT917

<400> SEQUENCE: 41

Met Gly Pro Gly Leu Ile Gly Pro Tyr Gly Pro Gly Ala Ser Ala Ala
1               5                   10                  15

Ala Ala Ala Gly Val Asn Gly Pro Gly Ser Gly Leu Ile Gly Pro Gly
            20                  25                  30

Val Ser Gly Val Tyr Gly Pro Gly Leu Ile Gly Pro Gly Leu Ile Gly
        35                  40                  45

Pro Gly Ser Ser Ala Ala Ala Ala Gly Pro Gly Val Tyr Gly Pro
    50                  55                  60

Gly Leu Ile Gly Pro Ser Ala Ser Ala Ala Ala Ala Gly Pro Gly
65                  70                  75                  80

Ser Gly Leu Ile Gly Pro Gly Ala Ser Gly Val Tyr Gly Pro Gly Leu
                85                  90                  95

Ile Gly Pro Gly Leu Ile Gly Pro Gly Ser Ser Ala Ala Ala Ala Ala
            100                 105                 110

Gly Val Tyr Gly Ser Gly Pro Gly Leu Ile Gly Pro Tyr Gly Ser Ala
        115                 120                 125

Ala Ala Ala Ala Gly Pro Gly Ser Gly Val Tyr Gly Val Gly Pro Tyr
    130                 135                 140

Gly Pro Gly Ala Ser Gly Pro Gly Val Tyr Gly Pro Gly Leu Ile Gly
145                 150                 155                 160

Pro Ser Ala Ser Ala Ala Ala Ala Gly Ser Gly Leu Ile Gly Pro
            165                 170                 175

Gly Val Tyr Gly Pro Tyr Ala Ser Ala Ala Ala Ala Gly Val Tyr
        180                 185                 190

Gly Ser Gly Pro Gly Leu Ile Gly Pro Tyr Gly Pro Gly Val Ser Gly
        195                 200                 205

Ser Gly Leu Ile Gly Pro Gly Leu Ile Gly Pro Tyr Ala Ser Ala Ala
    210                 215                 220

Ala Ala Ala Gly Pro Gly Leu Ile Gly Pro Tyr Gly Pro Gly Ser Ser
225                 230                 235                 240

Ala Ala Ala Ala Ala Gly Val Tyr Gly Tyr Gly Pro Gly Leu Ile Gly
            245                 250                 255

Pro Tyr Gly Pro Gly Ala Ser Gly Val Asn Gly Pro Gly Ser Gly Val
        260                 265                 270

Tyr Gly Pro Gly Leu Ile Gly Pro Gly Val Ser Ala Ala Ala Ala Ala
        275                 280                 285

Gly Pro Gly Leu Ile Gly Pro Tyr Gly Pro Gly Ala Ser Ala Ala Ala
    290                 295                 300

Ala Ala Gly Val Tyr Gly Pro Gly Leu Ile Gly Pro Gly Val Tyr Gly
305                 310                 315                 320

Pro Gly Ser Ser Gly Pro Gly Leu Ile Gly Pro Tyr Gly Pro Gly Ser
            325                 330                 335

Ser Ala Ala Ala Ala Ala Gly Val Tyr Gly Pro Gly Leu Ile Gly Pro
            340                 345                 350

Tyr Gly Pro Gly Val Ser Ala Ala Ala Ala Gly Val Tyr Leu Ile
        355                 360                 365

Gly Pro Gly Leu Ile Gly Pro Tyr Gly Pro Gly Ala Ser Gly Pro Gly
    370                 375                 380

Leu Ile Gly Pro Tyr Gly Pro Gly Ala Ser Ala Ala Ala Ala Ala Gly
385                 390                 395                 400

-continued

```
Pro Gly Val Tyr Gly Pro Gly Leu Ile Gly Pro Ser Ala Ser Ala Ala
                405             410             415

Ala Ala Ala Gly Val Tyr Gly Ser Gly Pro Gly Val Tyr Gly Pro Tyr
                420             425             430

Gly Pro Gly Val Ser Gly Pro Gly Ser Gly Leu Ile Gly Val Gly Pro
                435             440             445

Tyr Gly Pro Gly Ala Ser Ala Ala Ala Ala Gly Val Tyr Gly Pro
    450             455             460

Gly Leu Ile Gly Pro Tyr Gly Pro Gly Val Ser Ala Ala Ala Ala
465             470             475             480

Gly Pro Gly Ser Gly Val Tyr Gly Pro Gly Ala Ser Gly Val Asn Gly
                485             490             495

Pro Gly Ser Gly Val Tyr Gly Pro Gly Leu Ile Gly Pro Gly Val Ser
                500             505             510

Ala Ala Ala Ala Ala Gly Val Tyr Leu Ile Gly Pro Gly Leu Ile Gly
                515             520             525

Pro Tyr Gly Pro Gly Ala Ser Ala Ala Ala Ala Gly Val Tyr Gly
    530             535             540

Ser Gly Pro Gly Leu Ile Gly Pro Tyr Gly Pro Gly Val Ser Gly Ser
545             550             555             560

Gly Leu Ile Gly Pro Gly Leu Ile Gly Pro Tyr Ala Ser Ala Ala Ala
                565             570             575

Ala Ala Gly Pro Gly Ser Gly Leu Ile Gly Pro Gly Ala Ser
                580             585             590
```

```
<210> SEQ ID NO 42
<211> LENGTH: 587
<212> TYPE: PRT
<213> ORGANISM: Artificial Sequence
<220> FEATURE:
<223> OTHER INFORMATION: Met-PRT1028

<400> SEQUENCE: 42

Met Gly Pro Gly Ile Phe Gly Pro Tyr Gly Pro Gly Ala Ser Ala Ala
1               5               10              15

Ala Ala Ala Gly Thr Gly Pro Gly Ser Gly Ile Phe Gly Pro Gly Thr
                20              25              30

Ser Gly Thr Tyr Gly Pro Gly Ile Phe Gly Pro Gly Ile Phe Gly Pro
                35              40              45

Gly Ser Ser Ala Ala Ala Ala Ala Gly Pro Gly Thr Tyr Gly Pro Gly
    50              55              60

Ile Phe Gly Pro Ser Ala Ser Ala Ala Ala Ala Gly Pro Gly Ser
65              70              75              80

Gly Ile Phe Gly Pro Gly Ala Ser Gly Thr Tyr Gly Pro Gly Ile Phe
                85              90              95

Gly Pro Gly Ile Phe Gly Pro Gly Ser Ser Ala Ala Ala Ala Ala Gly
                100             105             110

Thr Tyr Gly Ser Gly Pro Gly Ile Phe Gly Pro Tyr Gly Ser Ala Ala
                115             120             125

Ala Ala Ala Gly Pro Gly Ser Gly Thr Tyr Gly Thr Gly Pro Tyr Gly
                130             135             140

Pro Gly Ala Ser Gly Pro Gly Thr Tyr Gly Pro Gly Ile Phe Gly Pro
145             150             155             160

Ser Ala Ser Ala Ala Ala Ala Ala Gly Ser Gly Ile Phe Gly Pro Gly
                165             170             175
```

-continued

```
Thr Tyr Gly Pro Tyr Ala Ser Ala Ala Ala Ala Gly Thr Tyr Gly
            180                 185                 190

Ser Gly Pro Gly Ile Phe Gly Pro Tyr Gly Pro Gly Thr Ser Gly Ser
            195                 200                 205

Gly Ile Phe Gly Pro Gly Ile Phe Gly Pro Tyr Ala Ser Ala Ala Ala
            210                 215                 220

Ala Ala Gly Pro Gly Ile Phe Gly Pro Tyr Gly Pro Gly Ser Ser Ala
225                 230                 235                 240

Ala Ala Ala Ala Gly Thr Tyr Gly Tyr Gly Pro Gly Ile Phe Gly Pro
                245                 250                 255

Tyr Gly Pro Gly Ala Ser Gly Thr Gly Pro Gly Ser Gly Thr Tyr Gly
            260                 265                 270

Pro Gly Ile Phe Gly Pro Gly Thr Ser Ala Ala Ala Ala Gly Pro
            275                 280                 285

Gly Ile Phe Gly Pro Tyr Gly Pro Gly Ala Ser Ala Ala Ala Ala Ala
            290                 295                 300

Gly Thr Tyr Gly Pro Gly Ile Phe Gly Pro Gly Thr Tyr Gly Pro Gly
305                 310                 315                 320

Ser Ser Gly Pro Gly Ile Phe Gly Pro Tyr Gly Pro Gly Ser Ser Ala
            325                 330                 335

Ala Ala Ala Gly Thr Tyr Gly Pro Gly Ile Phe Gly Pro Tyr Gly
            340                 345                 350

Pro Gly Thr Ser Ala Ala Ala Ala Ala Gly Thr Tyr Ile Phe Gly Pro
            355                 360                 365

Gly Ile Phe Gly Pro Tyr Gly Pro Gly Ala Ser Gly Pro Gly Ile Phe
            370                 375                 380

Gly Pro Tyr Gly Pro Gly Ala Ser Ala Ala Ala Ala Gly Pro Gly
385                 390                 395                 400

Thr Tyr Gly Pro Gly Ile Phe Gly Pro Ser Ala Ser Ala Ala Ala Ala
                405                 410                 415

Ala Gly Thr Tyr Gly Ser Gly Pro Gly Thr Tyr Gly Pro Tyr Gly Pro
            420                 425                 430

Gly Thr Ser Gly Pro Gly Ser Gly Ile Phe Gly Thr Gly Pro Tyr Gly
            435                 440                 445

Pro Gly Ala Ser Ala Ala Ala Ala Ala Gly Thr Tyr Gly Pro Gly Ile
            450                 455                 460

Phe Gly Pro Tyr Gly Pro Gly Thr Ser Ala Ala Ala Ala Ala Gly Pro
465                 470                 475                 480

Gly Ser Gly Thr Tyr Gly Pro Gly Ala Ser Gly Thr Gly Pro Gly Ser
            485                 490                 495

Gly Thr Tyr Gly Pro Gly Ile Phe Gly Pro Gly Thr Ser Ala Ala Ala
            500                 505                 510

Ala Ala Gly Thr Tyr Ile Phe Gly Pro Gly Ile Phe Gly Pro Tyr Gly
            515                 520                 525

Pro Gly Ala Ser Ala Ala Ala Ala Gly Thr Tyr Gly Ser Gly Pro
            530                 535                 540

Gly Ile Phe Gly Pro Tyr Gly Pro Gly Thr Ser Gly Ser Gly Ile Phe
545                 550                 555                 560

Gly Pro Gly Ile Phe Gly Pro Tyr Ala Ser Ala Ala Ala Ala Ala Gly
            565                 570                 575

Pro Gly Ser Gly Ile Phe Gly Pro Gly Ala Ser
            580                 585
```

<210> SEQ ID NO 43
<211> LENGTH: 601
<212> TYPE: PRT
<213> ORGANISM: Artificial Sequence
<220> FEATURE:
<223> OTHER INFORMATION: PRT917

<400> SEQUENCE: 43

Met His His His His His His Ser Ser Gly Ser Ser Gly Pro Gly Leu
1               5                   10                  15

Ile Gly Pro Tyr Gly Pro Gly Ala Ser Ala Ala Ala Ala Ala Gly Val
                20                  25                  30

Asn Gly Pro Gly Ser Gly Leu Ile Gly Pro Gly Val Ser Gly Val Tyr
            35                  40                  45

Gly Pro Gly Leu Ile Gly Pro Gly Leu Ile Gly Pro Gly Ser Ser Ala
        50                  55                  60

Ala Ala Ala Ala Gly Pro Gly Val Tyr Gly Pro Gly Leu Ile Gly Pro
65                  70                  75                  80

Ser Ala Ser Ala Ala Ala Ala Ala Gly Pro Gly Ser Gly Leu Ile Gly
                85                  90                  95

Pro Gly Ala Ser Gly Val Tyr Gly Pro Gly Leu Ile Gly Pro Gly Leu
            100                 105                 110

Ile Gly Pro Gly Ser Ser Ala Ala Ala Ala Gly Val Tyr Gly Ser
            115                 120                 125

Gly Pro Gly Leu Ile Gly Pro Tyr Gly Ser Ala Ala Ala Ala Gly
        130                 135                 140

Pro Gly Ser Gly Val Tyr Gly Val Gly Pro Tyr Gly Pro Gly Ala Ser
145                 150                 155                 160

Gly Pro Gly Val Tyr Gly Pro Gly Leu Ile Gly Pro Ser Ala Ser Ala
            165                 170                 175

Ala Ala Ala Gly Ser Gly Leu Ile Gly Pro Gly Val Tyr Gly Pro
            180                 185                 190

Tyr Ala Ser Ala Ala Ala Ala Ala Gly Val Tyr Gly Ser Gly Pro Gly
        195                 200                 205

Leu Ile Gly Pro Tyr Gly Pro Gly Val Ser Gly Ser Gly Leu Ile Gly
        210                 215                 220

Pro Gly Leu Ile Gly Pro Tyr Ala Ser Ala Ala Ala Ala Gly Pro
225                 230                 235                 240

Gly Leu Ile Gly Pro Tyr Gly Pro Gly Ser Ser Ala Ala Ala Ala
            245                 250                 255

Gly Val Tyr Gly Tyr Gly Pro Gly Leu Ile Gly Pro Tyr Gly Pro Gly
            260                 265                 270

Ala Ser Gly Val Asn Gly Pro Gly Ser Gly Val Tyr Gly Pro Gly Leu
            275                 280                 285

Ile Gly Pro Gly Val Ser Ala Ala Ala Ala Gly Pro Gly Leu Ile
        290                 295                 300

Gly Pro Tyr Gly Pro Gly Ala Ser Ala Ala Ala Ala Gly Val Tyr
305                 310                 315                 320

Gly Pro Gly Leu Ile Gly Pro Gly Val Tyr Gly Pro Gly Ser Ser Gly
            325                 330                 335

Pro Gly Leu Ile Gly Pro Tyr Gly Pro Gly Ser Ser Ala Ala Ala Ala
            340                 345                 350

Ala Gly Val Tyr Gly Pro Gly Leu Ile Gly Pro Tyr Gly Pro Gly Val
        355                 360                 365

-continued

```
Ser Ala Ala Ala Ala Ala Gly Val Tyr Leu Ile Gly Pro Gly Leu Ile
370             375             380

Gly Pro Tyr Gly Pro Gly Ala Ser Gly Pro Gly Leu Ile Gly Pro Tyr
385             390             395             400

Gly Pro Gly Ala Ser Ala Ala Ala Ala Gly Pro Gly Val Tyr Gly
            405             410             415

Pro Gly Leu Ile Gly Pro Ser Ala Ser Ala Ala Ala Ala Gly Val
            420             425             430

Tyr Gly Ser Gly Pro Gly Val Tyr Gly Pro Tyr Gly Pro Gly Val Ser
            435             440             445

Gly Pro Gly Ser Gly Leu Ile Gly Val Gly Pro Tyr Gly Pro Gly Ala
            450             455             460

Ser Ala Ala Ala Ala Ala Gly Val Tyr Gly Pro Gly Leu Ile Gly Pro
465             470             475             480

Tyr Gly Pro Gly Val Ser Ala Ala Ala Ala Gly Pro Gly Ser Gly
            485             490             495

Val Tyr Gly Pro Gly Ala Ser Gly Val Asn Gly Pro Gly Ser Gly Val
            500             505             510

Tyr Gly Pro Gly Leu Ile Gly Pro Gly Val Ser Ala Ala Ala Ala Ala
            515             520             525

Gly Val Tyr Leu Ile Gly Pro Gly Leu Ile Gly Pro Tyr Gly Pro Gly
            530             535             540

Ala Ser Ala Ala Ala Ala Ala Gly Val Tyr Gly Ser Gly Pro Gly Leu
545             550             555             560

Ile Gly Pro Tyr Gly Pro Gly Val Ser Gly Ser Gly Leu Ile Gly Pro
            565             570             575

Gly Leu Ile Gly Pro Tyr Ala Ser Ala Ala Ala Ala Gly Pro Gly
            580             585             590

Ser Gly Leu Ile Gly Pro Gly Ala Ser
            595             600

<210> SEQ ID NO 44
<211> LENGTH: 598
<212> TYPE: PRT
<213> ORGANISM: Artificial Sequence
<220> FEATURE:
<223> OTHER INFORMATION: PRT1028

<400> SEQUENCE: 44

Met His His His His His Ser Ser Gly Ser Ser Gly Pro Gly Ile
1               5               10              15

Phe Gly Pro Tyr Gly Pro Gly Ala Ser Ala Ala Ala Ala Gly Thr
            20              25              30

Gly Pro Gly Ser Gly Ile Phe Gly Pro Gly Thr Ser Gly Thr Tyr Gly
            35              40              45

Pro Gly Ile Phe Gly Pro Gly Ile Phe Gly Pro Gly Ser Ser Ala Ala
            50              55              60

Ala Ala Ala Gly Pro Gly Thr Tyr Gly Pro Gly Ile Phe Gly Pro Ser
65              70              75              80

Ala Ser Ala Ala Ala Ala Gly Pro Gly Ser Gly Ile Phe Gly Pro
            85              90              95

Gly Ala Ser Gly Thr Tyr Gly Pro Gly Ile Phe Gly Pro Gly Ile Phe
            100             105             110

Gly Pro Gly Ser Ser Ala Ala Ala Ala Gly Thr Tyr Gly Ser Gly
            115             120             125
```

```
Pro Gly Ile Phe Gly Pro Tyr Gly Ser Ala Ala Ala Ala Gly Pro
    130             135             140

Gly Ser Gly Thr Tyr Gly Thr Gly Pro Tyr Gly Pro Gly Ala Ser Gly
145             150             155             160

Pro Gly Thr Tyr Gly Pro Gly Ile Phe Gly Pro Ser Ala Ser Ala Ala
                165             170             175

Ala Ala Ala Gly Ser Gly Ile Phe Gly Pro Gly Thr Tyr Gly Pro Tyr
            180             185             190

Ala Ser Ala Ala Ala Ala Ala Gly Thr Tyr Gly Ser Gly Pro Gly Ile
        195             200             205

Phe Gly Pro Tyr Gly Pro Gly Thr Ser Gly Ser Gly Ile Phe Gly Pro
    210             215             220

Gly Ile Phe Gly Pro Tyr Ala Ser Ala Ala Ala Ala Gly Pro Gly
225             230             235             240

Ile Phe Gly Pro Tyr Gly Pro Gly Ser Ser Ala Ala Ala Ala Ala Gly
                245             250             255

Thr Tyr Gly Tyr Gly Pro Gly Ile Phe Gly Pro Tyr Gly Pro Gly Ala
        260             265             270

Ser Gly Thr Gly Pro Gly Ser Gly Thr Tyr Gly Pro Gly Ile Phe Gly
        275             280             285

Pro Gly Thr Ser Ala Ala Ala Ala Gly Pro Gly Ile Phe Gly Pro
    290             295             300

Tyr Gly Pro Gly Ala Ser Ala Ala Ala Ala Ala Gly Thr Tyr Gly Pro
305             310             315             320

Gly Ile Phe Gly Pro Gly Thr Tyr Gly Pro Gly Ser Ser Gly Pro Gly
            325             330             335

Ile Phe Gly Pro Tyr Gly Pro Gly Ser Ser Ala Ala Ala Ala Gly
            340             345             350

Thr Tyr Gly Pro Gly Ile Phe Gly Pro Tyr Gly Pro Gly Thr Ser Ala
        355             360             365

Ala Ala Ala Gly Thr Tyr Ile Phe Gly Pro Gly Ile Phe Gly Pro
    370             375             380

Tyr Gly Pro Gly Ala Ser Gly Pro Gly Ile Phe Gly Pro Tyr Gly Pro
385             390             395             400

Gly Ala Ser Ala Ala Ala Ala Gly Pro Gly Thr Tyr Gly Pro Gly
            405             410             415

Ile Phe Gly Pro Ser Ala Ser Ala Ala Ala Ala Gly Thr Tyr Gly
            420             425             430

Ser Gly Pro Gly Thr Tyr Gly Pro Tyr Gly Pro Gly Thr Ser Gly Pro
        435             440             445

Gly Ser Gly Ile Phe Gly Thr Gly Pro Tyr Gly Pro Gly Ala Ser Ala
    450             455             460

Ala Ala Ala Gly Thr Tyr Gly Pro Gly Ile Phe Gly Pro Tyr Gly
465             470             475             480

Pro Gly Thr Ser Ala Ala Ala Ala Gly Pro Gly Ser Gly Thr Tyr
            485             490             495

Gly Pro Gly Ala Ser Gly Thr Gly Pro Gly Ser Gly Thr Tyr Gly Pro
        500             505             510

Gly Ile Phe Gly Pro Gly Thr Ser Ala Ala Ala Ala Gly Thr Tyr
            515             520             525

Ile Phe Gly Pro Gly Ile Phe Gly Pro Tyr Gly Pro Gly Ala Ser Ala
    530             535             540

Ala Ala Ala Gly Thr Tyr Gly Ser Gly Pro Gly Ile Phe Gly Pro
```

-continued

```
545              550              555              560

Tyr Gly Pro Gly Thr Ser Gly Ser Gly Ile Phe Gly Pro Gly Ile Phe
                565              570              575

Gly Pro Tyr Ala Ser Ala Ala Ala Ala Ala Gly Pro Gly Ser Gly Ile
            580              585              590

Phe Gly Pro Gly Ala Ser
        595

<210> SEQ ID NO 45
<211> LENGTH: 252
<212> TYPE: PRT
<213> ORGANISM: Artificial Sequence
<220> FEATURE:
<223> OTHER INFORMATION: Collagen-type4-Kai

<400> SEQUENCE: 45

Met His His His His His Ser Ser Gly Ser Ser Lys Asp Gly Val
1               5              10              15

Pro Gly Phe Pro Gly Ser Glu Gly Val Lys Gly Asn Arg Gly Phe Pro
            20              25              30

Gly Leu Met Gly Glu Asp Gly Ile Lys Gly Gln Lys Gly Asp Ile Gly
        35              40              45

Pro Pro Gly Phe Arg Gly Pro Thr Glu Tyr Tyr Asp Thr Tyr Gln Glu
    50              55              60

Lys Gly Asp Glu Gly Thr Pro Gly Pro Pro Gly Pro Arg Gly Ala Arg
65              70              75              80

Gly Pro Gln Gly Pro Ser Gly Pro Pro Gly Val Pro Gly Ser Pro Gly
                85              90              95

Ser Ser Arg Pro Gly Leu Arg Gly Ala Pro Gly Trp Pro Gly Leu Lys
            100             105             110

Gly Ser Lys Gly Glu Arg Gly Arg Pro Gly Lys Asp Ala Met Gly Thr
            115             120             125

Pro Gly Ser Pro Gly Cys Ala Gly Ser Pro Gly Leu Pro Gly Ser Pro
        130             135             140

Gly Pro Pro Gly Pro Pro Gly Asp Ile Val Phe Arg Lys Gly Pro Pro
145             150             155             160

Gly Asp His Gly Leu Pro Gly Tyr Leu Gly Ser Pro Gly Ile Pro Gly
            165             170             175

Val Asp Gly Pro Lys Gly Glu Pro Gly Leu Leu Cys Thr Gln Cys Pro
            180             185             190

Tyr Ile Pro Gly Pro Pro Gly Leu Pro Gly Leu Pro Gly Leu His Gly
            195             200             205

Val Lys Gly Ile Pro Gly Arg Gln Gly Ala Ala Gly Leu Lys Gly Ser
        210             215             220

Pro Gly Ser Pro Gly Asn Thr Gly Leu Pro Gly Phe Pro Gly Phe Pro
225             230             235             240

Gly Ala Gln Gly Asp Pro Gly Leu Lys Gly Glu Lys
            245             250

<210> SEQ ID NO 46
<211> LENGTH: 310
<212> TYPE: PRT
<213> ORGANISM: Artificial Sequence
<220> FEATURE:
<223> OTHER INFORMATION: Resilin-Kai

<400> SEQUENCE: 46
```

-continued

```
Met His His His His His Pro Glu Pro Pro Val Asn Ser Tyr Leu
1               5                   10                  15

Pro Pro Ser Asp Ser Tyr Gly Ala Pro Gly Gln Ser Gly Pro Gly Gly
            20                  25                  30

Arg Pro Ser Asp Ser Tyr Gly Ala Pro Gly Gly Gly Asn Gly Gly Arg
            35                  40                  45

Pro Ser Asp Ser Tyr Gly Ala Pro Gly Gln Gly Gln Gly Gln Gly Gln
        50                  55                  60

Gly Gln Gly Gly Tyr Ala Gly Lys Pro Ser Asp Ser Tyr Gly Ala Pro
65                  70                  75                  80

Gly Gly Gly Asp Gly Asn Gly Gly Arg Pro Ser Ser Ser Tyr Gly Ala
                85                  90                  95

Pro Gly Gly Gly Asn Gly Gly Arg Pro Ser Asp Thr Tyr Gly Ala Pro
            100                 105                 110

Gly Gly Gly Asn Gly Gly Arg Pro Ser Asp Thr Tyr Gly Ala Pro Gly
        115                 120                 125

Gly Gly Gly Asn Gly Asn Gly Gly Arg Pro Ser Ser Ser Tyr Gly Ala
    130                 135                 140

Pro Gly Gln Gly Gln Gly Asn Gly Asn Gly Gly Arg Pro Ser Ser Ser
145                 150                 155                 160

Tyr Gly Ala Pro Gly Gly Gly Asn Gly Gly Arg Pro Ser Asp Thr Tyr
            165                 170                 175

Gly Ala Pro Gly Gly Gly Asn Gly Gly Arg Pro Ser Asp Thr Tyr Gly
            180                 185                 190

Ala Pro Gly Gly Gly Asn Asn Gly Gly Arg Pro Ser Ser Ser Tyr Gly
        195                 200                 205

Ala Pro Gly Gly Gly Asn Gly Gly Arg Pro Ser Asp Thr Tyr Gly Ala
    210                 215                 220

Pro Gly Gly Gly Asn Gly Asn Gly Ser Gly Gly Arg Pro Ser Ser Ser
225                 230                 235                 240

Tyr Gly Ala Pro Gly Gln Gly Gln Gly Gly Phe Gly Gly Arg Pro Ser
            245                 250                 255

Asp Ser Tyr Gly Ala Pro Gly Gln Asn Gln Lys Pro Ser Asp Ser Tyr
            260                 265                 270

Gly Ala Pro Gly Ser Gly Asn Gly Asn Gly Gly Arg Pro Ser Ser Ser
        275                 280                 285

Tyr Gly Ala Pro Gly Ser Gly Pro Gly Gly Arg Pro Ser Asp Ser Tyr
        290                 295                 300

Gly Pro Pro Ala Ser Gly
305                 310

<210> SEQ ID NO 47
<211> LENGTH: 282
<212> TYPE: PRT
<213> ORGANISM: Artificial Sequence
<220> FEATURE:
<223> OTHER INFORMATION: elastin short

<400> SEQUENCE: 47

Met His His His His His His Ser Ser Gly Ser Ser Leu Gly Val Ser
1               5                   10                  15

Ala Gly Ala Val Val Pro Gln Pro Gly Ala Gly Val Lys Pro Gly Lys
            20                  25                  30

Val Pro Gly Val Gly Leu Pro Gly Val Tyr Pro Gly Gly Val Leu Pro
        35                  40                  45
```

```
Gly Ala Arg Phe Pro Gly Val Gly Val Leu Pro Gly Val Pro Thr Gly
    50              55                  60

Ala Gly Val Lys Pro Lys Ala Pro Gly Val Gly Gly Ala Phe Ala Gly
65              70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
                100                 105                 110

Tyr Thr Thr Gly Lys Leu Pro Tyr Gly Tyr Gly Pro Gly Gly Val Ala
                115                 120                 125

Gly Ala Ala Gly Lys Ala Gly Tyr Pro Thr Gly Thr Gly Val Gly Pro
    130                 135                 140

Gln Ala Ala Ala Ala Ala Ala Ala Lys Ala Ala Ala Lys Phe Gly Ala
145                 150                 155                 160

Gly Ala Ala Gly Val Leu Pro Gly Val Gly Gly Ala Gly Val Pro Gly
                165                 170                 175

Val Pro Gly Ala Ile Pro Gly Ile Gly Gly Ile Ala Gly Val Gly Thr
                180                 185                 190

Pro Ala Ala Ala Ala Ala Ala Ala Ala Ala Lys Ala Ala Lys Tyr
                195                 200                 205

Gly Ala Ala Ala Gly Leu Val Pro Gly Gly Pro Gly Phe Gly Pro Gly
    210                 215                 220

Val Val Gly Val Pro Gly Ala Gly Val Pro Gly Val Gly Val Pro Gly
225                 230                 235                 240

Ala Gly Ile Pro Val Val Pro Gly Ala Gly Ile Pro Gly Ala Ala Val
                245                 250                 255

Pro Gly Val Val Ser Pro Glu Ala Ala Ala Lys Ala Ala Ala Lys Ala
                260                 265                 270

Ala Lys Tyr Gly Ala Arg Pro Gly Val Gly
    275                 280
```

<210> SEQ ID NO 48
<211> LENGTH: 468
<212> TYPE: PRT
<213> ORGANISM: Artificial Sequence
<220> FEATURE:
<223> OTHER INFORMATION: type I keratin 26

<400> SEQUENCE: 48

```
Met Ser Phe Arg Leu Ser Gly Val Ser Arg Arg Leu Cys Ser Gln Ala
1               5                   10                  15

Gly Thr Gly Arg Leu Thr Gly Gly Arg Thr Gly Phe Arg Ala Gly Asn
                20                  25                  30

Val Cys Ser Gly Leu Gly Ala Gly Ser Ser Phe Ser Gly Pro Leu Gly
            35                  40                  45

Ser Val Ser Ser Lys Gly Ser Phe Ser His Gly Gly Gly Gly Leu Gly
    50                  55                  60

Ser Gly Val Cys Thr Gly Phe Leu Glu Asn Glu His Gly Leu Leu Pro
65                  70                  75                  80

Gly Asn Glu Lys Val Thr Leu Gln Asn Leu Asn Asp Arg Leu Ala Ser
                85                  90                  95

Tyr Leu Asp His Val Cys Thr Leu Glu Glu Ala Asn Ala Asp Leu Glu
                100                 105                 110

Gln Lys Ile Lys Gly Trp Tyr Glu Lys Tyr Gly Pro Gly Ser Gly Arg
                115                 120                 125
```

```
Gln Leu Ala His Asp Tyr Ser Lys Tyr Phe Ser Val Thr Glu Asp Leu
    130                 135                 140

Lys Arg Gln Ile Ile Ser Val Thr Thr Cys Asn Ala Ser Ile Val Leu
145                 150                 155                 160

Gln Asn Glu Asn Ala Arg Leu Thr Ala Asp Asp Phe Arg Leu Lys Cys
                165                 170                 175

Glu Asn Glu Leu Ala Leu His Gln Ser Val Glu Ala Asp Ile Asn Gly
                180                 185                 190

Leu His Arg Val Met Asp Glu Leu Thr Leu Cys Thr Ser Asp Leu Glu
                195                 200                 205

Met Gln Cys Glu Ala Leu Ser Glu Glu Leu Thr Tyr Leu Lys Lys Asn
    210                 215                 220

His Gln Glu Glu Met Lys Val Met Gln Gly Ala Ala Arg Gly Asn Val
225                 230                 235                 240

Asn Val Glu Ile Asn Ala Ala Pro Gly Val Asp Leu Thr Val Leu Leu
                245                 250                 255

Asn Asn Met Arg Ala Glu Tyr Glu Asp Leu Ala Glu Gln Asn His Glu
                260                 265                 270

Asp Ala Glu Ala Trp Phe Ser Glu Lys Ser Thr Ser Leu His Gln Gln
    275                 280                 285

Ile Ser Asp Asp Ala Gly Ala Ala Met Ala Ala Arg Asn Glu Leu Met
    290                 295                 300

Glu Leu Lys Arg Asn Leu Gln Thr Leu Glu Ile Glu Leu Gln Ser Leu
305                 310                 315                 320

Leu Ala Met Lys His Ser Tyr Glu Cys Ser Leu Ala Glu Thr Glu Ser
                325                 330                 335

Asn Tyr Cys His Gln Leu Gln Gln Ile Gln Glu Gln Ile Gly Ala Met
                340                 345                 350

Glu Asp Gln Leu Gln Gln Ile Arg Met Glu Thr Glu Gly Gln Lys Leu
    355                 360                 365

Glu His Glu Arg Leu Leu Asp Val Lys Ile Phe Leu Glu Lys Glu Ile
    370                 375                 380

Glu Met Tyr Cys Lys Leu Ile Asp Gly Glu Gly Arg Lys Ser Lys Ser
385                 390                 395                 400

Thr Cys Tyr Lys Ser Glu Gly Arg Gly Pro Lys Asn Ser Glu Asn Gln
                405                 410                 415

Val Lys Asp Ser Lys Glu Glu Ala Val Val Lys Thr Val Val Gly Glu
                420                 425                 430

Leu Asp Gln Leu Gly Ser Val Leu Ser Leu Arg Val His Ser Val Glu
    435                 440                 445

Glu Lys Ser Ser Lys Ile Ser Asn Ile Thr Met Glu Gln Arg Leu Pro
    450                 455                 460

Ser Lys Val Pro
465
```

```
<210> SEQ ID NO 49
<211> LENGTH: 7
<212> TYPE: PRT
<213> ORGANISM: Artificial Sequence
<220> FEATURE:
<223> OTHER INFORMATION: His6Tag

<400> SEQUENCE: 49

Met His His His His His His
1               5
```